United States Patent [19]
Horwell et al.

[11] Patent Number: 5,846,942
[45] Date of Patent: Dec. 8, 1998

[54] CHOLECYSTOKININ ANTAGONISTS, THEIR PREPARATION AND THERAPEUTIC USE

[75] Inventors: David Christopher Horwell, Foxton; Edward Roberts, New Market, both of England; Ann Holmes, Dexter, Mich.; Janak Khimchand Padia, Ann Arbor, Mich.; William Howard Roark, Ann Arbor, Mich.; Bruce David Roth, Ann Arbor, Mich.; Bharat Kalidas Trivedi, Farmington Hills, Mich.; Jurgen Kleinschroth, Denzlingen, Germany

[73] Assignee: Warner-Lambert Company, Morris Plains, N.J.

[21] Appl. No.: 709,316

[22] Filed: Sep. 9, 1996

Related U.S. Application Data

[60] Division of Ser. No. 41,647, Apr. 1, 1993, Pat. No. 5,593,967, which is a continuation-in-part of Ser. No. 839,647, Feb. 21, 1992, abandoned, which is a continuation-in-part of Ser. No. 726,655, Jul. 12, 1991, abandoned, which is a continuation-in-part of Ser. No. 576,628, Aug. 31, 1990, abandoned.

[51] Int. Cl.$^6$ ...................... C07D 209/18; C07D 217/00; C07D 209/20; A61K 38/00
[52] U.S. Cl. ............................. 514/18; 514/18; 546/143; 546/146; 546/147; 548/496; 530/331
[58] Field of Search ................................. 514/18; 530/331

[56] References Cited

U.S. PATENT DOCUMENTS

| | | | |
|---|---|---|---|
| 4,275,153 | 6/1981 | Gargiulo et al. | 435/13 |
| 4,428,874 | 1/1984 | Svendsen et al. | 260/112.5 |
| 4,757,151 | 7/1988 | Horwell | 548/469 |
| 4,826,958 | 5/1989 | Sham et al. | 530/331 |

FOREIGN PATENT DOCUMENTS

| | | |
|---|---|---|
| 0230151 | 7/1987 | European Pat. Off. |
| 0336356 | 10/1989 | European Pat. Off. |
| 0405537 A1 | 1/1991 | European Pat. Off. |
| 0405537 | 2/1991 | European Pat. Off. ...... C07D 209/20 |
| 91/02719 | 3/1991 | WIPO. |
| 92/04322 | 3/1992 | WIPO. |
| 92/14751 | 9/1992 | WIPO. |

OTHER PUBLICATIONS

Johansson et al. Somatostatin immunoreactive cells in lesional psoriatic human skin during peptide treatment. Acta dermatol. Venerol., 74: 106–109, Jan. 1994.
Ngo et al In:The protein folding and tertiary structure predicion, K. Mertz and S. Le Grand, Eds. Birkhauser, Boston, 1994, pp. 491–495.
*Brain Research*, 288 (1983) 199–211. G. W. Roberts et al., "Peptides, the Limbic Lobe and Schizophrenia".
*Brain Research*, 406 (1987) 130–135. B. A. MacVicar et al., "Inhibition of synaptic transmission in the hippocampus by . . . ".
*British Medical Bulletin*, (1982), v. 38, No. 3, pp. 253–258, G.J. Dockray, "The Physiology of Cholecystokinin in Brain and Gut".
*Cancer Research*, 46, 1612–1616, Apr. 1986, P. Singh et al., "Role of Gastrin and Gastrin Receptors on the Growth of a Transplantable . . . ".
*CCK in the Nervous System*, Ch. 7, pp. 110–127, M.J. Sheehan et al., "Central Actions of Cholecystokinin: Behavioral and Release Studies".
*Gastroenterology*, 1988; v. 95, No. 6, pp. 1541–1548, J. Palmer Smith et al., "Effects of Gastrin, Proglumide, and Somatostatin . . . ".
*Gastrointestinal Hormones*, 1980, Ch. 7, pp. 169–221, Viktor Mutt, "Cholecystokinin: Isolation, Structure, and Functions".
*Ibid.*, Ch. 22, pp. 507–527, Leonard R. Johnson, "Effect of Gastrointestinal Hormones on Growth of Gastrointestinal Tissue".
*Ibid.*, Ch. 23, pp. 529–564, Stanislaw J. Konturek, "Gastrointestinal Hormones and Gastric Secretion".
*Ibid.*, Ch. 30, pp. 729–739, Fl. Stadil, "Gastrinomas".
*Life Sciences*, v. 27, pp. 355–368, John E. Morley, "The Neuroendocrine Control of Appetite: The Role of the Endogenous Opiates . . . ".
*Journal of Neurochemistry*, v. 32, pp. 1339–1341, "Immunochemical Evidence of Cholecystokinin Tetrapeptides in Hog Brain".
*Neuropharmacology*, v. 26, No. 4, pp. 289–300, 1987, R.G. Hill, et al., "Antinociceptive Action of Cholecystokinin Octapeptide (CCK 8) . . . ".
*Journal of Neuroscience*, Mar. 1998, 8(3):988–1000, H. Demeulemeester, et al., "Heterogeneity of GABAergic Cells in Cat Visual Cortex".
*Neuroscience*, v. 19, No. 1, pp. 181–192, 1986, S. Totterdell et al., "Cholecystokinin–immunoreactive Boutons in Synaptic Contacts . . . ".
*Peptides*, v. 4, pp. 749–753, 1983, L.H. Schneider et al., "CCK–8 Modulation of Mesolimbic Dopamine: Antagonism of Amphetamine–. . . ".
Goodman and Gilman's *The Pharmacological Basis of Therapeutics*, 7th ed (1985), Ch. 17, S.C. Harvey, "Hypnotics and Sedatives".
*Pharmacology Biochemistry & Behaviour*, v. 30, pp. 309–317, 1988, Friedbert Weiss, et al., "Opposite Actions of CCK–8 on . . . ".

(List continued on next page.)

*Primary Examiner*—Cecilia J. Tsang
*Assistant Examiner*—Michael Borin
*Attorney, Agent, or Firm*—Elizabeth M. Anderson

[57] ABSTRACT

Novel cholecystokinin antagonists useful as agents in the treatment of obesity, hypersecretion of gastric acid in the gut, gastrin-dependent tumors, or as antipsychotics are disclosed. Further, the compounds are antianxiety agents and antiulcer agents. They are agents useful for preventing the response to the withdrawal from chronic treatment with use of nicotine, diazepam, alcohol, cocaine, coffee, or opioids. The compounds of the invention are also useful in treating and/or preventing panic. Also disclosed are pharmaceutical compositions and methods of treatment using the antagonists as well as processes for preparing them and novel intermediates useful in their preparation. An additional feature of the invention is the use of the subject compounds in diagnostic compositions.

6 Claims, No Drawings

OTHER PUBLICATIONS

*Regulatory Peptides*, 14 (1986) 277–291, R. R. Schick et al., "Intracerebroyentricular injections of cholecystokinin . . . ".

*Science*, v. 206, Oct. 26, 1979, pp. 471–473, "Cholecystokinin Octapeptide: Continuous Picomole Injections into the Cerebral . . . ".

*Trends in Pharmacological Sciences*, v. 11, Jul. 1990, pp. 271–273, "Cholecystokinin and Anxiety".

Copending application USSN 07/576,308 filed Aug. 31, 1990.

Copending application USSN 07/576,296 filed Aug. 31, 1990.

Copending application USSN 07/576,315 filed Aug. 31, 1990.

Copending application USSN 07/576,024 filed Aug. 31, 1990.

Copending application USSN 07/576,297 filed Aug. 31, 1990.

Copending application USSN 07/545,222 filed Jun. 28, 1990.

Horwell, C.C., et al, *Eur J Med Chem,* 1990, 25:53–60.

A. G. S. Blommaert, et al., *J Med Chem*, 1993, 36, 2868–2877.

P. R. Boden, et al., *Br J Pharmacol*, 1994, 112:666–670.

Horwell, C.C., et al, *Eur J Med Chem*, 1990, 25:53–60.

CHOLECYSTOKININ ANTAGONISTS, THEIR PREPARATION AND THERAPEUTIC USE

CROSS-REFERENCE TO RELATED APPLICATIONS

This is a Divisional Application of U.S. Ser. No. 08/041,647 filed Apr. 1, 1993, now U.S Pat. No. 5,593,967, which is a Continuation-In-Part application of U.S. Ser. No. 07/839,647, filed Feb. 21, 1992, now abandoned, which is a Continuation-In-Part application of U.S. Ser. No. 07/726,655, filed Jul. 12, 1991, now abandoned, which is a Continuation-In-Part application of U.S. Ser. No. 07/576,628, filed Aug. 31, 1990, now abandoned.

BACKGROUND OF THE INVENTION

Agents acting at central cholecystokinin (CCK) receptors may induce satiety (Schick, Yaksh, and Go, *Regulatory Peptides* 14:277–291, 1986). They are also expected to act as analgesics (Hill, Hughes, and Pittaway, *Neuropharmacology* 26:289–300, 1987), and as anticonvulsants (MacVicar, Kerrin, and Davison, *Brain Research* 406:130–135, 1987).

Reduced levels of CCK-peptides have been found in the brains of schizophrenic patients compared with controls (Roberts, Ferrier, Lee, Crow, Johnstone, Owens, Bacarese-Hamilton, McGregor, O'Shaughnessey, Polak, and Bloom, *Brain Research* 288:199–211, 1983). It has been proposed that changes in the activity of CCK neurones projecting to the nucleus accumbens may play a role in schizophrenic processes by influencing dopaminergic function (Totterdell and Smith, *Neuroscience* 19:181–192, 1986). This is consistent with numerous reports that CCK peptides modulate dopaminergic function in the basal ganglia and particularly the nucleus accumbens (Weiss, Tanzer, and Ettenberg, *Pharmacology, Biochemistry and Behaviour* 30:309–317, 1988; Schneider, Allpert, and Iversen, *Peptides* 4:749–753, 1983). It may therefore be expected that agents modifying CCK receptor activity may have therapeutic value in conditions associated with disturbed function of central dopaminergic function such as schizophrenia and Parkinson's disease.

CCK and gastrin peptides share a common carboxy-terminal pentapeptide sequence and CCK peptides can bind to the gastrin receptor of the stomach mucosa and elicit acid secretion in many species including human (Konturek, *Gastrointestinal Hormones*, Ch. 23, pp 529–564, 1980, ed. G. B. J. Glass, Raven Press, NY). Antagonists of the CCK-B receptor would also be expected to be antagonists at the stomach gastrin receptor and this would also be of value for conditions involving excessive acid secretion.

CCK and gastrin peptides have trophic effects on the pancreas and various tissues of the gastrointestinal tract (Johnson, *ibid.,* pp 507–527), actions which are associated with increased DNA and RNA synthesis. Moreover, gastrin secreting cells are associated with certain gastrointestinal tumors as in the Zollinger-Ellison syndrome (Stadil, *ibid.,* pp 729–739), and some colorectal tumors may also be gastrin/CCK dependent (Singh, Walker, Townsend, and Thompson, *Cancer Research* 46:1612, 1986; Smith, J. P., *Gastroenterology* 95:1541, 1988). Antagonists of CCK/gastrin receptors could therefore be of therapeutic value as antitumor agents.

The CCK peptides are widely distributed in various organs of the body including the gastrointestinal tract, endocrine glands, and the nerves of the peripheral and central nervous systems. Various biologically active forms have been identified including a 33-amino acid hormone and various carboxyl-terminus fragments of this peptide (e.g., the octapeptide CCK26-33 and the tetrapeptide CCK30-33). (G. J. Dockray, *Br. Med. Bull.* 38(3):253–258, 1982).

The various CCK peptides are thought to be involved in the control of smooth muscle contractility, exocrine and endocrine gland secretion, sensory nerve transmission, and numerous brain functions. Administration of the native peptides cause gall bladder contraction, amylase secretion, excitation of central neurons, inhibition of feeding, anticonvulsive actions and other behavioral effects. (*Cholecystokinin: Isolation, Structure and Functions*, G. B. J. Glass, Ed., Raven Press, New York, 1980, pp 169–221; J. E. Morley, *Life Sciences* 27:355–368, 1980; *Cholecystokinin in the Nervous System*, J. de Belleroche and G. J. Dockray, Ed., Ellis Horwood, Chichester, England, 1984, pp 110–127.)

The high concentrations of CCK peptides in many brain areas also indicate major brain functions for these peptides (G. J. Dockray, *Br. Med. Bull.* 38(3):253–258, 1982). The most abundant form of brain CCK found is CCK26-33, although small quantities of CCK30-33 exist (Rehfeld and Gotterman, *J. Neurochem.* 32:1339–1341, 1979). The role of central nervous system CCK is not known with certainty, but it has been implicated in the control of feeding (Della-Fera and Baile, *Science* 206:471–473, 1979).

Currently available appetite suppressant drugs either act peripherally, by increasing energy expenditure (such as thyroxine), or in some other manner (such as the biguanides), or act by exerting a central effect on appetite or satiety.

Centrally acting appetite suppressants either potentiate central catecholamine pathways and tend to be stimulants (for example, amphetamine), or influence serotonergic pathways (for example, fenfluramine). Other forms of drug therapy include bulking agents which act by filling the stomach, thereby inducing a "feeling" of satiety.

CCK is known to be present in some cortical interneurones which also contain gamma-aminobutyric acid (GABA) (H. Demeulemeester et al, *J. Neuroscience* 8:988–1000, 1988). Agents that modify GABA action may have utility as anxiolytic or hypnotic agents (S. C. Harvey, *The Pharmacological Basis of Therapeutics* (7th ed.) 1985, pp 339–371, MacMillan). Thus, agents which modify CCK action may have parallel anxiolytic or hypnotic activities. The role of CCK in anxiety is disclosed in *TIPS* 11:271–273, 1990, and is fully detailed in Woodruff, G. N. and Hughes, J., 1991, *Ann. Rev. Pharmacol. and Toxicol.* 31, 469–501.

SUMMARY OF THE INVENTION

The invention relates to novel compounds of the formula

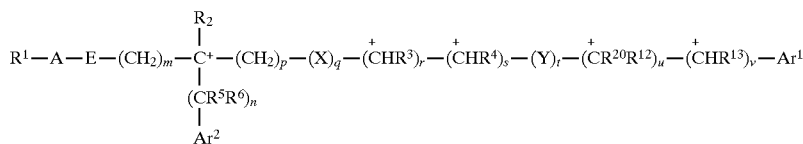

and the pharmaceutically acceptable salts thereof wherein $R^1$, $R^2$, $R^3$, $R^4$, $R^5$, $R^6$, $R^{12}$, $R^{13}$, $R^{20}$, A, X, Y, E, $Ar^1$, $Ar^2$, n, m, p, q, r, s, t, u, and v are as defined hereinbelow.

In commonly owned copending applications 07/576,308, 07/576,296, 07/576,315, 07/576,024, and 07/576,297 filed on Aug. 31, 1990, and now abandoned by Horwell, et al, the disclosures of which are incorporated herein by reference, CCK antagonists are disclosed.

In the continuation-in-part applications of the above applications also commonly owned and copending 07/726,656, 07/726,654, 07/726,653, 07/726,652, and 07/726,651 filed on Jul. 12, 1991, by Horwell, et al, the disclosures of which are incorporated herein by reference, CCK antagonists are disclosed. In like manner, the present invention relates to a pharmaceutical composition containing an effective amount of a compound according to formula I in combination with a pharmaceutically acceptable carrier in unit dosage form effective for appetite suppression.

The compounds are also useful as anxiolytics, antipsychotics, especially for treating schizophrenic behavior, as agents in treating disorders of the extrapyramidal motor system, as agents for blocking the trophic and growth stimulating actions of CCK and gastrin, and as agents for treating gastrointestinal motility.

Compounds of the invention are also useful as analgesics, and they potentiate the effect of morphine. They can be used as an adjunct to morphine and other opioids in the treatment of severe pain such as cancer pain, and reduce the dosage of morphine required in the treatment of pain where morphine is contraindicated.

An additional use for compounds of the invention is that a suitable radiolabeled isotope gives an agent suitable for treatment of gastrin dependent tumors such as those found in colonic cancers. I-125 radiolabeled compounds of the invention can also be used as diagnostic agents by localization of gastrin and CCK-B receptors in both peripheral and central tissue.

The invention further relates to a method of appetite suppression in mammals which comprises administering an amount effective to suppress appetite of the composition described above to a mammal in need of such treatment.

The invention also relates to a pharmaceutical composition for reducing gastric acid secretion containing an effective amount of a compound of formula I in combination with a pharmaceutically acceptable carrier in unit dosage form effective for reducing gastric acid secretion.

The invention also relates to a method for reducing gastric acid secretion in mammals which comprises administering an amount effective for gastric acid secretion reduction of the composition described above to a mammal in need of such treatment.

The invention also relates to a pharmaceutical composition containing an effective amount of a compound of formula I in combination with a pharmaceutically acceptable carrier in unit dosage form effective for reducing anxiety.

The invention also relates to a method for reducing anxiety in mammals which comprises administering an amount effective for anxiety reduction of the composition described above to a mammal in need of such treatment.

The invention also relates to a pharmaceutical composition containing an effective amount of a compound of formula I in combination with a pharmaceutically acceptable carrier in unit dosage form effective for treating gastrointestinal ulcers.

The invention further relates to a method for treating gastrointestinal ulcers in mammals which comprises administering an amount effective for gastrointestinal ulcer treatment of the composition as described above to a mammal in need of such treatment.

The invention also relates to a pharmaceutical composition containing an effective amount of a compound of formula I in combination with a pharmaceutically acceptable carrier in unit dosage form effective for treating psychosis, i.e., schizophrenia.

The invention further relates to a method for treating psychosis in mammals which comprises administering an amount effective for treating psychoses of a composition as described above to a mammal in need of such treatment.

The invention also relates to pharmaceutical compositions effective for stimulating or blocking CCK or gastrin receptors, for altering the activity of brain neurons, for schizophrenia, for treating disorders of the extrapyramidal motor system, for blocking the trophic and growth stimulating actions of CCK and gastrin, and for treating gastrointestinal motility.

The invention also relates to a pharmaceutical composition for preventing the withdrawal response produced by chronic treatment for abuse of drugs or alcohol.

The invention further relates to a method for treating the withdrawal response produced by withdrawal from chronic treatment or withdrawal from abuse of drugs or alcohol. Such drugs include benzodiazepines, especially diazepam, cocaine, alcohol, and nicotine. Withdrawal symptoms are treated by administration of an effective withdrawal treating amount of a compound of the invention.

The invention also relates to a pharmaceutical composition containing an effective amount of a compound of formula I in combination with a pharmaceutically acceptable carrier in unit dosage form effective for treating and/or preventing panic.

The invention also relates to a method for treating and/or preventing panic in mammals which comprises administering an amount effective for panic treatment and/or prevention of the composition described above to a mammal in need of such treatment.

The invention further relates to the use of the compounds of formula I to prepare pharmaceutical and diagnostic compositions for the treatment and diagnosis of the conditions described above.

The invention further provides processes for the preparation of compounds of formula I.

The invention further provides novel intermediates useful in the preparation of compounds of formula I and also provides processes for the preparation of the intermediates.

DETAILED DESCRIPTION

The compounds of the present invention are represented by the formula

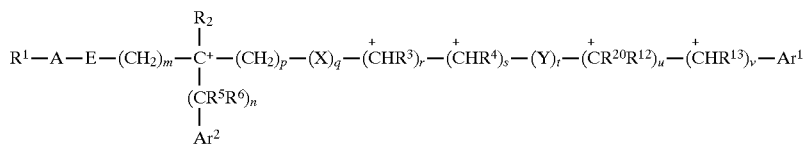

or a pharmaceutically acceptable salt thereof wherein:
$R^1$ is a cyclo or polycycloalkyl hydrocarbon or mono- or polyheterocycle moiety (wherein the hetero atom(s) can be N, O, and/or S of from 3 to 12 carbon atoms with from 0 to 4 substituents each independently selected from a straight or branched alkyl of from 1 to 6 carbon atoms, halogen, CN, OR*, SR*, $CO_2R^*$, $CF_3$, $NR^5R^6$, or $(CH_2)_nOR^5$ wherein R*, $R^5$, and $R^6$ are each independently hydrogen or a straight or branched alkyl of from 1 to about 6 carbon atoms;

m, n, p, q, r, s, t, u, and v are each independently an integer of from 0 to 6 with the proviso that q, r, and s are not all 1 when m, p, t, u, and v are all 0 except when X is not $CONR^9$ or A–E is not $(CH_2)_nCONH$—, $-SO_2NH$—, $-S(O)NH$—, $-NHCONH$, $-(CH_2)_n-OCO-NH-SCONH$—, $-O(CH_2)_nCO$— or $-HC=CHCONH$— wherein n is as above, A is a bond,
O,
S,
NR*,
$-(CH_2)_nCo-Z$,
$-SO_2-Z$,
$-SO-Z$,
$-S-Z$,
$-NHCO-Z$,

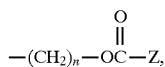

$-SCO-Z$,
$-O-(CH_2)_nCO-Z$,
$-HC=CHCO-Z$,
wherein Z is a bond, oxygen, sulphur, or $-NR^*-$
wherein R* is as defined above;
E is a bond,
an amino acid residue,
$-(CHR^3)_r-$,
$-(CHR^3)_r-(CHR^4)_s-$,
$-CONH-$,
$-NHCO-$,
$-OCO-$,
$-COO-$,
$-CH_2N(R^3)-$,
$-CH_2O-$,
$-CH_2S-$,
$-C=C-$,

$-SO_2NR^3-$,
$-NR^3SO_2-$, $-NHCONH-$,

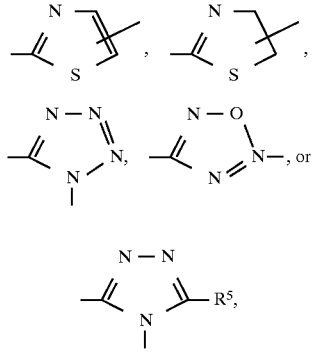

wherein r and s are independently as defined above;

$R^2$ and $R^{20}$ are each independently hydrogen, a straight or branched alkyl of from 1 to 6 carbon atoms, $-HC=CH_2$, $-C\equiv CH$, $-(CH_2)_nCH=CH_2$, $-(CH_2)_nC\equiv CH$, $-(CH_2)_nAr^1$, $-(CH_2)_nAr^2$, $-(CH_2)_nOR^*$, $-(CH_2)_nOAr$, $-(CH_2)_nCO_2R^*$, $-(CH_2)_nNR^5R^6$ wherein n, R*, $R^5$, and $R^6$ are as defined above, and $Ar^1$ and $Ar^2$ are as defined below;

X and Y are each independently:
$-CONH-$,
$-CONR^9$,
$-NHCO-$,
$-OCO-$,
$-COO-$,
$-CH_2N(R^3)-$,
$-CH_2O-$,
$-CH_2S-$,
$-OCH_2-$,
$-SCH_2-$,
$-C=C-$,

$-SO_2NR^3-$,
$-NR^3SO_2-$,
$-NHCONH-$,
$-CH(OR^*)CH_2-$,
$-COCH_2-$,
$-CH_2CO-$,

—NR³CH₂—,

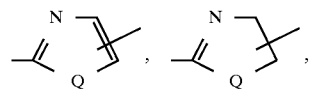

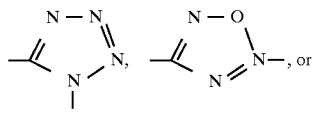

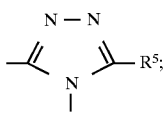

wherein Q is O, S, or NR⁹;

R³ and R⁴ are each independently the same as R² or —(CH₂)$_{n'}$—B—D wherein n' is an integer of from 0 to 3;

B is a bond,
—OCO(CH₂)$_n$—,
—O(CH₂)$_n$—,
—NHCO(CH₂)$_n$—,
—CONH(CH₂)$_n$—,
—NHCOCH=CH—,
—COO(CH₂)$_n$—,
—CO(CH₂)$_n$—,
—SO(CH₂)$_n$—,
—S(CH₂)$_n$—,
—SO₂(CH₂)$_n$—,

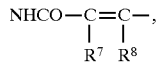

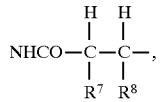

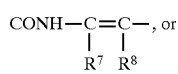

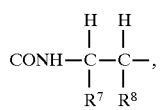

wherein R⁷ and R⁸ are each independently selected from hydrogen and R² or together form a ring (CH₂)$_m$ wherein m is an integer of from 1 to 5, D is —COOR*,
—CH₂OR*,
—CHR²OR*,
—CH₂SR*,
—CHR²SR*,
—CONR⁵R⁶,
—CN,
—NR⁵R⁶,
—OH,
—H, and acid replacements selected from: tetrazole;

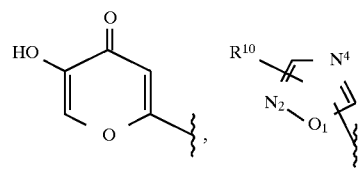

1,2,4 oxadiazole

R¹⁰ is OH, NH₂, CH₃, or Cl

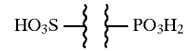

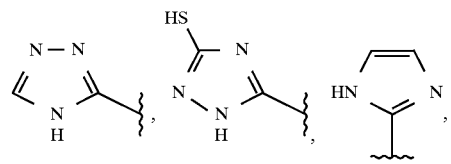

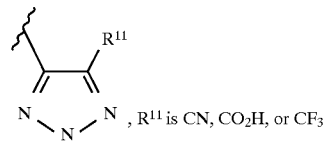

R¹¹ is CN, CO₂H, or CF₃

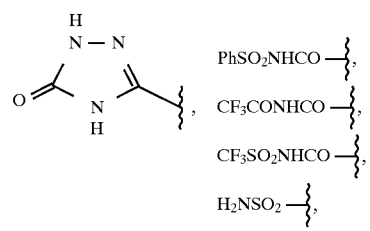

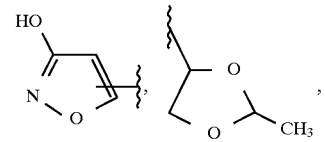

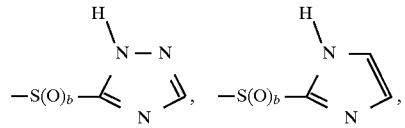

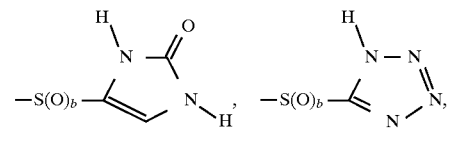

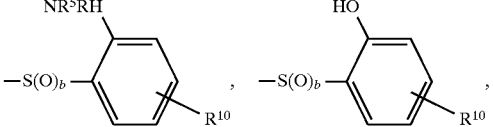

wherein b is an integer of from 0 to 2,
wherein R*, R², R⁵, and R⁶ are as defined above; R⁹ is H, or a straight or branched alkyl of from one to six carbon atoms, —(CH₂)$_n$CO₂R*, (CH₂)$_n$ OAr', (CH₂)$_n$Ar', (CH₂)$_n$NR⁵R⁶, wherein n, R*, R⁵, and R⁶ are as defined above or taken from R3 and Ar' is taken from Ar as defined below;

$R^{12}$ and $R^{13}$ are each independently hydrogen or taken together form a double bond, or are —$(CH_2)_n$—B—D as defined above; and $Ar^1$ and $Ar^2$ are each independently a mono- or polycyclic unsubstituted or substituted carbo- or heterocyclic aromatic or carbo- or heteroaromatic moiety; and Preferred $Ar^1$ is substituted phenyl, fused aryl, heterocycle, fused heterocycle, or perhydroaryl.

Preferred $Ar^1$ is 2 or 3-thienyl, 2 or 3-furanyl, 2, 3 or 4-pyridinyl or an unsubstituted or substituted benzene ring

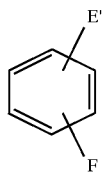

wherein $E^1$ and F are each independently hydrogen, fluorine, chlorine, bromine, iodine, methyl, methoxy, trifluoromethyl, nitro, hydroxy, $NH_2$, $OCF_3$, $NHCOCH_2CH_2OH$, or $CH_2CH_2CO_2H$.

Other preferred $Ar^1$ include pyrrolidinyl, cyclohexyl, cyclopentyl, bicyclo, and piperidinyl groups.

Preferred cycloalkyl or polycycloalkyl substituents have from six to ten carbon atoms.

Preferred compounds of the instant invention are those wherein cycloalkyl is a substituted or unsubstituted

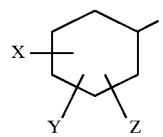

and wherein polycycloalkyl is selected from

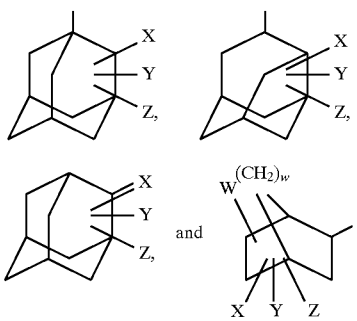

wherein W, X, Y, and Z are each independently hydrogen, a straight or branched alkyl of from one to six carbon atoms, $CF_3$, $NR^5R^6$, —$(CH_2)_nCO_2R^*$, or CN, F, Cl, Br, $OR^*$, $SR^*$, wherein $R^*$ is hydrogen or a straight or branched alkyl of from one to six carbon atoms and R5 and $R^6$ are as defined above and n is an integer of from 1 to 3.

Preferred mono- or polyheterocyclic moieties wherein the heteroatom can be W, 0, and/or mono- and polycyclic hydrocarbons include compounds wherein $R^1$ is

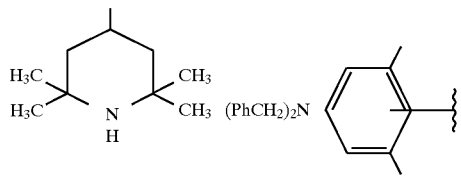

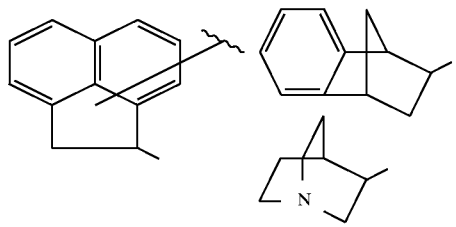

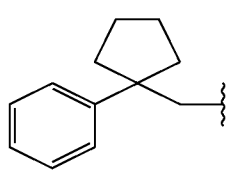

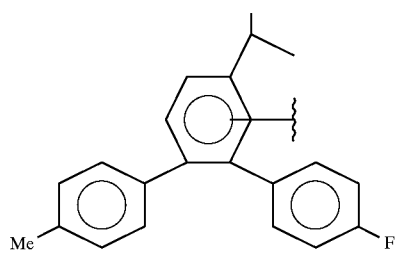

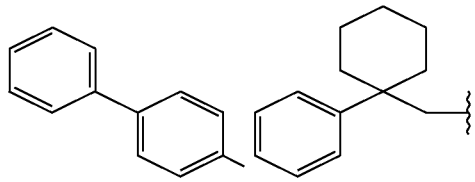

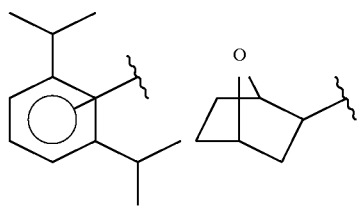

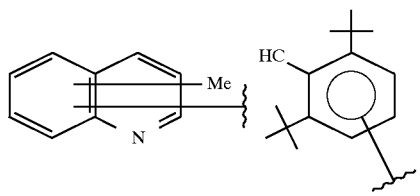

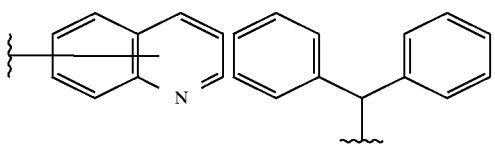

Other preferred compounds of the instant invention are those wherein

R¹ is 2-adamantyl or 1-(S)-2-endobornyl;
A is —NHCO—, —OCO—, —SO₂—, —S(=O)— or —CH₂CO—;
R² is —CH₃, —CH₂CO₂CH₃ or —CH₂C≡CH;
R³ is —(CH₂)ₙ—B—D or H; and
R⁴ is —(CH₂)ₙ—B—D or H.

More preferred compounds of the instant invention are those wherein
R¹ is 2-adamantyl or 1-(S)-2-endobornyl,
A is

R² is —CH₃;
R³ is H, —CH₂OH, —CH₂OCOCH₂CH₂CO₂H, —CH₂OCOCH=CHCO₂H, —CH₂CO₂H—, —CH₂SCH₂CO₂H—, —CH₂SCH₂CH₂CO₂H—, —CH₂NHCOCH₂CH₂CO₂H, or —CH₂NHCOCH=CHCO₂H and
R⁴ is H, -NHCOCH₂CH₂CO₂H ([D] configuration) or —NHCOCH=CHCO₂H ([D] configuration).

The D and the L configurations are possible at the chiral centers and are included in the scope of the invention:
1. Preferred is when R² is —CH₃[D] configuration;
2. Preferred is when R³ is —CH₂OCOCH₂CH₂CO₂H or —CH₂NHCOCH₂CH₂CO₂H with the [D] configuration at the Trp α-carbon atom and the [L] configuration at the Phe—α-carbon atom; and
3. Preferred is when R⁴ is —NHCOCH₂CH₂CO₂H[D] configuration or NHCOCH=CHCO₂H[D] configuration with the [D] configuration at the Trp α-carbon atom.

Most preferred compounds of the instant invention are:
Carbamic acid, [2-[[1-(hydroxymethyl)-2-phenylethyl]amino]-1-(1H-indol-3-ylmethyl)ethyl]-, tricyclo[3.3.1.1³,⁷]dec-2-yl ester, [S-(R*,S*)]-,
Carbamic acid, [2-[[1-(hydroxymethyl)-2-phenylethyl]amino]-1-(1H-indol-3-ylmethyl)ethyl-, tricyclo[3.3.1.1³,⁷]dec-2-yl ester, [S-(R*,R*)]-,
Tricyclo[3.3.1.1³,⁷]dec-2-yl[1-[[[1-hydroxy-methyl)-2-phenylethyl]carbonyl]amino]-2-(1H-indol-3-yl)ethyl]carbamate,
Carbamic acid, [2-[(2-hydroxy-2-phenylethyl)-amino]-1-(1H-indol-3-ylmethyl)-1-methylethyl]-, tricyclo[3.3.1.1³,⁷]dec-2-yl ester (hydroxy center is RS, other center is R),
Carbamic acid, [2-[[1-(hydroxymethyl)-2-phenyl-ethyl]amino]-1-(1H-indol-3-ylmethyl)-1-methylethyl]-, tricyclo[3.3.1.1³,⁷]dec-2-yl ester, [R-(R*,S*)]-, 4-methylbenzenesulfonate (1:1) (salt),
Benzenepropanol,:β-[[2-(1H-indol-3-yl)-2-[[tricyclo[3.3.1.1³,⁷]dec-2-yloxy)carbonyl]amino]-propyl]amino]-, acetate (ester), [R-(R*,S*)]-, 4-methylbenzenesulfonate (1:1) (salt),
Carbamic acid, [[2-[acetyl[1-(hydroxymethyl)-2-phenylethyl]amino]-1-(1H-indol-3-ylmethyl)-1-methyl]ethyl]-, tricyclo[3.3.1.1³,⁷]dec-2-yl ester, [R-(R*,S*)]-,
5,13-Dioxo-2,8-diazatetradec-10-enoic acid, 3-(1H-indol-3-ylmethyl)-3-methyl-4,9,12-trioxo-7-phenyl-, tricyclo[3.3.1.1³,⁷]dec-2-yl ester, [S-(R*,S*)]-,
5,13-Dioxo-2,8-diazatetradecanoic acid, 3-(1H-indol-3-ylmethyl)-3-methyl-4,9,12-trioxo-7-phenyl-, tricyclo[3.3.1.1³,⁷]dec-2-yl ester, [R-(R*,R*)]-,
Carbamic acid,[1-(1H-indol-3-ylmethyl)-1-methyl-2-[(1-oxo-4-phenylbutyl)amino]ethyl]-, tricyclo]3.3.1.1³,⁷]dec-2-yl ester (R)-, Carbamic acid, [2-(benzoylamino)-1-(1H-indol-3-ylmethyl)-1-methylethyl]-, tricyclo[3.3.1.1³,⁷]dec-2-yl ester, (R)-,
Carbamic acid, [1-(1H-indol-3-ylmethyl)-1-methyl-2-[(1-oxo-3-phenylpropyl)amino)ethyl]-, tricyclo[3.3.1.1³,⁷]dec-2-yl ester, (R)-,
Carbamic acid, [1-(1H-indol-3-ylmethyl)-1-methyl-2-[(2-phenylacetyl)amino]ethyl]-, tricyclo-[3.3.1.1³,⁷]dec-2-yl ester, (R)-,
Carbamic acid, [2-[[3-[[1-(hydroxymethyl)-2-phenylethyl]amino]-3-oxopropyl)amino]-1-(1H-indol-3-ylmethyl)-1-methyl-2-oxoethyl]-, [R,(R*,S*)]-,
Carbamic acid, [1-(1H-indol-3-ylmethyl)-2-[[3-[[1-(hydroxymethyl)-2-phenylethyl]amino]-3-oxopropyl]amino]-1-methyl-2-oxoethyl]-, tricyclo-[3.3.1.1³,⁷]dec-2-yl ester, [S-(R*,R*)]-,
D-Phenylalaninamide, α-methyl-N-[(tricyclo[3.3.1.1³,⁷]dec-2-yloxy)carbonyl]-D-tryptophyl-β-alanyl-,
L-Phenylalaninamide, α-methyl-N-[(tricyclo[3.3.1.1³,⁷]dec-2-yloxy)carbonyl]-D-tryptophyl-β-alanyl-,
L-Phenylalaninamide, α-methyl-N-[(tricyclo[3.3.1.1³,⁷]dec-2-yloxy)carbonyl]-L-tryptophyl-β-alanyl-,
D-Phenylalaninamide, α-methyl -N-[tricyclo[3.3.1.1³,⁷]dec-2-yloxy)carbonyl]-L-tryptophyl-β-alanyl-,
12-Oxo-2,5,9-triazatridecanoic acid, 3-(1H-indol-3-ylmethyl)-3-methyl-4,8,11-trioxo-10-(phenylmethyl)-, tricyclo[3.3.1.1³,⁷]dec-2-yl ester, [R,(R*,R*)]-,
L-Phenylalanine, N-[N-[α-methyl-N-[(tricyclo[3.3.1.1³,⁷]dec-2-yloxy)carbonyl]-D-tryptophyl]-β-alanyl]-, phenylmethyl ester,
Propanoic acid, 2-[[3-[[3-(1H-indol-3-yl)-2-methyl-1-oxo-2-[[(tricyclo[3.3.1.1³,⁷]dec-2-yloxy)carbonyl]amino]propyl]amino]-1-oxopropyl]-amino]-3-phenyl-, phenylmethyl ester, [S-(R*,R*)]-,
D-Phenylalanine, N-[N-[α-methyl-N-[(tricyclo[3.3.1.1³,⁷] dec-2-yloxy)carbonyl]-D-tryptophyl]-β-alanyl]-,
L-Phenylalanine, N-[N-[α-methyl-N-[(tricyclo[3.3.1.1³,⁷]dec-2-yloxy)carbonyl]-D-tryptophyl]-β-alanyl]-,
L-Phenylalanine, N-[N-[α-methyl-N-[(tricyclo[3.3.1.1³,⁷]dec-2-yloxy)carbonyl]-L-tryptophyl]-β-alanyl]-,
Benzenepropanoic acid, α-[[3-[[3-[(1H-indol-3-yl)-2-methyl-1-oxo-2-[[(tricyclo[3.3.1.1³,⁷]dec-2-yloxy)carbonyl]amino]propyl]amino]-1-oxopropyl]-amino]-, [S-(R*,S*)]-,
Glycine, N-[2-methyl-N-[(tricyclo[3.3.1.1³,⁷]dec-2-yloxy)carbonyl]-D-tryptophyl]-, phenylmethyl ester,
Carbamic acid, [3-(1H-indol-3-ylmethyl)-2,5-dioxo-1-(2-phenylethyl)-3-pyrrolidinyl]-, tricyclo[3.3.1.1 ³,⁷]dec-2-yl ester, (±)-,
Carbamic acid, [1-(1H-imidazol-4-ylmethyl)-1-methyl-2-oxo-2-[(2-phenylethyl)amino]ethyl]-, 1,1-dimethylethyl ester, (±)-,
Carbamic acid, [3-(1H-indol-3-yl)-1-methyl-1-[[(2-phenylethyl)amino]carbonyl]propyl]-, tricyclo[3.3.1.1³,⁷]dec-2-yl ester, (±)-,
Carbamic acid, [1-[[[1-hydroxymethyl)-2-phenylethyl]amino]carbonyl]-3-(1H-indol-3-yl)-1-methylpropyl]-, tricyclo[3.3.1.1³,⁷]dec-2-yl ester (hydroxymethyl center is S, other center is RS),
12-Oxa-2,5,8-triazatridec-10-enoic acid, 3-[2-(1H-indol-3-yl)ethyl]-3-methyl-4,5,12-trioxo-7-phenyl-, tricyclo[3.3.1.1³,⁷]dec-2-yl ester [TRP center is R/S mixture, other center is R],
L-Phenylalaninamide, N-[[(1,1-dimethylethoxy)-carbonyl]-α-methyl]-L-tryptophyl]-L-methionyl-L-α-aspartyl-,
Glycine, N-[2-methyl-N-[(tricyclo[3.3.1.1³,⁷]dec-2-yloxy)carbonyl]-D-tryptophyl]-L-phenylalanyl-, Carbamic acid, [1-[[[1-(hydroxymethyl)-2-phenylethyl] amino]carbonyl]-2-(1H-indol-3-yl)propyl]-, tricyclo [3.3.1.1$^{3,7}$]dec-2-yl ester (hydroxymethyl center S, other centers RS), 2,4-Heptadienoic acid, 6-[[3-(1H-indol-3-yl)-2-methyl-1-oxo-2-[[(tricyclo[3.3.1.1$^{3,7}$]dec-2-yloxy)-carbonyl]amino] propyl]amino]-7-phenyl-, [R,R*,S*-(E,E)]]-, Carbamic acid, [2-[(hexahydro-1H-azepin-1-yl)-amino]-1-(1H-indol-3-ylmethyl)-1-methyl-2-oxoethyl]-,tricyclo [3.3.1.1$^{3,7}$]dec-2-yl ester, (R)-, Carbamic acid, N-[2-[(2-hydroxycyclohexyl)-amino]-1-(1H-indol-3-ylmethyl)-1-methyl-2-oxo-ethyl]-,tricyclo [3.3.1.1$^{3,7}$]dec-2-yl ester, [1α(R),2β], Carbamic acid, [1-(1H-indol-3-ylmethyl)-1-methyl-2-(4-morpholinylamino)-2-oxoethyl]-,tricyclo-[3.3.1.1$^{3,7}$]dec-2-yl ester, (R)-, Carbamic acid, [1-(1H-indol-3-ylmethyl)-1-methyl-2-oxo-2-(1-piperidinylamino)ethyl]-,tricyclo-[3.3.1.1$^{3,7}$]dec-2-ylester, (R)-

Glycine, N-[2-methyl-N-[(tricyclo[3.3.1.1$^{3,7}$]dec-2-yloxy)carbonyl]-D-tryptophyl]-, phenylmethyl ester, Carbamic acid, [2-[(2-hydroxycyclohexyl)amino]-1-(1H-indol-3-ylmethyl)-1-methyl-2-oxoethyl]-,tricyclo-[3.3.1.1$^{3,7}$]dec-2-ylester Isomer 1
TRP Center is R; Other center unknown, and Carbamic acid, [2-[(2-hydroxycyclohexyl)amino]-1-(1H-indol-3-ylmethyl)-1-methyl-2-oxoethyl]-,tricyclo-[3.3.1.1$^{3,7}$]dec-2-ylester Isomer 2
TRP Center is R; Other center unknown, and Tricyclo[3.3.1.1$^{3,7}$]dec-2-yl ester [2S-(R*,S*)], N-[1-(1H-indol-3-ylmethyl)-2-[[2-(methoxymethyl)-1-pyrrolidinyl]amino]-1-methyl-2-oxoethyl]carbamate, Tricyclo[3.3.1.1$^{3,7}$]dec-2-yl[R-(R*,R*)]-[1-(1H-indol-3-ylmethyl)-2-[[2-(methoxymethyl)-1-pyrrolidinyl]amino]-1-methyl-2-oxoethyl]carbamate, (R)-1-[[3-(1H-indol-3-yl)-2-methyl-1-oxo-2- [[(tricyclo [3.3.1.1$^{3,7}$]dec-2-yloxy)carbonyl]amino]propyl]amino] cyclohexaneacetic acid,

[1S-[1α(S*),2B]] and [1R-[α(R*),2β]]$^{sp}$2-[[3-(1H-indol-3-yl)-2-methyl-1-oxo-2-[(tricyclo[3.3.1.1$^{3,7}$]-dec-2-yloxy) carbonyl]amino]propyl]amino]cyclohexane-carboxylic acid, Carbamic acid [2-[(2-cyanocyclohexyl)amino]-1-(1H-indol-3-ylmethyl)-1-methyl-2-oxoethyl]-1H-tricyclo-[3.3.1.1$^{3,7}$]dec-2-yl ester, Tricyclo[3.3.1.1$^{3,7}$]dec-2-yl ester[1-(1H-indol-3-ylmethyl)-1-methyl-2[(2-methylcyclohexyl) amino]-2-oxoethyl]carbamate, Tricyclo[3.3.1.1$^{3,7}$] dec-2yl ester [2-(bicyclo[2.2.1]hept-2-ylamino)-1-(1H-indol-3-ylmethyl) -1-methyl-2oxoethyl] carbamate, Tricyclo[3.3.1.1$^{3,7}$]dec-2-yl ester (R)[2-[[1-(hydroxymethyl)cyclopentyl]amino]-1-(1H-indol-3-ylmethyl)-1-methyl-2-oxoethyl]carbamate, 2-[[3-(1H-indol-3-yl)-2-methyl-1-oxo-2-[[(tricyclo [3.3.1.1$^{3,7}$] dec-2-yloxy)carbonyl]amino]propyl]amino] cyclohexanecarboxylic acid(R)$^{sp}$ 1- [[2-(1H-indol-3-ylmethyl)-2-methyl-1-oxo-2-[[(tricyclo-[3.3.1.1$^{3,7}$]dec-2-yloxy)carbonyl]amino]ethyl]amino]-cyclohexanoic acid, Tricyclo[3.3.1.1$^{3,7}$]dec-2-yl ester (R) [2-[1-(hydroxymethyl)cyclohexyl]amino]-1-(1H-indol-3-ylmethyl)-1-methyl-2-oxoethyl]carbamate, and Phenylmethyl ester [2S-[1(2S*,3R*),2R*]]-[3-[2[[(1,1-dimethylethyl)amino]carbonyl]-1-piperidinyl]-2-hydroxy-1-(phenylmethyl)propyl]carbamate.

Table I, below, illustrates representative compounds of the invention. The numbers on the left-hand column in Table I correspond to the compound numbers given above. All of the compounds shown in Table I have their stereochemical configurations shown.

In addition to the compounds shown in Table I, the compounds of the present invention include compounds of formula I wherein the indole moiety is a 2-indolyl.

The compounds of the invention include solvates and hydrates and pharmaceutically acceptable salts of the compounds of formula I.

TABLE I $$R^1-A-E-(CH_2)_m-\overset{R^2}{\underset{\underset{Ar^2}{(CR^5R^6)_n}}{C}}-(CH_2)_p-(X)_q-(CHR^3)_r-(CHR^4)_s-(Y)_t-\overset{+}{(CR^{20}R^{12})_u}-\overset{+CHR13)_v}{(}-Ar^1$$

| Ex. No. | R¹ | A | E | m | R² | P | X | q | R³ | r | R⁴ | s | y | t | R²⁰ | R¹² | R¹³ | u | v | Ar¹ | R⁵ | R⁶ | n | Ar² |
|---|---|---|---|---|---|---|---|---|---|---|---|---|---|---|---|---|---|---|---|---|---|---|---|---|
| 1 |  | OCONH | Null | O | H | 1 | NH | 1 | CH₂OH | 1 | H | 1 | Null | O | Null | Null | H | O | 1 | Ph | H | H | 1 |  |
| 2 |  | OCONH | Null | O | H | 1 | NH | 1 | CH₂OH | 1 | H | 1 | Null | O | Null | Null | H | O | 1 | Ph | H | H | 1 |  |
| 3 |  | OCOHH | Null | O | H | O | NHCO | 1 | CH₂OH | 1 | H | 1 | Null | O | Null | Null | H | O | 1 | Ph | H | H | 1 |  |
| 5 |  | OCONH | Null | O | Me | 1 | Null | 1 | H | 1 | OH | 1 | Null | O | Null | Null | H | O | 1 | Ph | H | H | 1 |  |

TABLE I-continued $$R^1-A-E-(CH_2)_m-\underset{\underset{Ar^2}{(CR^5R^6)_n}}{\overset{R^2}{\underset{|}{C}}}-(CH_2)_p-(X)_q-\overset{+}{(CHR^3)_r}-(CHR^4)_s-\overset{+}{(Y)_t}-\overset{+}{(CR^{20}R^{12})_u}-\overset{+CHR13)_v}{(\phantom{xxx})}-Ar^1$$

| Ex. No. | $R^1$ | A | E | m | $R^2$ | P | X | q | $R^3$ | r | $R^4$ | s | y | t | $R^{20}$ | $R^{12}$ | $R^{13}$ | u | v | $Ar^1$ | $R^5$ | $R^6$ | n | $Ar^2$ |
|---|---|---|---|---|---|---|---|---|---|---|---|---|---|---|---|---|---|---|---|---|---|---|---|---|
| 6 | adamantyl | OCONH | Null | O | Me | 1 | NH | 1 | CH$_2$OH | 1 | Null | O | Null | O | Null | Null | H | O | 1 | Ph | H | H | 1 | indolyl-phenyl |
| 7 | adamantyl | OCONH | Null | O | Me | 1 | NH | 1 | CH$_2$OAc | 1 | Null | O | Null | O | Null | Null | H | O | 1 | Ph | H | H | 1 | indolyl-phenyl |
| 8 | adamantyl | OCONH | Null | O | Me | 1 | NAc | 1 | CH$_2$OH | 1 | Null | O | Null | O | Null | Null | H | O | 1 | Ph | H | H | 1 | indolyl-phenyl |
| 11 | adamantyl | OCONH | Null | O | Me | O | COO | 1 | H | 1 | Ph | 1 | NHCO | 1 | H | — | — | 1 | 1 | CO$_2$Me | H | H | 1 | indolyl-phenyl |

TABLE I-continued $$R^1-A-E-(CH_2)_m-\underset{\underset{Ar^2}{\overset{\underset{R^2}{|}}{(CR^5R^6)_n}}}{C}-(CH_2)_p-(X)_q-(CHR^3)_r-(CHR^4)_s-(Y)_t-(CR^{20}R^{12})_u-(\overset{+CHR^{13}}{\phantom{l}})_v-Ar^1$$

| Ex. No. | $R^1$ | A | E | $(CH_2)_m$ | $R^2$ | p | X | q | $R^3$ | r | $R^4$ | s | y | t | $R^{20}$ | $R^{12}$ | $R^{13}$ | u | v | $Ar^1$ | $R^5$ | $R^6$ | n | $Ar^2$ |
|---|---|---|---|---|---|---|---|---|---|---|---|---|---|---|---|---|---|---|---|---|---|---|---|---|
| 12 | adamantyl | OCONH | Null | 0 | Me | 0 | COO | 1 | H | 1 | Ph | 1 | NHCO | 1 | H | H | H | 1 | 1 | CO$_2$Me | H | H | 1 | indole-like |
| 19 | adamantyl | OCONH | Null | 0 | Me | 1 | NHCO | 1 | H | 1 | H | 1 | Null | 0 | Null | O | H | 0 | 1 | Ph | H | H | 1 | indole-like |
| 20 | adamantyl | OCONH | Null | 0 | Me | 1 | NHCO | 1 | Null | 0 | Null | 0 | Null | 0 | Null | Null | Null | 0 | 0 | Ph | H | H | 1 | indole-like |
| 21 | adamantyl | OCONH | Null | 0 | Me | 1 | NHCO | 1 | H | 1 | Null | 0 | Null | 0 | Null | O | H | 0 | 1 | Ph | H | H | 1 | indole-like |

TABLE I-continued $$R^1-A-E-(CH_2)_m-\overset{R^2}{\underset{\underset{Ar^2}{(CR^5R^6)_n}}{C}}-(CH_2)_p-(X)_q-(CHR^3)_r-(CHR^4)_s-(Y)_t-(CR^{20}R^{12})_u-(CHR^{13})_v-Ar^1$$

| Ex. No. | R¹ | A | E | m | R² | p | X | q | R³ | r | R⁴ | s | y | t | R²⁰ | R¹² | R¹³ | u | v | Ar¹ | R⁵ | R⁶ | n | Ar² |
|---|---|---|---|---|---|---|---|---|---|---|---|---|---|---|---|---|---|---|---|---|---|---|---|---|
| 22 | adamantyl | OCONH | Null | 0 | Me | 1 | NHCO | 1 | H | 1 | Null | 0 | Null | 0 | Null | Null | H | 0 | 1 | Ph | H | H | 1 | indole-like |
| 23 | adamantyl | OCONH | Null | 0 | Me | 0 | CONH | 1 | H | 1 | H | 1 | CONH | 1 | CH₂OH | H | H | 1 | 1 | Ph | H | H | 1 | indole-like |
| 24 | adamantyl | CONH | Null | 0 | Me | 0 | CONH | 1 | H | 1 | H | 1 | CONH | 1 | CH₂OH | H | H | 1 | 1 | Ph | H | H | 1 | indole-like |
| 25 | adamantyl | OCONH | Null | 0 | Me | 0 | CONH | 1 | H | 1 | H | 1 | CONH | 1 | CONH₂ | H | H | 1 | 1 | Ph | H | H | 1 | indole-like |

TABLE I-continued $$R^1-A-E-(CH_2)_m-\overset{\overset{\displaystyle R^2}{|}}{\underset{\underset{\displaystyle Ar^2}{|}}{\underset{\displaystyle (CR^5R^6)_n}{|}}{C}}-(CH_2)_p-(X)_q-(CHR^3)_r-(Y)_t-(CR^{20}R^{12})_u-(CHR^{13})_v-Ar^1$$

| Ex. No. | R¹ | A | E | m | R² | P | X | q | R³ | r | R⁴ | s | y | t | R²⁰ | R¹² | R¹³ | u | v | Ar¹ | R⁵ | R⁶ | n | Ar² |
|---|---|---|---|---|---|---|---|---|---|---|---|---|---|---|---|---|---|---|---|---|---|---|---|---|
| 26 | adamantyl | OCONH | Null | O | Me | O | CONH | 1 | H | 1 | H | 1 | CONH | 1 | CONH₂ | H | H | 1 | 1 | Ph | H | H | 1 | indolyl-Ph |
| 27 | adamantyl | OCONH | Null | O | Me | O | CONH | 1 | H | 1 | H | 1 | CONH | 1 | CONH₂ | H | H | 1 | 1 | Ph | H | H | 1 | indolyl-Ph |
| 28 | adamantyl | OCONH | Null | O | Me | O | CONH | 1 | H | 1 | H | 1 | CONH | 1 | CONH₂ | H | H | 1 | 1 | Ph | H | H | 1 | indolyl-Ph |
| 29 | adamantyl | OCONH | Null | O | Me | O | NH | 1 | H | 1 | H | 1 | CONH | 1 | CO₂Me | H | H | 1 | 1 | Ph | S | S | 1 | indolyl-Ph |

TABLE I-continued $$R^1-A-E-(CH_2)_m-\underset{\underset{Ar^2}{\overset{(CR^5R^6)_n}{|}}}{\overset{R^2}{\underset{|}{C}}}-(CH_2)_p-(X)_q-(CHR^3)_r-(CHR^4)_s-(Y)_t-(CR^{20}R^{12})_u-(CHR^{13})_v-Ar^1$$

| Ex. No. | $R^1$ | A | E | m | $R^2$ | P | X | q | $R^3$ | r | $R^4$ | s | y | t | $R^{20}$ | $R^{12}$ | $R^{13}$ | u | v | $Ar^1$ | $R^5$ | $R^6$ | n | $Ar^2$ |
|---|---|---|---|---|---|---|---|---|---|---|---|---|---|---|---|---|---|---|---|---|---|---|---|---|
| 30 | adamantyl | OCONH | Null | 0 | Me | O | CONH | 1 | H | 1 | H | 1 | CONH | 1 | $CO_2O_2$ | H | H | 1 | 1 | Ph | H | H | 1 | indole |
| 31 | adamantyl | OCONH | Null | 0 | Me | O | CONH | 1 | H | 1 | H | 1 | CONH | 1 | $CO_2Bz$ | H | H | 1 | 1 | Ph | H | H | 1 | indole |
| 32 | adamantyl | OCONH | Null | 0 | Me | O | CONH | 1 | H | 1 | H | 1 | CONH | 1 | $CO_2H$ | H | H | 1 | 1 | Ph | H | H | 1 | indole |
| 33 | adamantyl | OCONH | Null | 0 | Me | O | CONH | 1 | H | 1 | H | 1 | CONH | 1 | $CO_2H$ | H | H | 1 | 1 | Ph | H | H | 1 | indole |

TABLE I-continued $$R^1-A-E-(CH_2)_m-\underset{\underset{Ar^2}{(CR^5R^6)_n}}{\overset{R^2}{\underset{|}{C}}}-(CH_2)_p-(X)_q-(CHR^3)_r-(CHR^4)_s-(Y)_t-(CR^{20}R^{12})_u-(CHR^{13})_v-Ar^1$$

| Ex. No. | R¹ | A | E | m | R² | P | X | q | R³ | r | R⁴ | s | y | t | R²⁰ | R¹² | R¹³ | u | v | Ar¹ | R⁵ | R⁶ | n | Ar² |
|---|---|---|---|---|---|---|---|---|---|---|---|---|---|---|---|---|---|---|---|---|---|---|---|---|
| 34 | adamantyl | OCONH | Null | O | Me | O | CONH₂ | 1 | H | 1 | H | 1 | CONH | 1 | CO₂H | H | H | 1 | 1 | Ph | H | H | 1 | indoline-Ar² |
| 35 | adamantyl | OCONH | Null | O | Me | O | CONH | 1 | H | 1 | H | 1 | CONH | 1 | CO₂H | H | H | 1 | 1 | Ph | H | H | 1 | indoline-Ar² |
| 36 | adamantyl | OCONH | Null | O | Me | O | CONH | 1 | H | 1 | Null | O | COO | 1 | Null | O | H | O | 1 | Ph | H | H | 1 | indoline-Ar² |
| 37 | adamantyl | OCONH | Null | O | —C(O)— | 1 | CON | 1 | H | 1 | Null | O | Null | O | Null | Null | H | O | 1 | Ph | H | H | 1 | indoline-Ar² |

TABLE I-continued $$R^1-A-E-(CH_2)_m-\overset{R^2}{\underset{\underset{Ar^2}{(CR^5R^6)_n}}{C}}-(CH_2)_p-(X)_q-(CHR^3)_r-(CHR^4)_s-(Y)_t-(CR^{20}R^{12})_u-(CHR^{13})_v-Ar^1$$

| Ex. No. | $R^1$ | A | E | m | $R^2$ | p | X | q | $R^3$ | r | $R^4$ | s | y | t | $R^{20}$ | $R^{12}$ | $R^{13}$ | u | v | $Ar^1$ | $R^5$ | $R^6$ | n | $Ar^2$ |
|---|---|---|---|---|---|---|---|---|---|---|---|---|---|---|---|---|---|---|---|---|---|---|---|---|
| 39 | adamantyl | OCONH | Null | 0 | Me | O | CONH | 1 | H | 1 | Null | O | Null | O | Null | Null | H | O | 1 | Ph | H | H | 2 | indole-like |
| 40 | adamantyl | O-NH-C(O) | Null | 0 | Me | O | CONH | 1 | CO$_2$OH | 1 | Null | O | Null | O | Null | Null | H | O | 1 | Ph | H | H | 2 | indole-like |
| 41 | adamantyl | H-N-C(O) | — | — | Me | O | NH | 1 | Ph | 1 | — | O | O NH | 1 | H | — | — | 1 | 1 | CO$_2$Me | H | H | 2 | indole-like |
| 43 | adamantyl | OCONH | Null | 0 | Me | O | CONH | 1 | CH$_2$Ph | 1 | Null | O | CONH | 1 | Null | Null | H | O | 1 | CO$_2$H | H | H | 1 | indole-like |

TABLE I-continued $$R^1-A-E-(CH_2)_m-\underset{\underset{Ar^2}{\overset{\overset{R^2}{|}}{\underset{|}{C^+}}(CR^5R^6)_n}}{}-(CH_2)_p-(X)_q-(CHR^3)_r-(CHR^4)_s-(Y)_t-(CR^{20}R^{12})_u-(\overset{+CHRl3}{})_v-Ar^1$$

| Ex. No. | R¹ | A | E | m | R² | P | X | q | R³ | r | R⁴ | s | y | t | R²⁰ | R¹² | R¹³ | u | v | Ar¹ | R⁵ | R⁶ | n | Ar² |
|---|---|---|---|---|---|---|---|---|---|---|---|---|---|---|---|---|---|---|---|---|---|---|---|---|
| 44 | adamantyl | OCONH | Null | O | H | O | CONH | 1 | CH₂OH | 1 | Null | O | Null | O | Null | Null | H | O | 1 | Ph | Me | H | 1 | 3-indolyl-CH(Me)- |
| 45 | adamantyl | OCONH | Null | O | Me | O | CONH | 1 | CH₂Ph | 1 | Null | O | Null | O | H | — | — | 1 | 1 | CH₂=CH₂ CO₂H | H | H | 1 | 2-indolyl-C(=CH₂)- |
| 46 | adamantyl | OCONH | Null | O | Me | O | CONH | 1 | H | 1 | Null | O | COO | 1 | Null | Null | H | O | 1 | Ph | H | H | 1 | 3-indolyl-CH(Me)- |

Other examples of compounds of the invention include:

Tricyclo[3.3.1.1$^{3,7}$]dec-2-ylcarbamic acid, 2-[[2-hydroxy-1-(hydroxymethyl)-2-phenylethyl]amino]-1-(1H-3-ylmethyl)-1-methyl-2-oxoethyl ester, N-[2-Hydroxy-1-(hydroxymethyl)-2-phenylethyl]-α-methyl-α-(2-oxo-2-tricyclo[3.3.1.1$^{3,7}$] dec-2-ylethoxy)-1H-indole-3-propanamide, N-[2-hydroxy-1-(hydroxymethyl)-2-phenylethyl]-α-(2-hydroxy-2-tricyclo[3.3.1.1$^{3,7}$]dec-2-ylethoxy)-α-methyl-1H-indole-3-propanamide,

[(Tricyclo[3.3.1.1$^{3,7}$]dec-2-ylamino)carbonyl]-sulfamic acid, 2-[[2-(hydroxy-1-(hydroxymethyl)-2-phenylethyl]amino]-1-(1H-indol-3-ylmethyl)-1-methyl-2-oxoethyl ester,

[(Tricyclo[3.3.1.1$^{3,7}$]dec-2-ylamino)sulfonyl]-carbamic acid, 2-[[2-hydroxy-1-(hydroxymethyl)-2-phenylethyl]amino]-1-(1H-indol-3-ylmethyl)-1-methyl-2-oxoethyl ester,

[[2-[[2-Hydroxy-1-(hydroxymethyl)-2-phenylethyl]amino]-1-(1H-indol-3-ylmethyl)-1-methyl-2-oxoethoxy]sulfonyl]carbamic acid, tricyclo[3.3.1.1$^{3,7}$]-dec-2-yl ester, N-[2-Hydroxy-1-(hydroxymethyl)-2-phenylethyl]-methyl-[[2-oxo-2-(tricyclo[3.3.1.1$^{3,7}$] dec-2-ylamino)-ethyl]amino]-1H-indole-3-propanamide, N-[2-Hydroxy-1-(hydroxymethyl)-2-phenylethyl]-α-methyl-α-[[(tricyclo[3.3.1.1$^{3,7}$] dec-2-ylamino)acetyl]-amino]-1H-indole-3-propanamide, N-[2-Hydroxy-1-(hydroxymethyl)-2-phenylethyl]-α-methyl-α-[(2-oxo-2-tricyclo[3.3.1.1$^{3,7}$]dec-2-ylethyl)amino]-1H-indole-3-propanamide, N-[2-Hydroxy-1-(hydroxymethyl)-2-phenylethyl]-α-[(2-hydroxy-2-tricyclo[3.3.1.1$^{3,7}$ ]dec-2-ylethyl)amino]-α-methyl-1H-indole-3-propanamide, N-[2-Hydroxy-1-(hydroxymethyl)-2-phenylethyl]-α-methyl-α-[[[[(tricyclo[3.3.1.1$^{3,7}$]dec-2-ylamino) -carbonyl]amino]sulfonyl]amino]-1H-indole-3-propanamide, N-[2-Hydroxy-1-(hydroxymethyl)-2-phenylethyl]-α-methyl-α-[[[[(tricyclo[3.3.1.1$^{3,7}$]dec-2-ylamino]-sulfonyl]amino]carbonyl]amino]-1H-indole-3-propanamide,

[[[2-[[2-Hydroxy-1-(hydroxymethyl)-2-phenyl-ethyl]amino]-1-(1H-indol-3-ylmethyl)-1-methyl-2-oxoethyl]amino]sulfonyl]carbamic acid, tricyclo[3.3.1.1$^{3,7}$]dec-2-yl ester,

[[[2-[[2-Hydroxy-1-(hydroxymethyl)-2-phenylethyl]amino]-1-(1H-indol-3-ylmethyl]-1-methyl-2-oxoethyl]amino]carbonyl]sulfamic acid, tricyclo[3.3.1.1$^{3,7}$]dec-2-yl ester, N-[2-Hydroxy-1-(hydroxymethyl)-2-phenylethyl]-α-methyl-α-[[(tricyclo[3.3.1.1$^{3,7}$]dec-2-ylamino)-sulfonyl]amino]-1H-indole-3-propanamide, N-[2-Hydroxy-1-(hydroxymethyl)-2-phenylethyl]-2-(1H-indol-3-ylmethyl)-2-methyl-N'-(tricyclo-[3.3.1.1$^{3,7}$]dec-2-ylmethyl)propanediamide, N-[2-Hydroxy-1-(hydroxymethyl)-2-phenylethyl]-2-(1H-indol-3-ylmethyl)-2-methyl]N'-tricyclo[3.3.1.1$^{3,7}$]-dec-2-ylpropanediamide, N-[2-Hydroxy-1-(hydroxymethyl)-2-phenylethyl]-α-[[imino(tricyclo[3.3.1.1$^{3,7}$]dec-2-ylamino)methyl]-amino]-α-methyl-1H-indole-3-propanamide, α- [[(Cyanoimino) (tricyclo[3.3.1.1$^{3,7}$]dec-2-ylamino)methyl]amino]-N-[2-hydroxy-1-(hydroxymethyl)-2-phenyl-ethyl]-α-methyl-1H-indole-3-propanamide, N-[2-Hydroxy-1-(hydroxymethyl)-2-phenylethyl]-α-methyl-α-[[(nitroimino) (tricyclo[3.3.1.1$^{3,7}$] dec-2-ylamino)methyl]amino]-1H-indole-3-propanamide,

[2-[[2-Hydroxy-1-(hydroxymethyl)-2-phenylethyl]amino]-1-(1H-indol-3-ylmethyl)-1-methyl-2 -oxoethyl]phosphoramidic acid, phenyl tricyclo[3.3.1.1$^{3,7}$]dec-2-yl ester, N-[2-[[2-Hydroxy-1-(hydroxymethyl)-2-phenylethyl]amino]-1-(1H-indol-3-ylmethyl)-1-methyl-2-oxoethyl]-N-tricyclo[3.3.1.1$^{3,7}$]dec-2-ylphosphorodiamidic acid phenyl ester, Tricyclo[3.3.1.1$^{3,7}$]dec-2-ylphosphoramidic acid, 2-[[2-hydroxy-1-(hydroxymethyl)-2-phenylethyl]amino]-1-(1H-indol-3-ylmethyl)-1-methyl-2-oxoethyl phenyl ester, and Phosphoric acid, 2-[[2-hydroxy-1-(hydroxy-methyl)-2-phenylethyl]amino]-1-(1H-indol-3-ylmethyl)-1-methyl-2-oxoethyl phenyl tricyclo[3.3.1.1$^{3,7}$]dec-2-yl ester.

The compounds of the present invention can have multiple chiral centers including those designated in the above formula I by the symbol †, depending on their structures. For example, when $R^3$ taken with $R^4$ and $R^{12}$ taken with $R^{13}$ form double bonds to their carbon atoms, they are no longer chiral. In addition, centers of asymmetry may exist on the other substituents. In particular, the compounds of the present invention may exist as diastereomers, mixtures of diastereomers, or as the mixed or the individual optical enantiomers. The present invention contemplates all such forms of the compounds. The mixtures of diastereomers are typically obtained as a result of the reactions described more fully below. Individual diastereomers may be separated from mixtures of the diastereomers by conventional techniques such as column chromatography or repetitive recrystallizations. Individual enantiomers may be separated by convention method well known in the art such as conversion to a salt with an optically active compound, followed by separation by chromatography or recrystallization and reconversion to the nonsalt form.

The compounds of the present invention can be formed by coupling individual substituted α-amino acids by methods well known in the art. (See, for example, standard synthetic methods discussed in the multi-volume treatise "The Peptides, Analysis, Synthesis, Biology," by Gross and Meienhofer, Academic Press, New York.) The individual substituted alpha amino acid starting materials are generally known or, if not known, may be synthesized and, if desired, resolved by methods within the skill of the art. (Synthesis of racemic [DL]-α-methyl tryptophan methyl ester - see Brana, M. F., et al, *J. Heterocyclic Chem.*, 1980, 17:829.)

A key intermediate in the preparation of compounds of formula I is a compound of formula

II

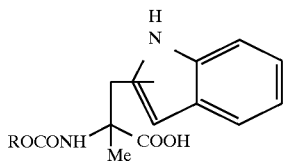

wherein R is selected from $R^1$, 9-fluorenylmethyl, Bz and other suitable N-blocking groups. These are useful as intermediates in the preparation of compounds of formula I. The compounds wherein R is 1-adamantyl, 2-adamantyl, 4-protoadamantyl, exo-bornyl, endo-bornyl, exo-norbornyl, endo-norbornyl, 2- methylcyclohexyl, 2-chlorocyclohexyl, or camphoryl are novel and are preferred.

The disclosure of U.S. Pat. No. 4,757,151 is hereby incorporated by reference. It describes the 9- fluorenylmethyl blocking group.

Compounds of formula II are prepared by reacting

ROH                                                          III wherein R is as defined above, with phosgene or a phosgene substitute to produce a corresponding compound of formula $$ROCOCl \qquad IV$$

and then reacting a compound of formula IV with α-methyltryptophan to produce the desired compound of formula II above.

Alternatively, a compound of formula IV can be reacted with an a-methyltryptophan methyl ester to produce

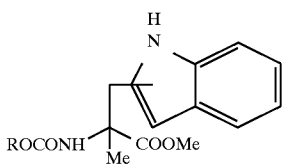

V which can be converted to a compound of formula II by known means such as hydrolysis with aqueous lithium hydroxide.

The schemes below illustrate procedures for preparing intermediates useful in producing final products of formula I.

Scheme 1 below illustrates preparative steps in the process of making compounds of the instant invention. Treatment of 2-adamantyloxycarbonyl-tryptophan 1 with N-methylmorpholine followed by isobutylchloroformate gave an intermediary mixed anhydride, this when mixed with N,O-dimethylhydro-acylamine hydrochloride gave the hydroxamate 2 which yielded the aldehyde 3 on reduction with LiAlH$_4$. Reductive amination of 3 with S-phenylalaninol and NaCNBH$_3$ gave the amino methylene 4 (Example 1). Example 2 (compound 5) was prepared in an exactly analogous manner. The intermediate mixed anhydride described above was treated with Me$_3$SiN$_3$ to make the acid azide which then reacted with p-nitrobenzyl alcohol in the presence of DABCO to give the bis urethane 6. Hydrogenation using Pearlman's catalyst to the monourethane, and treatment of the amine with the HOBT ester of 2-(acetoxymethyl)-3-phenylpropionic acid gave the compound 7, Example 3 after saponification of the ester with LiOH in aqueous THF. Example 4, compound 10 was prepared in three steps from 1. Here the mixed anhydride of 1 was treated with diazomethane to give the diazoketone 8. Reaction with HCl to the chloro ketone followed by reaction with sodium diethylbenzyl malonate gave a diester which, upon saponification, decarboxylated to the acid 10, Example 4.

SCHEME 1

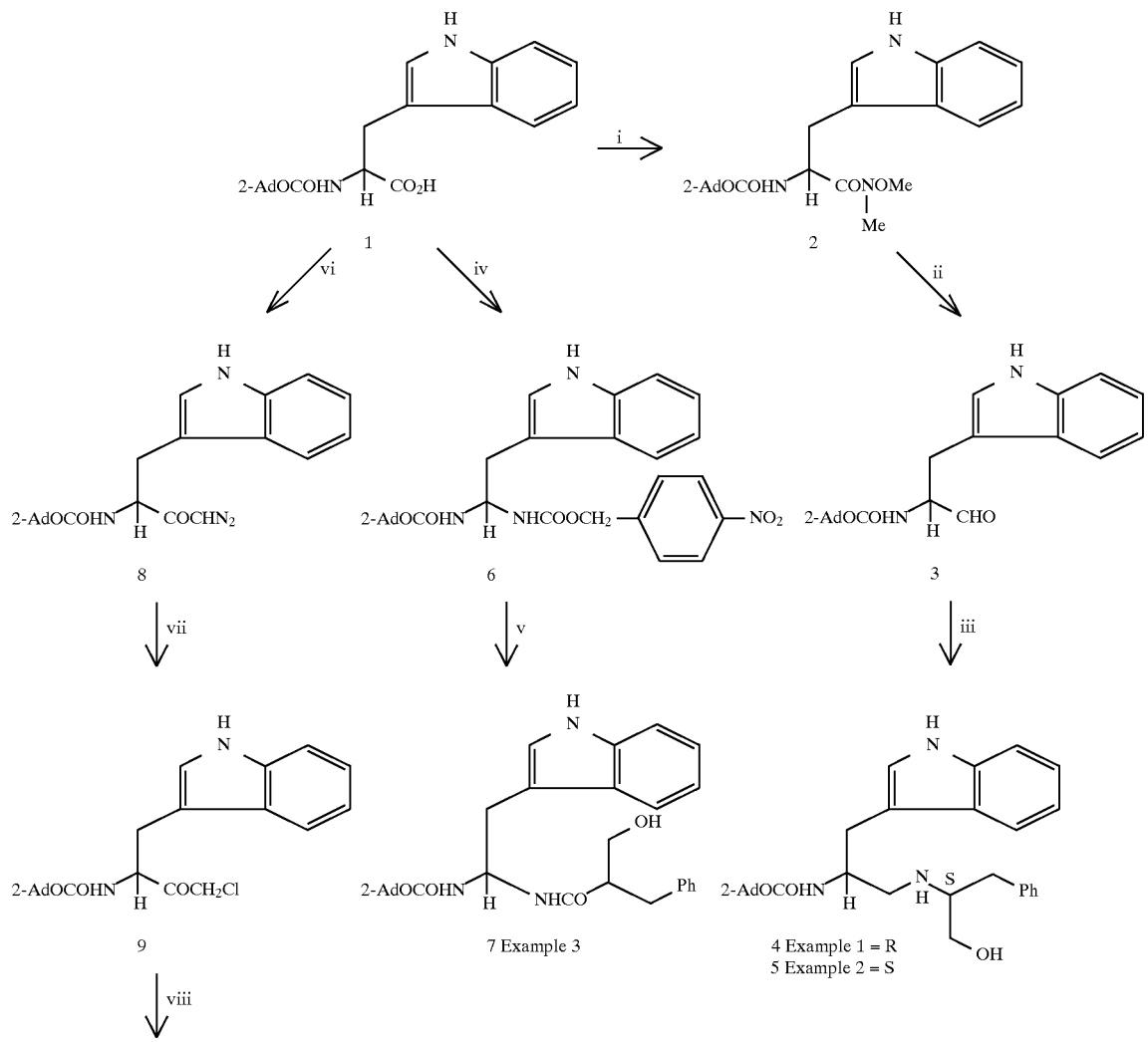

-continued
SCHEME 1

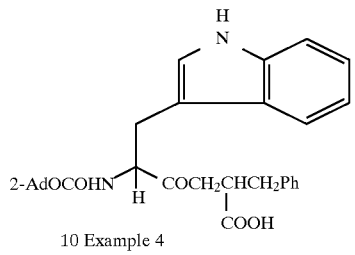

10 Example 4

KEY i) isobutylchloroformate, N-methyl morpholine, CH₃ONH(CH₃).HCl;
ii) LiAlH₄;
iii) S-phenylalaninol, NaCNBH₃;
iv) isobutylchloroformate, N-methylmorpholine, Me₃SiN₃ then 40° C. then para-NO₂—C₆H₄CH₂OH, DABCO;
    2,4-diazabicyclo-[2.2.2] octane (DABCO);
v) Pd(OH)₂H₂, then RS-HO₂CCCH(CH₂Ph)CH₂OAc; then LiOH, THF;
vi) isobutylchloroformate, N-methylmorpholine, CH₂N₂;
vii) HCl-dioxane;
viii) NaI, NaOME, then sodiodiethylbenzylmalonate, then NaOH, then HCl, then heat.

Scheme 2

Example 5, compound 12 was prepared by reduction of the amide in 11 using LiBH₄ and Me₃SiCl. Similarly, Example 6, compound 14 was prepared from 13. 14 was treated with acetylchloride to give Example 7, in the presence of base. The major product was compound 15a, which was hydrolyzed to Example 8, compound 16, on treatment with lithium hydroxide. The thiazoline 17, Example 9, was prepared by heating 13 with Lawesson's reagent.

SCHEME 2

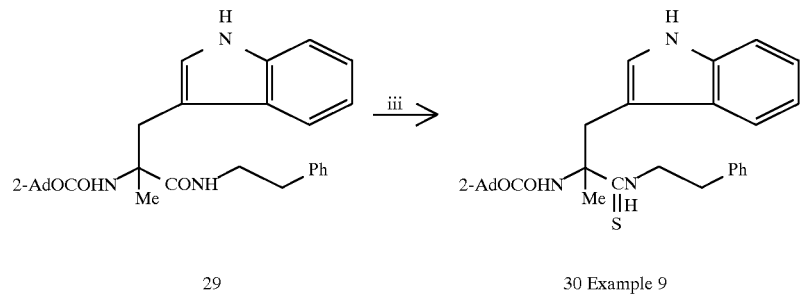

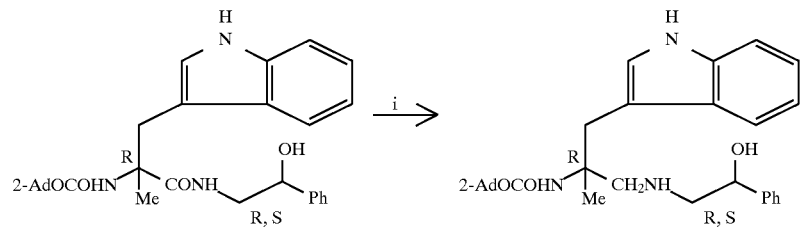

-continued
SCHEME 2

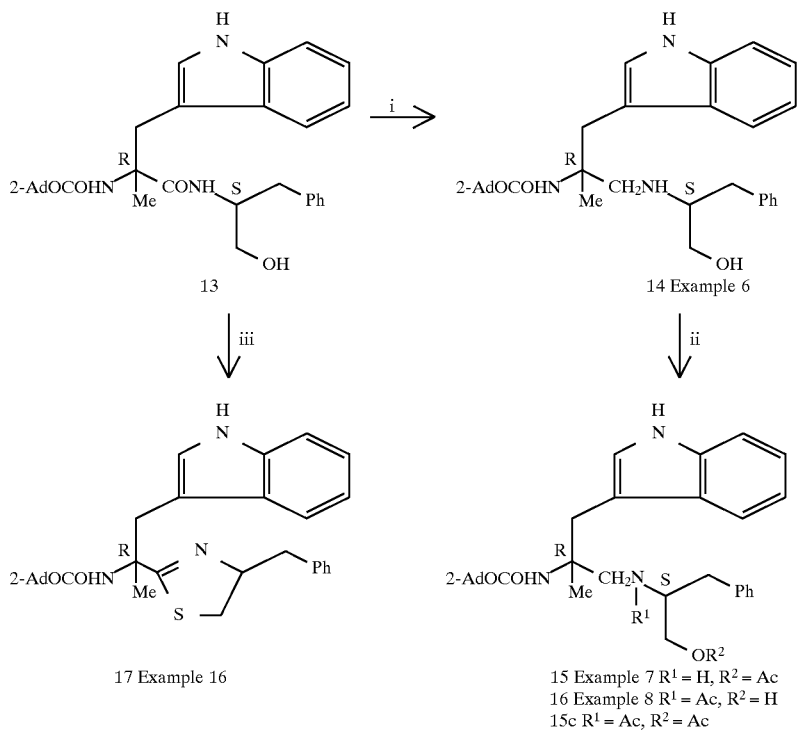

KEY i) LiBH$_4$, Me$_3$SiCl;
ii) CH$_3$COCl (Example 7); or CH$_3$COCl, Et$_3$N then LiOH (Example 8);
iii) Lawesson's Reagent.

Scheme 3 shows the synthesis of examples of ester isosteres. Monomethylfumarate was condensed with R-phenylglycinol via its HOBT ester to give 18. Further condensation of this with R- or S 2-Adoc-α-MeTrpOH in the presence of N,N'-carbonyldiimidazole gave Examples 10 (compound 19) and 11 (compound 20), respectively. In an exactly analogous way Example 12 (compound 22) was made except using monomethyl succinate.

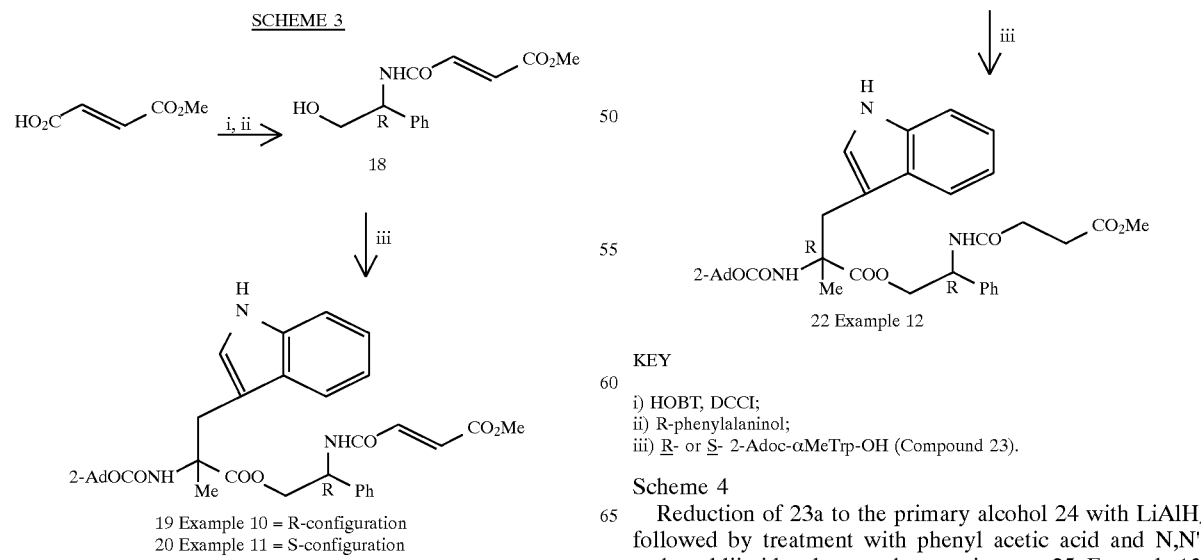

KEY i) HOBT, DCCI;
ii) R-phenylalaninol;
iii) R- or S- 2-Adoc-αMeTrp-OH (Compound 23).

Scheme 4

Reduction of 23a to the primary alcohol 24 with LiAlH$_4$ followed by treatment with phenyl acetic acid and N,N'-carbonyldiimidazole gave the ester isostere 25, Example 13.

Oxidation of 24 to the aldehyde 26 provided a very versatile intermediate. This aldehyde 26 was treated with Wittig reagents to give 27 (Example 14) and 29. Compound 29 was modified further to 30, Example 16 by hydrolysis of the ester and subsequent condensation with aniline. Treatment of aldehyde 26 with the Grignard reagent 3-phenylpropyl magnesium bromide afforded the secondary alcohol 28 (Example 15).

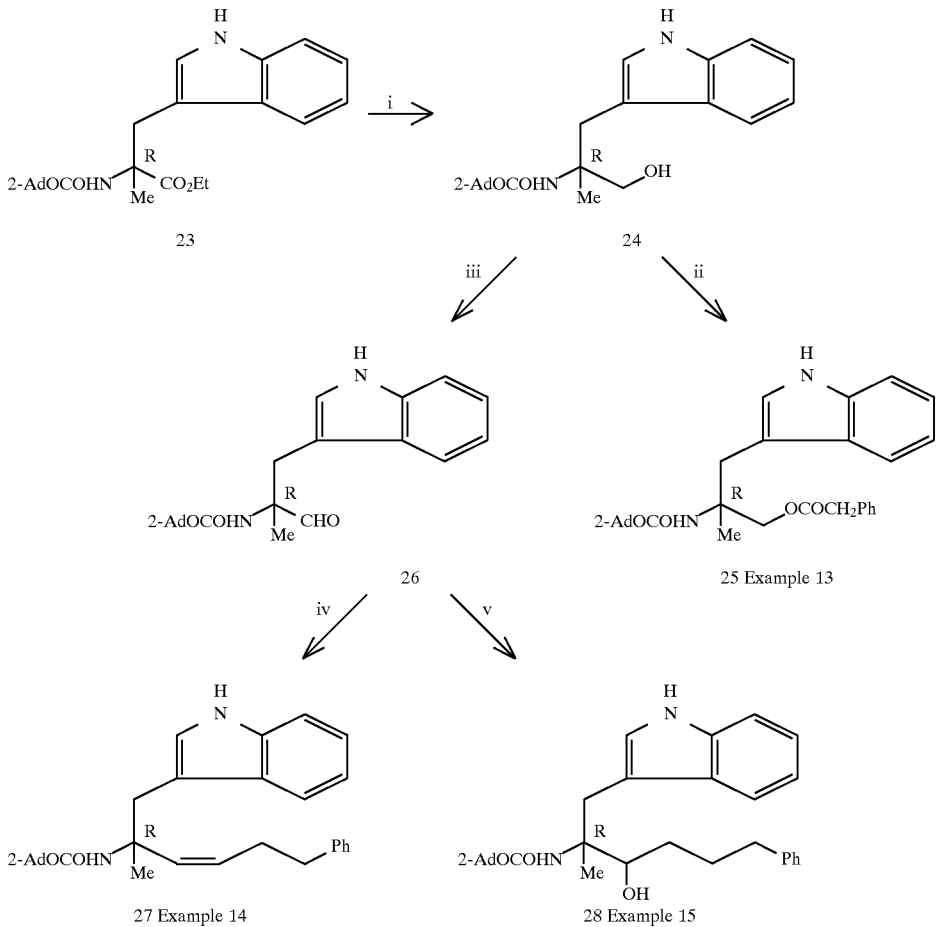

KEY i) LiAlH$_4$;
ii) PhCH$_2$CO$_2$H; carbonyldiimidazole;
iii) Tetrapropylammonium perruthenate;
iv) PhCH$_2$CH$_2$P$^+$Ph$_3$Br$^-$, NaH;
v) PhCH$_2$CH$_2$CH$_2$MgBr.

Scheme 5 shows the synthetic routes to some examples of homologated α-methyltryptophans, and their reverse amide isosteres. The mixed anhydride of 23b prepared by using isobutylchloroformate and N-methylmorpholine was treated with diazomethane to give the diazoketone 31, this as a solution in benzyl alcohol was treated with silver benzoate and Et$_3$N to yield the homologated benzyl ester 32. Hydrogenation afforded the acid 33 which was condensed in the usual way via the pentafluorophenyl ester with S-phenyl alaninol to give 34 (Example 18).

The amide of 23b, 35 was prepared by bubbling ammonia gas through a solution of the pentafluorophenyl ester. This amide was reduced to the amine 36 with Me$_3$SiCl/LiBH$_4$ in THF. This amine was subsequently reacted with phenyl acyl chlorides to give Examples 19–22 inclusive.

SCHEME 5

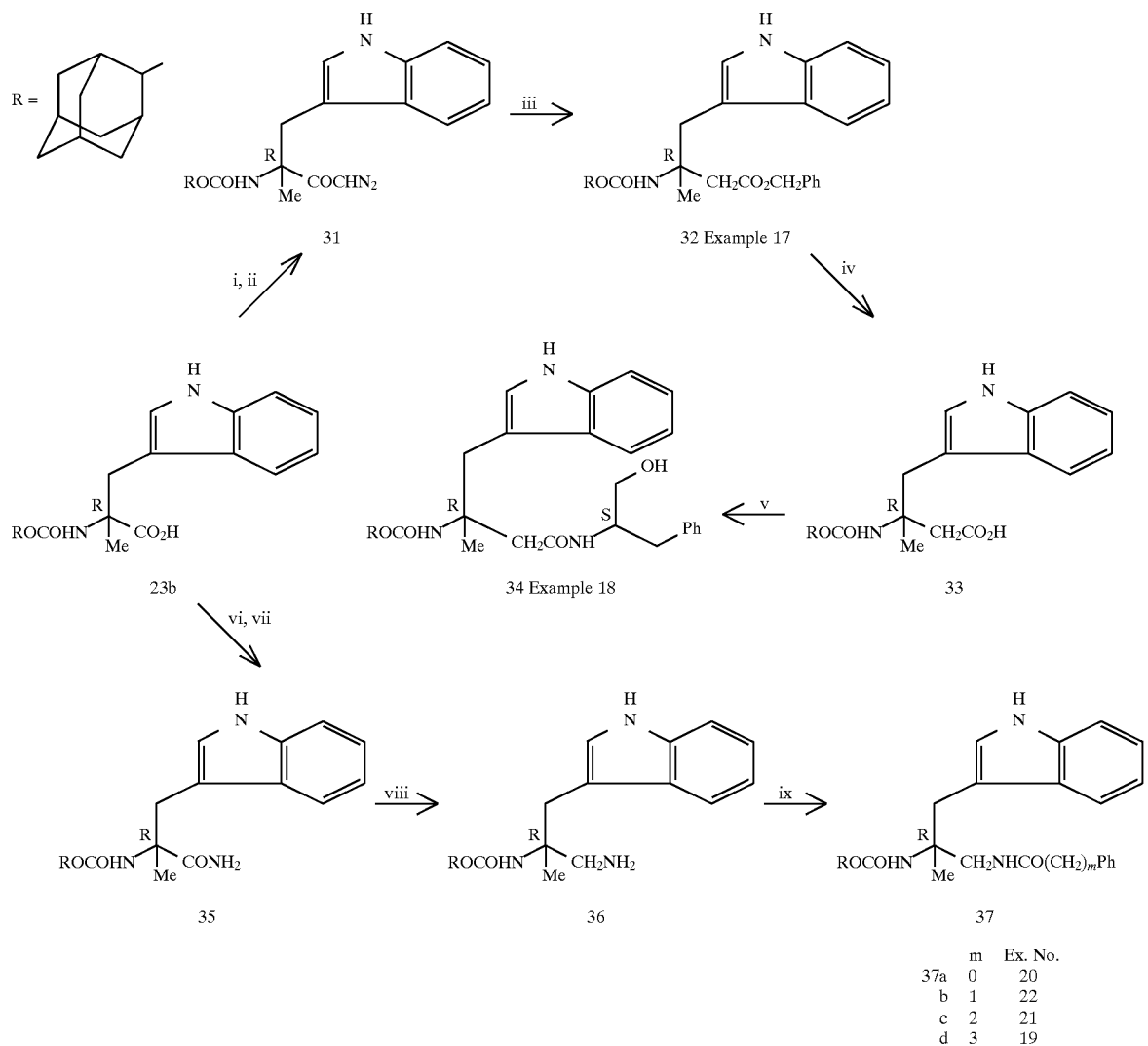

KEY Reagents:

i) isobutylchloroformate, NMM, THF;
ii) CH$_2$N$_2$, EtOAc;
iii) Ag$^+$ $^-$OCOPh, Et$_3$N, PhCH$_2$OH;
iv) H$_2$/Pd/C;
v) PFP, DCC, H$_2$NCH(CH$_2$OH)CH$_2$Ph, EtOAc;
vi) PFP, DCC, EtOAc;
vii) NH$_3$(g), THF;
viii) TMS-Cl, LiBH$_4$, THF;
ix) Ph(CH$_2$)$_m$COCl, pyridine, EtOAc.

Scheme 6 illustrates the synthesis of α-methyltryptophyl-β-alanine derivatives. The 2-adamantyl oxycarbonyl α-methyltryptophan 23b (R isomer) or 38 (S isomer) is condensed with β-alanine ester in the usual manner. This ester can then be hydrolyzed using standard methods (e.g., aqueous LiOH, etc) to afford the carboxylic acid 41 or 42. Either of these two isomers may be condensed with an appropriate amine to give Examples 23 and 24 (using S-phenyl alaninol), Examples 25–28 inclusive (using R and S phenyl alaninamide) and Examples 29–31 inclusive (using phenylalanine ester. Examples 29–31 and compound 52 may then be hydrolyzed using known methods to afford the products Examples 32–35 inclusive.

SCHEME 6

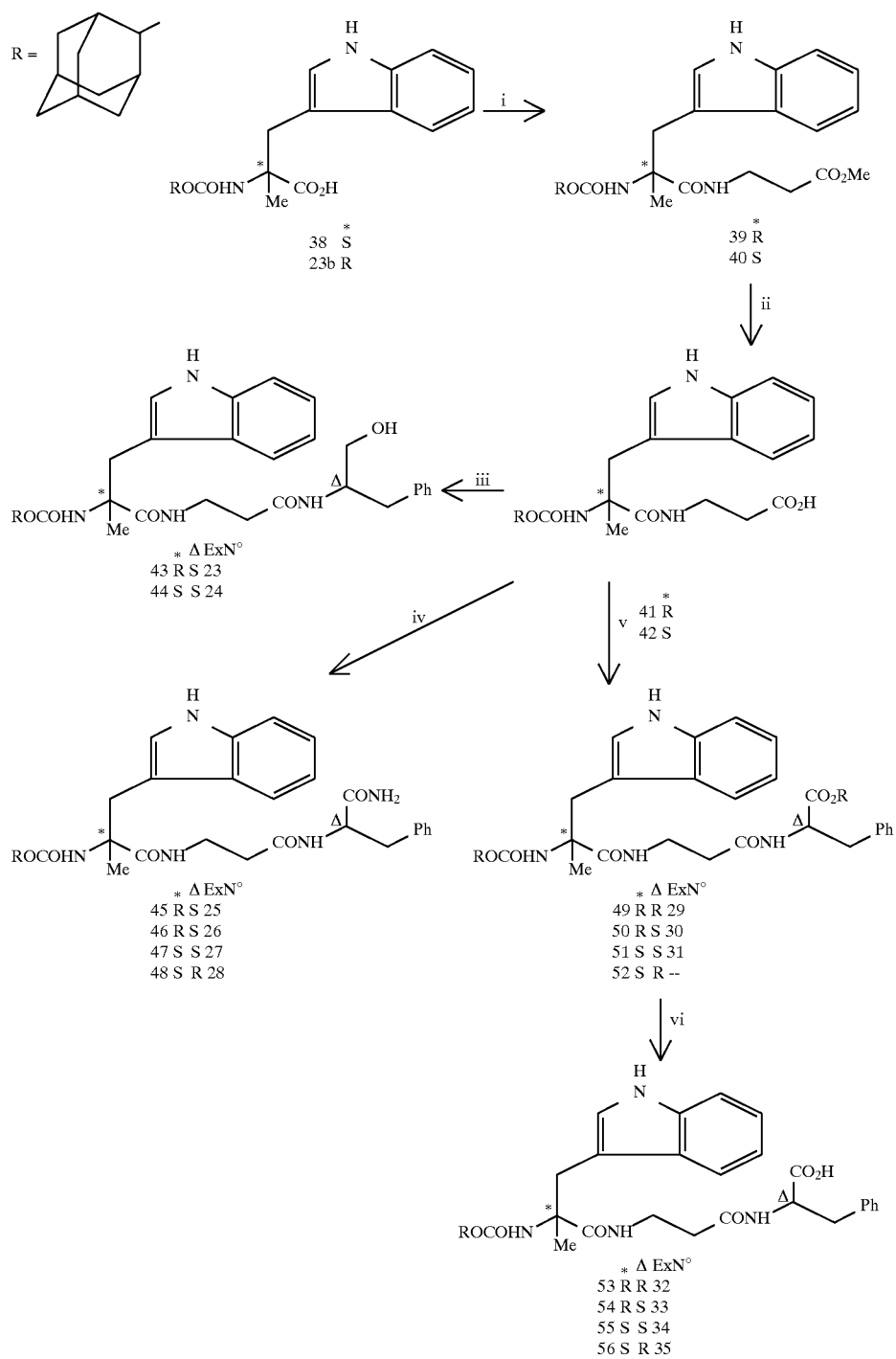

KEY Reagents: i) PFP, DCC, β-Alanine Me ester, EtOAc;
ii) LiOH, aq dioxan; iii) DCC, 2-amino-3-phenyl-1-propanol EtOAc; iv) PFP, DCC, phenylalaninamide, EtOAc; v) PFP, DCC, (S)-phenylalanine benzyl ester, EtOAc or PFP, DCC, (R)-phenylalanine methyl ester, EtOAC; vi) H₂, Pd/C, EtOH or LiOH, THF/H₂O.

Scheme 7 describes synthetic steps towards derivatives of α-methyl tryptophyl glycine. As an illustration, 2-Adoc-α-methyltryptophan 23b may be easily condensed with glycine benzyl ester via the pentafluorophenyl ester of 23b. Hydrogenation of this ester using 10% palladium on carbon in an ethanol solution affords the carboxylic acid 58 in high yield.

Treatment of this acid with N,N'dicyclohexyl-carbodiimide and pentafluorophenol gives the active ester which undergoes reaction with phenylalaninol readily to give the product compound 59, Example 37.

SCHEME 7

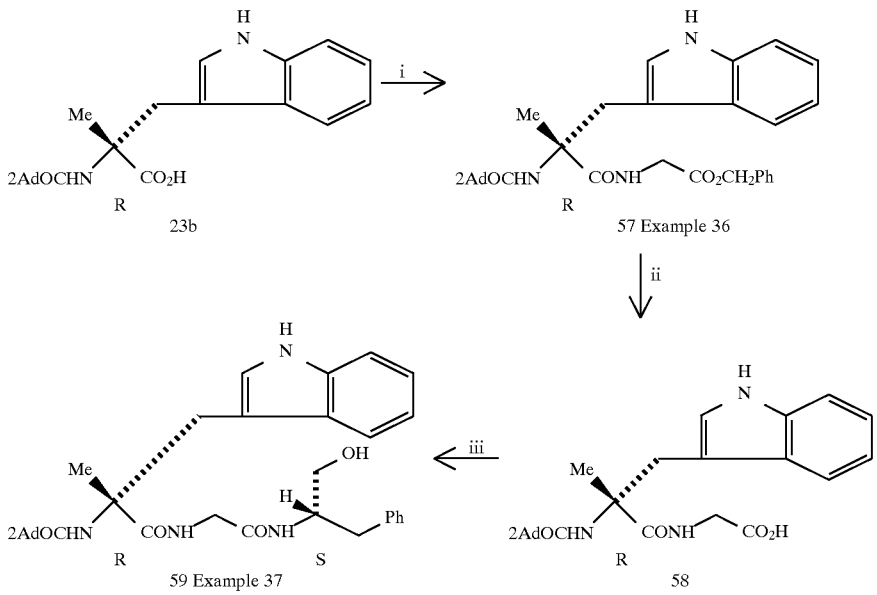

KEY  Reagents: i) PFP, DCC, glycine benzyl ester hydrochloride, Et₃N, EtOAc; ii) H₂ Pd/C, EtOH; iii) PFP, DCC, s-phenylalaninol, EtOAc.

Scheme 8 describes synthetic steps towards derivatives of α-methyltryptophyl-γ-aminobutyric acids. As an illustration, the carboxylic acid 23b may be condensed with γ-aminobutyric acid methyl ester to give 60, hydrolysis of this with LiOH affords acid 61. The product 62, Example 39 is produced when 61 is condensed with phenylalaninol via an active pentafluorophenyl ester.

SCHEME 8

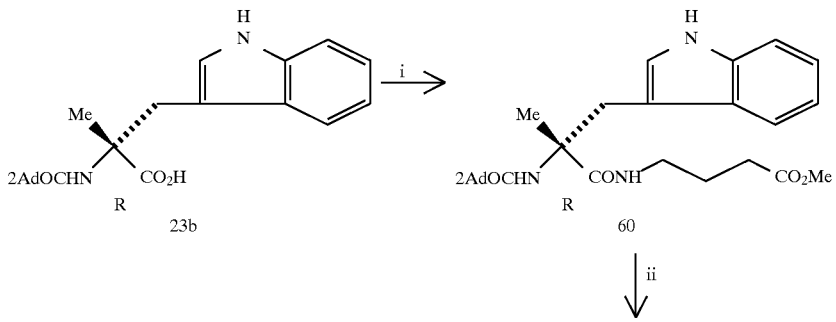

-continued
SCHEME 8

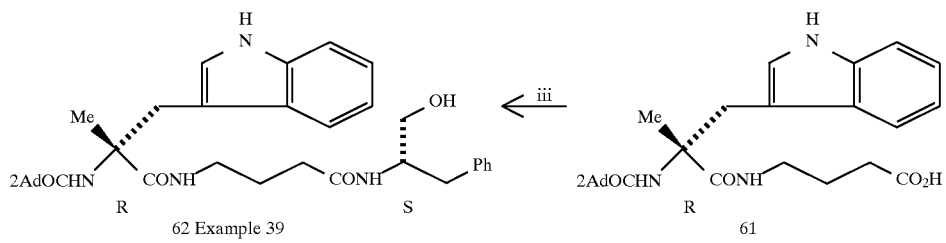

KEY Reagents: i) PFP, DCC, gamma-aminobutyric acid methylester hydrochloride, Et₃N, EtOAc; ii) LiOH, aq 1,4-dioxan; iii) PFP, DCC, s-phenylaleninol, EtOAc.

Scheme 9 outlines the synthesis of α-substituted tryptophanylphenethylamides and their intramolecular cyclizations to compound 68, Example 40. The isonitrile 63 (prepared by the method described in *Synthesis* 465, 1990) in ethanol at −5° C. was treated with ethanolic HCl to give the amine 64. This underwent coupling with 2-adamantylchloroformate to the urethane 65. Hydrogenation of 65 using 10% palladium on charcoal at 45 psi yielded the mono acid mono ester 66 which was condensed in the usual way to 2-phenethylamine giving 67. The product was formed by treatment of 67 with LiOH which abstracts the amide NH proton and cyclizes onto the ester group, liberating methoxide.

SCHEME 9

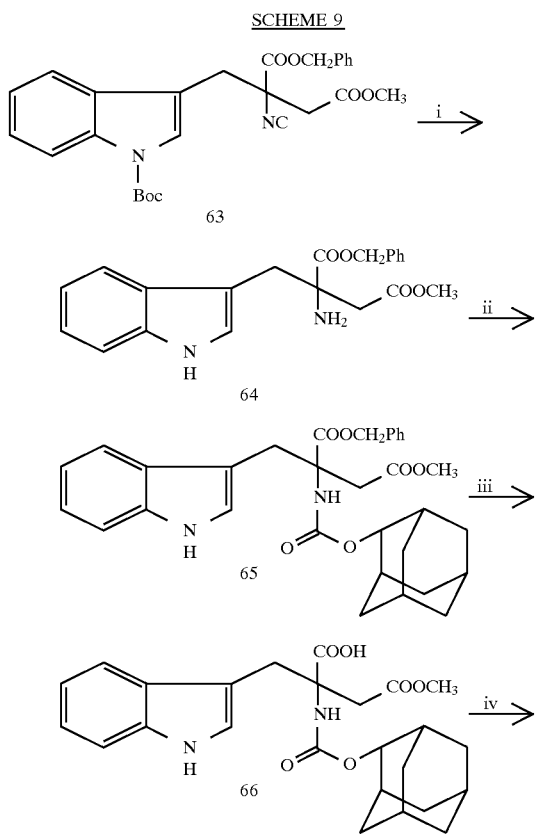

-continued
SCHEME 9

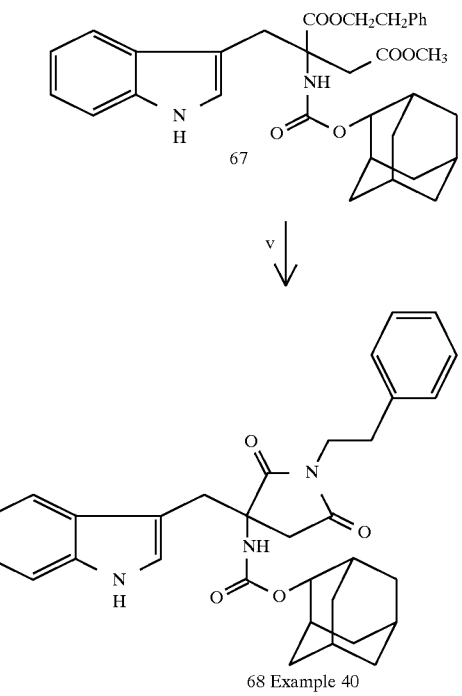

KEY Reagents: i) EtOH.hcL, 67%; ii) 2-adamantyl-OCOCl, Et₃N, EtOAC, 58%; iii) Pd/H₂, EtOH, 88%; iv) H₂NCH₂CH₂Ph, PFP, DCC, DMAP, EtOAc, 73%; v) LiOH (0.01M), 0° C., THF/H₂O, 79%.

Scheme 10 outlines the synthetic steps towards β-substituted tryptophan derivatives. Isopropylamine, when added to acetaldehyde and treated with KOH, gives 69 which reacts with indole in glacial acetic acid over 5 days to produce 70. The isopropylamino ethylidene 70 then reacts with 71 in the presence of NaOMe in hot toluene, yielding 72. Saponification and decarboxylation affords 74 as a mixture of separable diastereoisomers.

The amide 74 is dissolved in 4N sulphuric acid at reflux, then cooled to ambient temperature, and treated with 0.4N barium hydroxide until a pH of 8 is obtained, yielding the free amine 75 which reacts with 2-adamantyl chloroformate 76, yielding the urethane 77. This is then condensed with phenyl alaninol in the normal manner to give the product 78, Example 89.

SCHEME 10
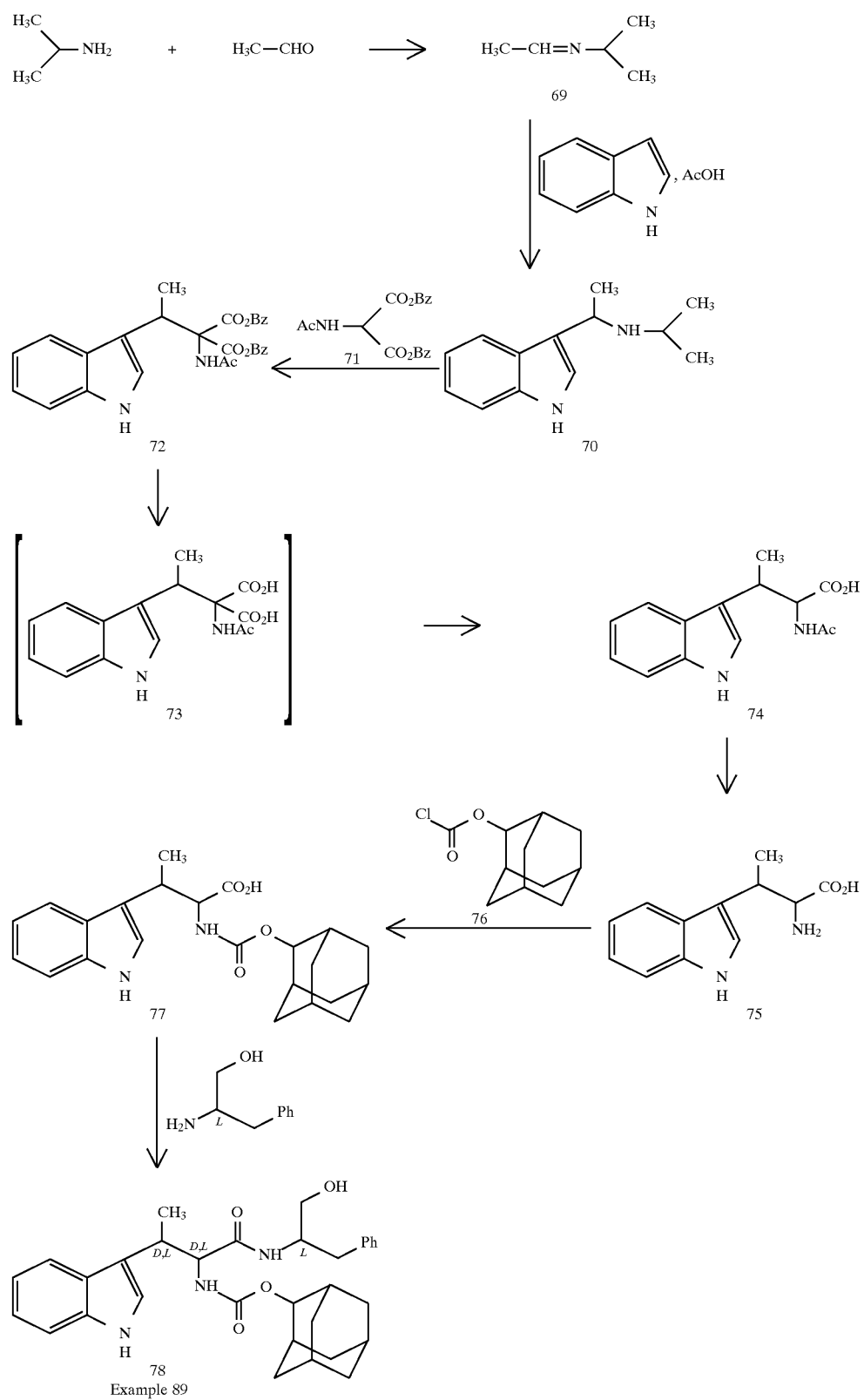
Example 89

GENERAL PROCESS FOR REACTION SCHEMES

Scheme 15a:

Cyano acetic esters or substituted derivatives 1 are alkylated with gramine and a base, e.g., NaOH in toluene, to compounds 2 in analogy to known methods. Compounds 2 are hydrogenated catalytically with Raney nickel alloy to the amino esters 3, which are reacted with chloro- or fluoroformates to the carbamic acid esters 4. The esters 4 are hydrolyzed to the acids 5, which are converted to activated esters, e.g., with pentafluorophenol and dicyclohexylcarbodiimide to the pentafluorophenyl esters. The activated esters are reacted with an appropriate amine to an amide of formula 6. Further conversions at the amide part of the molecules are done in analogy to known methods.

Compounds of general formula 15a

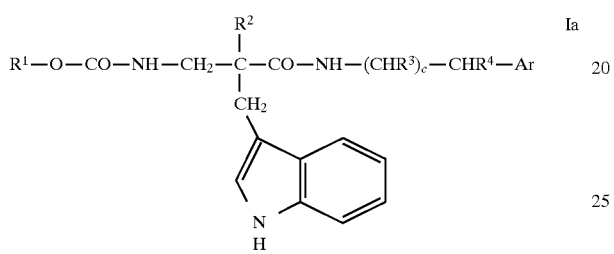

where $R^1$=1-adamantyl, 2-adamantyl, (1S)-2-endo-bornyl $R^2$=H or Me

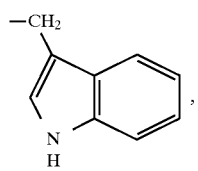

, c=0 or 1

$R^3$=H, —$CH_2OH$, —$CH_2$—O—CO—$(CH_2)_2CO_2H$ $R^4$ = H, —NH—$CO_2$—t—Bu,
—NH—CO—$CH_2$—$CH_2$—$CO_2$Bz, —NH—CO—$CH_2$—$CH_2$—$CO_2$H
—NH—CO—CH=CH—$CO_2$Me, —NH—CO—CH=CH—$CO_2$H
  t                          t are prepared according to Synthetic Scheme 15a:

SYNTHETIC SCHEME 15a

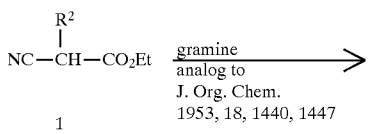

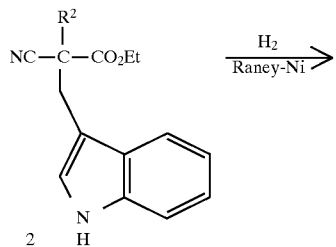

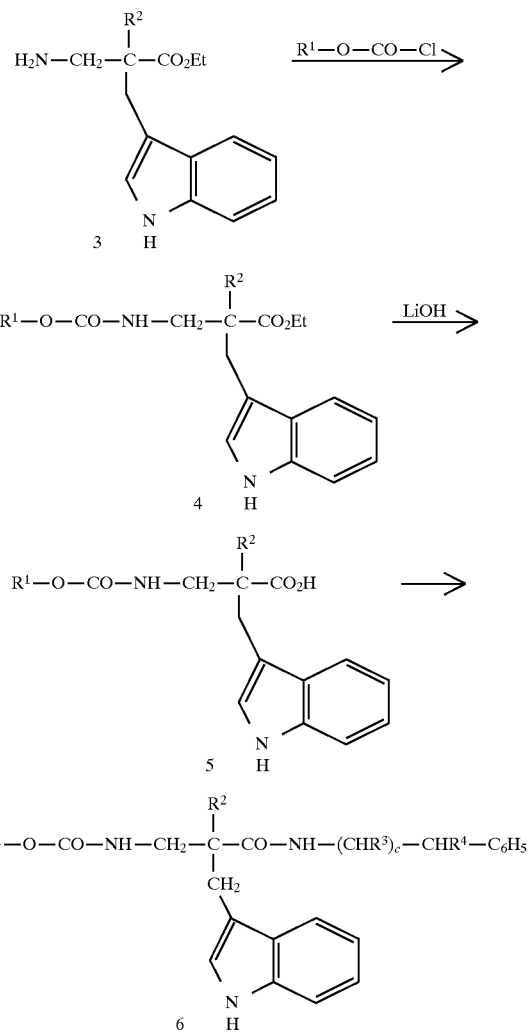

Scheme 15b:

Compounds of general formula Ia, where $R^2$, $R^2$, and $R^4$ are R are also prepared according to Synthetic Scheme 15b. Cyano acetic esters 7 are reacted with appropriate amines to the cyano acetamides 8, which are condensed with indole-3-carboxaldehyde and catalytic amounts of piperidine to compounds 9 in analogy to known methods, and thereafter hydrogenated catalytically with Raney nickel alloy to the 3-indolylmethyl substituted β-aminopropionamides 10. Reaction with chloro- or fluoroformates yields the carbamic acid ester derivatives 11.

SYNTHETIC SCHEME 15b

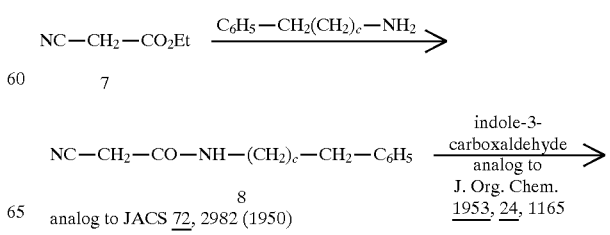

-continued
SYNTHETIC SCHEME 15b

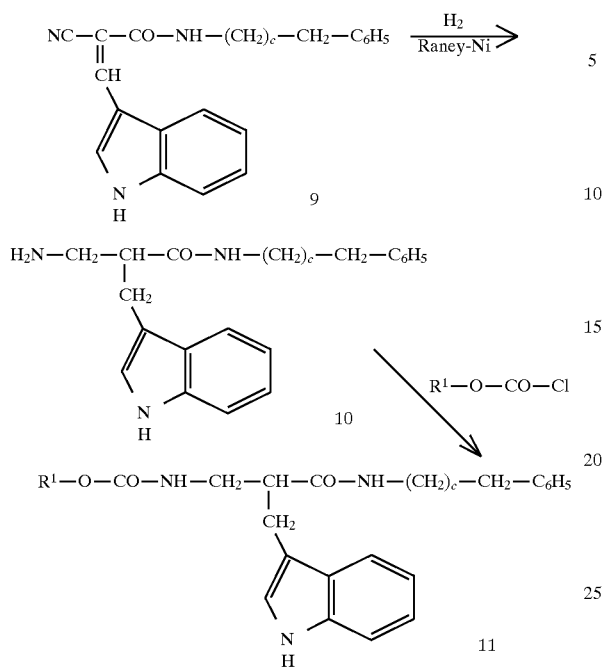

Scheme 15c:

Compounds of general formula Ia, where $R^2$=H or —$CH_2$

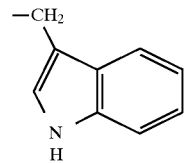

and $R^3$ and $R^4$ are H are also prepared according to Synthetic Scheme 15c. Cyano acetamides 8 are alkylated with gramine and a base, e.g., NaOH in toluene, to compounds 12 and 13, which are hydrogenated catalytically with Raney nickel alloy to the mono- or bis-(3-indolylmethyl) substituted 9-aminopropionamides 10 and 16. Reaction with chloro- or fluoroformates yields the carbamic acid ester derivatives 11 and 17.

SYNTHETIC SCHEME 15c

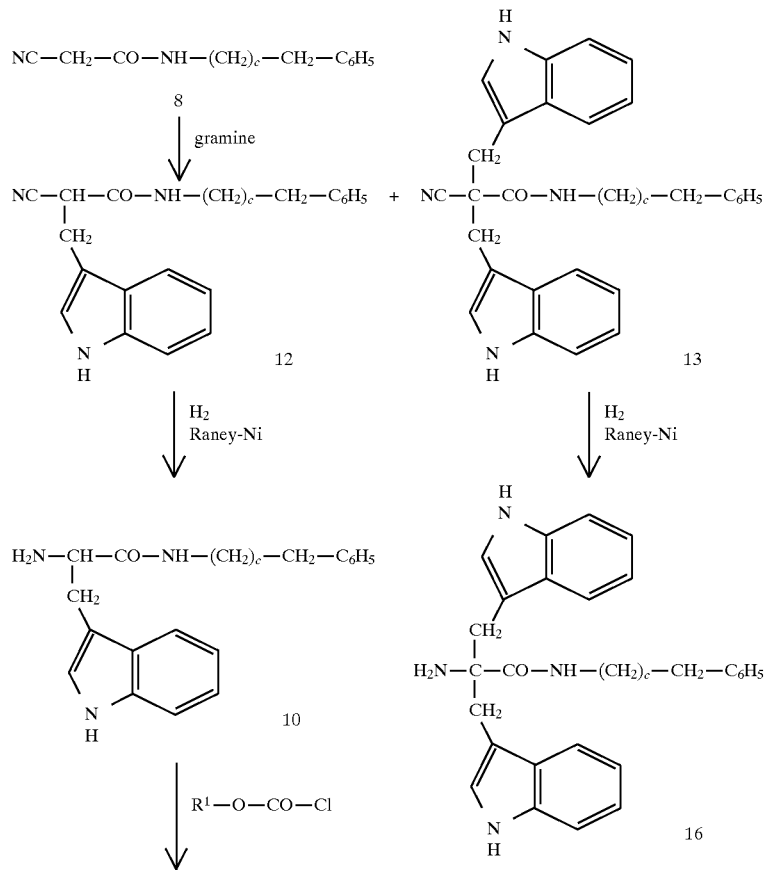

-continued
SYNTHETIC SCHEME 15c

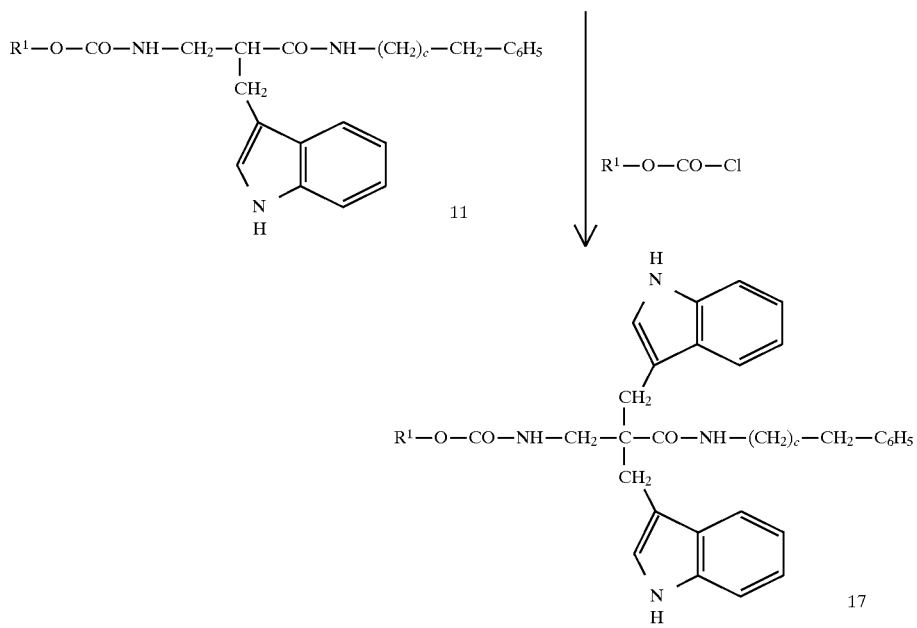

Scheme 16:
Compounds of the general formula Ib,

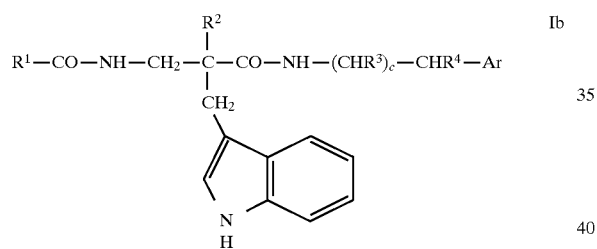

where $R^1$, $R^2$, $R^3$, $R^4$, and c are as defined above are prepared according to Synthetic Scheme 16. Aminoesters 3 are reacted with carboxylic acid chlorides to give the amides 18. The ester groups of compounds 18 are hydrolyzed with lithium hydroxide to the carboxylic acids 19, which are converted to activated esters, e.g., with pentafluorophenol and dicyclohexylcarbodiimide to the pentafluorophenyl esters. The activated esters are reacted with an appropriate amine to an amide of formula 20. Further conversions at $R^3$ and $R^4$ are done in analogy to known methods.

SYNTHETIC SCHEME 16

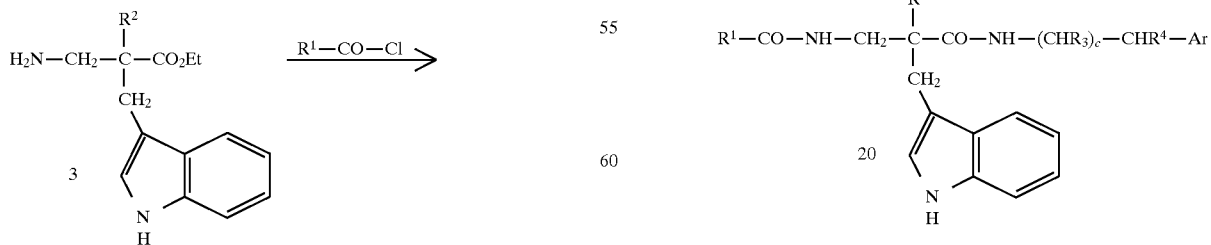

-continued
SYNTHETIC SCHEME 16

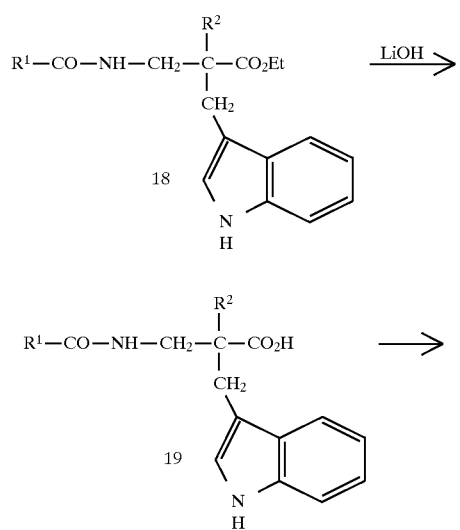

Scheme 17

Compounds of general formula Ic,

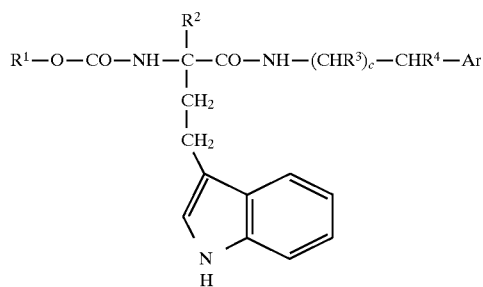

are prepared to Synthetic Scheme 17. 1-(3'-indolyl)-butan-3-one is converted with potassium cyanide and ammonium carbonate in a Bucherer synthesis to the hydantoin 21, which is hydrolyzed with aqueous sodium hydroxide to the amino acid 22, which is consequently esterified with methanol and hydrogen chloride to 23. Compound 23 is reacted with chloro- or fluoroformates to the carbamic acid esters 24. The ester groups of compounds 24 are hydrolyzed with lithium hydroxide to the carboxylic acids 25. Acids 25 are converted to activated esters, e.g., with pentafluorophenol and dicyclohexylcarbodiimide to the pentafluoro phenyl esters. The activated esters are reacted with an appropriate amine to an amide of formula 26. Further conversions at $R^3$ or $R^4$ are done in analogy to known methods.

SYNTHETIC SCHEME 17

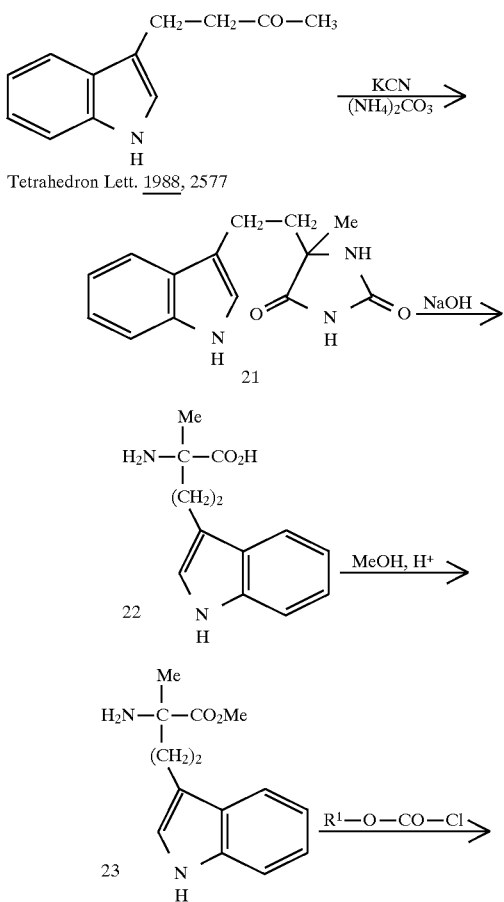

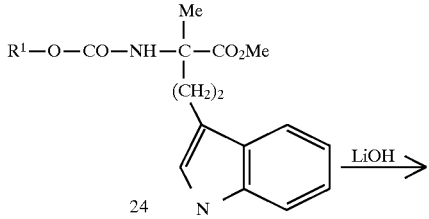

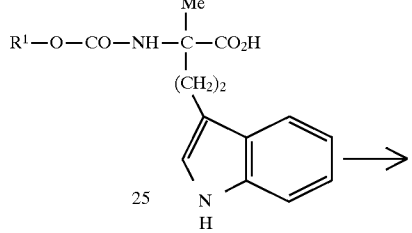

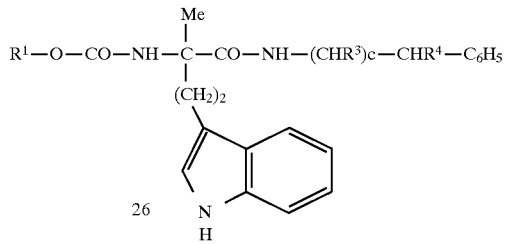

Scheme 18

Compounds of general formula Id,

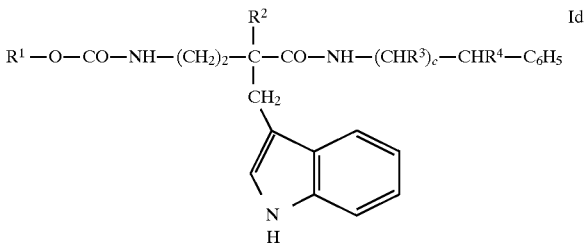

where $R^1$, $R^3$, $R^4$, and c are as defined above and $R^2$=Me are prepared according to Synthetic Scheme 18. Diethyl methylmalonate 27 is alkylated with gramine and a base, e.g., NaOH in toluene, to compound 28 by known methods. The diester 28 is hydrolyzed with potassium hydroxide to the mono acid 29. The ester group of 29 is selectively reduced with borane methyl sulfide complex to compound 30, which is esterified with methanol and sulfuric acid to the methyl ester 31. The hydroxy compound 31 is reacted with p-toluene-sulfonyl chloride and pyridine to the tosylate 32. Nucleophilic substitution with potassium cyanide gives the cyanoester 33, which is hydrogenated catalytically with Raney nickel alloy to the amino ester 34. The amino ester 34 is reacted with chloro- or fluoroformates to the carbamic acid esters 35. The ester groups of compounds 35 are hydrolyzed with lithium hydroxide to the carboxylic acids 36, which are converted to activated esters, e.g., with pentafluorophenol and dicyclohexylcarbodiimide to the pentafluorophenyl esters. The activated esters are reacted with an appropriate amine to an amide of formula 37. Further conversions at $R^3$ and $R^4$ are done in analogy to known methods.

SYNTHETIC SCHEME 18
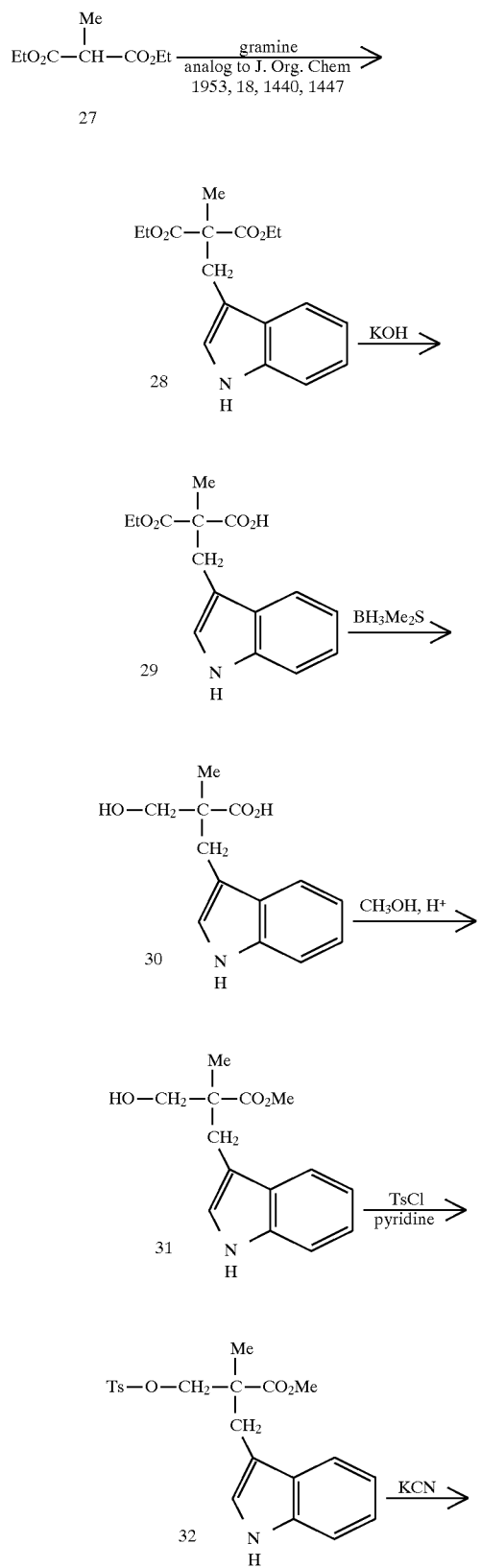
-continued
SYNTHETIC SCHEME 18
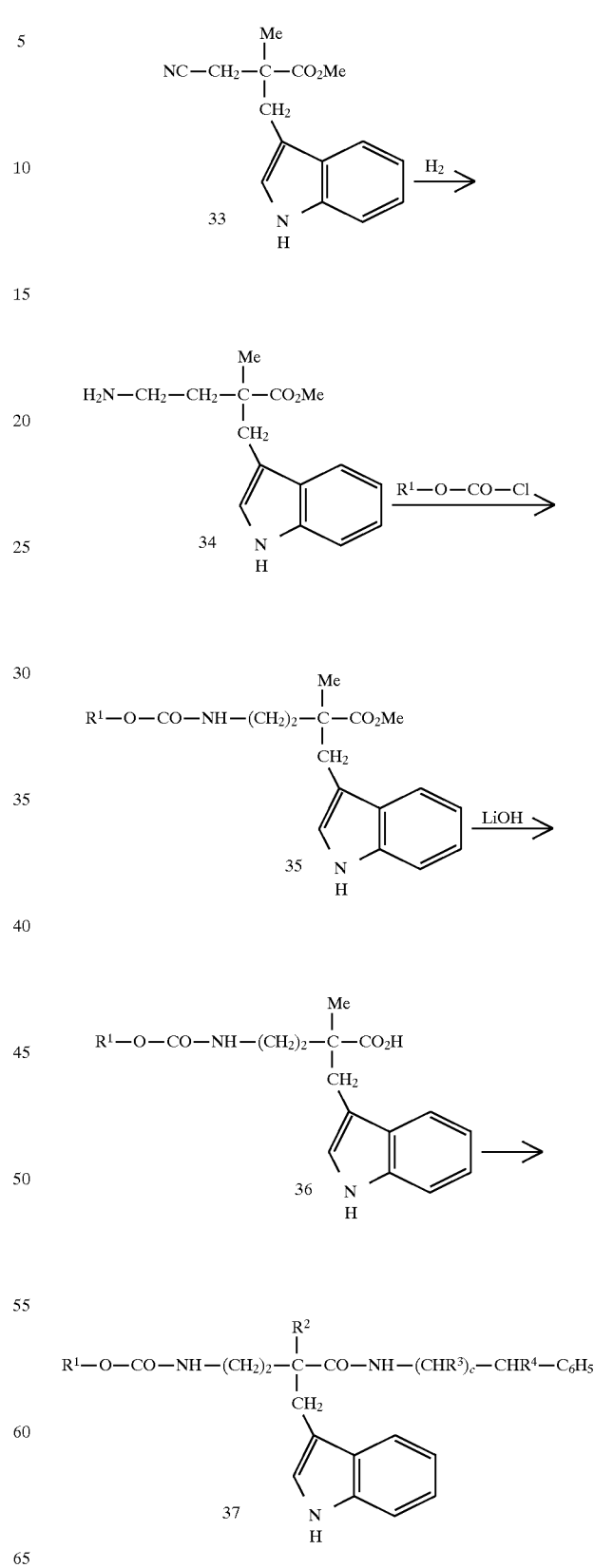

SYNTHETIC SCHEME 19
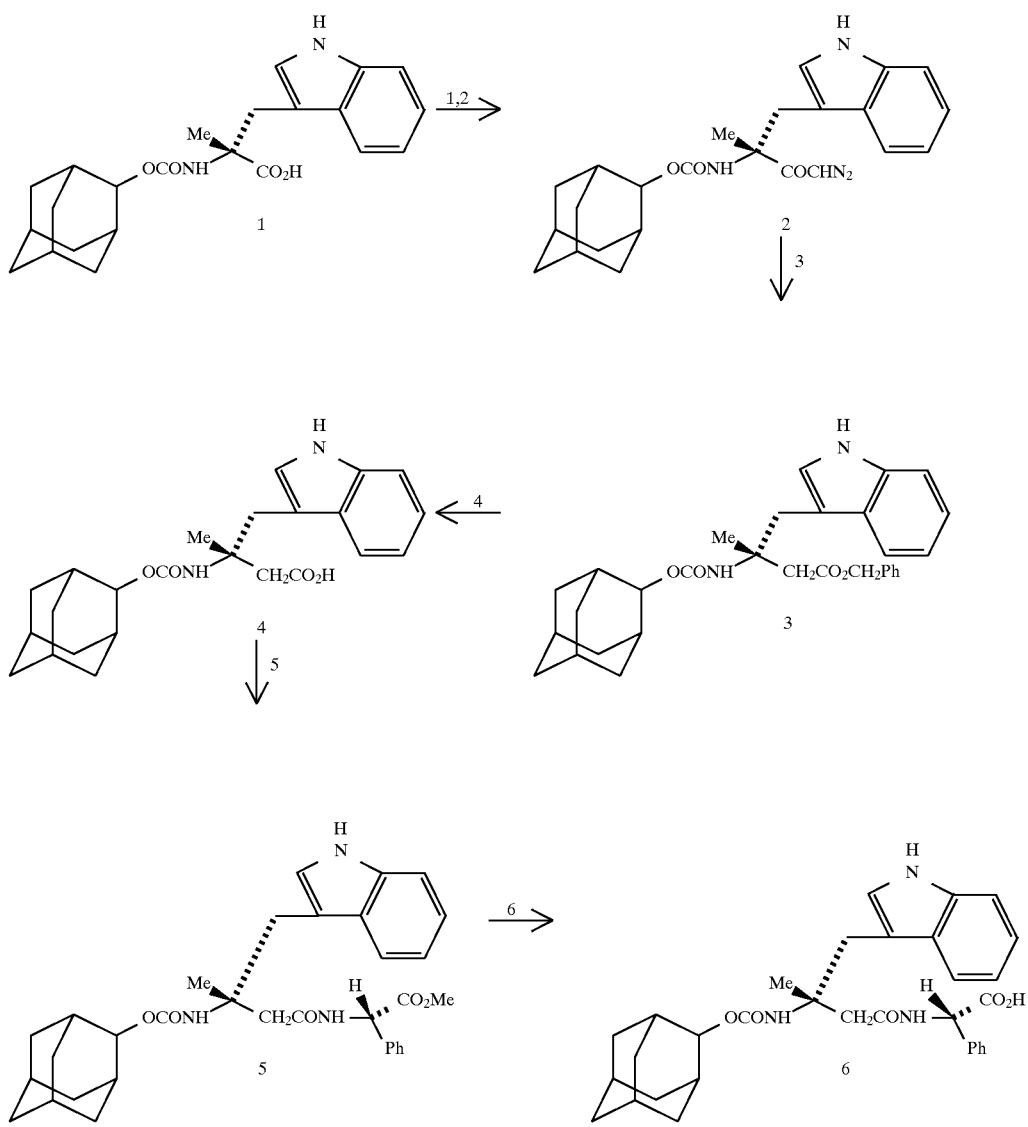
Reagents: 1) N-Methylmorpholine, iBuOCOCl; 2) CH₂N₂;
3) AgOCOPh, HOCH₂Ph, AgOCH₂Ph; 4) H₂Pd/C; 5) DPP, DCCi, Phenylglycine Methylester; 6) LiOH

SYNTHETIC SCHEME 20
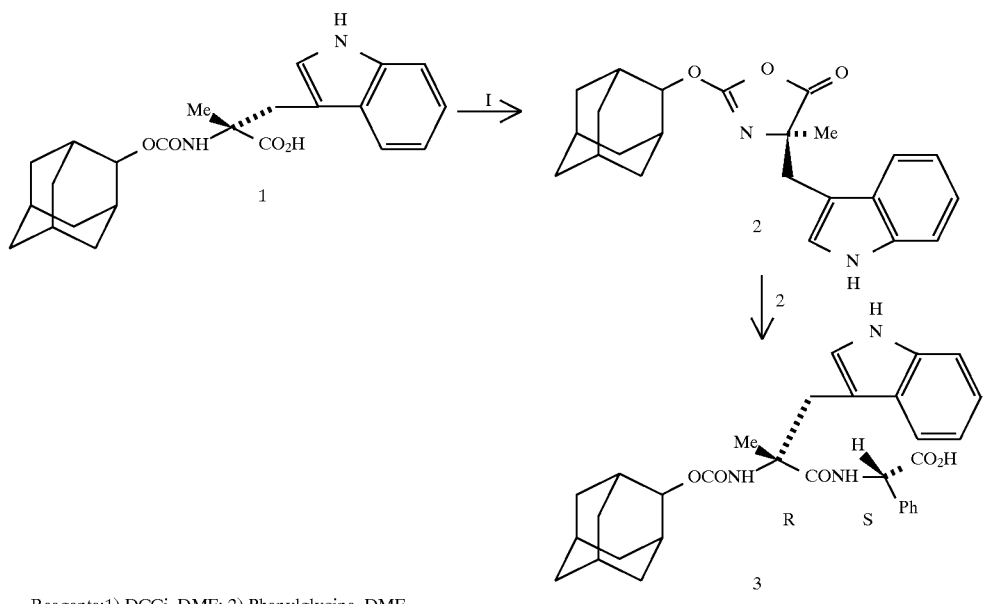
Reagents: 1) DCCi, DMF; 2) Phenylglycine, DMF
SYNTHETIC SCHEME 21
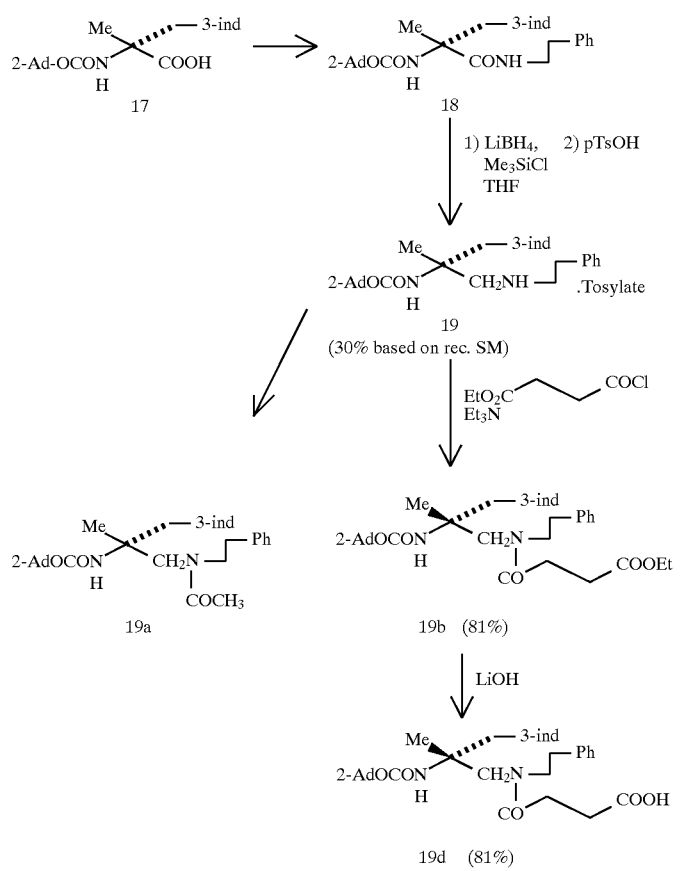

SYNTHETIC SCHEME 22
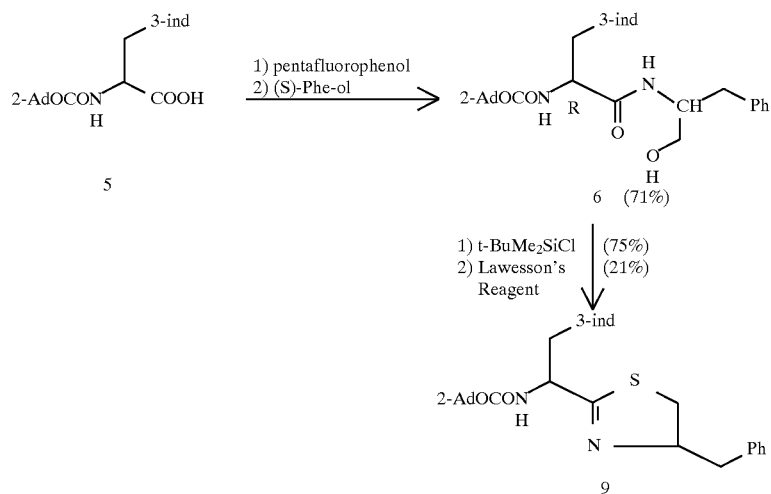
SYNTHETIC SCHEME 23
(See Examples 97–102)
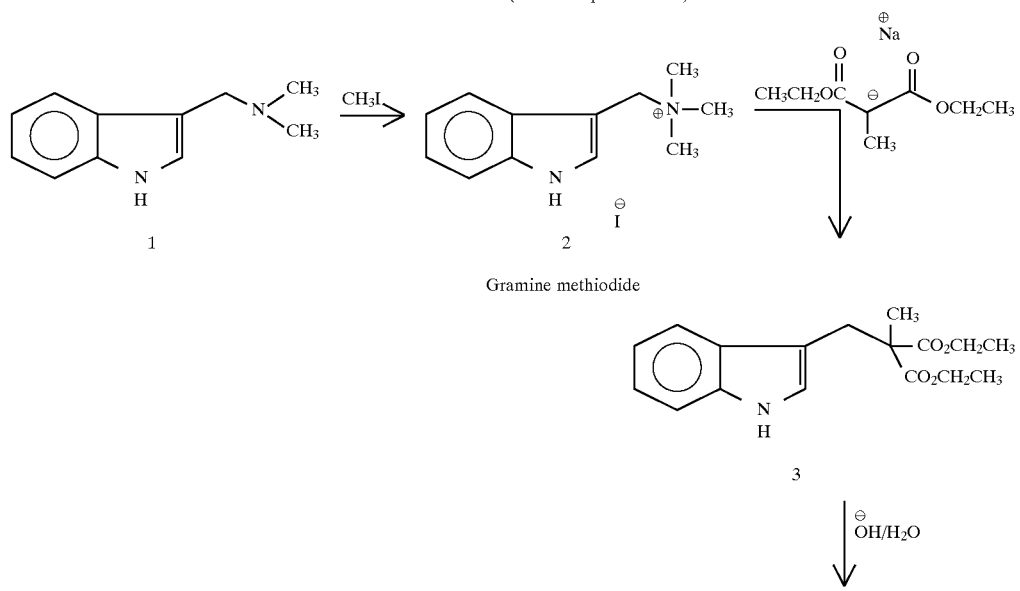
Gramine methiodide -continued
SYNTHETIC SCHEME 23
(See Examples 97–102)
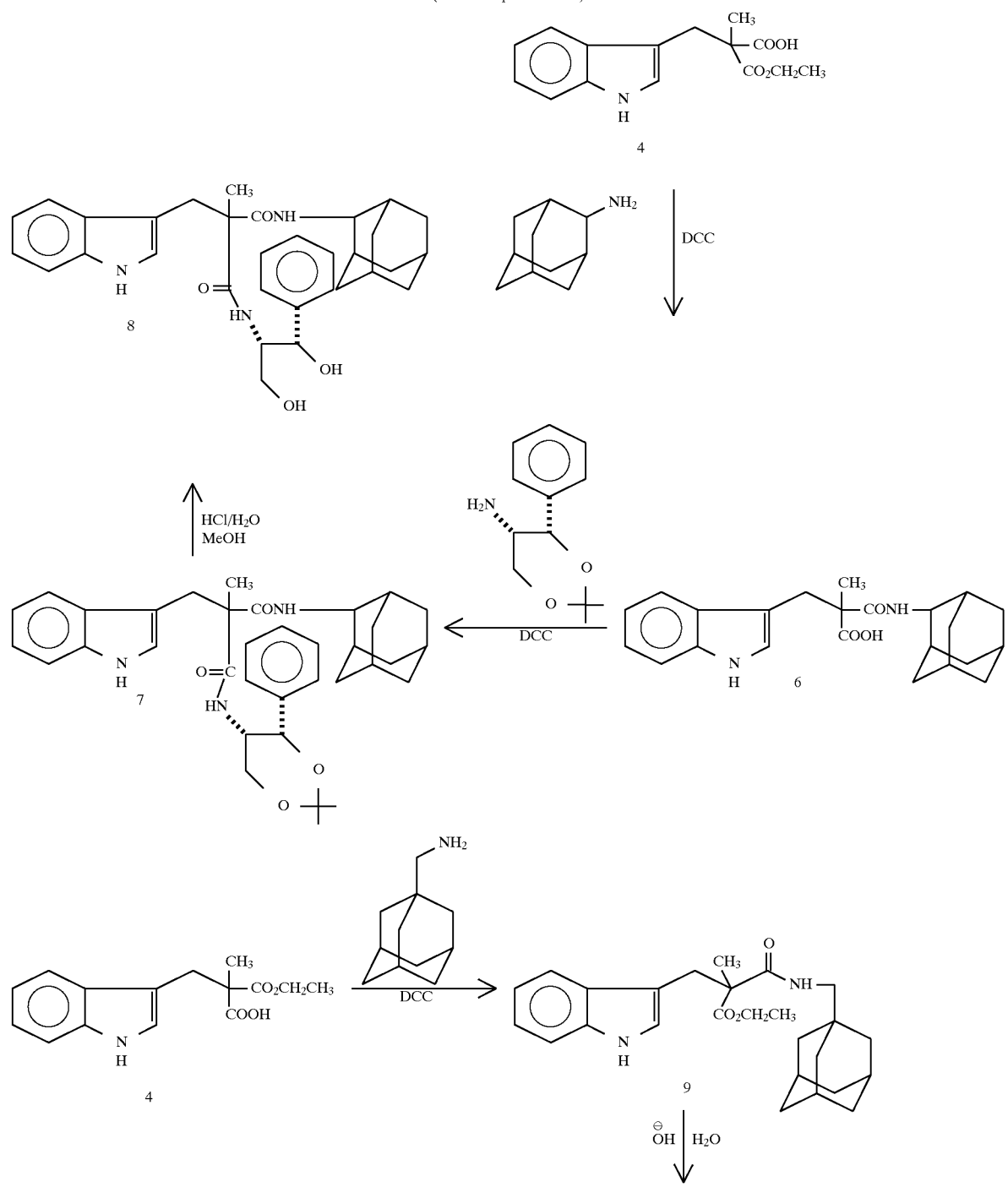

-continued
SYNTHETIC SCHEME 23
(See Examples 97–102)
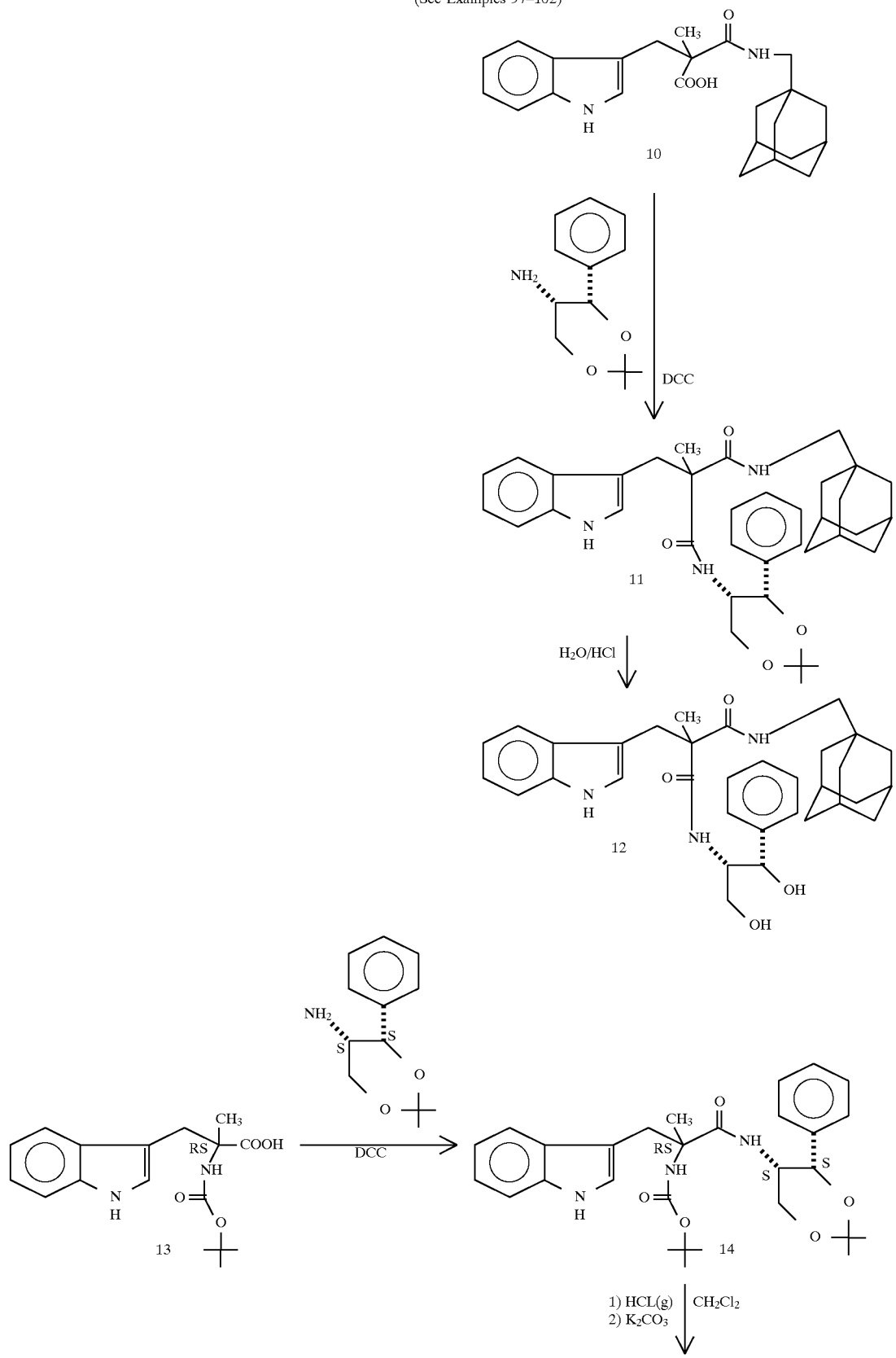

-continued
SYNTHETIC SCHEME 23
(See Examples 97–102)
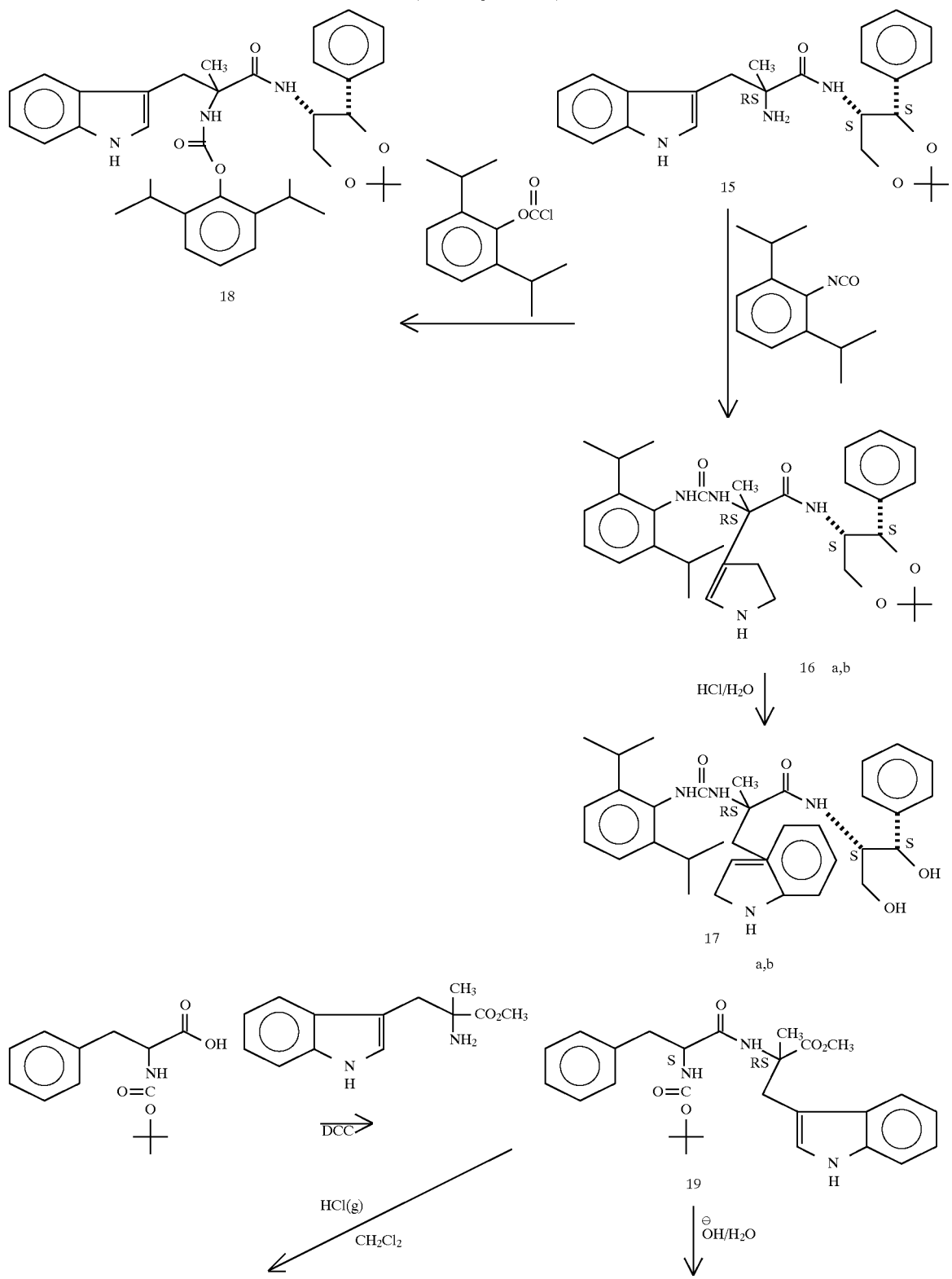

-continued
SYNTHETIC SCHEME 23

(See Examples 97–102)

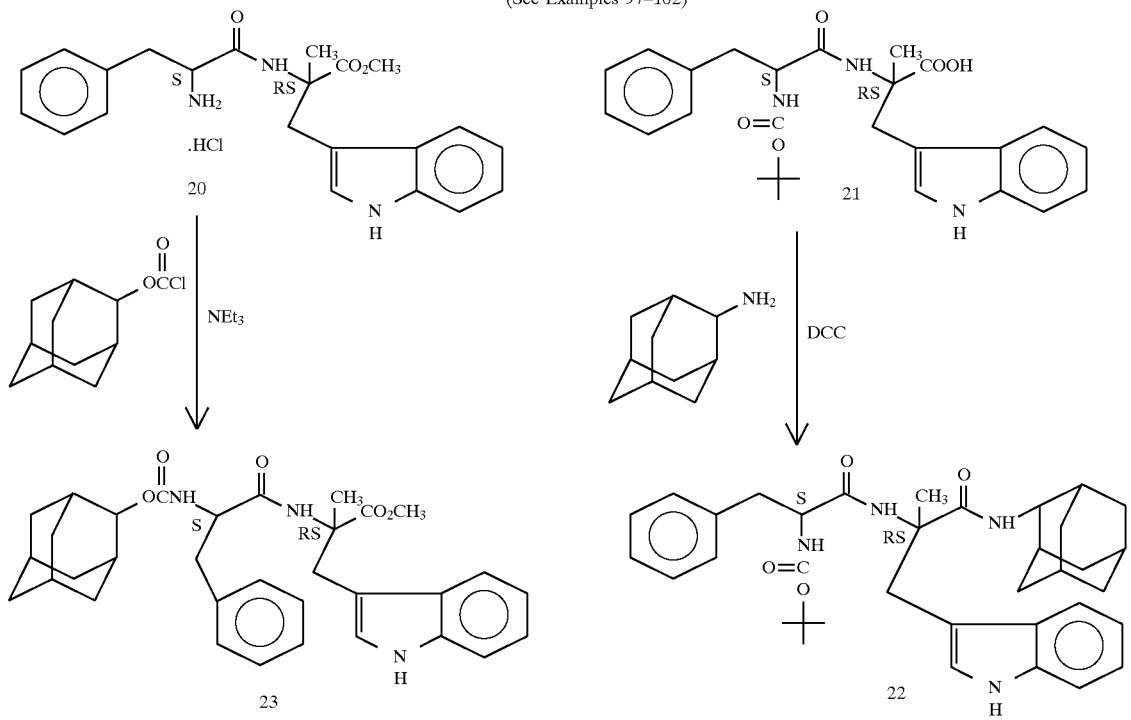

The individual diastereomers of Example 109 can be separated by HPLC. Alternatively, they can also be synthesized by utilizing enantiomeric pure trans-2-aminocyclohexanol which can be synthesized by following Synthetic Scheme 24. (See Overman L. E. and Sugar S., *J. Org. Chem.* 50:4154–4155, 1985).

SYNTHETIC SCHEME 24

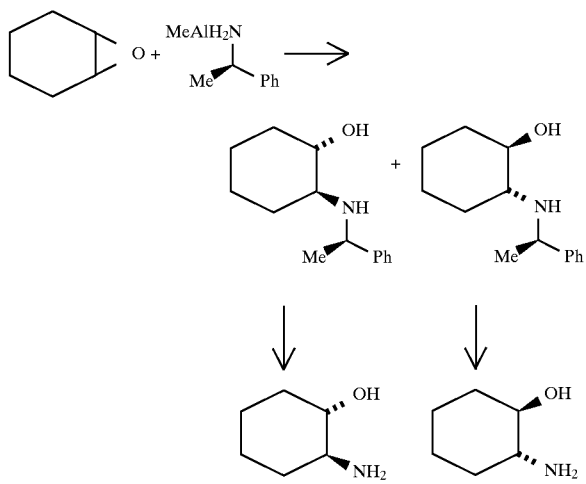

The biological activity of compounds of the present invention was evaluated employing an initial screening test which rapidly and accurately measured the binding of the tested compound to known CCK receptor sites. Specific CCK receptors have been shown to exist in the central nervous system. (See Hays et al, *Neuropeptides* 1:53–62, 1980; and Satuer et al, *Science* 208:1155–1156, 1980).

In this screening test, the cerebral cortices taken from male CFLP mice weighing between 30–40 g were dissected on ice, weighed, and homogenized in 10 volumes of 50 mM Tris-HCl buffer (pH 7.4 at 0°–4° C.). The resulting suspension was centrifuged, the supernate was discarded, and the pellet was washed by resuspension in Tris-HCl buffer followed by recentrifugation. The final pellet was resuspended in 20 volumes of 10 nM Hepes buffer (pH 7.2 at 23° C.) containing 130 mM NaCl, 4.7 nM KCl, 5 nM $MgCl_2$, 1 nM EDTA, 5 mg/mL bovine albumin, and bacitracin (0.25 mg/mL).

In saturation studies, cerebral cortical membranes were incubated at 23° C. for 120 minutes in a final volume of 500 $\mu$L of Hepes incubation buffer (pH 7.2) together with 0.2–20 n tritiated-pentagastrin (Amersham International, England).

In the displacement experiments, membranes were incubated with a single concentration (2 nM) of ligand, together with increasing concentrations ($10^{-11}$ to $10^{-14}$M) of competitive test compound. In each case, the nonspecific binding was defined as that persisting in the presence of the unlabeled octapeptide $CCK_{26-33}$ ($10^{-6}$M)

Following incubation, radioactivity bound to membranes was separated from that free in solution by rapid filtration through Whatman GF/B filters and washed three times with 4 mL of ice cold Tris-HCl buffer. Filters from samples incubated with tritiated-pentagastrin were placed in polyethylene vials with 4 mL of scintillation cocktail, and the radioactivity was estimated by liquid scintillation spectrometry (efficiency 47–52%).

The specific binding to CCK receptor sites was defined as the total bound tritiated-pentagastrin minus the amount of tritiated-pentagastrin bound in the presence of $10^{-6}$ octapeptide, $CCK_{26-33}$.

Saturation curves for specific tritiated-pentagastrin binding to mouse cortical membranes were analyzed by the methods of Scatchard (*Ann. New York Acad. Sci.* 51:660–672, 1949, and Hill (*J. Physiol.* 40:IV–VIII, 1910), to provide estimates for the maximum number of binding sites ($B_{max}$) and the equilibrium dissociation constant ($K_a$).

In displacement experiments, inhibition curves were analyzed by either logit-log plots or the iterative curve fitting computer program ALLFIT (DeLean, Munson and Redbard, 1978) to provide estimates of the $IC_{50}$ and nH (apparent Hill coefficient) values). ($IC_{50}$ values were defined as the concentration of test compound required to produce 50% inhibition of specific binding.)

The inhibition constant ($K_i$) of the test compound was then calculated according to the Cheng-Prusoff equation:

$$K_i = \frac{IC_{50}}{1 + [L]/K_a}$$

where [L] is the concentration of radiolabel and $K_a$ is the equilibrium dissociation constant.

The $K_i$ values for several representative compounds of the present invention are present in Table III.

The utility of the compounds of the present invention as appetite suppressants is tested according to the procedure described hereinbelow.

In the Palatable Diet Feeding assay, adult male Hooded Lister rats weighing between 200–400 g are housed individually and trained to eat a palatable diet. This diet consists of Nestlés sweetened condensed milk, powdered rat food and rat water which when blended together set to a firm consistency. Each rat is presented with 20–30 g of the palatable diet for 30 minutes per day during the light phase of the light-dark cycle over a training period of five days. The intake of palatable diet is measured by weighing the food container before and after the 30-minute access period (limits of accuracy 0.1 g). Care is taken to collect and correct for any spillage of the diet. Rats are given free access to pellet food and water except during the 30-minute test period.

After the training period, dose-response curves are constructed for CCK8 and several representative compounds of the present invention (n=8–10 rats per dose level). $MPE_{50}$ values (±95% confidence limits) are obtained for the anorectic effects of these compounds and are shown in Table III.

In therapeutic use as appetite suppression agents, the compounds of the instant invention are administered to the patient at dosage levels of from about 200 to about 2800 mg per day.

Table III below shows the binding data for

TABLE III

Binding Data on Cerebral Cortexes Taken From Male CFLP Mice

| Example Number | Binding to Central CCK Receptors Ki (nM) |
| --- | --- |
| 1 | 11500 |
| 3 Isomer 1 | 1230 |
| 3 Isomer 2 | 780 |
| 5 | 220 |
| 6 | 200 |
| 7 | 374 |
| 8 | 318 |
| 14 | NT |
| 9 | 808 |
| 11 | 260 |

TABLE III-continued

Binding Data on Cerebral Cortexes Taken From Male CFLP Mice

| Example Number | Binding to Central CCK Receptors Ki (nM) |
| --- | --- |
| 10 | 39 |
| 2 | 1120 |
| 4 | NT |
| 19 | 353 |
| 20 | 493 |
| 21 | >100 |
| 22 | 704 |
| 35 | 540 |
| 34 | 560 |
| 32 | 103 |
| 26 | 92 |
| 24 | 1100 |
| 31 | 1200 |
| 27 | 910 |
| 28 | 1400 |
| 29 | 240 |
| 30 | >$10^4$ |
| 25 | 550 |
| 33 | 22 |
| 23 | 800 |
| 37 | NT |
| 36 | 50 |
| 39 | NT |
| 17 | 17 |
| 56 | 23 |
| 57 | 93 |
| 58 | 110 |
| 90 | 942 |
| 91 | 110 |
| 112 | 73 |
| 113 | 2.5 |
| 115 | 1 |
| 116 | 3.5 |
| 117 | 39 |
| 118 | 53 |
| 119 | 180 |
| 120 | 40 |
| 121 | 2 |
| 122 | 59 |
| 123 | 17 |

NT = Not tested

Male Hooded Lister rats (175–250 g) are housed individually and are caused to fast overnight (free access to water). They are anesthetized with urethane (1.5 g/kg IP) and the trachea cannulated to aid spontaneous respiration. The stomach is perfused continuously using a modification of the original method of Ghosh & Schild in "Continuous recording of acid secretion in the rat", *Brit. J. Pharmac.* 13:54–61, 1956 as described by Parsons in "Quantitative studies of drug-induced gastric acid secretion". (Ph.D. Thesis, University of London, 1969). The cavity of the stomach is perfused at a rate of 3 mL/min with 5.4% w/v glucose solution through both the esophageal and body cannula. The fluid is propelled by a roller pump (Gilson, Minipuls 2), through heating coils to bring its temperature to 37°±1° C. The perfusion fluid is collected by the fundic collecting funnel and passed to a pH electrode connected to a Jenway pH meter (PHM6). An output is taken from the pH meter to a Rikadenki chart recorder for the on-line recording of the pH of the gastric perfusate.

Pentagastrin is stored as a frozen aliquot and diluted to the required concentrations with sterile 0.9% w/v NaCl. Novel compounds are dissolved in sterile 0.9% w/v NaCl on the day of the experiment. Drugs are administered IV through a cannulated jugular vein as a bolus in a dose volume of 1 mL/kg washed in with 0.15 mL 0.9% w/v NaCl. Basal pH is allowed to stabilize before administration of compounds is begun. Typically 30 minutes elapses between surgery and the first compound administration.

The compounds of the instant invention are also useful as antiulcer agents as discussed hereinbelow.

Aspirin-induced gastric damage is assessed in groups of 10 rats each.

All animals are made to fast for 24 hours before and during the experiment. Drug or vehicle is given 10 minutes before an oral dose of 1 mL of a 45-mg/mL suspension of aspirin in 0.5% carboxymethylcellulose (CMC).

The animals are sacrificed 5 hours after aspirin administration and the stomachs removed and opened for examination.

Gastric damage is scored as follows:

| Score | |
|---|---|
| 1 | Small hemorrhage |
| 2 | Large hemorrhage |
| 3 | Small ulcer |
| 4 | Large ulcer |
| 5 | Perforated ulcer |

The specific dosages may, however, be varied depending upon the patient, the severity of the condition being treated, and the activity of the compound employed. Determination of optimum dosages is within the skill of the art.

The compounds of the instant invention are also useful as anxiolytic agents as described and discussed below. Anxiolytic activity is assessed in the light/dark exploration test in the mouse (B. J. Jones, et al, *Brit. J. Pharmac.* 93:985–993, 1988).

The apparatus used is an open-topped box, 45 cm long, 27 cm wide, and 27 cm high, divided into a small (2/5) area and a large (3/5) area by a partition that extended 20 cm above the walls. There is a 7.5×7.5 cm opening in the partition at floor level. The small compartment is painted black and the large compartment white. The floor of each compartment is marked into 9 cm squares. The white compartment is illuminated by a 100-watt tungsten bulb 17 cm above the box and the black compartment by a similarly placed 60-watt red bulb. The laboratory is illuminated with red light.

All tests are performed between 13 hundred hours, 0 minutes and 18 hundred hours, 0 minutes. Each mouse is tested by placing it in the center of the white area and allowing it to explore the novel environment for five minutes. Its behavior is recorded on videotape and the behavioral analysis is performed subsequently from the recording. Five parameters are measured: the latency to entry into the dark compartment, the time spent in each area, the number of transitions between compartments, the number of lines crossed in each compartment, and the number of rears in each compartment.

In this test an increase in the time spent in the light area is a sensitive measure of, that is directly related to, the anxiolytic effects of several standard anxiolytic drugs. Drugs were dissolved in water or saline and administered either subcutaneously, intraperitoneally, or by mouth (PO) via a stomach needle.

The compounds of the instant invention are useful as antipsychotic agents and can be tested for their ability to reduce the effects of intra-accumbens amphetamine in the rat as described hereinafter.

Male Sprague Dawley (CD) Bradford strain rats are used. The rats are housed in groups of five at a temperature of 21°±2° C. on a 12 hour light-dark cycle of lights-on between 07 hours 00 minutes and 20 hours 00 minutes. Rats are fed CRM diet (Labsure) and allowed water ad libitum.

Rats are anesthetized with chloral hydrate (400 mg/kg SC) and placed in a Kopf stereotaxic frame. Chronically indwelling guide cannulae (constructed of stainless steel tubing 0.65 mm diameter held bilaterally in Parspex holders) are implanted using standard stereotaxic techniques to terminate 3.5 mm above the center of the nucleus accumbens (Ant. 9.4, Vert. 0.0, Lat. 1.6) or 5.0 mm above the central nucleus of the amygdala (Ant. 5.8, Vert. −1.8, Lat. ±4.5) (atlas of De Groot, 1959). The guides are kept patent during a 14-day recovery period using stainless steel stylets, 0.3 mm diameter, which extended 0.5 mm beyond the guide tips.

Rats are manually restrained and the stylets removed. Intracerebral injection cannulae, 0.3 mm diameter, are inserted and drugs delivered in a volume of 0.5 $\mu$L over 5 seconds (a further 55 seconds was allowed for deposition) from Hamilton syringes attached via polythene tubing to the injection units. Animals Are used on a single occasion only.

Behavioral experiments are conducted between 07 hours 30 minutes and 21 hours 30 minutes in a quiet room maintained at 22°±2° C. Rats are taken from the holding room and allowed 1 hour to adapt to the new environment. Locomotor activity is assessed in individual screened Perspex cages (25×15×15 cm (high)) (banked in groups of 30) each fitted with one photocell unit along the longer axis 3.5 cm from the side; this position has been found to minimize spurious activity counts due to, for example, preening and head movements when the animal is stationary. Interruptions of the light beam are recorded every 5 minutes. At this time animals are also observed for the presence of any nonspecific change in locomotor activity, e.g., sedation, prostration, stereotyped movements, that could interfere with the recording of locomotor activity.

The abilities of the compounds of the invention to inhibit the hyperactivity caused by the injection of amphetamine into the nucleus accumbens of the rat are measured.

An increase in locomotor activity followed the bilateral injection of amphetamine (20 $\mu$g) into the nucleus accumbens; peak hyperactivity (50 to 60 counts 5 minutes$^{-1}$) occurs 20 to 40 minutes after injection. This test is known to be predictive of antipsychotic activity (Costall, Domeney & Naylor & Tyers, *Brit. J. Pharmac.* 92:881–894).

The compounds of the instant invention prevent and treat the withdrawal response produced when chronic treatment by a drug is stopped or when alcohol abuse is stopped. These compounds are therefore useful as therapeutic agents in the treatment of chronic drug or alcohol abuse as discussed and described below.

The effect of the compounds of the instant invention is illustrated, for example, in the mouse "light/dark box" test wherein five animals are given nicotine, in a range of 0.1 to 100 mg/kg i.p. b.d. for 14 days. After a 24-hour withdrawal period, compound (20) is given at 1.0 mg/kg i.p. b.d. The increased time spent in the light area is a sensitive measure of the effect of compound (20) as an agent to treat withdrawal effects from nicotine.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

81

In powders, the carrier is a finely divided solid which is in a mixture with the finely divided active component. In tablets, the active component is mixed with the carrier having the necessary binding properties in suitable proportions and compacted in the shape and size desired.

For preparing suppository preparations, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

The powders and tablets preferably contain 50 to about 70% of the active component. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Preferred pharmaceutically acceptable salts are the N-methyl glucamine salt and sodium.

Pharmaceutically acceptable salts are acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, glucaptate, gluconate, glutamate, glycollylarsanilate, hexylresorcinate, hydrabamine, hydrobromide, hydrochloride, hydrochloride, hydroxynaphthoate, iodide, isethionate, lactate, lactobionate, malate, maleate, mandelate mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannata, tartrate, teoclate, triethiodide, benzathine, chloroprocaine, choline, diethanolamine, ethylenediamine, meglumine, procaine, aluminum, calcium, lithium, magnesium, potassium, sodium, and zinc.

The term "preparation" is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form preparations include solutions, suspensions, and emulsions. Sterile water or water- propylene glycol solutions of the active compounds may be mentioned as an example of liquid preparations suitable for parenteral administration. Liquid preparations can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

82

EXAMPLES

Example 1

Tricyclor[$3.3.1.1^{3,7}$]dec-2-yl(R)-[1-(1H-indol-3-yl-methyl)-2-(methoxymethylamino)-2-oxoethyl] carbamate (2)

To a solution of acid (1) (859 mg, 2.25 mmol) in dichloromethane (8 mL) was added N-methylmorpholine (495 μL, 4.50 mmol). The mixture was cooled to −15° C. ($CO_2$/benzyl alcohol) and isobutylchloroformate (292 μL, 2.25 mmol) was added. The mixture was stirred at −15° C for 15 minutes followed by the addition of N,O-dimethylhydroxylamine hydrochloride (219 mg, 2.25 mmol). The reaction mixture was stirred at −15° C. for 1 hour, then warmed to room temperature and stirred for a further 15 hours. The mixture was filtered and the filtrate washed sequentially with sodium hydrogen carbonate, water, 10% citric acid and brine, dried ($MgSO_4$) and evaporated to dryness. The crude material was purified by column chromatography to give hydroxamate (2) (694 mg, 730%) as a white foam; m.p. 72°–80° C. (Found: C, 67.4; H, 7.35; N, 9.8%. $C_{24}H_{31}N_3O_4$ requires C, 67.7; H, 7.3; N, 9.9%); $[\alpha]^{20}=-9.4°$ (C=0.3, $CHCl_3$); (S-ISOMER) $[\alpha]^{20}=+8.9°$ (C=0.3, $CHCl_3$)); $\upsilon_{max}$ (film); 1 695 (CO urethane), 1 657 (CO amide) 741 $cm^{-1}$ (disubstituted Ph); H ($CHCl_3$), δ6 1.30–2.01 (14H, m, adamantyl), 2.99–3.24 (5H, m, indole $CH_2$+NCH3), 3.58 (3H, s, $OCH_3$), 4.7 (1H, s, adamantyl 2-H), 5.00 (1H, br d, CH (NHR)CON⁻), 5.36 (1H br d, urethane NH), 6.92–7.17 (3H, m, indole 2,5,6-H), 7.27 (1H, d, J 8 Hz, indole 7-H), 7.53 (1H, d, J 8 Hz, indole 4-H), 7.99 (1H, s, indole NH).

Tricyclo[$3.3.1.1^{3,7}$]dec-2-yl(R)-[1-formyl-2-(1H-indol-3-yl)ethyl carbamate (3)

Lithium aluminum hydride (45 mg, 1.2 mmol) was added portionwise over a period of 30 minutes to a solution of the hydroxamate (2) (197 mg, 0.460 mol) in THF (3 mL) at 0° C. The mixture was stirred for a further 30 minutes, then ether (30 mL) was added followed by an ice cold solution of 10% citric acid (40 mL). The mixture was stirred vigorously for 30 minutes, then the layers were separated and the aqueous layer extracted with ether (5×10 mL). The ether extracts were combined and sequentially washed with saturated sodium hydrogen carbonate (25 mL), water (25 mL), 10% citric acid (25 mL), and brine (25 mL), dried ($Na_2SO_4$) and concentrated in vacuo to give aldehyde (3) (140 mg, 83%) as a white foam; $\upsilon_{max}$ (film) 1 725 sh (aldehyde C=O) and 1 693 $cm^{-1}$ (urethane C=O); H (300 M Hz; $CDCl_3$), υ1.47–2.13 (14H, m, adamantyl), 3.26 (2H, d of d, J 15 and 7 Hz, ind$CH_2$), 4.58 (1H, br d, CH(NHR)CHO), 4.84 (1H, s, adamantyl 2-H), 6.98–7.26 (3H, m), 7.35 (1H, d, J 8 Hz, indole 7-H), 7.60 (1H, br d, J 8 Hz, indole 4-H), 8.24 (lH, br s, indole NH), 9.64 (1H, s, CHO).

Tricyclo[$3.3.1.1^{3,7}$]dec-2-yl[S-(R)]- [2-[[1 - (hydroxymethyl)-2-phenylethyl]amino]-1-(1H-indol-3-ylmethyl) ethyl]carbamate (4). Example 1

Sodium cyanoborohydride (37 mg, 0.59 mmol) was added portionwise over a period of 15 minutes to a solution of aldehyde (3) (136 mg, 0.370 mmol) and (S)-2-amino-3-phenyl propanol (61 mg, 0.40 mmol) in methanol-acetic acid (99:1) (5 mL). The mixture was stirred for 2 hours at room temperature then chilled (ice bath). Saturated sodium hydrogen carbonate (30 mL) was added with stirring, followed by ethyl acetate (45 mL). The organic layer was separated, washed with brine (5 mL), dried ($Na_2SO_4$) and evaporated to dryness. The crude product was purified by column chromatography ($SiO_2$:dichloromethane-methanol (95:5) as eluant] to give amino alcohol (4) (60 mg, 32%) as a beige foam; m.p. 59°–61° C. (Found: C, 73.7; H, 7.8; N, 8.3%. $C_{31}H_{39}N_3O_3 \cdot 0.2H_2O$ requires C, 73.7; H, 7.9; N, 8.3%); $\upsilon_{max}$ (film) 3 325 (OH), 1 690 (CO urethane), 1 496 (N—H), 1 266 (OH), 1 048 (C—O), 740 and 701 cm$^{-1}$ (monosubstituted Ph); H (CDCl$_3$) δ1.31–2.04 (16H, m, adamantyl+NH+OH), 2.44–3.01 (7H, m, indCH$_2$, —CH$_2$NH—, CH$_2$Ph, NH—CH(CH$_2$OH)CH$_2$Ph), 3.21 (1H, dd, J 11 and 6 Hz, CH of CH$_2$OH), 3.47 (1H, dd, J 11 and 4 Hz, CH of CH$_2$OH), 3.97 (1H, m, —CH$_2$CH (NHCO$_2$R)CH$_2$NH—), 4.66 (1H, br d, urethane NH), 4.73 (1H, s, adamantyl 2-H), 6.87 (lH, d, J 2 Hz, indole 2-H), 6.96–7.24 (7H, m, indole 5,6-H +Ph), 7.29 (1H, d, J 8Hz, indole 7-H), 7.55 (1H, d, J 7 Hz, indole 4-H), 7.97 (1H, brs, indole NH).

Example 2

Tricyclo[3.3.1.1$^{3,7}$]dec-2-yl [S- (S)]-2- [[1 -(hydroxy-methyl)-2-phenylethyl]amino]-1-(1H-indol-3-ylmethyl)-ethyl]carbamate (5), Example 2

Compound 5 (253 mg, 23%) was synthesized using the same procedure as that described above for compound (4). White foam, m.p. 62°–63° C. (Found: C, 73.3; H. 7.8; N, 8.3%. $C_{31}H_{39}N_3O_3 \cdot 0.4\ H_2O$ requires C, 73.2; H, 7.9; N, 8.3%). $\upsilon_{max}$ (film) 3 331 (OH), 1 692 (CO urethane), 1 513 (N—H), 1360 (O—H), 1048 (C—O), 739 and 701 cm$^{-1}$ (monosubstituted Ph); H (CDCl$_3$), δ 1.47–2.10 (16H, m, adamantyl+NH+OH), 2.54–3.04 (7H, m, CH$^2$ indole, CH$_2$NH, CH$_2$Ph+CH$_2$CH(CH$_2$OH)CH$_2$Ph), 3.30 (1H, dd, J 11 and 6 Hz, CH of CH$_2$OH), 3.59 (1H, dd, J 11 and 4 Hz, CH of CH$_2$OH), 4.06 (1H, m, —CH$_2$CH(NHCO$_2$R) CH$_2$NH—), 4.81 (2H, br s, adamantyl 2-H+urethane NH), 6.86 (1H, brs, indole 2-H), 7.06–7.32 (7H, m, indole 5,6-H+Ph), 7.35 (1H, d, J 8 Hz, indole 7-H), 7.59 (1H, d, J 8 Hz, indole 4-H), 8.03 (1H, br s, indole NH).

Example 3

Tricyclo[3.3.1.1$^{3,7}$]dec-2-yl-[2-(1H-indol-3-yl)1-]]](4-nitrophenyl)methoxy]carbonyl]amino]ethyl]-carbamate (6)

To a solution of acid (1) (3.62 g, 9.74 mmol) in anhydrous THF (36 mL) at −10° C. was added N-methylmorpholine (1.15 mL, 10.4 mmol) and n-isobutyl chloroformate (1.35 mL, 10.4 mmol). This mixture was stirred for 20 minutes at −10° C. then filtered. Trimethylsilyl azide [Aldrich] (1.89 mL, 14.2 mmol) was added to the filtrate and the resulting solution stirred at −10° C. for 1 hour. The solvent was then removed in vacuo at 25° C. and the residue partitioned between ethyl acetate (100 mL) and saturated sodium hydrogen carbonate (100 mL). The layers were separated and the organic phase was washed with brine, dried (MgSO$_4$), and concentrated in vacuo at 25° C. The residue was taken up in toluene (100 mL) and treated at 40° C. until rearrangement to the isocyanate was complete. (IR: $\upsilon_{max}N_3$ 2139, $\upsilon_{max}$ NCO 2249 cm$^{-1}$). p-Nitrobenzylalcohol (2.20 g, 14.3 mmol) and DABCO (149 mg, 1.33 mmol) were added and the mixture left at 40° C. for 15 hours. The solvent was removed in vacuo and the crude product purified by column chromatography [SiO$_2$:ether-hexane (4:1) as eluant] to give (6) (2.12 g, 42%) as a yellow solid which was recrystallized from ether/hexane, m.p. 148°–1490C. $^1$H NMR (300 m Hz), δ1.39–2.03 (m 14H, adamantyl), 3.07 (brs, 12H, CH$_2$ ind+ H$_2$O/HOD), 4.64 (s, 1H, adamantyl 2-H), 5.14 (s, 2H, CH$_2$Ph), 5.37 (m, 1H, CH (NHCO$_2$)—NHCO$_2$), 6.90–7.29 (m, 4H, indole H-2, H-5, H-6, and NH), 7.34 (d, J 8 Hz, 2H, H-subst. Ph), 7.46–7.62 (m, 3H, ind H-4, ind H-7, NH), 8.16 (d, J 8 Hz, 2H, 4-subst. Ph), 10.61 (s, 1H, ind NH); IR (film): 2908+2855 (adamantyl), 1703 (br, CO urethane), 1520 (NO$_2$), 1347 (NO$_2$).

Anal. $C_{29}H_{32}N_4O_6$ requires C, 65.40; H, 6.06; N, 10.52. Found: C, 65.25; H, 6.03; N, 10.50.

Tricyclo[3.3.1.1$^{3,7}$]dec-2-yl [1-[[[1-hydroxymethyl)-2-phenylethyl]carbonyl]amino]-2-(1H-indol-3-yl) ethyl]-carbamate Compound (7), Example 3

The urethane (6) (190 mg, 0.357 mmol) in ethyl acetate (36 mL) was hydrogenated over palladium hydroxide on carbon (Pearlman's catalyst) at 45 psi and 30° C. for 1 hour. The mixture was filtered through celite to remove the catalyst into a flask containing the HOBT ester of 2-(acetoxymethyl)-3-phenylpropionic acid [the latter was generated via the reaction of 2-(acetoxymethyl)-3-phenylpropionic acid (81 mg, 0.36 mmol) in ethyl acetate (5 mL) with 1-hydroxybenzotriazole (57.5 mg, 0.426 mmol) and DCCI (85.9 mg, 0.416 mmol) at 0° C. for 30 minutes]. The resulting mixture was stirred at room temperature for 18 hours. The solution was concentrated in vacuo, chilled (ice-bath), filtered, and evaporated to dryness. the residue was taken up in THF:MeOH:H$_2$O (3:2:1) (6 mL), lithium hydroxide monohydrate (28 mg, 0.67 mmol) added, and the mixture stirred at room temperature for 18 hours. The reaction mixture was poured into 2N HCl (50 mL) and extracted with ethyl acetate (3×25 mL). The organic phase was washed with saturated NaCl, dried (MgSO$_4$), filtered, and evaporated to dryness. The crude product was purified by column chromatography [SiO$_2$: dichloromethane- methanol (95:5) as eluant] to given an approximately 50:50 mixture of diastereomeric alcohols (7) (16 mg total, 8%) as yellow oils. Isomer I: TLC Rf=0.24 (CH2Cl$_2$—MeOH (95.5)); $^1$H NMR (300 M Hz): δ1.43–2.04 (br m, 17H, adamantyl+H$_2$O), 2.42 (m, 1H, NHCO, CH), 2.67–3.22 (br m, 5H, CH$_2$ ind+CH$_2$Ph +OH), 3.67 (m, 2H, CH$_2$OH), 4.78 (s, 1H, adamantyl H=2), 5.40 (brs, 1H), 5.58 (brs, 1H), 6.26 (brs, 1H, amide NH), 6.82 (s, 1H, ind H-2), 7.02–7.37 (m, 9H, Ph+ind H-5, ind H-6, ind H-7, +CHCl$_3$), 7.44 (d, J 8 Hz, ind H-4), 8.16 (s, 1H, ind NH); IR (film): 3540–3140 (br, OH), 2910+2855 (adamantyl), 1695 (urethane Co), 1660 (amide CO); Isomer II: TLC Rf=0.19 [CH$_2$Cl$_2$—MeOH (95:5); $^1$H NMR (300 M Hz): δ1.47–2.08 (m, 17H, adamantyl+H$_2$O), 2.42 (m, 1H, NHCO·CH), 2.61–2.97 (m, 3H, CH$_2$+OH), 3.19 (d, J 7 Hz, CH$_2$), 4.68 (brs, 2H, CH$_2$OH), 4.75 (s, 1H, adamantyl H-2), 5.18 (brs, 1H), 5.49 (brs, 1H), 6.30 (brs, 1H, amide NH), 6.96 (s, 1H, ind H-2), 7.02–7.30 (m, 9H, Ph+ind H-5, ind H-6+CHCl$_3$), 7.37 (d, J 8 Hz, 1H, ind H-7), 7.57 (d, J 8 Hz, 1H, ind H-4), 8.12 (s, 1H, ind NH); IR (film): 3520–3160 (br, OH), 2907+2855 (adamantyl), 1696 (urethane CO), 1660 (amide CO).

Example 4

2-Adamantyloxycarbonyltryptophandiazoketone (8) Preparation of diazomethane.

CAUTION! DIAZOMETHANE IS HIGHLY TOXIC AND EXPLOSIVE (NO GROUND GLASS JOINTS). HANDLE WITH CARE IN A FUME HOOD. n-METHYLNITROSUREA IS HIGHLY TOXIC AND CARCINOGENIC. HANDLE IN A FUME HOOD USING A FULL FACE MASK AND GLOVES.

A solution of 40% potassium hydroxide (4.5 mL, 32 mmol) was added dropwise to a suspension of N-methylnitrosurea (1.5 g, 15 mmol) in ether (25 mL), cooled in an ice-salt bath. After all the solid had dissolved (additional base is added if necessary), the ethereal solution of diazomethane was dried over solid potassium hydroxide. This drying process was repeated twice more and the diazomethane used immediately.

To a solution of 2-adamantyloxycarbonyltryptophan (1) (1.77 g, 4.61 mmol) in THF (25 mL) at 0° C. was added N-methylmorpholine (557 µL, 5.07 mmol) and isobutylchloroformate (658 µL, 5.07 mmol). The mixture was stirred for 20 minutes at 0° C., then filtered. To the filtrate was added a solution of diazomethane (10 mmoL) in ether (produced from N-methylnitrosurea (1.0 g, 10 imol)). The resulting solution was stirred for 15 minutes at 0° C., then for 15 hours at room temperature. The solvent was removed in vacuo and the residue taken up in ethyl acetate (100 mL). This solution was washed with water (2×10 mL), 5% citric acid (2×10 mL), 1N $NaHCO_3$ (10 mL), and brine (10 mL). It was dried ($MgSO_4$) and the solvent removed in vacuo. The crude product was purified by column chromatography [$SiO_2$:hexane-ethyl acetate (5:4) as eluant] to give diazoketone (8) (1.35 g, 72w) as a yellow foam, m.p. 72°–75° C. $v^{max}$ ($CDCl_3$ film) 2 109 ($N_2$); 1 697 (CO) and 740 $cm^{-1}$ (disubstituted Ph); H ($d_6$-acetone), δ1.39–2.02 (14H, m, adamantyl), 3.13 (1H, dd, J 15 and 8 Hz, CH of $CH_2$ indole), 3.29 (1H, dd, J 15 and 5 Hz, CH of $CH_2$indole), 4.51 (1H, m, $CH_2$C-H(NHR)CO), 4.69 (1H, S, adamantyl 2-H); 5.90 (1H, brs, $CHN_2$); 6.41 (1H, s, NH CO); 7.01 (1H, t, J 7 Hz, indole 5 or 6-H), 7.09 (1H, t, J. 7 Hz, indole 7-H), 7.61 (1H, d, J 9 Hz, indole 4-H), 10.05 (1H, brs, indole NH).

2-Adamantyloxycarbonyltryptophanyl Chloromethyl Ketone (9)

Hydrochloric acid (11.1 mL of a 0.30 M solution in dioxane) was added dropwise with stirring to a solution of diazoketone (8) (1.35 g, 3.32 mmol) in THF (100 mL) at 0° C. The reaction was monitored by infrared for the disappearance of the $N_2$ peak (2 109 $cm^{-1}$) in the starting material. When all the diazoketone had gone (ca 60 minutes) the reaction mixture was quenched with saturated sodium hydrogen carbonate (20 mL). The mixture was concentrated in vacuo and the residue partitioned between ethyl acetate (100 mL) and saturated sodium hydrogen carbonate (1090 mL). The layers were separated and the aqueous extracted further with ethyl acetate (2×100 mL). The combined ethyl acetate fraction was washed with brine (50 mL), dried ($MgSO_4$), and the solvent removed in vacuo. The crude product was recrystallized from ethyl acetate-hexane to give chloroketone (9) (1.29 g, 94%), m.p. 138°–140° C. (Found: C, 66.6; H, 6.7; Cl, 8.3; N, 6.9%. $C_{23}H_{27}ClN_2O_3$ requires C, 66,6; H, 6.6; Cl, 8.5; N, 6.75%). $v_{max}$ ($CDCl_3$ film), 1 740 (CO α chloroketone), 1 698 (CO urethane), and 736 $cm^{-1}$ (disubstituted Ph); H ($CDCl_3$) δ1.45–2.06 (14H, m, adamantyl), 3.27 (2H, m, $CH_2$ind), 3.96 (1H, d, J 16 Hz, CH of $CH_2$Cl), 4.11 (1H, d, J 16 Hz, CH of $CH_2$Cl), 4.83 (2H, m, $CH_2$CHCO and adamantyl 2-H), 5.35 (1H, d, J 7 Hz, NH), 7.00 (1H, d, J 2 Hz, indole 2-H), 7.14 (1H, t, 6 Hz, indole 5 or 6-H), 7.22 (1H, t, J 6 Hz, indole 5 or 6-H), 7.37 (1H, d, J 8 Hz, indole 7-H), 7.61 (1H, d J 8 Hz, indole 4-H), 8.20 (1H, s, indole NH).

α-[4- (1H-indole-3-yl)-2-oxo-3-[[(tricyclo[3.3.1.1$^{3,7}$]-dec-2-yloxy)carbonyl]amino]butyl]benzene propanoic acid. Compound (10), Example 4

Sodium iodide (Aldrich) (51 mg, 0.34 mmol) was added to a solution of chloroketone (126) (112 mg, 0.27 mmol) in anhydrous DME (5 mL) at room temperature. This mixture was stirred at room temperature for 15 minutes, then an aliquot (800 µL, 0.30 mmol) of an anion solution [generated by the reaction of sodium hydride (60w dispersion in oil) (88 mg, 2.2 mmol) in anhydrous DME (5 mL) with diethylbenzylmalonate (950 µL, 4.0 mmol) at room temperature] was added. The resulting solution was stirred at room temperature for 2 hours. The solvent was removed in vacuo, the residue taken up in dichloromethane (50 mL), washed with brine, dried ($MgSO_4$), and evaporated under reduced pressure. The crude material was purified by column chromatography [$SiO_2$:hexane-ethyl acetate (2:1) as eluant] to yield ketodiester (100 mg, 59w); m.p. 49°–54° C. (Found: C, 70.8; H, 7.2; N, 4.4%. $C_{37}H_{44}N_2O_7$ requires C, 70.7; H, 7.05; N, 4.5%). $v_{max}$ ($CH_2Cl_2$ film) 1 728 $cm_{-1}$ (CO); H ($CDCl_3$δ1.42–2.08 (14H, m, adamantyl), 2.98 (1H, d, J 19 Hz), 3.18 (1H, dd, J 15 and 6 Hz, $CH_2$ind), 3.24 (1H, dd, J 15, and 6 Hz), $CH_2$ind), 3.34 (2H, s, $CH_2$), 4.18 (4H, m, 2×$CH_2$), 4.62 (1H, m, $CH_2$CH(CO)NH), 4.79 (1H, s, adamantyl 2-H), 5.30 (1H, d, J 8 Hz, NH), 6.84 (2H, d, J 7 Hz, Ph 2,6-H), 6.92 (1H, d, J 2 Hz, indole 2-H), 7.07–7.25 (5H, m, indole 5, 6-H, Ph 3,4,5-H), 7.34 (1H, d, J 8 Hz, ind 7-H), 7.62 (1H, d, J 8 Hz, indole 4-H), 8.07 (1H, s, indole NH).

A solution of the keto diester (1.19 g, 1.89 mmol) in ethanol (5 mL), and 6N NaOH (946 µL, 5.67 mmol) was stirred at room temperature for 1 hour. The solvent was removed in vacuo and the residue diluted with $H_2O$ (10 mL). This aqueous solution was acidified to pH 2 with concentrated HCl, then extracted with ethyl acetate (3×50 mL). The organic extract was washed with saturated sodium chloride solution, dried ($MgSO_4$) and concentrated in vacuo. The residue was taken up in dioxane (30 mL) and refluxed for 18 hours. The solvent was removed in vacuo and the crude material purified by column chromatography [$SiO_2$: tolueneacetic acid (9:1) as eluant] to give ketoacid (10) (783 mg, 78%) as a yellow foam, m.p. 66°–80° C. $^1$H NMR (300 m Hz): γ1.38–2.22 (m, 16H, adamantyl+$H_2O$), 2.55–3.25 (vbr m, 12H, $CH_2$ind, $CH_2$Ph CO, $CH_2$CH+$H_2O$/HoD), 4.26 (m, 1H, NHCHCO), 4.57 (s, 1H, adamantyl 2-H), 6.95–7.37 (m, 10H, Ph+ind 2-H, ind 5-H, ind 6H, ind 7-H+NH), 7.49 (d, J 8 Hz, 1H, ind 4-H), 10.58 (s, 1H, ind NH). IR (film): 3460–3200 (br, OH), 2920+2856 (adamantyl) 1707 (br, ester ketone CO, acid CO, urethane CO). Anal. $C_{32}H_{36}N_2O_5$ requires C, 72.70; H, 6.86; N, 5.30%. Found C, 73.18; H, 6.98; N, 5.05%.

Example 5

Tricyclo[3.3.1.1$^{3,7}$]dec-2-yl [1- [(2-hydroxy-2-phenyl-ethyl)amino]-3-(1H-indol-3-yl)-2-methylprop-2-yl]-carbamate (12)

This compound was prepared by a route similar to that used to make compound (14) (Example 6) except that compound (11) was used. Recovered 0.42 g (43%); m.p. 78°–80° C.; IR (neat) 2910, 1694 (C=O urethane) $cm^{-1}$ ; NMR ($CDCl_3$) δ 8.1 (1H, br s, indole NH), 7.6 (1H, d, J 8 Hz, indole H-4), 7.4–7.1 (8H, m, Ph+indole H-5, H-6, H-7), 7.0 (1H, m, indole H-2), 5.0–4.6 (3H, m, adamantane H-2+urethane NH+CHOH), 3.5–2.6 (6H, m, 3×$CH_2$), 2.1–1.5 (15H, m, adamantane+OH) 1.4 (3H, s, $CH_3$); $[α]_D$+ 18° ($CHCl_{31}$, 22° C., c=0.2); FABMS ($m^+$/e)502 ($m^+$+H); anal $C_{31}H_{39}N_3O_3$. 0.5 $H_2O$; requires C 72.91%, H 7.90%, N 8.23%; found: C 72.56%, H 7.84%, N 7.95%.

Example 6

Tricyclo[3.3.1.1$^{3,7}$]dec-2-yl[R-(R*,S*)]-1- [[1 (hydroxy-methyl)-2-phenylethyl]amino]-3-(1H-indol-3-yl)-2-methylprop-2-ylcarbamate (14)

To a solution of lithium borohydride (4 mL, 2M solution, 8 mmol) in dry tetrahydrofuran under nitrogen was added a solution of chlorotrimethylsilane (1.75 g, 16.0 mmol) in dry tetrahydrofuran (5 mL). A white ppt of lithium chloride was observed. After 2 minutes a solution of Compound (13), (1 g, 2 mmol) in tetrahydrofuran (15 mL) was added slowly (over 3 to 4 minute period) and the reaction was stirred for 20 hours at ambient temperature. The reaction was treated cautiously with methanol (5 mL) and the volatiles were removed in vacuo (40° C.). The residue was purified by flash chromatography on normal phase silica gel using hexane/ ethyl acetate eluant (a gradient elution technique was employed, ranging from 80% hexane:20% ethyl acetate to 100% ethyl acetate). Recovered 0.60 g starting material and 0.26 g (27%) desired product (14) as a white foam; IR (neat) 2900, 1694 (C=O urethane)cm$^{-1}$; NMR (CDCl$_3$) δ 8.1 (1H, br s, indole NH), 7.6 (1H, d, J 8 Hz, indole H-4), 7.4–7.1 (8H, m, Ph+indole H-5, H-6, H-7), 6.9 (1H, d, J 2 Hz, indole H-2), 4.9 (1H, s, urethane NH), 4.8 (1H, s, adamantane H-2), 3.6–3.3 (2H, m, CH$_2$—QH), 3.1 (2H, m, CH$_2$-indole), 3.0–2.6 (5H, m, 2×CH$_2$+1×CH), 2.1–1.5 (15H, m, adamantane+OH), 1.25 (3H, s, CH$_3$).

A mono-4-toluenesulphonate salt was prepared by dissolving (14) (0.2 g, 0.4 mmol) and 4-toluenesulphonic acid monohydrate (0.074 g, 0.40 nmol) in acetone (10 mL) and subsequent removal of solvent in vacuo to give a white solid; m.p. 110°–113° C. IR (neat) 2915, 1790 (C=O urethane) cm$^{-1}$; [α]$_D$+20° (CHCl$_3$, 23° C., c=1) λ FAB MS (m$^+$/e) 516 (m$^+$+H); anal: C$_{32}$H$_{41}$N$_3$O$_3$·C$_7$H$_8$SO$_3$·0.5H$_2$O Requires: C, 67.22; H. 7.23; N, 6.03; S, 4.60.
Found: C, 67.23; H, 7.26; N, 5.84; S, 4.36.

Example 7

[R- (R*,S*)]-β- [[2-(1H-indol-3-ylmethyl)-2-[ [tricyclo-[3.3.1.1$^{3,7}$]dec-2-yloxvcarbonyl]amino] propyl]amino]-benzenepropanol acetate (15)

To a solution of (14) (0.05 g, 0.10 mmol) in dichloromethane (10 mL) at ambient temperature was added acetyl chloride (0.10 mL, 1.4 mmol) and the reactants were stirred for 1 hour, the volatiles were removed in vacuo (40° C.) and the residue purified by flash chromatography using 80% hexane : 20% ethyl acetate as eluant. Recovered 0.024 g, (44%) of (88) as an amorphous white solid. IR (neat) 2910, 1739 (C=O ester), 1700 (C=O urethane)cm$^{-1}$; NMR (CDCl$_3$) δ 8.2 (1H, s, indole NH), 7.6 (1H, d, J 8 Hz, indole H-4), 7.4–7.0 (8H, m, Ph+indole H-5, H-6, H-7), 6.9 (1H, d, J 2 Hz, indole H-2), 5.1 (1H, s, urethane NH), 4.8 (1H, s, adamantane H-2), 3.9 (2H, d, J 4 Hz, CH$_2$OCO), 3.1 (2H, m, CH$_2$-indole), 3.0–2.5 (4H, m, CH$_2$Ph+CH$_2$N), 2.1–1.4 (17H, m, CH$_3$CO+adamantane), 1.3 (3H, s, CH$_3$).

A mono-4-toluenesulphonate salt was prepared by dissolving (15) (0.02 g, 0.04 mmol) and 4-toluenesulphonic acid monohydrate (0.007 g, 0.04 mmol) in acetone (5 mL) and subsequent removal of solvent in vacuo to give a white solid, m.p. 98°–101° C.; [α]$_D$+32° (CHCl$_3$, 24° C., C=0.5); FAB MS (m$^+$/e) 558.5 (m$^+$ +H); anal: C$_{34}$H$_{43}$N$_3$O$_4$·C$_7$H$_8$SO$_3$·H$_2$O requires C 65.84%, H 7.14%, N 5.62%, S 4.29%. Found: C 65.48%, H 7.08%, N 5.53%, S 4.31%.

Example 8

[R- (R*,S*) ]-β-[acetyl[2- (1H-indol-3-vlmethyl) -2-[[tricyclo [3.3.1.1$^{3,7}$]dec-2-yloxycarbonyl]amino] -propyl]amino]benzene propanol acetate (15a)

To a solution of (14) (0.05 g, 0.10 mmol) in dichloromethane (10 mL) at ambient temperature was added triethylamine (1 mL, 7 mmol) followed by acetyl chloride (0.1 mL, 1.4 mmol) and the reactants stirred for 1 hour. The volatiles were removed in vacuo and the residue purified by flash chromatography using hexane:ethyl acetate as eluant. Recovered 0.043 g, (74%) of (88a) as an amorphous solid; IR (neat) 2920, 1740 (C=O ester), 1709 (C=O urethane), 1632 (C=O amide) cm$^{-1}$.

Tricyclo[3.3.1.1$^{3,7}$]dec-2-yl[R-(R*,S*)]-[acetyl[1- (hydroxymethyl)-2-phenylethyl]amino]-2-(1H-indol-3-ylmethyl)prop-2-ylcarbamate (16)

To a solution of (15a) (0.03 g, 0.05 mmol) in tetrahydrofuran (5 mL) was added a solution of lithium hydroxide (0.1 g, 2.4 mmol) in water (5 mL) and the reactants stirred for 15 min. The reaction was then acidified with hydrochloric acid (2N aq) and the products extracted with ethyl acetate (50 mL). The extract was dried (magnesium sulphate) and evaporated in vacuo (40° C.). The residue was purified by flash chromatography using hexane:ethyl acetate eluant. Recovered 0.024 g (860%) of (89) as a white solid; m.p. 109°–112° C., [α]$_D$+31° (22° C., CHCl$_3$, c=0.5); IR (neat) 2900, 1694 (C=O urethane), 1621 (C=O amide)cm$^{-1}$ ; NMR (CDCl$_3$) δ8.1 (1H, s, indole NH), 7.5 (1H, d, J 8 Hz, indole H-4), 7.4–7.0 (8H, m, Ph+indole H-5, H-6, H-7), 6.9 (1H, s, indole H-2), 5.3 (1H, br, urethane NH), 4.8 (1H, br, adamantane H-2), 4.4 (1H, s, OH), 3.9 (1H, d, J 12 Hz, one of CH$_2$OH), 3.8–3.7 (2H, m, one of CH$_2$OH+one of CH$_2$N), 3.5 (1H, m, CH), 3.4 (1H, d, J 14 Hz, one of CH$_2$ indole), 3.3 (1H, d, J 13 Hz, one of CH$_2$N), 3.1 (2H, d, J 8 Hz, CH$_2$Ph), 2.8 (1H, d, J 14 Hz, one of CH$_2$-indole), 2.0 (3H, s, CH$_3$CO), 1.9–1.4 (14H, m, adamantane), 1.1 (3H, s, CH$_3$); anal C$_{34}$H$_{43}$N$_3$O$_4$·0.5 H$_2$O; requires C 72.06% H 7.82% N 7.41%; found C 72.20% H 7.73% N 7.30%; FAB MS (m/e) 558 (m$^+$ +H).

Example 9

Tricyclo[3.3.1.1$^{3,7}$]dec-2-yl (R)-[1-(1H-indol-3-ylmethyl)-2-methyl-2- [(2-phenylethyl)amino]-2-thioxoethyl]carbamate To a solution of (29) (0.1 g, 0.2 mmol) in toluene (10 mL) was added Lawesson's reagent (0.10 g, 0.25 mmol) and the reaction was heated to reflux for 1 hour. The reaction was allowed to cool to ambient temperature and was purified by flash chromatography (dichloromethane/ether eluant). Recovered 0.065 g (63%) of 30) as a white foam, m.p. 81-85° C; IR (neat) 2916, 1703 (C=O methane), 1520 (C=S) cm$^{-1}$; NMR (CDCl$_3$) γ8.1 (1H, br, indole NH), 7.8 (1H, br, this amide NH), 7.6 (1H, d, J 8 Hz, indole H-4), 7.5–6.9 (9H, m, indole H-5, H-6, H-7, H-2,+phenyl), 5.3 (1H, br, urethane NH), 4.7 (1H, brs, adamantane H-2), 3.8 (2H, m, CH$_2$-N), 3.6 (1H, d, J 14 Hz, one of CH$_2$-indole), 3.4 (1H, d, J 14 Hz, one of CH$_2$-indole), 2.6 (2H, m, CH$_2$—Ph), 2.0–1.6 (14H, m, adamantane), 1.5 (3H, s, CH$_3$); R$_f$ (30% ethyl acetate/hexane) 0.3.

Example 10

Methyl (R)-4-[(2-hydroxy-1-phenylethyl)amino]-4-oxo-2-butenoate (18)

To a solution of monomethyl fumarate (3.0 g, 23 mmol) in ethyl acetate (40 mL) was added 1-hydroxybenzotriazole hydrate (3.0 g, 22 mmol), followed by N,N'-dicyclohexylcarbodiimide (4.5 g, 22 mmol) and the reaction stirred at ambient temperature for 1 hour. The solid was filtered off and discarded. To the filtrate was added (R)-α- phenylglycinol (3.0 g, 22 mmol) and stirring continued for 20 minutes. The volatiles were removed in vacuo (40° C.) and the residue purified by flash chromatography on normal phase silica gel using hexane:ethyl acetate (1:1) as eluant. Recovered 2.5 g (46%) of (18) as a white solid, m.p. 75°–77° C.; IR (neat) 3250 (OH), 1729 (C=O ester), 1666 (C=O amide), 1640 (C=C)cm$^{-1}$; NMR (CDCl$_3$) δ 7.3–7.4 (5H, m, Ph), 7.0 (1H, d, J 15 Hz, trans alkene), 6.8 (1H, d, J 15 Hz, trans alkene), 6.6 (1H, br d, NH), 5.2 (1H, m, CH), 3.9 (2H, t, J 3 Hz, CH$_2$), 3.8 (3H, s, CH$_3$), 2.3 (1H, t, J 5 Hz, OH); [α]$_D$–53° (CHCl$_3$, 24° C., c=1); anal C$_{13}$H$_{15}$NO$_4$; requires C 62.64% H 6.07% N 5.62%; found C 62.72% H 5.92% N 5.48%.

Tricyclo[3.3.1.1$^{3,7}$]dec-2-yl 3-[(1H-indol-3-yl) methyl]-3-methyl-4,9-dioxo-7-phenyl-5,13-dioxa-2 8-diaze-tetradec-10-enoate (19)

To a solution of N,N'-carbonyldiimidazole (0.15 g, 0.90 mmol) in dichloromethane (40 mL) was added (23b) (0.25 g, 0.63 mmol). After 20 minutes stirring at ambient temperature (18) (0.2 g, 0.8 mmol) was added and the reaction was heated to reflux for 10 hours. On cooling to ambient temperature the volatiles were removed in vacuo (40° C.) and the residue was purified by flash chromatography (hexane/ethyl acetate eluant). Recovered 0.28 g (71%) of (19) as a white solid, m.p. 96°–99° C. IR (neat) 2910, 1730 (C=O ester), 1695 (C=O urethane), 1670 (C=O amide+ C=C) cm$^{-1}$: NMR (CDCl$_3$ γ 8.3 (1H, br, indole, NH), 7.5 (1H, d, J 8 Hz, indole H-4), 7.4 (1H, d, J 8 Hz, indole H-5), 7.3–6.9 (10H, m, indole H-6, H-7, H-2+phenyl+amide NH+one of alkene CH), 5.3 (1H, br, one of CH2—O), 5.1 (1H, s, urethane NH), 5.0 (1H, br, CH), 4.8 (1H, brs, adamantane H-2), 4.1 (1H, dd, J 11 Hz, 4 Hz, one of CH$_2$—O), 3.8 (3H, s, CH$_3$), 3.5 (1H, d, J 14 Hz, one of CH$_2$-indole), 3.3 (1H, d, J 14 Hz, one of CH$_2$-indole), 2.1–1.4 (18H, m, adamantane+CH$_3$): [α]$_D$+25° (CHCl$_3$, 24° C., C=0.2): FAB MS (m$^+$/e) 6281 (m$^+$ +H) : Anal; C$_{36}$H$_{41}$N$_3$O$_7$ requires C 68.88%; H, 6.58%; N, 6.69%; found C, 68.56%; H, 6.83%; N, 6.57%.

Example 11

Tricyclo[3.3.1.1$^{3,7}$]dec-2-yl 3-[(1H-indol-3-yl) methyl]-3-methyl-4.9-dioxo-7-phenyldioxa-2.8-diazatetradec-10-enoate (20)

Prepared by a route similar to that used to make compound (19). Recovered 0.30 g (76%) of (20) as a white solid, m.p. 104°–105° C.; IR (neat) 2920, 1728 (C=O ester), 1720 (C=O) urethane), 1700 (C=C), 1670 (C=O amide) cm$^{-1}$; NMR (CDCl$_3$; δ 8.3 (1H, br, indole NH), 7.5 (1H, d, J 8 Hz, indole H-4), 7.4 (1H, d, J 8 Hz, indole H-5), 7.3–7.1 (7H, m, indole H-6, H-7+phenyl), 7.1–6.7 (4H, m, indole H-2+amide NH+alkenes), 5.3 (2H, br, urethane NH+one of CH$_2$—O), 4.8 (1H, br, adamantane H-2), 4.7 (1H, m, CH), 4.1 (1H, dd, J 11 Hz, 4 Hz, one of CH$_2$—O), 3.8 (3H, s, ester, CH$_3$), 3.4 (1H, d, T 14 Hz, one of CH$_2$-indole), 3.2 (1H, d, J 14 Hz, one of CH$_2$-indole), 2.1–1.5 (17H, m, adamantane+CH$_3$): [α]$_D$–36° (CHCl$_3$, 22° C., C=1). FAB MS (m$^+$/e) 628 (m$^+$ +H) : Anal; C$_{36}$H$_{41}$N$_3$O$_7$ requires C, 68.88%; H, 6.58%; N, 6.69%; found: C, 68.86%; H, 6.57%; N, 6.77%.

Example 12

Methyl (R)-4- [(2-hydroxy-1-phenylethvl)amino]-4-oxobutanoate (21)

Prepared by a route similar to that used to make compound (18) (see Example 10). Recovered 3.6 g, (65%) of (21); m.p. 59°–61° C.; IR (neat) 3250 (OH), 1737 (C=O ester), 1651 (C=O amide)cm$^{-1}$; NMR (CDCl$_3$) δ 7.2–7.4 (5H, m, Ph), 6.4 (1H, br d, NH), 5.1 (1H, m, CH), 3.7 (3H, s, CH$_3$), 2.8–2.5 (6H, m, 3×CH$_2$), 1.7 (1H, br, OH); [α]$_D$–53° (CHCl$_3$, 22° C., c=1); anal C$_{13}$H$_{17}$NO$_4$; requires C 62.14% H 6.82% N 5.57%; found C 62.21% H 7.13% N 5.73%.

Tricyclo[3.3.1.1$^{3,7}$]dec-2-yl 3-[(1H-indol-3-yl) methyl]-3-methyl-4,9-dioxo-7-phenyl-5,13-dioxo-2, 8-diazatetra-decanoate (22)

To a solution of 1,3-dicyclohexylcarbodiimide (0.3 g, 1.5 mmol) and 4-dimethylaminopyridine (0.05 g, 0.40 mmol) in dichloromethane (40 mL) was added (23) (0.50 g, 1.3 mmol. After stirring for 20 minutes at ambient temperature (21) (0.30 g, 12 mmol) was added and the reaction was heated to reflux for 2 hours. The volatiles were removed in vacuo (40° C. and the residue purified by flash chromatography (hexane/ethyl acetate eluant). Recovered 0.41 g (52%) as a white solid, m.p. 69°–71° C. IR (neat 2920, 1739 (C=O ester), 1700 (C=O urethane), 1660 (C=O amide): NMR δ (CDCl 8.3 (1H, br, indole NH), 7.5 (1H, d, J 8 Hz, indole H-4), 7.4–6.9 (10H, m, indole H-5, H-6, H-7, H-2+amide NH+phenyl), 5.3 (1H, m, CH), 5.2 (1H, brs, urethane NH), 4.8 (2H, br, adamantane H-2+one of CH$^2$—O), 4.1 (1H, m, one of CH$_2$—O), 3.7 (3H, s, ester CH$_3$), 3.4 (2H, M, CH$_2$-indole), 2.7–2.5 (4H, m, 2×CH$_2$), 2.1–1.5 (17H, m, adamantane+CH$_3$): [α]$_D$–18° (CHCl$_3$, 22° C., C=1). FAB MS (m$^+$/e), 630.0 (m$^+$+H); Anal: C$^{36}$N$_{43}$N$_3$O$_7$·0.5H$_2$O requires C, 67.69; H, 6.94; N, 6.58; found C, 67.36; H, 6.99; N, 6.51.
NOTE: some small peaks at δ4.4–4.2 in the NMR spectrum may indicate the presence of a small amount of another isomer.

Example 13

Tricyclo[3.3.1.1$^{3,7}$]dec-2-yl (R)-[2-hydroxy-1-(1H-indol-3-ylmethyl)-1-methylethyl]carbamate (24)

To a solution of (23) (R=Me) (1.0 g, 2.4 mmol) in dry THF (20 mL) at 0° C. under a nitrogen atmosphere was added a solution of lithium aluminum hydride in ether (3 mL of a 1M solution, 3 mmol) and the reaction was stirred for 20 minutes. Ethyl acetate (20 mL) was added cautiously and the resulting solution was washed with acid (2N HCl, 2×100 mL), dried over magnesium sulfate, and evaporated to dryness. Recovered 0.85 g (91%) of (24) as a white solid, m.p. 72°–74° C.; IR (neat 2918, 1693 (C=O urethane) cm$^{-1}$; NMR (CDCl$_3$) δ 8.1 (1H, br, indole NH), 7.6 (1H, d, J 8 Hz, indole H-4), 7.35 (1H, d, J 8 Hz, indole H-5), 7.2–7.0 (3H, m, indole H-6, H-7, H-2), 4.85 (1H, br s, urethane NH), 4.8 (1H, br, adamantane H-2), 4.0 (1H, br, OH), 3.8 (2H, m, CH$_2$—O), 3.25 (1H, d, J 14 Hz, one of CH$_2$-indole), 3.0 (1H, d, J 14 Hz, one of CH$_2$-indole), 2.1–1.5 (14H, m, adamantane), 1.2 (3H, s, CH$_3$); [α]$_D$+42° (CHCl$_3$, 22° C., C=1); FAB MS (m/e) 383 (m$^+$ +H); Anal: C$_{23}$H$_{30}$N$_2$O$_3$·0.5H$_2$O requires C, 70.56%; H, 7.98%; N, 7.15%; found: C, 7.35%; H, 7.83%; N, 6.94%.

3-(1H-indole-3-yl)-2-methyl-2- [[(tricyclo[3.3.1.1$^{3,}$ $_7$]-dec-2-yloxy)carbonyl]amino]propyl (R)-benzeneacetate (25)

To a solution of N,N'-carbonyldiimidazole (0.40 g, 2.5 nmmol) in dichloromethane (20 mL) was added phenylacetic acid (0.30 g, 2.2 mmol). After 10 minutes stirring at ambient temperature alcohol (24) (0.3 g, 0.8 mmol) was added and stirring was continued for 40 hours. The volatiles were removed in vacuo and the residue was purified by flash chromatography (hexane/5% ethyl acetate eluant). Recovered 0.30 g (77%) of (25) as a white foam, m.p. 57°–60° C.; IR (neat) 2917, 1722 (C=O ester), 1700 (C=O urethane) cm$^{-1}$; NMR (CDCl$_3$) δ 8.05 (1H, br, indole NH), 7.5 (1H, d, J 8 Hz, indole H-4), 7.4–7.2 (6H, m, indole H-5+phenyl), 7.16 (1H, t, J 7 Hz, indole H-6), 7.07 (1H, t, J 7 Hz, indole H-7), 6.9 (1H, d, J 2 Hz, indole H-2), 4.8 (1H, br, adamantane H-2), 4.6 (1H, br, urethane NH), 4.3 (1H, d, J 11 Hz, one of CH$_2$—O), 4.2 (1H, d, J 11H, one of CH$_2$—O), 3.7 (2H, s, CH$_2$—Ph), 3.2 (1H, d, J 14 Hz, one of CH$_2$-indole), 3.0 (1H, d, J 14 Hz, one of CH$_2$-indole), 2.1–1.4 (14H, m, adamantane), 1.2 (3H, S, CH$_3$); [α]$^D$+13° (CHCl$_3$, 22° C., C=0.5); FAB MS 501 (m$^+$ +H). Anal: C$_{31}$H$_{36}$N$_2$O$_4$ requires C, 74.37%; H, 7.25%; N, 5.60%; found: C, 74.20%; H, 7.32%; N, 5.52%.

Tricyclo[3.3.1.1$^{3,7}$[dec-2-yl (R)-[1-formyl-2-(1H-indol-3-ylmethyl)-1-methylethyl]carbamate (26)

To a solution of (24) (0.03 g, 0.08 mmol) in dichloromethane (40 mL) at ambient temperature under argon was added N-methylmorpholine-N-oxide (0.1 g, 0.9 mmol), molecular sieves (4A activated powder, 0.5 g), and tetra-n-propylammonium perruthenate (0.01 g, 0.03 mmol). After stirring for 30 minutes the volatiles were removed in vacuo (40° C.). The residue was taken up in ethyl acetate and purified by flash chromatography (hexane/5% ethyl acetate eluant). Recovered 0.2 g (67%) of (24) as a white solid, m.p. 178°–179° C.; IR (neat) 2900, 1732 (C=O aldehyde), 1692 (C=O urethane) cm$^{-1}$; NMR (CDCl$_3$), δ 9.6 (1H, s, CHO), 8.1 (1H, br s, indole NH), 7.6–6.9 (5H, m, indole), 5.2 (1H, br, urethane NH), 4.8 (1H, s, adamantane H-2), 3.3 (2H, br, CH$_2$-indole), 2.1–1.3 (17H, m, adamantane+CH$_3$); [α]$^D$+ 22D (CHCl$_3$, 22° C., C=1); FAB MS (m$^+$/e) 381 (m$^+$+H). Anal: C$_{23}$H$_{28}$N$_2$O$_3$ requires C, 72.61%; H, 7.42%; N, 7.36%; found: C, 72.31%; H, 7.46%; N, 7.31%.

Example 14

Tricyclo[3.3.1$^{3,7}$]dec-2-yl [R-(Z)]-[1-(1H-indol-3-yl-methyl)-1-methyl-5-phenyl-2-pentenyl]carbamate (27)

A mixture of triphenylphosphine (0.35 g, 1.3 mmol) and 1-bromo-3-phenylpropane (0.27 g, 1.3 mmol) was heated to 110° C., at which point the molten reactants solidified. On cooling to ambient temperature and trituration with hexane a white solid was recovered (0.4 g, 65%). This was added to a suspension of sodium hydride (50 mg of 50% in oil dispersion, 1 mmol) in toluene (40 mL) and the reaction was refluxed for 20 minutes. Aldehyde (0.2 g, 0.5 mmol) was added and heating continued 1 hour. The volatiles were removed in vacuo and the residue purified by flash chromatography (hexane/10% ethyl acetate eluant). Recovered 0.20 g (79%) of (27) as a white solid, m.p. 49°–52° C.; IR (neat) 2904, 1696 (C=O urethane), 1683 (C=C) cm$^{-1}$; NMR (CDCl$_3$): δ 8.3 (1H, s, indole NH), 7.6 (1H, d, J 8 Hz, indole H-4), 7.3–7.0 (8H, m, indole H-5, H-6, H-7+phenyl), 6.9 (1H, s, indole H-2), 5.6 91H, d, J 12hz, CH by a-centre), 5.4 (1H, dt, J 5, 12 Hz, CH—CH$_2$), 4.8 (2H, m, urethane NH+adamantane H-2), 3.3 (1H, d, J 14 Hz), one of CH$_2$-indole), 3.1 (1H, d, J 14 Hz, one of CH$_2$-indole), 2.6–2.4 (4H, m, 2×CH$_2$), 2.1–1.4 (14H, m, adamantane), 1.4 (3H, s, CH$_3$).

Example 15

Tricyclo[3.3.1.1$^{3,7}$]dec-2-yl [2-hydroxy-1-(1H-indol-3-ylmethyl)-1-methyl-5-phenylpentyl]carbamate (28)

To a stirred mixture of magnesium metal (0.5 g, 21 mmol) and dry ether (20 mL) at 0° C. under a nitrogen atmosphere was added 1-bromo-3-phenylpropane (0.20 mL, 0.26 g, 1.3 mmol) and one crystal of iodine. After 20 minutes the reaction mixture became colorless, so the solution was removed by syringe and added to a solution of (26) (0.30 g, 0.8 mmol) in dry ether at 0° C. under a nitrogen atmosphere. After 20 minutes the reaction was allowed to warm to ambient temperature and was quenched in dilute hydrochloric acid (2N, 50 mL). The products were extracted with ethyl acetate (50 mL), dried over magnesium sulfate, and evaporated in vacuo. The residue was purified by flash chromatography (hexane:ethyl acetate eluant); recovered 0.31 g (79%) of (28) as an oil which appears to be a 1:1 mixture of the possible diastereomers. Further chromatography gave a single diastereoisomer: IR (neat) 2908, 1690 (C=O urethane): NMR (CDCl$_3$) δ 8.1 (1H, br, indole NH), 7.6 (1H, d, J 8 Hz, indole H-4), 7.4–6.9 (9H, n, indole H-5, H-6, H-7, H-2+phenyl), 4.8 (1H, br, adamantane H-2), 4.7 (1H, br s, urethane NH), 3.6 (1H, m, CH—OH), 3.5 (1H, d, J 14 Hz, one of CH$_2$-indole), 3.1 (1H, d, J 14 Hz, one of CH$_2$-indole), 2.7 (2H, m, CH$_2$-Ph), 2.1–1.3 (19H, m, adamantane+2× CH$_2$+OH), 1.1 (3H, s, CH$_3$).

Example 16

Tricyclo[3.3.1.1$^{3,7}$]dec-2-ylR-(R*,S*)]-[4,5-dihydro-4-(phenylmethyl)-2-thiazolyl]-2-(1H-indol-3-yl)-1-methylethyl]carbamate (17)

To a solution of (13) (0.1 g, 0.2 mmol) in toluene (10 mL) was added Lawesson's reagent (0.10 g, 0.25 mmol) and the reaction was heated to reflux for 1 hour. The reaction mixture was allowed to cool to ambient temperature and was purified by flash chromatography (dichloromethane/ether eluant). Obtained 0.07 g (70%) of the product; IR (neat) 2910, 1697 (C=O urethane), 1620 (C=N) cm$^{-1}$: NMR (CDCl$_3$ δ 8.1 (1H, br, indole NH), 7.7 (1H, d, J 8 Hz, indole H-4), 7.4–6.9 (9H, m, indole H-5, H-6, H-7, H-2+phenyl), 5.8 (1H, br, urethane NH), 4.9 (1H, br, adamantane H-2), 4.6 (1H, m, CH), 3.7 (1H, m, one of CH$_2$—S), 2.9 (1H, m, one of CH$_2$—S), 2.8 (1H, br, one of CH$_2$—Ph), 2.2 (1H, br, one of CH$_2$—Ph), 2.1–1.4 (14H, m, adamantane), 1.3 (3H, s, CH$_3$); FAB MS (m$^+$/e) 529 (m$^+$_H), 47%), 398 (m$^+$-(indole-CH$_2$), 44%), 130 (indole-CH$_2$), 100%): R$_f$ (30% ethyl acetate/hexane), 0.85.

Example 17

Phenylmethyl (R)-β-methyl-β- [[(tricyclor3.3.1.1$^{3,7}$] dec-2-yloxy)carbonyl]amino]-1H-indole-3-butanoate Step 1

A solution of N-methyl morpholine (253 mg, 2.50 mmol) and 2-Adoc-αMe-R-TrpOH (23b) (990 mg, 2.50 mmol) in anhydrous THF (20 mL) was cooled to 0° C. and treated with a solution of i-butylchloroformate (360 mg, 2.5 mmol) in anhydrous THF (10 mL) dropwise over 10 mm. This was stirred at 0° C. for a further 20 minutes and filtered. A solution of diazomethane (6 mmol) in Et$_2$O was added to the filtrate and left at 0° C. for 4 hours, then allowed to warm slowly to room temperature over 12 hours. Excess diazomethane was quenched with acetic acid and the solvents removed in vacuo. The residue was chromatographed using 25% EtOAc in n-hexane to give the diazoketone (300 mg, 29%); IR (film) 3400–3200, 2913, 2854, 2106, 1693, and 1353 cm$^{-1}$; NMR (CDCl$_3$) δ 1.49 (3H, s), 1.50–1.60 (2H, m,), 1.70–2.05 (12H, m), 3.30–3.40 (2H, br s), 4.86 (1H, br,s), 5.20–5.40 (1H, br s), 5.56 (1H, s), 6.95 (1H, d, J 2 Hz), 7.08 (1H, t, J 7 Hz), 7.16 (1H, t, J 7 Hz), 7.33 91H, d, J 8 Hz), 7.55 (1H, d, J 8 Hz), 8.50 (1H, s).

Step 2

A solution of the diazoketone (Scheme 5, No. 31) (1.04 g, 2.50 mmol) in benzyl alcohol (10 mL) was treated with a solution of silver benzoate (4 mL, 17 mmol) in triethylamine (5 mL) portionwise, and left to stir for 1 hour. EtOAc (30 mL) was then added and this solution treated with activated charcoal and filtered through a filter and the solvent was removed in vacuo and the residue chromatographed using 30% EtOAc in n-Hexane as eluant to give the benzyl ester (44.0 mg, 35%); IR (film) 3500–3200, 2907, 2855, 1720 and 1698 cm$^{-1}$; NMR (CDCl$_3$) δ 1.37 (3H, s), 1.50–1.55 (2H, m), 1.65–1.85 (8H, m), 1.90–2.05 (4h, m), 2.67 (1H, d, J 14.5 Hz, 2.97 (1H, d, J 14.5 Hz), 3.22 91H, d, J 14 Hz), 3.29 (1H, d, J 14 Hz), 4.68 (1H s), 4.82 (1H, s), 5.09 (2H, s), 6.95 (1H, d, J 2 Hz), 7.06 (1H, dt, J 7.5 and 1 Hz), 7.15 (1H, dt, J 7.5 and 1 Hz), 7.25–7.35 (6H, m), 7.57 (1H, d, J 8 Hz), 8.28 (1H, s).

Example 18

Tricyclo[3.3.1.1$^{3,7}$]dec-2-yl [R-(R*,S*)] [3- [[1- (hydroxymethyl)-2-phenylethyl]amino]-1-(1H-indol- 3-ylmethyl]-1-methyl-3-oxopropyl]carbamic acid

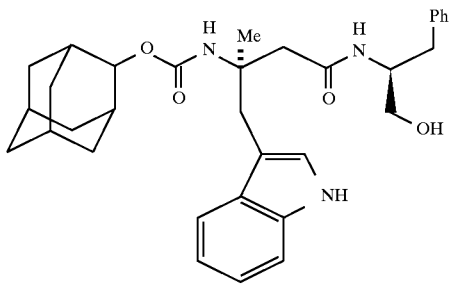

Step 1

A solution of benzyl ester (Example 17, Scheme 5 No. 32) (440 mg, 0.88 mmol) in absolute EtOH (100 mL) was treated with Pd/C (50 mg, Ca 10%) and put under an atmosphere of hydrogen at 50 psi and 30° C. with agitation for 16 hours. The reaction mixture was filtered through a filter aid and the filtrate evaporated to dryness in vacuo. The residue was chromatographed over reverse phase silica using 25% H$_2$O in MeOH as eluant to give the acid (180 mg 50%), m.p. 91°–99° C. (MeOH/H$_2$O); [α]$^D$+20.0° (C=1, MeOH); IR (film) 3500–3300, 2912, 2856, 1704 cm$^{-1}$; NMR (CDCl$_3$) δ 1.41 (3H, s), 1.53 (1H, s), 1.57 (1H, s), 1.70–1.85 (9H, m), 1.95–2.10 (4H, m), 2.69 (1H, d, J 14.5 Hz), 3.05 (1H, d, J 14.5 Hz), 3.21 (1H, d, J 14.5 Hz), 3.32 (1H, d, J 14.5 Hz), 4.86 (1H, s), 5.10–5.30 (1H, br s), 7.04 (1H, d, J 2hz), 7.07–7.20 (2H, m), 7.35 (1H, d, J 8 Hz), 7.60 (1H, d, J 8 Hz), 8.16 (1H, s).

Step 2

A solution of the carboxylic acid (Step 1, Scheme 5, No. 33) (160 mg, 0.39 mmol) and pentafluorophenol (72 mg, 0.39 mmol) in EtOAc (20 mL) was cooled to 0° C. and treated with a solution of N,N'-dicyclohexylcarbodiimide (80 mg, 0.39 mmol) in EtOAc (5 mL) and left stirring at 0° C. for 18 hours. After this time it was filtered and S-phenyl alaninol added (121 mg, 0.8 mmol), and the mixture left at room temperature for 24 hours. The solvent was then removed in vacuo and the residue chromatographed using 30% EtOAc in n-Hexane as eluant to give the product as a white solid (140 mg, 66%); IR (film) 3500–3200, 2909, 2855, 1694, 1651, and 1570 cm$^{-1}$; NMR (CDCl$_3$) δ 1.27 (3H, s), 1.51 (1H, s), 1.55 (1H, s), 1.70–2.05 (12H, m), 2.46 (1H, d, J 13.5 Hz), 2.75–2.81 (2H, m), 2.87 (1H, d, J 13.5 Hz), 2.90–3.05 (1H, br), 3.08 (1H, d, J 14 Hz), 3.28 (1H, d, J 14 Hz), 3.50 (1H, dd, J 11 and 5 Hz), 3.61 (1H, dd, J 11 and 3.5 Hz), 4.10–4.20 (1H, m), 4.81 (1H, s), 5.14 (1H, s), 6.26 (1H, d, J 8 Hz), 6.99 (1H, d, J 2 Hz), 7.08 (1H, t, J 7 Hz), 7.10–7.30 (6H, m), 7.33 (1H, d, J 8 Hz), 7.58 (1H, d, J 8 Hz), 8.32 (1H, s).

Example 19

Carbamic acid, [1-(1H-indol-3-ylmethyl)-1-methyl- 2-[(1-oxo-4-phenylbutyl)amino]ethyl]-, tricyclo- [3.3.1.1$^{3,7}$]dec-2-yl ester (R)-

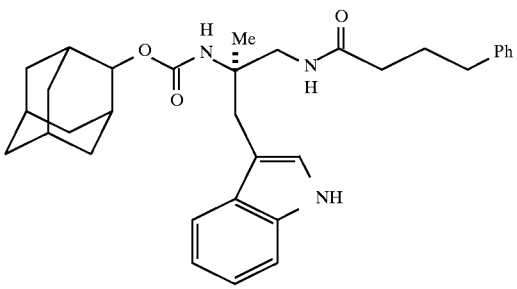

This was prepared in the same manner as described in Example 21. Scheme 5 No. 37d, m.p. 70°–75° C. (foam); [α]$^D$–9.2 (C=1, MeOH); IR (film) 3400–3100, 2908, 2853, 694, 1645, and 1526 cm$^{-1}$; NMR (CDCl$_3$) δ 1.24 (3H, s), 1.50–2.10 (16H m), 2.20 (2H, t, J 7 Hz), 2.64 (2H, t, J 7 Hz), 2.98 (1H, d, J 14.5 Hz), 3.25 (1H, d, J 14.5 Hz), 3.55 (1H, dd, J 14 and 6 Hz), 3.70 (1H, dd, J 14 and 6 Hz), 4.81 (1H, s), 4.94 (1H, s), 6.50–6.60 (1H, br s), 7.00 (1H, d, J 2 Hz), 7.05–7.30 (7H, m), 7.35 (1H, d, J 8 Hz), 7.57 (1H, d, J 8 Hz), 8.17 (1H, s); Anal. C$_{33}$H$_{41}$N$_3$O$_3$, C, H, N.

Example 20

Carbamic acid, [2- (benzoylamino)-1-(1H-indol-3- ylmethyl)-1-methylethyl]-, tricyclo[3.3.1.1$^{3,7}$]dec-2- yl ester, (R)-

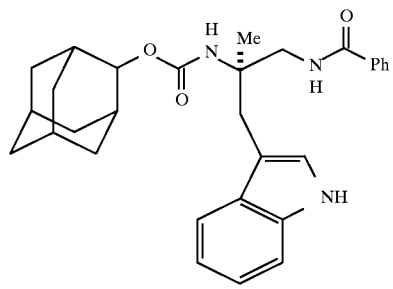

This was prepared in the same manner as described in Example 21. Scheme 5 No. 37a, m.p. 220.0°–220.1° C. (MeOH); [α]$_D$+24° C. (C=0.25, MeOH); IR (film) 3500- 3200-2907, 2855, 1695, 1646, and 1533 cm$^{-1}$; NMR (CDCl$_3$) δ 1.30 (3H, s), 1.50–1.60 (2H, m), 1.70–2.10 (12H, m), 3.07 (1H, d, J 14.5 Hz), 3.31 (1H, d, J 14.5 Hz), 3.76 (1H, dd, J 14 and 6 Hz), 3.89 (1H, dd, J 14 and 6 Hz), 4.84 (1H, s), 5.03 (1H, s), 7.01 (1H, d, 2 Hz), 7.05–7.20 (2H, m), 7.35–7.50 (4H, m), 7.60 (1H, d, J 8H, 7.77 (2H, d, J 7 Hz), 7.60–7.90 (1H, br), 8.39 (lH, s); FAB MS m/e 486.3 (34), 355.3 (63), 290.3 (29), 177.2 (37), 154.1 (100); Anal. C$_{30}$H$_{35}$N$_3$O$_3$; C, H, N.

Example 21

Carbamic acid, [1-(1H-indol-3-ylmethyl)-1-methyl-2-[(1-oxo-3-phenylpropyl)amino]ethyl-, tricyclo-[3.3.1.1$^{3,7}$]dec-2-vl ester, (R)-

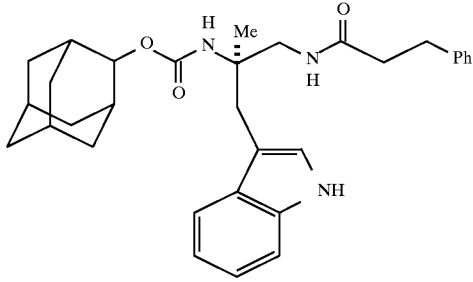

Step 1

Carbamic acid, [2-amino-1-(1H-indol-3-ylmethyl)-1-methyl-2-oxoethyl]-, tricyclo[3.3.1.1$^{3,7}$]dec-2-yl ester, (R)- AdOC-α-Me)DTrp-NH$_2$ (See Scheme 5, No. 35 2-Adoc-α-Me-R-Trp NH$_2$)

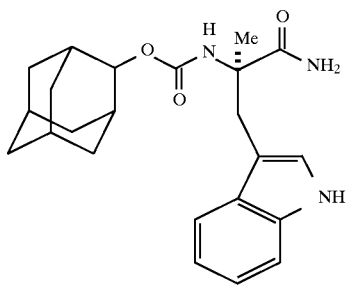

2-Adoc-α-Me-R-TrpOH (23b) (9.5 g, 24 nmuol) as a solution in EtOAc (150 mL) was treated with pentafluorophenol (4.4 g, 24 mmol) and cooled to 0° C. A solution of N,N'-dicyclohexylcarbodiimide (5.15 g, 25 mmol) in EtOAc (20 mL) was added dropwise and the resultant mixture allowed to stir 6 hours, then left a further 12 hours at 4° C. This was then filtered and the filtrate evaporated to dryness in vacuo. The residue was redissolved in THF (100 mL) and ammonia gas bubbled through at 0° C. for 1 hour. The solvent was removed in vacuo and the residue chromatographed over reverse phase silica using 30% H$_2$O in MeOH as eluant to give the amide (35, Scheme 5) (9.2 g, 97%) as white crystals, m.p. 136°–149° C. (MeOH); [α]$_D$+42.1 (C=1), MeOH); IR (film) 3351, 2906, 2855, 1675, and 1588 cm$^{-1}$; NMR (CDCl$_3$) δ 1.50–1.60 (2H, m), 1.58 (3H, s), 1.70–2.05 (12H, m), 3.33 (1H, d, J 14.5 Hz), 3.51 (1H, d, J 14.5 Hz), 4.86 (1H, s), 5.24 (1H, s), 5.40–5.55 (1H, br), 6.20–6.35 (1h, br), 7.04 (1H, d, J 2 Hz), 7.08–7.21 (2H, m), 7.36 (1H, d, J 8 Hz), 7.63 (1H, d, J 8 Hz), 8.24 (1H, s); MS (FAB) m/e 396 (100); Anal. C$_{23}$H$_{29}$N$_3$O$_3$; C, H, N.

Step 2 (See Scheme 5, No. 36)

Trimethylsilylchloride (4.34 g, 40 mmol) was added dropwise to a solution of LiBH$_4$ (11 mL of a 2M solution, 22 mmol) in THF under an atmosphere of nitrogen. A solution of 2-AdocαMe-R-TrpNH$_2$ (Scheme 5, N°35) from the previous step (3.95 g, 10.0 mmol) in anhydrous THF (20 mL) was added dropwise over 20 mm and the reaction mixture stirred 10 minutes at room temperature, then at gentle reflux for 3 hours. This was then cooled to 0° C. and MeOH (16.5 mL) added with caution. All solvents were then removed in vacuo and the residue chromatographed over reverse phase silica using 30% H$_2$O in MeOH as eluant to give 1.25 g (32%) of starting amide and 1.29 g (34%) of the product amine, m.p. 138°–144° C. (MeOH); [α]$^D$+51.6° (C=1, MeOH); IR (film) 2912, 2854 and 1690 cm$^{-1}$; NMR (CDCl$_3$) δ 1.32 (3H, s), 1.40–1.55 (2H, m), 1.65–2.05 (12H, m), 3.04 (1H, d, J 14 Hz), 3.20–3.30 (2H, m), 3.40–3.50 (1H, m), 4.78 (1H, s), 5.10–5.30 (1H, br s), 7.00–7.20 (3H, m), 7.34 (1H, d, J 8 Hz), 7.52 (1H, d, J 8 Hz), 8.56 (1H, s), 8.67 (2H, br s); FAB MS m/e 382.3 (100).

Step 3 (See Scheme 5, No. 37c)

A solution of 3-phenylpropionic acid (75 mg, 0.5 mmol) in EtOAc (5 mL) was treated with pentafluorophenol (92 mg, 0.5 mmol) and cooled to 0° C. A solution of N,N'-dicyclohexylcarbodiimide (103 mg, 0.5 mmol) in EtOAc (2 mL) was added and the mixture left 12 hours at 4° C. This mixture was then filtered and solid amine (from Step 2, Scheme 5 N°36) (198 mg, 0.5 mmol) added, and left at room temperature for 24 hours. The reaction mixture was washed with 1M citric acid solution (2×10 mL), NaHCO$_3$ (2×10 mL of a 1M solution), and H$_2$O (2×10 mL) and the organic phase dried over MgSO$_4$. The solvent was then removed in vacuo and the residue chromatographed over silica gel using 20 MeOH in CH$_2$Cl$_2$ eluant to give the product (230 mg, 90%) as white crystals, m.p. 171°–175° C. (MeOH); [α]$°_D$–12.3° (C=0.56, MeOH); IR (KBr) 3400–3100, 2906, 2854, 1694, 1649, an 1528 cm$^{-1}$; NMR (CDCl$_3$) δ 1.13 (3H, s), 1.50–2.10 (14H, m), 2.50 (2H, t, J 7 Hz), 2.90 (1H, d, J 14 and 6 Hz), 3.65 (1H, dd, J 14 and 6 Hz), 4.81 (1H, s), 4.88 (1H, s), 6.40–6.60 (1H, br), 6.96 (1H, d, J 3 Hz), 7.05–7.30 (7H, m), 7.35 (1H, d, J 8 Hz), 7.53 (1H, d, J 8 Hz), 8.15 (1H, s); FAB MS m/e 514.4 (8), 383.3 (32), 205.2 (32), 170.2 (47), 135.2 (100); Anal. C$_{32}$H$_{39}$N$_3$O$_3$; C, H, N.

Example 22

Carbamic acid, [1-(1H-indol-3-ylmethyl)-1-methyl-2-[(2-phenylacetyl)amino]ethyl]-, tricyclo[3.3.1.1$^{3,7}$]-dec-2-yl ester. (R)-

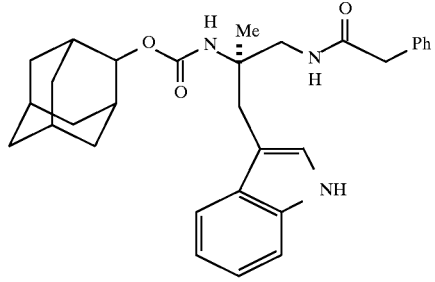

This was prepared in the same manner as described in Example 21 (see Scheme 5, No. 37b), m.p. 176.5°–180° C. (MeOH); [α]D$_1$–1.6° (C=O 56, MeOH); IR (film) 3400–3100, 291, 2854, 1694, 1656, and 1520 cm$^{-1}$ ; NMR (CDCl$_3$) δ 1.16 (3H, s), 1.50–2.10 (14H, m), 2.90 (1H, d, J 14 Hz), 3.16 (1H, d, J 14 Hz), 3.50 (1H, dd, J 14.and 6 Hz), 3.57 (2H, s), 3.65 (1H, dd, J 14 and 6 Hz), 4.73 (1H, s), 4.80 (1H, s), 6.30–6.40 (1H, brs), 6.94 (1H, d, J 2 Hz), 7.07 (1H, t, J 8 Hz), 7.16 (1H, t, J 8 Hz), 7.25–7.40 (6H, m), 7.48 (1H, d, J 8 Hz), 8.11 (1H, s); FAB MS m/e 500.5 (100), 369.3 (87); Anal. C$_{31}$H$_{37}$N$_3$O$_3$; C, H, N.

Example 23

Carbamic acid, [2- [[3-[[1- (hydroxymethyl)-2-phenyl-ethyl]amino]-3-oxopropyl]amino]-1-(1H-indol-3-ylmethyl)-1-methyl-2-oxoethyl]-, tricyclo-[3.3.1.1$^{3,7}$]dec-2-vl ester. [R-(R*.S*)]-

The acid as prepared in Example 30, Step 2 (1.17 g, 2.80 mmol) and pentafluorophenol (461 mg, 2.5 mmol) as a solution in EtOAc (50 mL) was treated with dicyclohexyl carbodiimide (542 mg, 2.60 mmol) and left at 0° C. for 18 hours. This was filtered and the filtrate treated with s-phenylalaninol (454 mg, 3.00 mmol) and the reaction mixture left stirring 18 hours at room temperature. This was then concentrated in vacuo and the residue chromatographed over reverse phase silica using 75t MeOH in H$_2$O as eluant to give the product as a white, noncrystalline solid (1.17 g, 78%); m.p. 94°–98° C.; [α]$_{D20}$+14.7° (c=1), MeOH); IR (film) 3306, 2904, 2854, 1693, and 1651 cm$^{-1}$; NMR (DMSO-d$_6$) δ .29 (3H, s), 1.60–2.00 (14H, m), 2.05–2.25 (2H, m), 2.62 (1H, dd, J 14 and 8 Hz), 2.83 (1H, dd, J 14 and 6 Hz), 3.10–3.40 (5H, m), 3.85–3.95 (1H, m), 4.70–4.80 (2H, m), 6.70 (1H, br s), 6.90–7.35 (9H, m), 7.44 (1H, d, J 8 Hz), 7.70 (1H, d, J 8 Hz), 7.75 (1H, br s), 10.85 (1H, s); FAB MS m/e 601 (m+1), 100); Anal. C$_{35}$H$_{44}$N$_4$O$_5$·0.25H$_2$O; C, H, N.

Example 24

Carbamic acid, [1-(1H-indol-3-ylmethyl)-2-[[3-[[1-hydroxymethyl)-2-iphenylethyl]amino]-3-oxopropyl]-amino]-1-methyl-2-oxoethyl]-, tricyclo [3.3.1.1$^{3,7}$]dec-2-ylester, [S- (R*,R*)]-

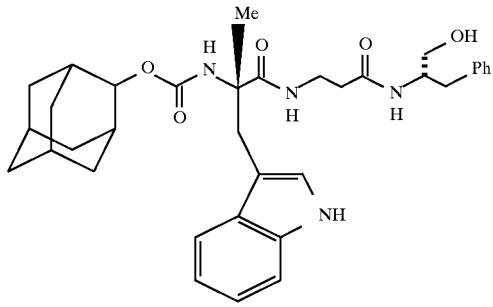

This was prepared in the same manner as described in Example 23 (see Scheme 6, No. 44), m.p. 95°–97° C. (MeOH/H$_2$O); [α]$_D^{20}$–31.3° (c=1), MeOH); IR (film) 3314, 2910, 2856, 1696, and 1651 cm$^{-1}$; NMR (CDCl$_3$) δ 1.53 (5H, s), 1.70–2.05 (12H, m), 2.10–2.30 (2H, M), 2.79 (2H, d, J 7 Hz), 3.25 (1H, d, J 14.5 Hz), 3.35 (1H, d, J 14.5 Hz), 3.30–3.55 (3H, m), 3.65–3.70 (1H, m), 4.10–4.20 (1H, m), 4.79 (1H, s), 5.26 (1H, s), 6.20–6.35 (1H, br s), 6.69 (1H, t, J Hz), 6.97 (1H, d, J 2 Hz), 7.06–7.29 (7H, m), 7.34 (1H, d, J 8 Hz), 7.57 (1H, d, J 8 Hz), 8.49 (1H, s); FAB MS m/e 601 (100); Anal. C$_{35}$H$_{44}$N$_4$O$_5$·0.25H$_2$O; C, H, N. MS FAR m/e 614 (m+1) and 217 (100); Anal. C$_{35}$H$_{43}$N$_5$O$_5$·0.5H$_2$O; C, H, N.

Example 25

D-Phenylalanamide, α-methyl-N- [(tricyclo [3.3.1.1$^{3,7}$]-dec-2-yloxv)carbonyl]-D-tryotophyl-β-alanyl-

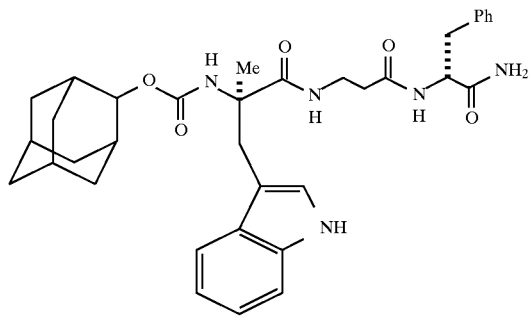

This was prepared using a method similar to Example 26. The acid from Example 30, Step 2 (117 mg, 0.25 mmol) and pentafluorophenol (46 mg, 0.25 mmol) as a solution in EtOAc (10 mL) was treated with dicyclohexylcarbodiimide (52 mg, 25 mmol) and left stirring at room temperature for 2 hours before being filtered. S-Phenylalaninamide (50 mg, 0.3 mmol) was then added and the mixture left stirring at room temperature for 72 hours. The reaction mixture was then washed with 1M HCl (10 mL), H$_2$O (10 mL), 1M NaOH (10 ml), and H$_2$O (10 ml). The organic phase was dried over MgSO$_4$ and concentrated in vacuo. The residue was chromatographed over reverse phase silica gel using 75% MeOH in H$_2$O as eluant to give the product as a white noncrystalline solid (130 mg, 85%); m.p. 113°–118° C.; [α]$_D^{20}$+27.5° (C=0.5, MeOH); IR (film) 3311, 3055, 2908, 1700, and 1659 cm$^{-1}$; NMR (CDCl$_3$) δ 1.49 (2H, s), 1.52 (3H, s), 1.60–2.05 (12H, m), 2.19 (2H, t, J 6 Hz), 3.01 (1H, dd, J 7.5 and 14 Hz), 3.08 (1H, dd, J 7.5 and 14 Hz), 3.27 (1H, d, J 14.5 Hz), 3.42 (1H, d, J 14.5 Hz), 3.35–3.50 (2H, m), 4.59 (1H, dd, J 15 and 7 Hz), 4.80 (1H, s), 5.29 (1H, s), 5.47 (1H, s), 6.20 (1H, s), 6.50 (1H, d, J 7 Hz), 6.76 (1H, t, J 6 Hz), 6.96 (1H, d, J 2 Hz), 7.05–7.35 (7H, m), 7.34 (1H, d, J 8 Hz), 7.57 (1H, d, J 8 Hz), 8.36 (1H, s).

Example 26

L-Phenylalaninamide, α-methyl-N-[(tricyclo [3.3.1.1$^{3,7}$]-dec-2-yloxy)carbonyl]-D-tryptophvl-β-alanyl-

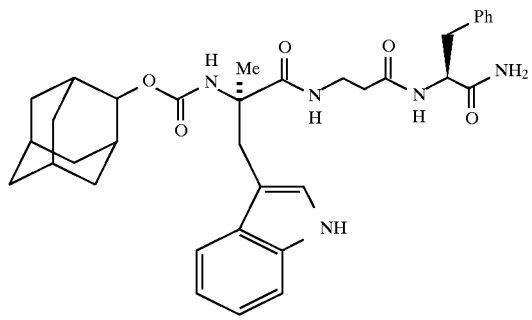

m.p. 112°–118° C. (MeOH/H$_2$O); [α]$_D^{20}$+16.3° (c=1, MeOH); IR (film) 3309, 2907, 2855, 1690, 1652 cm$^{-1}$; NMR (CDCl$_3$) δ 1.50–2.05 (17H, m), 2.10–2.20 (2H, m), 2.98 (1H, dd, J 14 and 8 Hz), 3.09 (1H, dd, J 14 and 7 Hz), 3.24 (1H, d, J 14.5 Hz), 3.35 (1H, d, J 14.5 Hz), 3.25–3.55 (2H, m), 4.58 (1H, dd, J 15 and 7.5 Hz), 4.78 (1H, s), 5.28 (1H, s), 5.48 (1H, s), 6.27 (1H, br s), 6.54 (1H, br s), 6.75 (1H, m), 6.99 (1H, d, J 2 Hz), 7.05–7.30 (7H, m), 7.34 (1H, d, J 8 Hz), 7.58 (1H, d, J 8 Hz), 8.41 (1H, s); FAB MS m/e 614.3 (100); Anal. C$_{35}$H$_{43}$N$_5$O$_5$0.75H$_2$O; C, H, N.

Example 27

L-Phenylalaninamide α-methyl-N- [(tricyclo[3.3.1.1$^{3,7}$]-dec-2-yloxy)carbonyl]-L-tryptophy-β-alanyl-

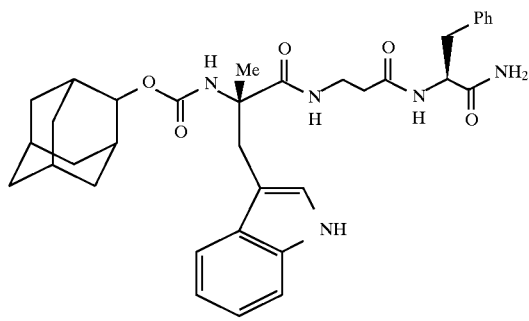

m.p. 114°–119° C. (MeOH/H$_2$O); [α]$_D^{20}$-15.2° (c=0.5, MeOH); IR (film) 3323, 2909, 2855, 1700–1640 cm$^{-1}$; NMR (CDCl$_3$) δ 1.50 (2H, s), 1.54 (3H, s), 1165–2.00 (12H, m), 2.10–2.20 (2H, br s), 2.95 (1H, dd, J 14 and 8 Hz), 3.10 (1H, dd, J 14 and 6 Hz), 3.23 (1H, d, J 14 Hz), 3.32 (1H, d, J 14H), 3.20–3.30 (1H, m), 3.40–3.50 (1H, m), 4.55 (0.5H, 0, J 8 Hz), 4.60 (0.5H, d, J 8 Hz), 4.78 (1H, 8), 5.35 (1H, s), 5.68 (1H, s), 6.41 (1H, s), 6.65–6.85 (1H, m), 6.82 (1H, t, J 6 Hz), 6.97 (1H, d, J 2 Hz), 7.05–7.30 (7H, m), 7.33 (1H, d, J 8 Hz), 7.57 (1H, d, J 8 Hz), 8.55 (1H, s); FAB MS m/e 614.3 (50.7), 236.1 (100); Anal. C$_{35}$H$_{43}$N$_5$O$_5$ ·0.5H$_2$O; C, H, N.

Example 28

D-Phenylalaninamide, α-methyl-N-[tricyclo[3.3.1.1$^{3,7}$]-dec-2-yloxy)carbonyl]-L-tryptophyl-β-alanyl-

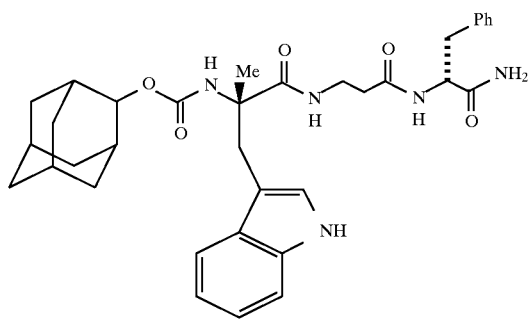

m.p. 113°–118° C. (MeOH/H$_2$O); [α]$_D^{20}$-30° (c=0.5, MeOH); IR (film) 3313, 2909, 2856, 1694–1652 br. cm$^{-1}$; NMR (CDCl$_3$) δ 1.45 (3H, s), 1.50 (2H, s), 1.65–2.00 (12H, m), 2.14 (2H, s), 2.90 (1H, dd, J 14 and 8 Hz), 3.06 (1H, d, J 14 and 5.5 Hz), 3.2–3.4 (4H, m), 4.56 (0.5H, d, J 7.5 Hz), 4.60 (0.5H, d, J 7.5 Hz), 4.80 (1H, s), 5.54 (1H, s), 6.14 (1H, s), 6.70 (1H, s), 6.87 (1H, s), 7.00–7.30 (10H, m), 7.51 (1H, d, J 8 Hz), 8.87 (1H, s); FAB MS 636.4 (100), 614.4 (61); Anal. C$_{35}$H$_{43}$N$_5$O$_5$·0.5H$_2$O; C, H, N.

Example 29

12-Oxa-2,5,9-triazatridecanoic acid, 3-(1H-indol-3-ylmethyl)-3-methyl-4.8.11-trioxo-10-(phenvlmethyl)-, tricyclo[3.3.1.1$^{3,7}$]dec-2-vl ester, [R-(R*,R*)]-
(See Scheme 6, No. 49)

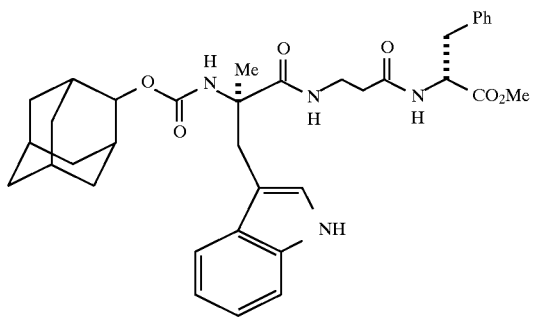

In a manner similar to Example 30, the following was prepared, m.p. 86°–90° C. (foam); [α]$_D^{20}$+17.4° (c=0.5, MeOH); IR (film) 1738, 1698, and 1656 cm$^{-1}$; NMR (CDCl$_3$) δ 1.55 (3H, s), 1.50–1.60 (2H, br s), 1.65–2.05 (12H, m), 2.10–2.35 (2H, m), 2.99 (1H, dd, J 14 and 8 Hz), 3.11 (1H, dd, J 14 and 5 Hz), 3.20–3.30 (1H, m), 3.31 (2H, s), 3.55–3.65 (1H, m), 3.68 (3H, s), 4.73 (1H, dd, J 13 and 8 Hz), 4.80 (1H, s), 5.33 (1H, s), 6.40–6.60 (1H, br s), 6.90 (1H, br s), 6.98 (1H, d, J 2 Hz), 7.05–7.35 (8H, m), 7.59 (1H, d, J 8 Hz), 8.45 (1H, s); MS FAB m/e 629.2 (100); Anal. C$_{36}$H$_{44}$N$_4$O$_6$·0.25H$_2$O; C, H, N.

Example 30

L-Phenylalanine,N-[N-[α-methyl-N-[(tricyclo[3.3.1.1$^{3,7}$]dec-2-yloxy)carbonyl]-d-tryotoohyl]-β-alanyl]-phenylmethyl ester Step 1 (See Scheme 6, No. 39)

A solution of 2-Adamantyloxycarbonyl-α-methyl-R-tryptophan (8.0 g, 20 mmol) in EtOAc (100 mL) was treated with pentafluorophenol (3.68 g, 20.0 mmol) and cooled to 0° C. Dicyclohexylcarbodiimide (4.33 g, 21.0 mmol) was then added and the mixture left to stir for 18 hours at 0° C. After this time the mixture was filtered and S-alanine methyl ester (2.47 g, 240 mmol) added and the mixture left stirring a further 18 hours at room temperature, filtered, and the filtrate washed with 1M HCl (3×30 mL), H$_2$O (2×30 mL), saturated NaHCO$_3$ solution (3×30 mL) H$_2$O (2×30 mL). The organic phase was dried over MgSO$_4$ and concentrated in vacuo and the product crystallized from ether to give the ester (7.8 g, 81%); IR (film) 3700–3200, 3000–2800), 2723, 1695, and 1659 cm$_{-1}$.

Step 2 (See Scheme 6, No. 41)

β-Alanine,N-[α-methyl-N-[(tricyclo[3.3.1.1$^{3,7}$]dec-2-yloxy)carbonyl]-D-tryptophyl]

The ester from Step 1 (5.20 g, 10.8 mmol) as a solution in 1.4 dioxane (300 mL) was treated with a solution of LiOH·H$_2$O (454 mg, 10.8 mmol) in H$_2$O (100 mL) dropwise at room temperature and left stirring 18 hours. 1M HCl (10.8 mL) was added and the mixture distilled to dryness in vacuo and the residue chromatographed over reverse phase silica gel using 70% MeOH in H$_2$O; as eluant to give the product (3.23 g, 51%) along with starting ester (1 g); m.p. 98°–103°

C. (MeOH/H$_2$O); [α]$_D^{20}$+29° (c=1, MeOH); IR(film)3351, 2911, 2855, 1706, and 1658 cm$^{-1}$; NMR (CDCl$_3$) δ 1.50–2.00 (17H, m), 2.39 (2H, br s), 3.26 (1H, d, J 15 Hz), 3.40–3.50 (3H, m), 4.80 (1H, s), 5.42 (1H, br s), 6.75 (1H, t, J 6 Hz), 6.99 (1H, d, J 2 Hz), 7.05–7.20 (2H, m), 7.33 (1H, d, J 8 Hz), 7.57 (1H, d, J 8 Hz), 8.37 (1H, s); FAB MS m/e 468 (m+1) and 217 (100); Anal. C$_{26}$H$_{33}$N$_3$O$_5$·0.25H$_2$O; C, H, N.

Step 3

A solution of the acid from Step 2 (467 mg, 1.00 mmol) and pentafluorophenol (184 mg, 1.00 mmol) in EtOAc (50 mL) was treated with dicyclohexyl-carbodiimide (206 mg, 1.00 mmol) at 0° C. and left 18 hours. This was then filtered and S-phenyl alanine benzyl ester (306 mg, 1.20 mmol) added and left stirring 18 hours at room temperature. This was then washed with 1M HCl (2×20 mL), H$_2$O (20 mL), saturated NaHCO$_3$ solution (2×20 mL), and H$_2$O (20 mL). The organic phase was dried over MgSO$_4$ and concentrated in vacuo and the residue chromatographed over reverse phase silica gel using 75% to 85% MeOH in H$_2$O as eluants to give the product (500 mg, 71%); m.p. 75°–82° C. (MeOH/H$_2$O); [α]$_D^{20}$+28.1° (c=0.45, MeOH); IR (film) 3324, 2908, 2855, 1737, 1698, and 1657 cm$^{-1}$; NMR (CDCl$_3$) δ 1.50 (3H, s), 1.50–1.55 (2H, m), 1.70–2.00 (12H, m), 2.10–2.30 (2H, m), 3.06 (1H, dd, J 14 and 7 Hz), 3.14 (1H, dd, J 14 and 6 Hz), 3.29 (1H, d, J 15 Hz), 3.25–3.60 (3H, m), 4.75–4.85 (2H, m), 5.08 (1H, d, J 12 Hz), 5.15 (1H, d, J 12 Hz), 5.29 (1H, br s), 6.20–6.30 (1H, br m), 6.81 (1H, br m), 6.95 (1H, d, J 2 Hz), 7.00–7.35 (13H, m), 7.57 (1H, d, J 8 Hz), 8.20 (1H, s) ; Anal. C$_{42}$H$_{48}$N$_4$O$_6$; C, H, N.

Example 31

In a manner similar to Example 30 the following was prepared, m.p. 77°–82° C. (foam); [α]$_D^{20}$–19.2° (c=0.5, MeOH); IR (film) 3305, 2906–2857, 1735, 1696, and 1658 cm$^{-1}$; NMR (CDCl$_3$) δ 1.51 (3H, s), 1.50–1.60 (2H, m), 1.70–2.10 (12H, m), 2.10–2.30 (2H, m), 3.01 (1H, dd, J 14 and 8 Hz), 3.12 (1H, dd, J 14 and 5 Hz), 3.20–3.30 (1H, m), 3.31 (1H, s), 3.55–3.65 (1H, m), 4.75–4.85 (2H, m), 5.07 (1H, d, J 12 Hz), 5.15 (1H, d, J 12 Hz), 5.28 (1H, br s), 6.30–6.50 (1H, br s), 6.80–6.90 (1H, br), 6.97 (1H, d, J 2 Hz), 7.05–7.35; MS FAB m/e 705.2 (71) and 327.2 (100); Anal. C$_{42}$H$_{48}$N$_4$O$_6$; C, H. N.

Example 32

D-Phenylalanine, N-[N-[α-methyl-N-[(tricyclo-[3.3.1.1$^{3,7}$]dec-2-yloxy)carbonyl]-D-tryptophyl]-β-alanyl]-

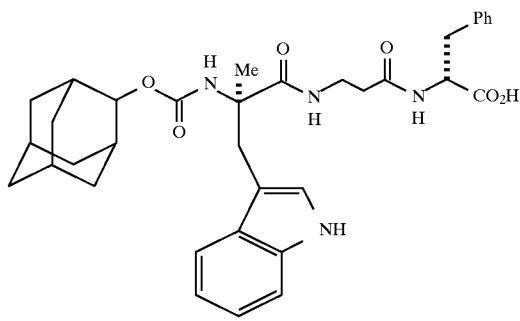

This was prepared in a manner similar to that described in Example 33, m.p. 119°–129° C. (MeOH/H$_2$O); [α]$_D^{20}$+5.8° (c=0.5, MeOH);IR (film) 2907, 2855, 1700, 1651 cm$^{-1}$; NMR (CDCl$_3$+CD$_3$OD) δ 1.53 (5H, s), 1.70–2.05 (12H, m), 2.10–2.30 (2H, br s), 2.95–3.05 (1H, m), 3.15–3.60 (5H, m), 4.65 (1H, s), 7.00–7.40 (9H, m), 7.57 (1H, d, J 8 Hz); FAB MS m/e 615.2 (58), 216.9 (100); Anal. C$_{35}$H$_{42}$N$_4$O$_6$·0.5H$_2$O; C, H, N.

Example 33

S-Phenylalanine N-[N-[α-methyl-N-[(tricyclo-[3.3.1.1$^{3,7}$]dec-2-yloxy)carbonyl]-R-tryptophyl]-β-alanyl]

A solution of the benzyl ester (450 mg, 0.64 mmol) in absolute EtOH (100 mL) was treated with 100 Pd/C (45 mg, 10% w/w) and put under an atmosphere of hydrogen at 50 psi for 2 hours with agitation. The mixture was then filtered through a filter aid and concentrated in vacuo and the residue chromatographed over reverse phase silica gel using 70% MeOH in H$_2$O as eluant to yield the product as a white, noncrystalline solid (300 mg, 76%); m.p. 114°–119° C.; [α]$_D^{20}$+37.8° (c=1), MeOH); IR (film) 3331, 2911, 2856, 1700, and 1656 cm$^{-1}$; NMR (CDCl$_3$) δ 1.41 (3H, s), 1.45–1.55 (2H, m), 1.70–2.00 (12H, m), 2.10–2.20 (2H, m), 3.01 (1H, dd, J, 14 and 8 Hz), 3.15–3.50 (5H, m), 4.00–5.00 (1H, v.br), 4.66 (1H, dd, J 13 and 7 Hz), 4.82 (1H, s), 5.46 (1H, br s), 6.50–6.70 (1H, br s), 6.87 (2H, br s), 7.00–7.30 (8H, m), 7.52 (1H, d, J 8 Hz), 8.44 (1H, s); Anal. C$_{35}$H$_{42}$N$_4$O$_6$; C, H, N.

Example 34

L-Phenylalanine, N-[N-[α-methyl-N-[(tricyclo-[3.3.1.1$^{3,7}$]dec-2-yloxy)carbonyl]-L-tryptophyl]-β-alanyl]-

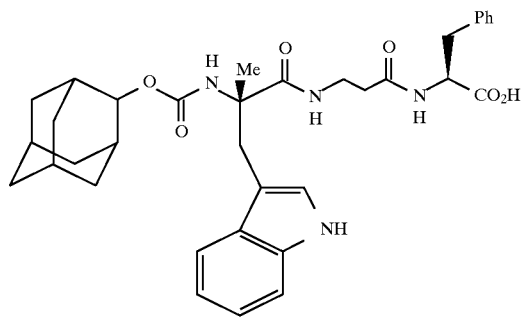

This was prepared in a manner similar to that described in Example 33, m.p., 115°–120° C. (MeOH/H$_2$O); [α]$_D^{20}$–7.2° (c=0.5, MeOH); IR (film) 3391, 2906, 2854, 1700, and 1646(s) cm$^{-1}$; NMR (CDCl$_3$+CD$^3$OD) δ 1.51 (3H, s), 1.54 (1H, s), 1.57 (1H, s), 1.70–2.05 (12H, m), 2.15–2.30 (2H, m), 2.99 (1H, dd, J 14 and 8 Hz), 3.15–3.55 (5H, m), 4.66 (1H, dd, J 8 and 5 Hz), 4.79 (1H, s, 7.00–7.40 (9H, m), 7.56 (1H, d, J 8 Hz); FAB MS m/e 615 (100); Anal. C$_{35}$N$_{42}$N$_4$O$_6$; C, H, N.

Example 35

Benzenepropanoic acid, α-[[3- [[3-[(1H-indol-3-yl)-2-methyl-1-oxo-2-[[(tricyclo[3.3.1.1³,⁷]dec-2-yloxy)-carbonyl]amino]propyl]amino]-1-oxopropyl]amino-, [S-(R*,S*)]-

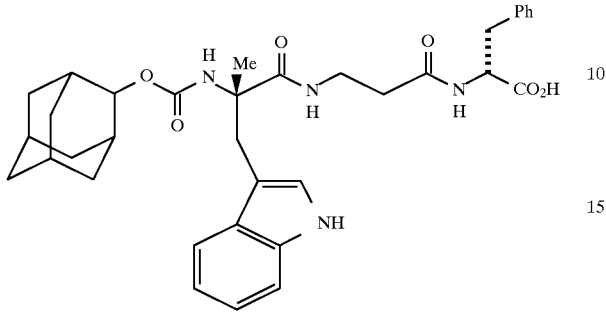

m.p., 116°–124° C. (MeOH/H₂O); $[\alpha]_D^{20}$ –35° (c=0.5, MeOH); IR (film) 3500–3200, 2912, 2856, 1700, and 1654 cm⁻¹; NMR (CDCl³) δ 1.42 (3H, s), 1.47 (1, s), 1.51 (1H, s), 1.6514 2.20 (14H, m), 2.90–3.00 (1H, m), 3.10–3.50 (5H, m), 3.50–4.50 (br, CO₂H and H₂O), 4.61 (1H, s), 4.82 (1H, s), 5.45 (1H, s), 6.50–6.80 (1H, br s), 6.85–7.30 (11H, m), 7.52 (1H, d, J 8 Hz), 8.58 (1H, s); FAB MS m/e 615.2 (100; Anal. $C_{35}H_{42}N_4O_6 \cdot 0.4H_2O$; C, H, N.

Example 36

Glycine, N-[2-methyl-N-[(tricyclo[3.3.1.1³,⁷]dec-2-yloxy)carbonyl-D-tryptophyl]-, phenylmethyl ester

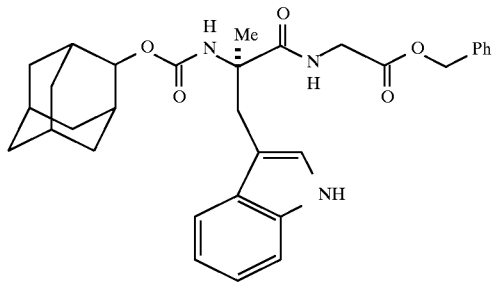

A solution of 2-Adocα-Me-R-TrpOH (Scheme 7, N°23b) (3.0 g, 7.6 mmol) in EtOAc (40 mL) was treated with pentafluorophenol (1.39 g, 7.6 mmol), and cooled to 0° C. A solution of N,N'-dicyclohexylcarbodiimide (1.56 g, 7.6 mmol) in EtOAc (10 mL) was then added dropwise and stirred 12 hours at 4° C. and filtered. Glycine benzyl ester hydrochloride (1.8 g, 9.0 mmol) was added followed by the dropwise addition of triethylamine (0.9 g, 9.0 mmol) in EtOAc (10 mL). This was allowed to stir 18 hours at room temperature. The reaction mixture was then washed with 1M citric acid solution (2×50 mL), 1M NaHCO₃ solution (2×50 mL) and H₂O (2×50 mL). The organic phase was dried over MgSO₄ and evaporated to dryness in vacuo. The residue was chromatographed over reverse phase silica using 25% H₂O in MeOH as eluant to give the product as a white foam (2.83 g, 68%) along with 0.9 g starting active ester, m.p. 76°–82° C. (foam); $[\alpha]_D^{20}$ +36° (c=1, MeOH); IR (film) 3500–3200, 2908, 2855, 1745, 1702, and 1665 cm⁻¹; NMR (CDCl₃) δ 1.45–1.60 (4H, m), 1.69–2.00 (13H, m), 3.30 (1H, d, J 14.5 Hz), 3.50 (1H, d, J 14.5 Hz), 3.95–4.10 (2H, m), 4.84 (1H, s), 5.13 (2H, s), 5.21 (1H, s), 6.79 (1H, s), 7.01 (1H, d, J 2 Hz), 7.08 (1H, t, J 7 Hz), 7.15 (1H, t, J 7 Hz), 7.30–7.40 (6H, m), 7.57 (1H, d, J 8 Hz), 8.26 (1H, s); FAB MS 544.4 (11), 414.3 (11), 348.2 (36), 135.2 (100); Anal.; $C_{32}H_{37}N_3O_5$; C, H, N.

Example 37

Carbamic acid, [2- [[2-[[1-(hydroxymethyl)-2-phenylethyl]amino]-2-oxoethyl]amino]-1-(1H-indol-3-ylmethyl)-1-methyl-2-oxoethyl]-, tricyclo[3.3.1.1³,⁷]-dec-2-yl ester, [R-(R*,S*)]- AdOC-(α-Me)DTrp-Gly-NH((S)-1-(hydroxymethyl)-2-phenylethyl)

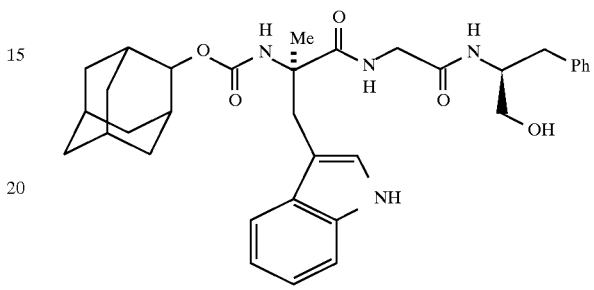

Step 1. Glycine, N-[3-(1H-indol-3-yl)-2-methyl-1-oxo-2-[[(tricyclo[3.3.1.1³,⁷]dec-2-yloxy) carbonyl]amino]-propyl]-, (R)- AdOC-(α-Me)DTrp-Gly

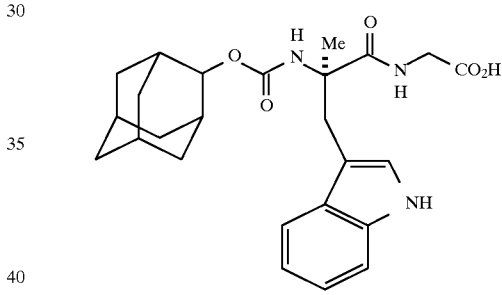

A solution of the benzyl ester (Example 36, Scheme 7, No. 57) (2.5 g, 4.6 nmol), in absolute EtOH (100 mL) was treated with 10% Pd/C (250 mg, 10% w/w) and put under an atmosphere of hydrogen at 50 psi and 20° C. for 5 hours with agitation. The reaction mixture was filtered through a filter aid and the filtrate concentrated in vacuo. The residue was then chromatographed over silica gel using 0.5% AcOH, 0.5% MeOH in CH₂Cl₂ as eluant to give the product (1.87–3 g, 90%) as a white solid; m.p. 112°–117° C. (MeOH/H₂O); $[\alpha]_D^{20}$+40° (c=1, MeOH); IR (film) 3500–3200, 2910, 2856, 1702, 1660, and 735 cm⁻¹; NMR (CDCl₃) δ 1.26 (1H, s), 1.51 (1H, s), 1.58 (3H, s), 1.70–2.00 (12H, m), 3.00–4.00 (1H, br), 3.28 (1H, d, J 14.5 Hz), 3.45 (1H, d, J 14.5 Hz), 3.94 (2H, d, J 5 Hz), 4.85 (1H, s), 5.35–5.50 (1H, br s), 6.85 (1H, br t), 7.04 (1H, d, J 2 Hz), 7.05–7.18 (2H, m), 7.32 (1H, d, J 8 Hz), 7.56 (1H, d, J 8 Hz), 8.39 (1H, s); Anal. $C_{25}H_{31}N_3O_5$; C, H, N.

Step 2

A solution of the acid (Scheme 7, No. 59, Step 1) (226 mg, 0.5 nmol) and pentafluorophenol (92 mg, 0.5 mmol) in EtOAc (20 mL) was cooled to 0° C. and treated with a solution of N,N'-dicyclohexyl-carbodiimide (108 mg, 0.525 mmol), in EtOAc (5 mL). This was left 12 hour at 0° C., filtered and the filtrate treated with S-phenylalaninol (91 mg, 0.6 mmol). This reaction mixture was stirred at room temperature for 18 hours, evaporated to dryness in vacuo and the residue chromatographed using 30% n-hexane in EtOAc as eluant to give the product (202 mg, 66%); IR (film) 3500–3200, 2911, 2855, 1695, and 1658 cm$^{-1}$; NMR (CD$_3$OD) δ 1.44 (3H, s), 1.52–1.62 (2H, m), 1.70–2.10 (14H, m), 2.78 (1H, dd, J 13.5 and 8 Hz), 2.93 (1H, dd, J 13.5 and 6 Hz), 3.24 (1H, d, J 14.5 Hz), 3.41 (1H, d, J 14.5 Hz), 3.53 (2H, d, J 5.5 Hz), 3.57 (1H, d, J 17 Hz), 3.71 (1H, d, J 17 Hz), 4.05–4.15 (1H, m), 4.88 (1H, s), 6.98 (1H, dt, J 7.5 and 1 Hz), 7.00–7.25 (7H, m), 7.32 (1H, d, J 8 Hz), 7.50 (1H, d, J 8 Hz).

Example 39

Carbamic acid, [2-[[4-[[1-(hydroxymethyl)-2-phenylethyl]amino]-4-oxobutyl]amino]-1-(1H-indol-3-ylmethyl)-1-methyl-2-oxoethyl]-, tricyclo[3.3.1.1$^{3,7}$]-dec-2-yl ester, [R-(R*,S*)]-

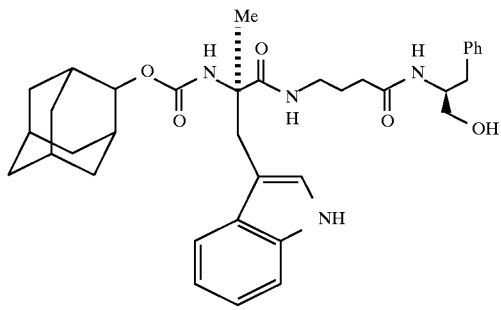

Step 1. Butanoic acid, 4-[[3-(1H-indol-3-yl)-2-methyl-1-oxo-2-[[(tricyclo[3.3.1.1$^{3,7}$]dec-2-yloxy)-carbonyl]amino]propvyl]amino]-, (R)-

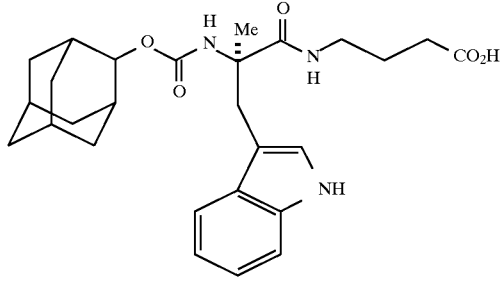

A solution of the methyl ester (Example 38, Scheme 8, No. 60) (2.6 g, 5.2 mmol) in 1,4-dioxan (500 mL) was treated dropwise with a solution of LiOH (104 mL of a 0.05M solution, 5.20 mmol) over 24 hours with vigorous stirring. This mixture was stirred at room temperature for 24 hours and quenched with 1M HCl (5.2 mL). The solvent was removed in vacuo and the residue chromatographed using 0.5% AcOH, 5% MeOH in CH$_2$Cl$_2$ to give 80 mg of starting ester along with 1.32 g of product, 550 yield, 77% conversion, m.p. 92°–96° C. (CH$_2$Cl$_2$); [α]$_D^{20}$ +29.3° (c=, MeOH); IR(film)3600–3200, 2909, 2856, 1702, and 1651 cm$^{-1}$; NMR (CDCl$_3$) δ 1.50–1.55 (2H, min), 1.61 (3H, s), 1.62–2.00 (14H, m), 2.10–2.25 (2H, m), 3.20–3.40 (2H, m), 3.24 (1H, d, J 14.5 Hz), 3.45 (1H, d, J 14.5 Hz), 4.84 (1H, s), 5.47 (1H, s), 6.58–6.65 (1H, br m), 7.03 (1H, d, J 2 Hz), 7.09 (1H, t, J 7 Hz), 7.17 (1H, t, J 7 Hz), 7.35 (1H, d, J 8 Hz), 7.57 (1H, d, J 8 Hz), 8.59 (1H, s); Anal. C$_27$H$_35$N$_3$O$_5$·0.2$_H$20; C, H, N.

Step 2

A solution of the acid (Step 1, Scheme 8, No. 61) (240 mg, 0.5 mmol), and pentafluorophenol (92 mg, 0.8 mmol) in EtOAc (20 mL) was cooled to 0° C. and treated with a solution of N,N'-dicyclohexyl-carbodiimide (108 mg, 0.55 mmol) in EtOAc (5 mL). This mixture was left at 0° C. for 12 hours, filtered, and the filtrate treated with S-phenylalaninol. This reaction mixture was left stirring at room temperature for 24 hours, the solvent removed in vacuo, and the residue chromatographed using 10% MeOH in CH$_2$CL$_2$ as eluant to give the product as a white solid (153 mg, 50%); IR (film) 3500–3200, 207, 2850, 1692, and 1642 cm$^{-1}$; NMR (CD$_3$OD) δ 1.43 (3H, s), 1.50–1.70 (4H, m), 1.75–1.95 (8H, m), 2.00–2.15 (6H, m), 2.7s (1H, dd, J 14 and 8 Hz), 2.91 (1H, dd, J 14 and 6 Hz), 2.95–3.35 (3H, m), 3.45–3.50 (3H, m), 4.07–4.17 (1H, m), 4.81 (1H+HOD), 6.93–7.09 (3H, m), 7.10–7.30 (5H, m), 7.31 (1H, d, J 8 Hz), 7.53 (1H, d, J 8 Hz).

Example 40

Tricyclo[3.3.1.1$^{3,7}$]dec-2-yl-(±)- [3-(1H-indol-3-yl-methyl)-2.5-dioxo-1-(2-phenylethyl)-3-pyrrolidinyl]-carbamate (68)

Step 1. Methyl-(±)-β-amino-β-[(phenylmethoxy -carbonyl]-1H-indole-3-butanoate (64)

1-Methyl-(±)-β-cyano-1-[1,1-dimethylethoxy)-carbonyl] -1H-indole-3-butanoate (63) (0.241 g, 0.50 mmol) was dissolved in ethanol (5 mL). The solution cooled to −5° C. in an acetone-ice bath and ethanolic HCl was added dropwise. H$_2$O (0.1 mL) was added and the reaction was warmed to room temperature. The solution was left to stir for 24 hours, and the solvent evaporated off in vacuo. The oil was dissolved in ethyl acetate (50 mL) and washed with 10% Na$_2$CO$_3$ (50 mL) solution. The organic layer was dried (MgSO$^4$), filtered, and evaporated to dryness. The product was isolated by flash chromatography (ethyl acetate:hexane, 1:1) to yield the wanted product. (0.120 g, 67%) as a yellow oil, υ$_{max}$ (cm$^{-1}$, thin film) 3350 (NH); 3425 (NH br); 1741 (CO ester), H (300 M Hz, CDCl$_3$), δ 2.12 (2H, brs, NH2); 3.17 (1H, d, J 18 Hz, CH$_2$CO$_2$CH$_3$); 3.28 (1H, d, J 18 Hz, CH$_2$CO$_2$CH$_3$); 3.37 (1H, d, J 15 Hz, indole-CH$_2$); 3.43 (3H, s, OCH$_3$); 3.53 (1H, d, J 15 Hz, indole-CH$_2$); 4.82 (1H, d, J 12 Hz, CH$^2$Ph); 4.92 (1H, d, J 12 Hz, CH$_2$Ph); 6.73 (1H, d, J 2 Hz, 2-H); 6.95–7.21 (8H, m, 5-H+6-H+7-H+H$_{arom}$); 7.47 (1H, s, 4-H); 8.42 (1H, s, NH).

Step 2. Methyl-(±)-β-[(phenylmethoxy)carbonyl]-β-[(tricyclo-[3.3.1.1$^{3,7}$]dec-2-vloxy)carbonyl]-amino]-1H-indole-3-butanoate (65)

Methyl-(±)-β-amino-β-[(phenylmethoxy)carbonyl]-1H-indole-3-butanoate (64) (120 mg, 0.33 mmol) was dissolved in dry THF (10 mL) under argon. Triethylamine (55 μL, 0.40 mmol) was injected. The solution was cooled to 0° C. in an ice- alt bath and 2-adamantyl chloride (77 mg, 0.36 mmol) dissolved in THF (5 mL) was injected. The solution was stirred for 12 hours at room temperature before triethylamine hydrochloride was filtered off. Dichloromethane (50 mL) was added and the solution was washed with water (2×25 mL). The organic payer was dried (MgSO$_4$), filtered, and evaporated to dryness. The product was isolated by flash chromatography (ether: hexane, 1:1), to furnish the title compound (105 mg, 58%), m.p. 61.5°–62.5° C. υ$_{max}$: (cm$^{-1}$, thin film) 3412 (NH), 1738 (CO), H (300M Hz, CDCl$_3$), 1.49–2.09 (14H, m, adamantyl-H); 3.12 (1H, d, J 15 Hz, CHH$_2$CO$_2$CH$_3$); 3.30 (1H, d, J 15 Hz, CH$_2$CO$_2$CH$_3$); 3.38

(s, 3H, OCH$_3$); 3.72 (1H, d, J 15 Hz, indole-CH$^2$); 3.80 (1H, d, J 15 Hz, indole-CH$^2$); 4.83 (1H, brs, CH); 4.98 (1H, d, J 112 Hz, PhCH$_2$); 5.11 (1H, d, J 12 Hz, PhCH$_2$); 6.88 (1H, s, NH); 6.79 (1H, s, 2-H); 7.03 (1H, t, J 7 Hz, 6-H); 7.14 (1H, t, J 7 Hz, 5-H); 7.17–7.34 (6H, m, 7-H, H$_{arom}$), 7.48 (1H, d, J-8 Hz, 4-H), 8.30 (1H, s, NH). m/z (FAB) 545 (M+1); 501; 130. Found: C, 70.6%; H, 6.8%; N, 5.0%; C$_{32}$H$_{36}$N$_2$O$_6$ requires C, 70.6%; H, 6.7%; N, 5.1%).

Step 3. Methyl-(±)-β-carboxy-β-[[(tricyclo-[3.3.1.1$^{3,7}$]dec-2-yloxy)carbonyl]amino]-1H-indole-3-butanoate (66)

In a 250-mL glass vial, methyl-(±)-β-[(phenyl-methoxy)carbonyl]-β-[[(tricyclo[3.3.1.1$^{3,7}$]dec-2-yloxy)carbonyl[amino]-1H-indole-3-butanoate (65) (105 mg; 0.19 mmol). Palladium on charcoal (10%, Ca 20 mg) and ethanol (75 mL) was added. The vessel was sealed in a Parr Hydrogenation Apparatus and charged with H$_2$ gas (45 psi). Shaking was initiated after pressurization and continued for 12 hours. Upon completion, palladium on charcoal (10%) was filtered of and the filtrate evaporated to dryness. The product was isolated by flash chromatography (methanol: water, 2:1) to yield a white powder (77 mg, 88%), m.p. 108°–9° C. υ$_{max}$ (cm$^{-1}$, thin film) 3413 (NH); 1733 (CO). υ H (300M Hz, CDCl$_3$), 1.47–2.07 (14H, m, adamantyl-H); 3.14 (1H, d, J 16 Hz, CH$_2$CO$_2$CH$_3$); 3.26 (1H, d, J 16 Hz, CH$_2$CO$_2$CH$_3$); 3.64 (3H, s, OCH$_3$); 3.76 (1H, d, J 15 Hz, indole-CH$^2$); 3.84 (1H, d, J 15 Hz, indole-CH$_2$); 4.83 (1H, brs, CH); 5.75 (1H, brs, OH); 5.96 (1H, s, NH); 6.98–7.04 (2H, m, 2-H+6-H); 7.10 (1H, t, J 7 Hz, 5-H); 7.28 (1H, d, J 8 Hz, 7-H); 7.61 (1H, d, J 8 Hz, 4-H); 8.34 (1H, s, NH). δ c (75.5M Hz, CDCl$_3$) 27.0, 27.2 31.3, 31.7, 32.1, 36.4, 37.4, 39.7, 51.8, 62.4, 78.0, 108.9, 111.1, 118.7, 119.4, 121.7, 124.1, 128.2, 135.7, 154.8, 171.3, 176.2. m/z (FAB) 455 (M+1), 411, 217, 135, 130. Found: C, 65.7%; H, 6.7%; N, 6.0%. C$_{25}$H$_{30}$N$_2$O$_6$ requires C, 66.1%; H, 6.65%; N, 6.2%.

Step 4. Methyl-(±)-β-[[(2-phenylethyl)amino] carbonyl-β-[[(tricyclo[3.3.1.1$^{3,7}$]dec-2-yloxy) carbonyl]amino]-1H-indole-3-butanoate (67)

Methyl-(±)-β- [[(tricyclo[3.3.1.1$^{3,7}$]dec-2-yloxy)-carbonyl[amino]-1H-indole-3-butanoate (66) (200 mg, 0.44 mmol) was dissolved followed by dicyclohexyl-carbodiamide (100 mg, 0.48 mmol). The solution was left stirring for 2 hours before phenylethylamine (60 mg, 0.50 mmol) was injected to the solution. The mixture was left stirring overnight. The solution was evaporated down to dryness, ethyl acetate added, and dicyclohexylurea filtered off. The filtrate was evaporated down to dryness and the product was isolated by flash chromatography (hexane:ethyl acetate, 3:1) to give a white solid (180 mg, 73%), m.p. 78.0–79.5° C. υ$_{max}$ (cm$^{-1}$, thin film), 3333 (NH), 1730 (CO), 1659 (CO amide), H (300M Hz, CDCl$_3$), δ 1.51–2.04 (14H, m, adamantyl-H); 2.61 (2H, m, CH$_2$NH); 2.94 (1H, d, J 16 Hz, CH$^2$CO$_2$CH$_3$); 3.21 (1H, d, J 16 Hz, CH$_2$CO$_2$CH$_3$); 3.37 (1H, d, J 7 Hz, CH$_2$Ph); 3.41 (1H, d, J 7 Hz, CH$_2$Ph); 3.46 (1H, d, J 15 Hz, indole-CH$_2$); 3.57 (1H, d, J 15 Hz, indole-CH$_2$); 3.62 (3H, s, OCH$_3$); 4.78 (1H, brs, CH); 5.88 (1H, brs, NH urethane); 6.58 (1H, brs, NH amide); 6.92 (1H, d, J 2 Hz, 2-H); 7.03–7.26 (7H, m, 5-H+6-H+H$_{arom}$); 7.33 (1H, d, J 8 Hz, 7-H); 7.56 (1H, d, J 8 Hz, 4-H). mz/ (FAB). 558 (M+1), 362, 331, 231, 135, 130, 105. (Found: C, 69.0; H, 6.8; N, 7.2. C$_{33}$H$_{39}$N$_3$O$_5$·0.75H$_2$O requires C, 69.4; H, 7.1; N, 7.4).

Step 5. Tricyclo[3.3.1.1$^{3,7}$]dec-2-yl-(±)-[3-(1H-indol-3-yl-methyl)-2,5-dioxo-1-(2-phenylethyl)-3-pyrrolidinyl]-carbamate (68)

The ester (67) above (110 mg, 0.20 mmol) was dissolved in 20 mL THF and cooled to 0° C. Lithium hydroxide (21 mL, 0.01 M) was added dropwise to the solution over a 3-hour period. The solution was kept stirring for a further 1 hour and then allowed to warm to room temperature. Hydrochloric acid (2.1 mL, 0.1 M) was added and the solution extracted with ethyl acetate (3×20 mL). The organic layers were combined, dried with MgSO$_4$, filtered, and evaporated to dryness, to afford (105 g, 98%) of crude product. The product was isolated by flash chromatography (methanol:water, 4:1) as a white powder (84 mg, 78.5%). υ$_{max}$ (cm$^{-1}$, thin film). 3347 (NH), 2912 (CH); 1781 (CO), 1701 (CO). H (300M Hz, CDCl$_3$) δ 1.55–1.97 (14H, m, adamantyl-H); 2.38 (2H, m, NHCH$_2$); 3.00 (1H, d, J 18 Hz, CH$_2$CON); 3.05 (1H, d, J 15 Hz, indole-CH$_2$); 3.47 (2H, t, J 8 Hz, CH$^2$Ph); 4.80 (1H, s, CH); 5.49 (1H, s, NH); 7.04–7.35 (8H, m, 5-H +6-H+7H+H$_{arom}$; 7.56 (1H, d, J 8 Hz, 4-H); 8.68 (1H, s, NH). C (75.5M Hz, CDCl$_3$), 26.9, 27.1, 31.7, 32.0, 36.3, 37.3, 39.8, 40.2, 59.95, 76.4, 107.3, 111.4, 118.6, 120.2, 122.7, 123.7, 126.4, 127.4, 128.7, 136.0, 138.0, 154.9, 174.1, 176.1. m/z (C.I.) 528 (M+1). 527, 526, 374, 331, 130. Found: C, 72.6%; H, 6.7%; N, 7.9%; C$_{32}$H$_{35}$N$_3$O$_4$0.25H$_2$O requires C, 72.5%; H, 6.7%; N, 7.9%).

Example 41

(R$^2$ =Me. see Scheme 15a)

A suspension of powdered sodium hydroxide (2 g, 50 mmol) and ethyl 2-cyanopropionate (20 g, 157 mol) in 150 mL toluene was heated under nitrogen atmosphere to 100° C. and gramine (30.1 g, 172 mmol) added in portions. After 30 minutes the temperature was raised to 130° C. (oil bath) and the mixture gently refluxed for 16 hours. Then 100 mL water and 200 mL ethyl acetate were added, the mixture neutralized with acetic acid, the organic layer separated, washed with water (100 mL), dried (sodium sulfate) and evaporated. The residue was purified by chromatography over silica gel using toluene/ethyl acetate (1:1, v/v, Rf 0.4). 2a was isolated as a light brown viscous oil (34.5 g, 860%). MS (70eV): m/z 256 (M$^+$, 8%), 130 (100%).

Example 42

(R$^2$ =Me, see Scheme 15a)

Compound 2a (5 g, 19.5 mmol) in 250 mL dioxane, saturated with ammonia, was hydrogenated (100 bar, 80° C.) with Raney nickel alloy (0.95 g) in an autoclave for 1 hour. After filtration and evaporation the residue was purified by chromatography over silica gel using dichloromethane/methanol (95:5, v/v, Rf 0.1). 3a was isolated as a colorless viscous oil (4.76 g, 94%). MS (70eV): m/z 260 (M$^+$, 17), 130 (100), 117 (48).

Example 43

(R$^1$=2-adamantyl, R$^2$ =Me, see Scheme 15a)

To a stirred solution of 2-adamantylchloroformate (4.45 g, 20.7 mmol) in dry THF (50 mL) under N$_2$ atmosphere was added a solution of 3a (4.76 g, 18.3 mmol) in dry THF (100 mL) followed by a solution of triethylamine (3.7 g, 36.6 nunol) in dry THF (50 mL) dropwise. After 15 minutes the reaction mixture was filtered, the solvent removed and the residue column chromatographed on silica gel using CH$_2$Cl$_2$/MeOH (98:2) as eluents to yield 4a as a colorless amorphous solid (7.8 g, 97%). MS (70eV): m/z 438 (M$^+$, 20), 130 (100).

Example 44

(R$^1$=2-adamantyl, R$^2$=Me. see Scheme 15a)

To a solution of 4a (3.9 g, 8.9 mmol) in dioxane/H$_2$O 2:1 (60 mL) was added an excess of LiOH (0.325 g, 13.5 nmmol) and stirred at room temperature for 72 hours. After removing the solvent in vacuo the residue was suspended in water (50 mL), neutralized with acetic acid, extracted with $CH_2Cl_2$ and the organic layer separated and dried (sodium sulfate). After filtration and evaporation the residue was chromatographed using $CH_2Cl_2$/MeOH 95:5 (v/v, Rf 0.3) as eluents to yield the acid 5a as a colorless, amorphous solid (2.5 g. 69%). MS (70eV): m/z 410 ($M^+$, 4), 130(100).

Example 45
($R^1$=2-adamantyl, $R^2$=Me. $R^3$=—$CH_2OH$. c=1, $R^4$=H, see Scheme 15a)

Carbamic acid, [3- [[1-r(hydroxymethyl)-2-phenylethyl]amino]-2-(1H- indol-3-ylmethyl)-2-methyl-3-oxopropyl]-, tricyclo[3.3.1.1$^{3,7}$]dec-2-yl ester [S-(R*,RS)]-

To a solution of 5a (1 g, 2.44 mmol) in dry ethyl acetate (40 mL) was added pentafluorophenol (0.45 g, 2.44 mmol) and stirred for 10 minutes. The reaction mixture was cooled to 0° C. and a solution of dicyclohexylcarbodiimide (0.505 g, 2.44 mmol) in ethyl acetate (10 mL) was added dropwise. This solution was stirred for one hour at 0° C. then at room temperature for four hours before leaving it at 4° C. overnight. The mixture was filtered and the precipitate washed with cold ethyl acetate (10 mL) and a solution of (S)-(-)-phenylalaninol (0.405 g, 2.68 mmol) in ethyl acetate (25 mL) was added dropwise to the combined filtrates. The mixture was left to stir for 4 days at room temperature. The reaction mixture was diluted with ethyl acetate (100 mL), washed with water (100 mL), dried (sodium sulfate) and evaporated. The residue was chromatographed on silica gel using $CH_2Cl_2$/MeOH (98:2) as eluants to yield 6a as a colorless amorphous solid (0.780 g, 59%, mixture of two diastereomers), m.p. 85°–95° C. CI-MS (70eV, NH3): m/z 544 ($MH^+$, 100), 392 (76).

In an analogous manner Examples 46-57 are prepared: (C*=configuration at the chiral C-atom of the substituted 2-phenylethylamide residue, $R^2$ center is always RS)

Example 46
($R^1$ =(1S)-2-bornyl, $R^2$=Me, $R^3$=$R^4$=H, c=1)

Carbamic acid, [2-(1H-indol-3-ylmethyl)-2-methyl-3-oxo-3-[(2-phenylethyl)amino]propyl-, 1,7,7-trimethylbicyclo[2.2.1]hept-2-yl ester (Bicyclo system is 1S-endo. chain center is RS)
m.p. 60°–70° C., MS (70eV): m/z 515 ($M^+$,5), 130 (100)

Example 47
($R^1$=1-adamantyl, $R^2$=Me, $R^3$=$R^4$=H, c=1)

Carbamic acid, [2-(1H-indol-3-ylmethyl)-2-methyl-3-oxo-3-[(2-phenylethyl)amino]-propyl-, tricyclo-[3.3.1.1$^{3,7}$]dec-1-yl ester, (±)-
m.p. 75°–85° C., MS (70eV): m/z 513(M+,100), 305(91)

Example 48
($R^1$=2-adamantyl, $R^2$=Me, $R^3$=$R^4$=H, c=1)

Carbamic acid, [2-(1H-indol-3-ylmethyl)-2-methyl-3-oxo-3- [(2- phenylethvl)amino]propyl]-, tricyclo [3.3.1.1$^{3,7}$]dec-2-yl ester, (±)- m.p. 75°–85° C., MS (70eV): m/z 513 ($M^+$,25), 305 (88), 134 (100)

Example 49
($R^1$=(1S)-2-bornyl, $R^2$=Me, $R^3$=$CH_2OH$, $R^4$=H, c=1. C*=S)

Carbamic acid, [3-[[1-(hydroxymethyl)-2-phenylethyl]amino]-2-(1H-indol-3-ylmethyl)-2-methyl-3-oxopropyl]-1.7.7-trimethylbicyclo [2.2.1] hept-2-yl ester (Bicyclo system is 1S-endo, hydroxymethyl center is S, other center is RS)
m.p. 75°–85° C., MS (70eV): m/z 545 ($M^+$,7), 130 (22), 95 (77), 44 (100)

Example 50
($R^1$=2-adamantyl, $R^2$=Me, $R^3$=H, $R^4$=NHCOCH$_2$CH$_2$CO$_2$Bz, c=1, C*=R)

14-Oxa-2,6.9-triazapentadecanoic acid, 4-(1H-indol-3-ylmethyl-4-methyl-5,10,13-trioxo-8,15-diphenyl-, tricyclo[3.3.1.1$^{3,7}$]-dec-2-yl ester. [R-(R*,R*)]-
m.p. 80°–90° C., CI-MS (CH$_4$): m/z 611 (21), 459 (21), 135 (100)

Example 51
($R^1$=2-adamantyl, $R^2$=Me, $R^3$=H, $R^4$=NHCOCH=CHCO$_2$Me, c=1, C*=R)

14-Oxa-2,6,9-triazapentadec-11-enoic acid, [4-(1H-indol-3-yl-methyl)-4-methyl-5,10,13-trioxo-8-phenyl-, tricyclo[3.3.1.1$^{3,7}$]dec-2-vl ester. [R-[R*, R*-(E)]-
m.p. 105°–120° C., CI-MS (CH$_4$): m/z 641 ($MH^+$, 1), 151 (18), 135 (100)

Example 52
($R^1$=2-adamantyl, $R^2$=Me, $R^3$=H, $R^4$=NHCO$_2$-t-Bu, c=1, C*=R)

11-Oxa-2,6,9-triazatridecanoic acid, 4-(1H-indol-3-ylmethyl)-4,12,12-trimethyl-1,5,10-trioxo-8-phenyl-, tricyclo[3.3.1.1$^{3,7}$] dec-2-yl ester. [R-(R*,R*)]-
m.p. 100°–110° C., CI-MS (CH$_4$): m/z 629 ($MH^+$, 8), 135 (100)

Example 53
($R^1$=2-adamantyl, $R^2$=Me, $R^3$=H, $R^4$=NHCOCH$_2$CH$_2$CO$_2$H, c=1, C*=R)

Butanoic acid, 4- [[2- [[2-(1H-indol-3-ylmethyl)-2-methyl-1-oxo-3- [[(tricyclo[3.3.1.1$^{3,7}$]dec-2-yloxy)carbonyl]amino]-propyl]amino]-1-phenylethyl]amino]-4-oxo-, [R-(R*,R*)]-
m.p. 110°–125° C., CI-MS (CH$_4$): m/z 628 ($M^-$, 21), 164 (100)

Example 54
($R^1$=2-adamantyl, $R^2$=Me, $R^3$=H, $R^4$=NHCOCH=CH—CO$_2$H, c=1, C*=R)

2-Butenoic acid, 4-[2-[[2-(1H-indol-3-ylmethyl)-2-methyl-1-oxo-3-[[(tricyclo[3.3.1.1$^{3,7}$]dec-2-yloxy)carbonyl]amino]-propyl]amino]-1-phenylethyl]-4-oxo- (Trp center RS; other center R: double bond E)
m.p. 210°–220° C., CI-MS (CH$_4$): m/z 626 ($M^-$,7), 474 (100), 164 (88)

Example 55
($R^1$=2-adamantyl, $R^2$=Me, $R^4$=H, c=0)

Carbamic acid, [2-(1H-indol-3-ylmethyl)-2-methyl-3-oxo-3-[(phenyl methyl)amino]-propyl]-, tricyclo [3.3.1.1$^{3,7}$]dec-2-yl ester. (±)-
m.p. 80°–90° C., MS (70eV): m/z 499 ($M^+$,25), 291 (47), 130 (100)

Example 56
($R^1$=(1S)-2-bornyl, $R^2$=Me, $R^3$=CH$_2$OCOCH$_2$CH$_2$CO$_2$H, R4=H, c=1, C*=S)

Butanedioic acid, mono 2-[[2-(1H-indol-3-ylmethyl)-2-methyl-1-oxo-3-[[(1,7,7-trimethylbicyclo[2.2.1]hept-2-yloxy)carbonyl]-amino]propyl]amino]-3-phenylpropyl ester (Bicyclo system is 1S-endo, phenvlmethyl center is S. other center is RS)
m.p. 115–130, CI-MS (CH$_4$): m/z 646 ($MH^+$, 34), 528 (78), 101 (100)

Example 57
($R^1$=2-adamantyl, $R^2$=Me, $R^3$=$CH_2OCOCH_2CH_2CO_2H$, $R^4$=H, c=1, C*=S)

Butanedioic acid, [2-[[2-(1H-indol-3-ylmethyl)-2-methyl-1-oxo-3-[[(tricyclo[3.3.1.1$^{3,7}$]dec-2-yloxy)carbonyl]amino]proloyl]-amino]-3 phenylpropyl ester (Trp center RS; other center S)

m.p. 85°–95° C., CI-MS ($C_4H_{10}$): m/z 643 (M⁻, 16), 642 (19), 235 (100)

The conversion of compound 5a ($R^1$=2-adamantyl, $R^2$=Me) to the compounds 6f, 6g, 6h, 6i, 6k, and the conversion of compounds 6a and 6e to the compounds 6m and 6n has been done in analogy to already described procedures. Compounds of general formula Ia, where $R^2$, $R^3$ and $R^4$ are H are also prepared according to synthetic scheme 15b:

Example 58

(c=1, see Scheme 15b)

A solution of N-(β-phenylethyl)cyanoacetamide (8a, 18.8 g, 0.1 mol), indole-3-carboxaldehyde (14.5 g, 0.1 mol) and piperidine (5 drops) in ethanol (100 mL) was refluxed for 16 hours. After cooling to room temperature the precipitate was filtered off, washed with ethanol (2×20 mL) and dried to give 9a as yellow crystals (29 g, 92%). MS (70ev): m/z 315 (M⁺,14), 195 (100).

Example 59
(c=1, see Scheme 15b)

Compound 9a (3.15 g, 10 mmol) in 50 mL dioxane, saturated with ammonia, was hydrogenated (100 bar, 80° C.) with Raney nickel alloy (0.5 g) in an autoclave for 17 hours. After filtration and evaporation the residue was chromatographed on silica gel using $CH_2Cl_2$/MeOH 9:1 (v/v) as eluents. 10a was obtained as colorless crystals from ethyl acetate (1.16 g, 36%). MS (70eV): m/z 321 (M⁻, 46), 170 (93); 130 (100).

Example 60
($R^1$=2-adamantyl. c=1, see Scheme 15b)

Carbamic acid, [2-(1H-indol-3-ylmethyl)-3-oxo-3-[(2-phenylethyl)amino]propyl]-, tricyclo[3.3.1.1$^{3,7}$]dec-2-yl ester, (±)-

The conversion of 10a to 11a was done according to the conversion of 3a to 4a. After chromatographic separation using $CH_2Cl_2$/MeOH 98:2 as eluents 11a was isolated as a colorless amorphous solid (87%), m.p. 115°–140° C. MS (70eV): m/z 499 (M⁺, 3), 291 (100).

Examples 61 and 62
(c=1, see Scheme 15c)

A suspension of powdered sodium hydroxide (0.5 g, 12.5 mmol) and N-(β-phenylethyl)cyanoacetamide (8a, 8 g, 42.5 mmol) in 50 mL toluene was heated under nitrogen atmosphere to 100° C. and gramine (7.4 g, 42.5 mmol) added in portions. After 30 minutes the temperature was raised to 130° C. (oil bath) and the mixture gently refluxed for 2 hours. Then 50 mL water and 200 mL ethyl acetate were added, the mixture neutralized with acetic acid, the organic layer separated, washed with water (100 mL), dried (sodium sulfate) and evaporated. The residue was separated by chromatography on silica gel using $CH_2Cl_2$/EtOAc 9:1 (v/v) as eluents.

1. fraction: compound 13a as colorless crystals (4.5 g, 47%) MS (70eV): m/z 446 (M⁺, 4), 130 (100).

2. fraction: compound 12a, colorless crystals from ethanol (3.05 g, 23%). MS (70eV): m/z 317 (M⁺, 18), 130 (100).

Example 63
($R^1$=2-adamantyl, c=1)

Carbamic acid, [2.2-bis(1H-indol-3-ylmethyl)-3-oxo-3-[(2-phenylethyl)amino]propyl]-, tricyclo[3.3.1.1$^{3,7}$)-dec-2-yl ester The conversion of 13a (c=1) to 17a ($R^1$=2-adamantyl, c=1) was completed in analogy to the conversion of 2a to 4a. After purification by chromatography on silica gel using $CH_2Cl_2$/MeOH 98:2 17a was isolated as a colorless amorphous solid (yield 50% from 13a), m.p. 105°–110° C. CI-MS ($NH_3$): m/z 629 (MH⁺, 100%).

Example 64
($R^1$=1-adamantyl, $R^2$=Me, see Scheme 16)

To a stirred solution of 3a (3 g, 11.5 mmol) in anhydrous THF (100 mL) at room temperature was added adamantane-1-carbonyl chloride (2.28 g, 11.5 mmol), followed by a solution of triethylamine (3.2 mL, 23 mmol) in THF (20 mL) dropwise. The reaction was complete after 30 minutes as assayed by thin layer chromatography. The reaction mixture was filtered and the solvent removed in vacuo. The residue was purified by chromatography over silica gel using $CH_2Cl_2$/MeOH 98:2 as eluents. 18a was isolated as a colorless amorphous solid (3.25 g, 67%). MS (70eV): m/z 422 (M⁺, 35), 293 (34), 130 (100).

Example 65
($R^1$=1-adamantyl, $R^2$=Me, see Scheme 16)

To a solution of 18a (3.25 g, 7.7 mmol) in 1.4-dioxane/$H_2O$ (2:1, 90 mL) was added an excess of LiOH (0.37 g, 15.4 mmol) and the solution stirred at room temperature for 48 hours. After removing the solvent in vacuo the residue was dissolved in water (150 mL), acidified with citric acid (10% in water) and extracted with dichloromethane (2×100 mL). The organic layer was dried ($Na_2SO_4$) and evaporated. 19a was isolated as a colorless, amorphous solid (3 g, ≈100% ). TLC (silica gel): Rf 0.2 ($CH_2Cl_2$/MeOH 95:5).

Example 66
($R^1$=1-adamantyl, $R^2$=Me, $R^3$=—$CH_2OH$, c=1, $R^4$=H, see Scheme 16)

1H-Indole-3-prolanamine, N-[1-(hydroxymethyl)-2-phenylethyl]-α- methyl-α-[[(tricyclo[3.3.1.1$^{3,7}$]dec-2-ylcarbonyl)amino]methyl]- (indole center is RS, other center is S)

The conversion of 19a to 20a was done in analogy to the conversion of 5a to 6a. After purification by chromatography on silica gel using $CH_2Cl_2$/MeOH 98:2 20a was isolated as a colorless amorphous solid (52%), m.p. 85°–95° C. MS (70eV): m/z 527 (Me⁺, 30), 335 (100).

There is obtained in an analogous manner:

Example 67
($R^1$=1-adamantyl, $R^2$=Me, $R^3$=H, c=1, $R^4$ =H)

1H-Indole-3-propanamide, α-methyl-N-(2-phenylethyl)-α-[[(tricyclo[3.3.1.1$^{3,7}$]dec-2-ylcarbonyl)amino]methyl], (±)-

A colorless amorphous solid, m.p. 80°–90° C. MS (70eV): m/z 497 (M⁺,9), 305 (43), 184 (56), 135 (64), 130 (100).

Example 68

(See Scheme 17)

In an autoclave 1-(3'-indolyl)-butan-3-one (12.32 g, 65.9 mmol), potassium cyanide (4.7 g, 72.3 mmol), ammonium carbonate (6.9 g, 71.8 mmol) and ammonium hydroxide (25%, 13 mL) in water (25 mL) and methanol (75 mL) were heated to 60° C. for 16 hours with stirring. The solution was diluted with water (100 mL), the methanol evaporated and the residual mixture acidified (2n HCl). The precipitated hydantoin 21 was filtered off, washed with water and dried. Yield: 15.2 g (90%) colorless crystals. MS (70eV): m/z 257 (M$^+$, 22), 144 (96), 130 (100).

Example 69

(See Scheme 17)

In an autoclave 21 (10 g, 38.9 nmol) in 5% aqueous sodium hydroxide (125 mL) was heated to 150° C. for 16 hours. After cooling to room temperature, the solution was neutralized with hydrochloric acid (37%) and if necessary filtered immediately to remove traces of hydantoin 21. The solution was stirred at room temperature for 2 hours and the precipitated amino acid 22 filtered off, washed with water (20 mL) and dried. 22 was isolated as pale beige crystals (8.52 g, 94%). MS (70eV): m/z 232 (M$^+$, 26), 144 (100), 130 (92).

Example 70

(See Scheme 17)

A solution of 22 (5 g, 21.5 mmol) in dry methanol (375 mL) was warmed to 40° C. and saturated with hydrogen chloride (1 hour). After stirring at 40°–45° C. for 5 hours and at room temperature for another 15 hours the solvent was evaporated. Water (100 mL) was added, the mixture neutralized with aqueous sodium carbonate and extracted with ethyl acetate (2×100 mL). The organic layer was washed with diluted sodium bicarbonate solution (50 mL) then with water (50 mL) and dried (Na$_2$SO$_4$). After removing the solvent the residue was chromatographed on silica gel using CH$_2$Cl$_2$/MeOH 98:2 (v/v) as eluents. 23 was isolated as beige crystals (4.0 g, 75%). MS (70eV): m/z 246 (M$^+$, 25), 144 (71), 130 (100).

Example 71

(R$^1$=2-adamantyl. see Scheme 17)

The reaction of aminoester 23 with 2-adamantyl-chloroformate was done according to the conversion of 3a to 4a. 24a was isolated in 86% yield as a colorless amorphous powder. MS (70eV): m/z 424 (M$^+$, 42), 281 (41), 144 (100), 135 (78).

Example 72

(R$^1$=2-adamantyl. see Scheme 17)

The hydrolysis of 24a with lithium hydroxide was done according to the hydrolysis of 4a to 5a. 25a was isolated without chromatography as a pale beige amorphous powder in quantitative yield, pure enough to be used in the next step (see Example 73) without further purification. MS (70eV): m/z 410 (M$^+$, 5), 130 (100).

Example 73

(R$^1$=2-adamantyl, R$^3$=R$^4$=H, c=1, see Scheme 17)

Carbamic acid, [3-(1H-indol-3-yl)-1-methyl-1-[[(2-phenylethyl)amino]carbonyl]-provyl]-, tricyclo-[3.3.1.1$^{3,7}$]dec-2-yl ester, (±)-

The conversion of 25a with 2-phenylethylamine to 26a was done according to the conversion of 5a to 6a. After chromatographic separation on silica gel using CH$_2$Cl$_2$/MeOH 98:2 (v/v) 26a (Rf 0.2) was isolated in 69% yield as a colorless amorphous powder, m.p. 75°–85° C. MS (70eV): m/z 513 (M$^+$, 1), 370 (67), 130 (100).

In analogous manner are prepared:

(C*=configuration at the chiral C-atom of the substituted 2-phenylethylamide residue, other center is always RS)

Example 74

(R$^1$=2-adamantyl, R$^3$=CH2OH, R$^4$=H, c=1, C*=S)

Carbamic acid, [1-[[[1- (hydroxymethyl)-2-phenylethyl]-amino]carbonyl]-3-(1H-indol-3-yl)-1-methylpropyl]-, tricyclo[3.3.1.1$^{3,7}$]dec-2-vl ester (hydroxymethyl center is S, other center is RS)

m.p. 80°–90° C., CI-MS (C$_4$H$_{10}$): m/z 544 (MH+, 2), 392 (100)

Example 75

(R$^1$=(1S)-2-bornyl, R$^3$=R$^4$=H, c=1)

Carbamic acid, [3-(1H-indol-3-yl)-1-methyl-1-[[(2-phenylethyl)-amino]carbonyl]propyl]-, 1.7,7-trimethyl-bicyclo[2.2.1]hept-2-yl ester, [1R-[1α,2α (S), 4α]]- m.p. 70°–80° C., CI-MS (CH$_4$): m/z 516 (MH$^+$, 2), 362 (100)

Example 76

(R$^1$=2-adamantyl, R$^3$=H, R$^4$=NHCOCH=CHCO$_2$Me, c=1, C*=R)

13-Oxa-2,5,8-triazatetradec-10-enoic acid, 3-[2-(1H-indol-3-yl) ethyl]-3-methyl-4,5,12-trioxo-7-phenyl-, tricyclo-[3.3.1.1$^{3,7}$]dec-2-yl ester (TRP center is R/S mixture, other center is R. double bond E)

m.p. 117°–123° C., CI-MS(C4H10): m/z 640(M$^-$,19), 487 (100)

Example 77

(R$^1$=2-adamantyl, R$^3$=H, R$^4$=NHCOCH2CH2CO2Bz, c=1, C*=R)

13-Oxa-2,5,8-triazatetradecanoic acid, 3-[2-(1H-indol-3-yl)ethyl]-3-methyl-4,9,12-trioxo-7,14-diphenyl-, tricyclo-∂3.3.1.1$^{3,7}$]dec-2-vl ester (TRP center is R/S mixture, other center is R)

m.p. 85°–95° C., CI-MS (C$_4$H$_{10}$): m/z 627 (20), 475(100), 251(44)

Example 78

(R$^1$=(1S)-2-bornyl, R$^3$=CH$_2$OH, R$^4$=H, c=1, C*=S)

Carbamic acid, [2-[[[1-(hydroxymethyl)-2-phenylethyl]amino]-carbonyl]-3-(1H-indol-3-yl)-1-methylpropyl]-, 1,7,7-trimethylbicyclo-[2.2.1]hept-2-yl ester (Bicyclo system is 1S-endo, hydroxymethyl center is S, other center is RS)

m.p. 75°–85° C., CI-MS (CH$_4$): m/z 546 (MH$^+$, 82), 153 (100)

Example 79

(R$^1$=2-adamantyl, R$^3$=H, R$^4$=NHCOCH$_2$CH$_2$CO$_2$H, c=1, C=R))

Butanoic acid, 4-[[2-[[4-(1H-indol-3-yl)-2-methyl-1-oxo-2-[[(tricyclo[3.3.1.1$^{3,7}$]dec-2-yloxy)carbonyl]-amino]butyl]amino]-1-phenylethyl]amino]-4-oxo-(indole center is RS, other center is R)

m.p. 115°–125° C., CI-MS (C$_4$H$_{10}$): m/z 629 (MH$^+$, 1), 191 (28), 135 (100)

Example 80
($R^1$=2-adamantyl, $R^3$=H, $R^4$=—NHCOCH=CHCO2H, c=1, C*=R)

2-Butenoic acid, 4-[2-[[2-[2-(1H-indol-3-yl)ethyl]-2-methyl-1-oxo-3-[[(tricyclo[3.3.1.1$^{3,7}$]dec-2-yloxy)-carbonyl]amino]propyl]amino]-1-phenylethyl]-4-oxo-(indole center is RS, other center is R. double bond E)

m.p. 190°–200° C., Cl-MS (NH$_3$): m/z 626 (M$^-$, 24), 201 (60), 151 (100)

The conversion of 26d to 26h and the conversion of 26e to 26g were done in analogy to already described procedures.

Example 81
(See Scheme 18)

The method is as described for 2a (compare lit. *J. Org. Chem.* 18:1440, 1447, 1953). Alkylation of diethyl methylmalonate with gramine provided compound 28 after chromatographic separation on silica gel using CH$_2$Cl$_2$/MeOH 98:2 (v/v) as eluents as a light red brown syrup (yield 90%). MS (70eV): m/z 303 (M$^-$, 11), 130 (100).

Example 82
(See Scheme 18)

To a solution of the diester 28 (31 g, 0.102 mol) in dry ethanol (80 mL) was added a solution of potassium hydroxide (6.5 g, 0.116 mol) in ethanol (65 mL) dropwise at room temperature (1 hour) and stirred for another 16 hours. The reaction mixture is filtered and the filtrate evaporated. The residue is suspended in water (700 mL), neutralized with hydrochloric acid and extracted with ether (3×250 mL). The ether solution was dried (Na$_2$SO$_4$), evaporated and the residue purified by chromatography on silica gel using CH$_2$Cl$_2$/MeOH 95:5 (v/v) as eluents. The monoacid 29 (Rf 0.1) was isolated as a light redbrown syrup (18 g, 64%). MS (70eV): m/z 275 (M$^+$, 9), 130 (100).

Example 83
(See Scheme 18)

To a solution of compound 29 (37 g, 0.134 mol) in dry tetrahydrofuran (500 mL) at 0° C. under nitrogen was added dropwise a 2 M solution of borane-methyl sulfide complex in tetrahydrofuran (100 mL, 0.2 mol) (45 min.) and stirred for 3 hours at 0° C. Then water (100 mL) was added dropwise, the mixture diluted with more water (400 mL) and ethyl acetate (800 mL). The organic layer was separated, washed with water (3×150 mL), dried (Na$_2$SO$_4$) and evaporated. The residue was suspended in CH$_2$Cl$_2$ (100 mL), the precipitated 29 filtered off and washed with CH$_2$Cl$_2$ (30 mL). 29 was isolated as colorless, sometimes slightly red crystals (26.74 g, 85%), pure enough to be used in the next step. TLC (silica gel): Rf 0.15 (toluene/tetrahydrofuran 1:1).

Example 84
(See Scheme 18)

To a solution of 30 (26.6 g, 0.114 mol) in dry methanol (1.5 l) were added 4 mL sulfuric acid (95–97%) and the solution stirred at room temperature for 2 days. The solution was neutralized with sodium bicarbonate solution, partially evaporated to remove the methanol, diluted with water (500 mL) and extracted with ethyl acetate (2×500 mL). The organic layer was washed with water (250 mL), dried (Na$_2$SO$_4$) and evaporated. The residue was chromatographed on silica gel using toluene/ethyl acetate 3:1 (v/v) as eluents. 31 was isolated as a colorless, viscous syrup (25.7 g, 91%). MS (70eV): m/z 247 (M$^+$, 8), 130 (100).

Example 85
(See Scheme 18)

To a solution of 31 (5.0 g, 20.2 mmol) and pyridine (3.2 g, 40.4 mmol) in dry dichloromethane (100 mL) at 0° C. was added p-toluene sulphonyl chloride (5.0 g, 26.3 mmol) in small portions. The solution was allowed to stand for 4 days in the refrigerator at 0°–5° C. The solution was washed with sodium bicarbonate solution (2×50 mL), dried (Na$_2$SO$_4$) and evaporated. The residue was chromatographed on silica gel using toluene/ethyl acetate 95:5 (v/v) as eluents. Compound 32 (Rf 0.3) was isolated as a viscous oil, which was recrystallized from diisopropyl ether to yield colorless crystals (6.94 g, 85%). MS (70eV): m/z 401 (M$^+$, 8), 130 (100).

Example 86
(See Scheme 18)

Compound 32 (3.5 g, 8.13 mmol) and potassium cyanide (0.850 g, 13.1 mmol) in dry dimethylformamide (60 mL) were stirred at 110° C. for 16 hours. The solution was evaporated in vacuo and the residue dissolved in ethyl acetate (200 mL) and water (200 mL). The organic layer was separated, dried (Na$_2$SO$_4$) and evaporated. The residue was purified by chromatography on silica gel using toluene/ethyl acetate 9:1 (v/v) as eluents. Compound 33 was isolated (Rf 0.4 in toluene/ethyl acetate 4:1) as a colorless syrup (1 g, 45%). MS (70eV): m/z 256 (M$^+$, 8) 130 (100).

Example 87
($R^1$=2-adamantyl, $R^3$=$R^4$=H, c=1, see scheme 18)

Carbamic acid, [3-(1H-indol-3-ylmethyl)-3-methyl-4-oxo-4-[[(2-phenylethyl)amino]butyl]-, tricyclo-[3.3.1.1$^{3,7}$]dec-2-yl ester, (±)-

The conversion of compound 33 to compounds 37 has been done in analogy to the conversion of compounds 2 to compounds 6 (see synthetic scheme 15a). 37a has been isolated after chromatographic separation on silica gel using CH$_2$Cl$_2$/MeOH 98:2 (v/v) as eluents as a colorless amorphous solid in 52% yield, m.p. 70°–80° C. MS (70eV): m/z 527 (M$^+$, 2), 130 (100).

Example 88
($R^1$=2-adamantyl, $R^3$=—CH$_2$OH, $R^4$=H, c=1, see Scheme 18)

Carbamic acid, [4-[[1- (hydroxymethyl)-2-phenylethyl]-amino]-3-(1H-indol-3-ylmethyl)-3-methyl-4-oxobutyl]-, tricyclo-[3.3.1.1$^{3,7}$]dec-2-yl ester In an analogous manner to the synthesis of 37a, compound 37b has been isolated after chromatographic separation on silica gel using CH$_2$Cl$_2$/MeOH 98:2 (v/v) as eluents as a colorless amorphous solid in 52% yield, m.p. 70°–80° C. MS (70eV): m/z 527 (M$^+$, 2), 130 (100). 37b is a mixture of two diastereomers (S-configuration at the chiral center derived from (S)-(−)-phenylalaninol).

Example 89
Ethylidene-isopropylamine (69)

Isopropylamine (85 mL, 1.0 mol) was added gradually dver a period of 1 hour to acetaldehyde (56 mL, 1.0 mol) cooled in an ice bath. After the addition was complete, the mixture was stirred for an additional 20 minutes. Potassium hydroxide flakes were added until the solution separated into two layers. The organic phase was separated and stored over crushed potassium hydroxide at 0° C. The dried material was distilled under vacuum at room temperature to yield the title compound (1) (51.4 g, 60%), b.p. 25°–30° C./10 mm; δ H (300 M Hz; CDCl₃); 1.09 (6H, d, J 6.3 Hz, 2CH₃), 1.88 (3H, d, J 4.8 Hz, CH₃CH).

3-(Isopropyl-aminoethylidene)-indole (70)

A solution of indole (25.0 g, 0.213 mol) in glacial acetic acid (150 mL) was cooled in an ice bath and ethylidene-isopropylamine (69) (17.3 g, 0.203 mol) in toluene (50 mL) added dropwise, with stirring over a period of 1 hour. The resulting mixture was kept at 0° C. for 5 days. After this period the mixture was poured onto an ice-ether mixture. The ether layer was separated and extracted with 1N potassium hydrogen sulphate (2×100 mL). The combined aqueous phase was washed with ether (2×50 mL), then made basic with 10N sodium hydroxide (keeping the temperature below 25° C.). The alkaline solution was extracted with ether (4–250 mL). The organic phase was dried (MgSO₄) and evaporated to dryness to give the title compound (2) (24.6 g, 60%), m.p. 107°–112° C. (lit.,[1] 108°–114° C.); $\upsilon_{max}$ (film) 3 479 cm⁻¹ (indole NH); δ H (300 M Hz, CDCl₃), 1.01 (3H, d, J 6 Hz, CH₃), 1.09 (3H, d, J 6 Hz, CH₃), 1.52 (1.52 (3H, d, J 6.6 Hz, CH₃), 2.88 (1H, septet, J 6 Hz, CH(CH₃), 4.27 (1H, q, J 6.6 Hz, indCH)CH₃), 7.08–0.25 (4H, m), 7.35 (1H, s, J 8 Hz, NH), 7.71 (1H, d, J 8 Hz, indole 4-H), 8.21 (1H, brs, indole NH).

Dibenzylacetamidomalonate (71)

Diethylacetamidomalbonate (9.1 g, 42 mmol) [Aldrich] in benzyl alcohol (26 mL, 0.25 mmol) was heated in an oil bath at 200° C. A slow stream of nitrogen was bubbled through the solution and the ethanol distilled out. After 4 hours the reaction mixture was cooled to room temperature and the excess benzyl alcohol removed in vacuo with the oil bath temperature being slowly raised to 185°–190° C., at which point distillation became very slow. The solution was cooled to room temperature and the resulting precipitate recrystallized from isopropanol to yield the title compound (71) (12.2 g, 85%); m.p. 111°–112° C. (lit.,[1] 110°–113° C.); $\upsilon_{max}$ (film) 1752, 1734 (ester C=0), 1651 (amide C=0), 740 and 694 cm⁻¹ (mono substituted pH); 6 H (300 M Hz, CDCl₃), 2.05 (3H, s, CH₃CO), 5.17 (2H, s, CH₂Ph), 5.18 (2H, s, CH₂Ph), 5.29 (1H, d, J 7 Hz, CHCO₂CH₂Ph)₂), 6.53 (1H, brd, J 6 Hz, NH), 7.27 (10H, m, 2Ph), δ c (75.5 M Hz, CDCl₃), 22.5, 56.5, 68, 128.5, 134.5, 166, 170.

Dibenzyl (3-indolylethylidene)acetamidomalonate (72)

The amine (70) (5.41 g, 26.7 mmol), diester (71) (9.12 g, 26.7 mmol) and sodium methoxide (38 mg, 0.70 mmol) were heated in toluene (30 mL) at 85°–95° C. (bath temperature) while a slow stream of nitrogen was bubbled through the solution. The reaction mixture was kept at this temperature for 5 hours, then cooled to −40° C. (freezer). The crude product was filtered and recrystallized from isopropanol to yield the title compound (72) (8.22 g, 64%), m.p. 162°–163° C. (Pr$^i$OH) (lit.,[1] 161°–163° C.); $\upsilon_{max}$ 1737 (ester C=0), 1672 (amide C=0), 743 and 697 cm⁻¹ (monosubstituted Ph); δ H (300 M Hz, CDCl₃), 1.57 (3H, d, J 7 Hz, CH₃), 1.97 (3H, s, CH₃CO), 4.32 (1H, q, J 7 Hz, CH CH₃)), 4.72 (1H, d, J 12 Hz, one of CH₂Ph), 4.89 (1H, d, J 12 Hz, one of CH₂OH):, 5.08 (1H, d, J 12 Hz, one of CH₂Ph), 5.20 (1H, d, J 12 Hz, one of Ch₂Ph), 6.56 (1H, s, NH), 6.86 (1H, d, J 2 Hz, indole 2-H), 7.02–7.33 (13H, m, indole+2Ph), 7.54 (1H, d, J 8 Hz, indole 4-H), 8.15 (1H, br s, indole NH), δ C (75.5 M Hz, CDCl₃), 18, 23, 37, 68, 70, 111.5, 115, 119.5, 122, 122.5, 127, 128, 134.5, 136, 167, 168, 169.5.

(3-Indolylethylidene)acetamidomalonic acid (73)

The diester (72) (930 mg, 1.92 mmol), palladium hydroxide on carbon (Pearlman's catalyst) (125 mg) and 95% ethanol (110 mL) were placed in a Parr hydrogenation vessel and subjected to a hydrogen pressure of 45 psi at 25° C. for 3 hours (until the uptake of hydrogen ceased). The reaction mixture was filtered through Celite to remove the catalyst, then evaporated to dryness to give the title compound (73) (576 mg, 99%) which was used without further purification. δ H (300 M Hz; D₂O), 1.55 (3H, d, J 7 Hz, CH₃), 1.99 (3H, S, CH₃CO), 4.09 (1H, brd, J 7 Hz, CH,(CH₃), 7.12–7.24 (3H, m), 7.49 (1H, d, J 8 Hz, indole 7-H), 7.71 (1H, d, J 8 Hz, indole 4-H).

2-Acetamido-3-(3-indolyl)butanoic acid (74)

The malonic acid (73) (5.48 g, 18.0 mmol) was refluxed in pyridine/water (1:1) (20 mL) until no diacid remained (S$_i$O₂:EtOH—EtOAc (1:1) +1% ACOH; rf 0.26). The reaction mixture was cooled, diluted with water (50 mL), and acidified with 10% sulphuric acid (50 mL). The resulting solution was left at 0° C. overnight to crystallize. The brown solid was filtered off and dried to yield 2-acetamido-3-(3-indolyl)butanoic acid isomer A (74A) (1.30 g, 28%); δ H (300 M Hz; d₆-DMSO), 1.32 (3H, J 9 Hz, CH₃), 1.84 (3H, s, CHH₃CO), 3.46–3.55 (1H, m, indCH(CH₃)—), 4.58–4.67 (1H, m, CH(COOH)NHAc), 6.93–7.19 (3H, m), 7.34 (1H, d, J 8 Hz, amide NH), 7.54 (1H, J 8 Hz, indole 7-H), 8.04 (1H, d, J 9 Hz, indole-4H), 10.81 (1H brs, indole NH), ca 12.4 (vbrs, CO₂H). The filtrate was extracted with ethyl acetate (4×100 mL). The ethyl acetate extracts were combined and washed with water (2×50 mL) then extracted with 10% sodium hydrogen carbonate (2×100 mL). The sodium hydrogen carbonate extract was acidified with 4N sulphuric acid then extracted with ethyl acetate (2×75 mL). The ethyl acetate solution was washed with water (2×25 mL) then evaporated to dryness to give a beige foam, 2-acetamido-3-(3-indolyl)butanoic acid isomer B (74B) (2.17 g, 46%); 6 H (300 M Hz, d₆-DMSO), 1.32 (3H, d, J 7 Hz, CH₃), 1.84 (3H, s, CH₃CO), 3.50 (1H, M, ind CH(CH₃)—), 4.66 (1H, m, CH(COOH)NHAc), 6.93–719 (3H, m), 7.34 (1H, d, J 8 Hz, amide NH), 7.63 (1H, d, J 8 Hz, indole 7-H), 7.84 (1H, d, J 9 Hz, indole 4-H), 10.83 (1H, s, indole NH), ca 12.5 (vbrs, CO₂H).

Deacetylation of acids (74A) and (74B)

The acids (74A) and (74B) were deacetylated separately by the same procedure. Nitrogen was bubbled through a mixture of acid (74B) (3.96 g, 15.2 mmol) in 4N sulphuric acid (25 mL) for 30 minutes, then the mixture was refluxed until all the solid dissolved. The solution was cooled to room temperature and neutralized to pH 8 with 0.4N barium hydroxide. The barium salts were precipitated with solid carbon dioxide, the mixture heated to boiling point and filtered hot. The solvent was removed in vacuo and the crude product purified by reverse phase column chromatography [methanol-water (1:6) as eluant] to give 2-amino-3-(3-indolyl)butanoic acid (75) (2.34 g, 71%) in a ratio of 1:3 (75A:75B), m.p. 198°–212° C. (lit.[1], 218°–225° C. dec); isomer A δ H (300 M Hz, D₂O), 1.33 (3H, d, J 7 Hz, CH₃), 3.66–3.75 (2H, m, indCH(CH₃)- +CH(Co₂H)NH₂), 7.20–7.34 (2H, m), 7.57 (1H, d, J 8 Hz, indole 7-H), 7.87 (1H, d, J 8 Hz, indole 4-H), isomer B, δ H (300 M Hz, D₂O), 1.37 (3H, d, J 7 Hz, CH₃), 3.30–3.42 (2H, m, ind CH(CH₂)- + —CH(CO₂H)NH₂), 7.09–7.24 (3H, m), 7.48 (1H, d, J 8 Hz, indole 7-H), 7.73 91H, d, LJ 8 Hz, indole 4-H).

2-Adamantylchloroformate

A solution of 2-adamantanol (10.1 g, 66.5 mmol) in dichloromethane (200 mL) was cooled in an ice bath. Bis(trichloromethyl)carbonate (triphosgene) (7.55 g, 25.4 mmol) was added followed by dropwise addition of pyridine (6.2 mL, 77 mmol) at such a rate that the temperature remained below 20° C. After a further 10 minutes the mixture was warmed to room temperature and stirred for a further 2.5 hours. The dichloromethane was removed in vacuo without heating and the residue slurried with ethyl acetate (50 mL). The pyridinium hydrochloride was filtered off and the filtrate evaporated to dryness without heating to yield 2-adamantylchloroformate (76) (13.7 g, 96%); δ H (300 M Hz, CDCl$_3$, 1.48–2.32 (14H, m, adamantyl), 5.01 (1H, t, J 3 Hz, adamantyl 2-H); (lit.,[2] δ H (CCl$_4$) 1.3–2.4 (14H, m), 4.95 (lH, s).

2-(2-Adamantyloxycarbonyl)amino-3-(3-indolyl)butanoic acid (77)

Percent amino acid (75) (449 mg, 2.29 mmol) in 1N sodium hydroxide (2.29 mL) was added to sodium hydrogen carbonate (211 mg, 2.5 mmol). This mixture was cooled to 0° C. (ice bath), dioxan. (2.29 mL) was added, followed by dropwise addition with stirring of a solution of the chloroformate (76) (742 mg, 34.46 mmol) in dioxan (2.29 mL). When all the amino acid had gone (TLC SiO$_2$:4% methanol in dichloromethane), the dioxan was removed in vacuo and the residue partitioned between 10% citric acid and ethyl acetate. The aqueous phase was extracted further with ethyl acetate. The organic extracts were combined, dried (MgSO$_4$), and evaporated to dryness. The crude acid was purified by column chromatography on normal silica [hexane:ethyl acetate (3:20+0.5% acetic acid as eluant] to give 2-(2-adamantyloxy-carbonyl)amino-3-(3-indolyl) butanoic acid (77) (570 mg, 63%); δ H (300 M Hz, d$_6$-DMSO), 1.34 (3H, d, J 8Jz. CH$_3$), 1.68–2.00 (14H, m, adamantyl), 3.40–3.53 (1H, m, indCH(CH$_3$)), 4.36 (1H, brt, CH(CO$_2$H)), 4.59 (1H, s, adamantyl 2-H), 6.73 (1H, d, J 9 Hz, urethane NH), 6.96 (1H, t, J 7 Hz, indole 5-H), 7.06m (1H, t, J 7 Hz, indole 6-H), 7.17 (1H, brs, indole 2-H), 7.33 (1H, d, J 8 Hz, indole 7-H), 7.60 (1H, d, J 8 Hz, indole 4-H), 10.83 (1H, s, indole NH)m, ca 12.6 (vbrs, CO$_2$H).

2-Adamantyloxycarbonyl-D,L-β-methyl-D,L-tryptophan-L-phenylalaninol (78)

The carboxylic acid (77) (288 mg, 0.726 mmol), N,N'-dicyclohexyl-carbodiimide (DCCI) (173 mg, 0.838 mmol) and 1-hydroxybenzotriazole (HOBT) 9121 mg, 0.895 mmol) in ethyl acetate (5 mL) were stirred for 1 hour at 0° C. Dimethylaminopyridine (DMAP) (23 mg, 0.19 nmol) and phenylalaninol (163 mg, 1.08 nmol) were added, and the mixture stirred for a further 2 hours at 0° C. then for 48 hours at room temperature. The mixture was filtered and the filtrate washed with 5% citric acid (2×10 mL), saturated sodium hydrogen carbonate (10 mL), 5% citric acid again (10 mL), and brine (10 mL), dried (MgSO$_4$), and evaporated to dryness. The crude product was purified by column chromatography on normal silica [ethyl acetate:hexane (1:1) as eluant] to yield 2-adamantyloxvcarbonyl-D,L-β-methyl-D,L-trvytophan-L-phenylalaninol (78) (45 mg, 12%); m.p. 99°–101° C. (Found: C, 71.7; H, 7.65; N, 7.4. C$_{32}$H$_{39}$N$_3$O$_4$·0.5H$_2$O requires C, 71.35; H, 7.5; N, 7.8%); $\upsilon_{max}$ (film) 3360 (OH), 1 695 (urethane C=O), 1658 (amide C=O), 746 and 702 cm$^{-1}$ (monosubstituted Ph); δ H (300 M Hz, CDCl$_3$), 1.42 (3H, d, J 7 Hz, CH$_3$), 1.45–2.10 (14H, m, adamantyl), 2.20 (1H, brs, OH), 2.43–2.69 (2H, m, CH$_2$Ph), 2.84 (1H, brs, ind CH(CH$_3$—), 3.39 (2H, br, m, CH$_2$OH), 3.86 (1H, brs, CH(CH$_2$Ph)CH$_2$OH), 4.49 (1H, m, CH(NMR)(CONH—), 4.79 (1H, s, adamantyl 2-H), 5.49 (1H, brs, urethane NH), 6.87 (1H, brs, amide NH), 6.95–7.38 (9H, m, indole+ Ph), 7.69 (1H, d, J 7 Hz, indole 4-H), 8.26 (1H, s, indole NH); m/z (FAB) 530 (M$^+$+1), 257, 232, 217, 181, 144, 126 (100%), 109.

Example 90

N-[D-3-(1H-indol-3-ylmethyl)-3-methyl-N- [(tricyclo [3.3.1.1$^{3,7}$]dec-2-yloxy)carbonyl]-β-alanyl] -L-2-phenylglycine, AdOC-((D)-3-(1H-indol-3-ylmethyl)bAla-(L) -2-phenyl)Gly Step 1. Synthesis of 2AdocuMeRTrp CHN$_2$ (diazoketone).

A solution of N-methylmorpholine (253 mg, 2.50 mmol) and 2ADOCαMe-R-TrpOH (990 mg, 2.50 mmol) in anhydrous THF (20 mL) at 0° C. was treated dropwise with a solution of iso-butyl chloroformate (340 mg, 2.50 mmol) in anhydrous THF (10 mL) and left stirring for 20 minutes). The reaction mixture was then filtered and a solution of diazomethane (6 mmol) in ether was added to the filtrate. This was then allowed to warm to room temperature and left 12 hours. Excess diazomethane was quenched with ACOH (1 mL) and the mixture evaporated to dryness in vacuo. The residue was then separated by silica gel chromatography using n-hexane:EtOAC (4:1 then 3:1) as eluants to give the diazoketone (Scheme 19, No. 2) as yellow crystals. M.p. 182.2°–182.7° C. (MeOH); [α]$_D^{20}$=+64° (c=0.5, MeOH); IR (film) 3400–3200, 2913, 2854, 2106, 1693 and 1352 cm$^{-1}$; NMR (CDCl$_3$) δ 1.49 (3H, s), 1.50–1.60 (2H, m), 1.70–2.05 (12H, m), 3.30–3.40 (2H, br s), 4.86 (1H, s), 5.20–5.40 (1H, br s), 5.56 (1H, s), 6.95 (1H, d, J 2 Hz), 7.08 (1H, t, J 7 Hz), 7.16 (1H, t, J 7 Hz), 7.33 (1H, d, J 8 Hz), 7.55 (1H, d, J 8 Hz), 8.50 (1H, s); MS 71e (FAB) 421.3 (11), 393.2 (54), 351.2 (9), 307.2 (22) and 259.1 (100);

Analysis for C$_{24}$H$_{28}$N$_4$O$_3$:
Calc.: C, 68.55; H, 6.71; N, 13.32%
Found: C, 68.51; H, 6.73; N, 13.26%

Phenylmethyl (R)-β-methyl-β-[[(tricyclo[3.3.1.1$^{3,7}$] dec-2-yloxy)carbonyl]amino]-1H-indole-3-butanoic acid Step 2. Synthesis of the above compound (Scheme 19, No. 3)

A solution of the diazoketone (as prepared in Step 1) (4–20 g, 10.0 mmol) in benzyl alcohol (30 mL) was treated with a solution of silver benzoate (6 mL of a solution containing 1 g silver benzoate in 10 mL Et$_3$N) at room temperature. This was stirred for 4 hours, treated with activated charcoal and filtered through gypsum. The benzyl alcohol was removed in vacuo and the residue separated by silica gel chromatography using CH$_2$Cl$_2$ as eluant to give the benzyl ester (Scheme I, No. 2) as a glass (3.3 g, 66w); m.p. 47°–52° C.; [α]$_D^{20}$=+17.6° (c=1, MeOH); IR(film) 3500–3200, 2908, 2855, 1750–1680 cm$^{-1}$; NMR (CDCl$_3$)δ 1.39 (3H, s), 1.51 (1H, s), 1.54 (1H, s), 1.70–2.05 (12H, m), 2.68 (1H, o, J 14.3 Hz), 2.97 (1H, d, J 14.3 Hz), 5.10 (3H, s), 6.99 (1H, d, J 2.3 Hz), 7.08 (1H, t, J 7 Hz), 7.16 (1H, b, J 7 Hz), 7.30–7.35 (6H, m), 7.58 (1H, d, J 7.8 Hz), 8.05 (1H, s); MS M/e (FAB) 501.3 (28), 370.3 (24), 326.3 (29), 306.2 (32) and 135.2 (100);

Analysis for C$_{31}$H$_{36}$N$_2$O$_4$:
Calc.: C, 74.37; H, 7.25; N, 5.60%
Found: C, 74.44; H, 7.20; N, 5.75%

(R)-β-methyl-β-[[(tricyclo[3.3.1.1$^{3,7}$]dec-2-yloxy) carbonyl]amino]-1H-indole-3-butanoic acid, AdOC-(α-Me)DTrp Step 3. Synthesis of the above compound (Scheme 19 No. 4)

A solution of the benzyl ester (as prepared in Step 2) 1.0 g, 2 mmol) in absolute ethanol (100 mL) was treated with 10% palladium on carbon (100 mg, 10% w/w) and the resulting suspension subjected to an atmosphere of hydrogen at 50 psi for 4 hours with agitation at temperature of 30° C. This reaction mixture was then filtered through gypsum and the solvent removed in vacuo. The residue was column chromatographed over reverse phase silica using MeOH:H$_2$O (3:1) as eluant and the solid product recrystallized from chloroform to give the acid as a white solid (700 mg, 85%), m.p. 198°–201° C. (CHCl$_3$); [α]$_D^{20}$=+20° (c=1, MeOH); IR (film) 3500–3300, 2912, 2856, 1704 and 734 cm$^{-1}$; NMR (CDCl$_3$)δ 1.41 (3H, s), 1.53 (1H, s), 1.57 (1H, s), 1.70–1.85 (9H, m), 1.95–2.10 (4H, m), 2.69 (1H, d, J 14.3 Hz), 3.05 (1H, d, J 14.3 Hz), 3.21 (1H, d, J 14.3 Hz), 3.32 (1H, d, J 14.4 Hz), 4.86 (1H, s), 5.10–5.30 (1H, br s), 7.04 (1H, d, J 2.2 Hz), 7.07–7.20 (2H, m), 7.;35 (1H, d, J 8 Hz), 7.60 (1H, d, J 7.7 Hz), 8.16 (1H, s); MS M/e (FAB) 411.5 (9) and 217.2 (100);
Analysis for $C_{24}H_{30}N_4O_4$:
Calc.: 70.22; H, 7.37; N, 6.82%
Found: 70.03; H, 7.38; N, 6.78%

Methyl N-[D-3-(1H-indol-3-ylmethyl)-3-methyl-N-[(tricyclo[3.3.1.1$^{3,7}$]dec-2-yloxy)carbonyl]-β-alanyl]-L-2-phenylglycine Step 4. Synthesis of the above compound (Scheme 19 No. 5)

A stirred solution of the acid (as prepared in Step 3) (500 mg, 1.20 mmol) and pentafluorophenol (224 mg, 1.20 mmol) in EtOAC (50 mL) at 0C was treated with N, N'-dicyclohexylcarbodiimide (263 mg, 1.30 mmol). This mixture was stirred 18 hours at 0° C., filtered and S-phenyl glycine methyl/ester (303 mg, 1.50 mmol) added to the filtrate. This reaction mixture was left at room temperature for 48 hours, washed with 1M citric acid solution (2×20 mL), saturated $NaHCO_3$ solution (2×20 mL) and $H_2O$ (2×20 m). The dried ($MgSO_4$) organic phase was evaporated to dryness in vacuo and the residue separated by reverse phase silica gel chromatography using $MeCH:H_2O$ (3:1) as eluant to give the ester (Scheme 1 No. 5) as a noncrystalline solid (600 mg, 90%); m.p. 72°–82° C.; $[α]_D^{22}$=+55.3$^6$ (c=1, MeOH); IR(film)3500–3200, 2916, 2856, 1743, 1694, 1657 and 1504 cm$^{-1}$; NMR (CDCl$_3$) δ 1.35 (3H, s), 1.40–1.55 (2H, m), 1.70–2.05 (12H, m), 2.54 (1H, d, J 13.3 Hz), 3.04–3.15 (2H, m), 3.31 (1H, d, J 14.2 Hz), 3.71 (3H, s), 4.71 (1H, s), 5.09 (1H, s), 5.48 (1H, d, J 6.6 Hz), 6.85 (1H, d, J 6.1 Hz), 7.04 (1H, d, J 2 Hz), 7.08 (1H, g, J 7 Hz), 7.17 (1H, g, J 7 Hz), 7.30–7.40 (6H, m), 7.59 (1H, d, J 7.6 Hz), 8.14 (1H, s); MS M/e (FAB), 558.3 (12), 383 (11), 198.1 (34), 170.1 (27) and 135.1 (100);
Analysis for $C_{32}H_{39}N_3O_5$:
Calc.: C, 71.07, H, 7.05; N, 7.53%
Found: C, 71.31; H, 7.30; N, 7.28

Glycine. N-[D-3-(1H-indol-3-ylmethyl)-3-methyl-N-[(tricyclo[3.3.1.1$^{3,7}$]dec-2-yloxy)carbonyl]-β-alanyl]-L-2-phenyl-AdOC-((D)-3-(1H-indol-3-ylmethyl)bAla-((L)-2 -phenyl) Gly

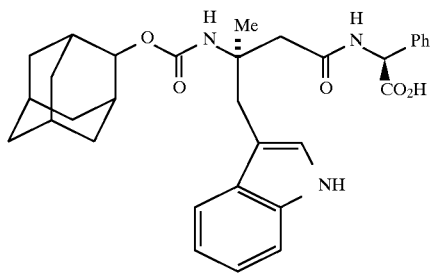

Step 5. Synthesis of Example 90, Scheme 19, No. 6)

A stirred solution of the ester (as prepared in Step 4) (399 mg, 0.70 mmol) in THF (20 mL) was treated with a solution of ClOH (30 mg, mmol) in $H_2O$ (5 mL) at room temperature. After 2 hours the mixture was made acidic to pH paper by adding 1M HCl solution. The solvent was then removed under vacuum and the residue separated by reverse phase silica gel chromatography using $MeOH:H_2O$ (3:1) as eluant to give the product (Example 90) as a noncrystalline solid (200 mg, 53%); m.p. 120°–125° C.; $[α]_D^{20}$=+49.2° (c=0.5, MeOH); IR (film) 3450–3250, 2916, 2856, 1750–1600, 1510 and 1256 cm$^{-1}$; NMR (CDCl$_3$) δ 1.34 (3H, s), 1.50–1.55 (2H, m), 1.60–200 (12H, m), 2.58 (1H, d, J 12.7 Hz), 3.00–3.25 (3H, m), 2.50–4.00 (1H, br), 4.60–4.75 (1H, br s), 4.90–5.20 (1H, br s), 5.54 (1H, d, J 6.5 Hz), 7.00–7.60 (10H, m), 7.58 (1H, d, J 7.9 Hz), 8.14 (1H, s);
Analysis for $C_{32}H_{37}N_3O_5·O_3·H_2O$:
Calc.: C, 70.00; H, 6.90; N, 7.65%
Found: C, 69.97; H, 6.85; N, 7.64%

Example 91

[R-(R*,S)]-α-[[3-(1H-indol-3-yl)-2-methyl-1-oxo-2-[[(tricyclo[3.3.1.1$^{3,7}$]dec-2-yloxy)carbonyl]amino] proipyl]amino]benzeneacetic acid, [R-(R*,S*)]-AdOC-(α-Me)DTrp-L-phenylglycine (See Scheme 20)

Step 1. Synthesis of oxazolone (R)(4-(lH-indol-3-ylmethyl)-4-methyl-2-(tricyclo[3.3.1.1$^{3,7}$]dec-2-yloxy)-5(4H)-oxazolone) (No. 2, Scheme 20)

A solution of AdOCαMe-R-TrpOH (1.0 g, 2.5 mmol) and N,N'dicyclohexylcarbodiimide (0.52 g, 2.5 mmol) in anhydrous DMF (5 mL) was stirred for 1 hour at room temperature. This mixture was then filtered and the filtrate evaporated to dryness in vacuo. The residue was chromatographed on silica gel using hexane:EtOAC (6:1) as eluant to give the oxazoline (2, Scheme 20) as white crystalline needles (850 mg, 90%). M.p. 150.5°–150.9° C. (hexane); $[α]_D^{20}$=+9.0° (c=1, MeOH); IR (film), 2910, 2857, 1823, 1681 and 1399 cm$^{-1}$; NMR (CDCl$_3$) δ 1.10–1.20 (1H, m), 1.30 (15H, m), 2.04 (1H, s), 3.20 (1H, d, J 14.5 Hz), 3.25 (1H, J 14.5 Hz), 4.72 (1H, t, J 3.5 Hz), 6.99 (1H, d, J 2.4 Hz), 7.07 (1H, dt, J 7.1 Hz), 7.14 (1H, dt, J 7.5 and 1 Hz), 7.29 (1H, d, J 7.3 Hz), 7.64 (1H, d, J 7.6 Hz), 8.02 (1H, s); MS M/Le (CI) 379.2 (52), 178.3 (47), 163.3 (61), 135.2 (74) and 130.2 (100);
Analysis for $C_{23}H_{26}N_2O_3$:
Calc.: C, 72.99; H, 6.92; N. 7.40%
Found: C, 72.88; H, 6,96; N, 7.37%

Step 2

A suspension of S-phenylglycine (42 mg, 0.28 mmol), $NaHCO_3$ (23 mg, 0.28 mmol) and the oxazolone (Scheme 20, No. 2) (100 mg, 0.26 mmol) in $DMF:H_2O$ (1:1) (10 mL) was stirred at room temperature for 18 hours. The solvent was then removed in vacuo and the residue suspended between EtOAC (20 mL) and 1 M citric acid solution (20 mL). The aqueous phase was partitioned and extracted with EtOAC (2×20 mL) and the combined organic phases washed with $H_2O$ (3×10 mL), dried over $MgSO_4$ and the solvent removed in vacuo. The residue was then subject to silica gel chromatography using 3% MeOH in $CH_2Cl_2$ then 5% MeOH, 0.5% $H_2OH$ in $CH_2Cl_2$ to give the product (Example 91) as a noncrystalline solid (106 mg, 77%). M.p. 138°–143° C.; $[α]_D^{24}$=+82° (c=1, MeOH); IR (film) 3500–3200, 2913, 2855, 1696, 1666 and 1499 cm$^{-1}$; NMR (CDCl$_3$) δ 1.40–1.50 (2H, m), 1.56 (3H, s), 160–1.95 (12H, m), 3.26 (1H, d, J 14.6 Hz), 3.40 (1H, d, J 14.6 Hz), 4.73 (1H, s), 5.68 (1h, d, J 6.8 Hz), 5.40–5.80 (1H, br), 6.90 (1H, s), 7.00–7.15 (2H, m), 7.20–7.30 (6H, s), 7.35 (1H, d, J 6.8 Hz), 7.53 (1H, d, J 7.5 Hz), 8.41 (1H, s); MS M/e (FAB) 530.5 (13), 217.2 (38);
Analysis for $C_{31}H_{35}N_3O_5O2H_2O$:
Calc.: C, 69.83; H, 6.69; N, 7.88%
Found: C, 69.85; H, 6.66; N, 7.74%

Example 92

Tricyclo[3.3.1.1$^{3,7}$]dec-2-yl(r)-[2-[2-phenylethyl)-amino]-1-(1H-indol-3-yl)-1-methylethyl]carbamate (See Scheme 21)

To a solution of lithium borohydride (4 mL, 2 M solution, 8 mmol) in dry THF under a nitrogen atmosphere was added a solution of chlorotrimethyl-silane (1.75 g, 16.0 mmol) in dry THF (5 ML). A white precipitate (of lithium chloride) was observed. After 2 minutes a solution of (18) (1 g, 2 mmol) in THF (15 mL) was added slowly (over 3–4 minute period) and the reaction mixture was stirred for 20 hours at ambient temperature. The reaction was treated cautiously with MeOH (5 mL) and the volatiles were removed in vacuo at 40° C. The residue was purified by silica gel chromatography using hexane:ethyl acetate (80:20) as eluant to give (19) (0.14 g, 14%) as a colorless oil, and recovered (18) (0.52 g; yield of (19) based on recovered starting material 30%). The amine (19) (0.14 g, 0.28 mmol) was taken dissolved up in MeOH (5 mL) and treated with 4-toluenesulfonic acid hydrate (0.054 g, 0.28 mmol). The solution was evaporated to leave a white solid. $[\alpha]_D$=+22° (c=0.25, MeOH) IR (film) 2928 and 1708 (c=urethane). NMR (DMSO-d$_6$) δ 1.2 (3μ, s, CH$_3$), 1.4–2.1 (14H, m, adamantyl), 2.3 (3H, s, CH$_3$Ph), 2.9–3.7 (8H, m, 4×CH$_2$), 4.7 (1H, br s, adamantyl H-2), 6.9–7.6 (15H, m, aromatics), 8.3 (1H, br, one of NH$_2^+$), 8.5 (1H, br, one of NH$_2^+$), 11.0 (1H, s, indole NH); MS M/e (FAB) 486 (m+ +H) (100), 136 (52);
Analysis for C$_{31}$H$_{39}$N$_3$O$_2$·C$_7$H$_8$SO$_3$·0.75H$_2$O:
Calc.: C, 67.98; H, 7.28; N, 6.26
Found: C, 67.96; H, 7.31; N, 600. M.p. 90°–93° C.

Ethyl[R-(R*,S*)]-4-[[2-phenylethyl]-[3-(1H-indol-3-yl)-2-methyl-2-[[(tricyclo[3.3.1.1$^{3,7}$]dec-2-yloxy)carbonyl]amino]propyl]amino]-4-oxo-butanoate (19b, Scheme 21).

Prepared by a similar method to compound (19a). Recovered a white solid 0.102 g (81%); $[\alpha]_D^{21}$=+26° (c=0.5, CHCl$_3$); IR (film) 2905, 2853, 1732, 1711, 1634 cm$^{-1}$; NMR (CDCl$_3$) δ 1.2 (6H, m), 1.3–2.1 (14H, m), 2.6 (4H, br s), 2.9 (2H, m), 3.0 (1H, d, J 14 Hz), 3.3–3.8 (4H, m), 4.0–4.2 (3H, m), 4.8 (1H, br s), 5.3 (1H, br), 6.9–7.6 (10H, m), 8.1 (1H, br s); MS M/e (FAB) 614 (36) (M$^+$ +H), 483 (100), 419 (24);
Analysis for C$_{37}$H$_{47}$N$_3$O$_5$:
Calc.: C, 72.40; H, 7.72; N, 6.85%
Found: C, 72.11; H, 7.87; N, 6.16%. M.p. 67°–70° C.

Tricyclo[3.3.1.1$^{3,7}$]dec-2-yl[R-(R*,S*)]-[2-acetyl[2-phenylethyl]amino]-1-(1H-indol-3-ylmethyl)-1-methylethyl]carbamate (19a in Scheme 21)

To a solution of (19) (0.1 g, 0.2 mmol) in dichloromethane (20 mL) at 0° C. was added acetyl chloride (0.3 mL, 4 mmol), followed by triethylamine (4 drops). Stirring was continued at 0° C. for 20 minutes, then the reaction mixture was dissolved in ethyl acetate (50 mL), washed (HCl aq, H$_2$O, NaHCO$_3$ ag), dried (MgSO$_4$) and evaporated to dryness. The residue was purified by column chromatography using hexane-ethyl acetate eluent to give an off-white solid (0.092 g, 85%). $[\alpha]_D^{21}$=+24° (c=0.25, CHCL$_3$), IR (film) 2909, 2855, 1709, 1610 cm$^{-1}$; NMR (CDCl$_3$) δ 1–3 (3H, s), 1.4–2.1 (17H, m), 2.8 (2H, m), 3.1 (1H, d, J 14 Hz), 3.3–3.7 (4H, m), 4.0 (1H, d, J 14 Hz), 4.8 (1H, s), 5.5 (1H, br s), 6.9–7.7 (10H, m), 8.1 (1H, br s); MS M/e (FAB) 528 (45) (M$^+$ +H), 397 (100), 333 (27).

4-[[3-(1H-indol-3-yl)-2-methyl-2-[[(tricyclo-[3.3.1.1$^{3,7}$]dec-2-yloxy)carbonyl]amino]propyl](2-phenylethyl)amino]-4-oxobutanoic acid (19d, Scheme 21)

To a stirred solution of (19b) (0.04 g, 0.06 mmol) in THF (5 mL) was added methanol (5 mL), water (5 mL) and lithium hydroxide monohydrate (0.1 g, 2.4 mmol). The reaction mixture was stirred for 40 minutes at ambient temperature, then acidified (2NHCl aq, 50 mL) and the products extracted into ethyl acetate (50 mL). The organic phase was dried with magnesium sulphate and evaporated in vacuo (40° C.). The oily residue was purified by column chromatography using dichloromethane/methanol (9:1) as eluent. Recovered 0.031 g (81%) of a white solid; IR (film) 340 (br), 2912, 2852, 1714, 1700, 1635 cm$^{-1}$; NMR (MeOH-d$_4$) δ 1.1–.2 (17H, m, CH$_3$ +adamantane), 2.6–3.2 (6H, m, 3×CH$_2$), 3.4–4.1 (6H, m, 3×CH$_2$), 4.8 (1H, br, adamantane H-2), 7.0–7.6 (10H, m, aromatics); $[\alpha]_D$+4° (MeOH, C=0.2, 22° C.); FAB MS 586 (51) m$^+$ +H), 455 (100), 391 (24)%
Analysis of C$_{35}$H$_{43}$N$_3$O$_5$·0.25 H$_2$O:
Calc.: C, 71.22, H, 7.43; N, 7.12
Found: C, 71.24; H, 7.46; N, 6.87%, m.p. 99°–96° C.

Example 93

Tricyclo[3.3.1.1$^{3,7}$]dec-2-yl [R-(R*,S*)]-[2-[[1-(hydroxymethyl)-2-phenylethyl]amino]-1-(1H-indol-3-ylmethyl)-2-oxoethyl]carbamate (Scheme 22 No. 9)

The carboxylic acid 5 (380 mg, 1.0 mmol) and N,N'-icyclohexylcarbodiimide (230 mg, 1.1 mmol) and pentafluorophenol (200 mg, 1.1 mmol) were suspended in EtOAC (25 mL) and stirred for 2 hours then treated with (S)-2-amino-3-phenyl-1-propanol (150 mg, 1.0 nmmol) and stirred at 40° C. for 18 hours. The mixture was filtered and the filtrate was washed with sat aqueous citric acid followed by sat aq NaHCO$_3$ followed by H$_2$O. The organic layer was dried (MgSO$_4$), filtered, concentrated in vacuo and purified by reverse-phase silica gel chromatography (LiChroprep® RP-18) using MeOH:H$_2$O (4:1) as eluant to give the product 6 (0.36 g, 71%); $[\alpha]_D^{20}$=20.4° (c=0.25, CH$_2$Cl$_2$); NMR (CDCl$_3$) δ 1.8 (14H, m), 2.60 (2H, d); 3.30 (4H, m), 4.05 (1H, m), 4.42 (1H, q, J), 4.78 (1H, m), 5.45 (1H, br s), 6.15 (1H, br s), 7.30 (8H, m), 7.37 (1H, d, J), 7.67 (1H, d), 8.25 (1H, br s).

Hydroxyamide (6) (See Scheme 22) (517 mg, 1.00 mmol), imidazole (146 mg, 2.15 mmol), and tertiarybutyldimethylsilyl chloride (354 mg, 2.35 mmol) in DMF (6 mL) were stirred at room temperature for 18 hours. The reaction was quenched with H$_2$O (40 mL). The emulsion was extracted with ether (80 mL). The ether was washed with brine, dried (MGSO$_4$), filtered and concentrated in vacuo. The crude material was purified by column chromatography [SiO$_2$:hexane-ethyl acetate (2:1) as eluant] to give the silyl protected amide (474 mg, 75%) as a white foam. $^1$H NMR (CDCl$_3$) δ 8.12 (1H, s, indNH), 7.76 (1H, d, J 7 Hz, ind H-4), 7.40 (1H, d, J 8 Hz, ind H-7), 7.34–7.06 (8H, m, Ph+ind H-2, H-5, H-6), 6.98 (1H, s), 5.91 (6H, br s, NH?), 5.44 (0.4H, br s, NH?), 4.90 (1H, s, adamantyl H-2), 4.53 (1H, m, NHCH(CH$_2$ind)CO), 4.14 (1H, m, NHCH(CH$_2$OSi) CH$_2$Ph), 3,39 (2H, m, CH$_2$ind), 3.22 (2H, br, m, CH$_2$Ph), 2.12–1.54 (14H, br, m, adamantyl), 0.88 (2, 9H, $^t$Bu), 0.02 (6H, s, 2×CH$_3$); IR (film) vmax 2927+2856 (adamantyl), 1703 (CO rethane), 1663 cm$^{-1}$ (CO amide).

Silyl protected amide (418 mg, 0.664 mmol) and Lawesson's reagent [Aldrich] (268 mg, 0.663 mmol) were refluxed in toluene (10 mL) for 30 minutes. The solution was cooled to room temperature and poured onto a column of silica gel. The column was eluted with CH$_2$Cl$_2$ to remove the toluene and a high rf (0.74) Lawesson's reagent by-product. Elution was then continued with a hexane-ethyl acetate gradient (0–30%) to give thiazolene (9) (73 mg, 21%) as a white foam. M.p. 56°–63° C. $^1$H NMR (CDCl$_3$) δ 8.16 (1H, s, ind NH), 7.63 (1H, d, J 8 Hz, ind H-4), 7.38–6.96 (9H, m, ind H-7, H-6, H-5, H-2+Ph), 5.44 (1H, br, d, J 7 Hz, urethane NH), 4.88 (1H, br s, ind CH$_2$CH), 4.82 (1H, s, adamantyl H-2), 4.62 (1H, m, NCHCH$_2$Ph), 3.44–2.83 (5H, m, ind CH$_2$+PhCH$_2$+CH of CH$_2$S), 2.68 (1H, dd, J 9, 14 Hz, CH of CH$_2$S), 2.09–1.43 (14H, m, adamantyl); IR film) vmax 2909+2854 (adamantyl), 1698 (CO urethane), 1621 cm$^{-1}$ (C=N); MS (M/e;

Analysis for C$_{31}$H$_{35}$N$_3$SO$_2$:
Calc.: C, 72.48; H, 6.87; N, 8.18; S, 6.24%
Found: C, 72.32; H, 7.09; N, 7.75; S, 6.09%

Example 94

(1-Phenylcyclopentyl)methyl[1S-[1R*(R*),2R*]] and [1S-[1R*(S*),2R*]]-[2-[[2-hydroxy-1-(hydroxymethyl)-2-phenylethyl]amino]-1-(1H-indol-3-ylmethyl)-1-methyl-2-oxoethyl]carbamate (1-Phenylcyclopentyl)methyl carbonochloroidate Step A. To a stirred solution of 1-phenyl cyclopentyl-methanol (0.53 g, 3.0 mmol) in methylene chloride (15 mL) was added bis (trichloromethyl) carbonate (0.33 g, 1.1 mmol) followed by pyridine (0.24 g, 3.3 mmol) in methylene chloride at 0° C. The reaction mixture was warmed to room temperature and stirred for an hour. The reaction mixture was concentrated and diluted with ethyl acetate (25 mL). The pyridinium hydrochloride precipitate was filtered off and filtrate was concentrated to give semisolid (0.65 g, 90%), $^1$H NMR (200 MHz, CDCl$_3$) δ 7.50–7.10 (5H, m), 4.30 (2H, s), 2.10–1.90 (4H, m), 1.90–1.75 (4H, m).

α-Methyl-N-[[(1-phenylcyclopentyl)methyl]carbonyl]-DL-tryptophan methyl ester

Step B. To a stirred solution of 1-phenyl 1-cyclopentyl methylchloroformate (0.65 g, 2.75 mmol) in dry THF (10 mL) was added a solution of a-methyl- DL-tryptophan methyl ester (0.60 g, 2.5 mmol) followed by triethylamine (0.5 g, 5.0 mmol) in dry THF. The reaction mixture was stirred for 30 minutes and then filtered, concentrated and chromatographed to give an oil (0.9 g, 90%). $^1$H NMR (200 MHz, CDCl$_3$) δ 8.0 (1H, br s), 7.50 (1H, d, J 7 Hz), 7.40–7.0 (8H, m), 6.6 (1H, br s), 5.35 (1H, br s), 4.15 (2H, s), 3.65 (3H, s), 3.6–3.0 (2H, m), 2.10–1.85 (4H, m), 1.85–1.60 (4H, m), 1.55 (3H, s).

α-Methyl-N-[[(1-phenvlcyclopentyl)methyl]carbonyl]-DL-tryptophan

Step C. To a stirred solution of intermediate B (0.87 g, 2 mmol) in aqueous 1,4-Dioxane (1:2) (6 mL) was added LiOH (0.13 g, 3 mmol) and stirred at room temperature overnight. The reaction mixture is concentrated, diluted with water (50 mL), acidified with dilute HCl, extracted with ethyl acetate and chromatographed to give a white foam (0.8 g, 95%). $^1$H NMR (200 MHz, CDCl$_3$), 8.05 (1H, br s), 7.55 (1H, d, J 7 Hz), 7.45–7.00 (9H, m), 5.25 (1H, br s), 4.20–3.90 (2H, s), 3.35–3.05 (2H, m), 2.00–1.85 (4H, m), 1.85–1.65 (4H, m), 1.50 (3H, br s).

(1-Phenvlcyclopentyl)methvl[1S-[1R*(R*),2R*]]] and [1S-[1R*(S*), 2R*]]-[2-[[2-hydroxy-1-(hydroxymethyl)-2-phenylethyl]amino]-1-(1H-indol-3-ylmethyl)-1-methyl-2-oxoethyl]carbamate Step D. A solution of intermediate C (0.42 g, 1.0 nmol) in ethyl acetate (10 mL) was treated with dicyclohexylcarbodiimide (0.23 g, 1.1 mmol) and 1-hydroxybenzotriazole hydrate (0.17 g, 1.1 mmol). After stirring for an hour at room temperature, it was filtered. To this filtrate, 2-amino-1-phenyl-1,3-propanediol (0.18 g, 1.05 mmol) in 1:1 mixture of methylene chloride and ethyl acetate was added and stirred overnight. The reaction mixture was filtered, concentrated and chromatographed to yield (0.25 g, 44%) of the title compound as a white foam. m.p. 78° 83° C.

Example 95

(4-Nitrophenyl)methyl [4S-[4α,α5((R*)]] and [4S-[4α,5α(S*)]]- [2-[(2.2-dimethyl-4-phenyl-1.3-dioxan-5-yl)amino]-1-(1H-indol-3-ylmethyl-1-methyl-2-oxoethyl]-carbamate α-Methyl-N-[[(4-nitrophenyl)methoxy]carbonyl]-DL-tryptophan methyl ester Step A. The method was as described in Step B. Example 94, except p-nitro benzyl chloroformate was used. The title compound was obtained as a semisolid (2.5 g, 49%). $^1$HNMR (250 MHz, CDCl$_3$) δ 8.20 (2H, d, J 8.5 Hz), 8.10 (1H, br s), 7.60–6.80 (7H, m), 5.64 (1H, br s), 5.2–5.0 (2H, m), 3.71 (3H, s), 3.55 (1H, d, J 14 Hz), 3.35 (1H, d, J 14 Hz), 1.72 (3H, s).

α-Methyl-N-[[(4-nitrophenyl)methoxy]carbonyl]-DL-tryptophan

Step B. The method was as described in Step C, Example 94, except the product of Step A was used. The title compound was obtained as a foam (1.8 g, 75%). $^1$HNMR (250 M[]z, CDCl$_3$) δ 8.15–7.95 (3H, m), 7.60–6.9 (7H, m), 5.53 (1H, br s), 5.20 (2H, s), 3.60–3.20 (2H, m), 1.73 (3H, br s).

(4-Nitrophenyl)methyl [4S-[4α,5α(R*)]] and [4S-[4α,5α(S*)]]-[2-[(2,2-dimethyl-4-phenyl-1.3-dioxan-5-yl)amino]-1-(1H-indol-3-ylmethyl-1-methyl-2-oxoethyl]carbamate Step C. The method was as described in Step D, Example 94, except the product of Step B and 5-amino-2,2-dimethyl-4-phenyl-1,3-dioxan instead of the product of Step C and 2-amino-1-phenyl-1,3-propanediol, respectively. The title compound was obtained as a foam (2.3 g, 85%). m.p. 92°–102° C.

Example 96

[4S-[4α,5α(R*)]] and [4S-[4α,5α(S*)]]-N-(2,2-dimethyl-4-phenyl-1,3-dioxan-5-yl)-α-methyl-α-[[[(1-phenyl-cyclopentyl)methyl]amino]carbonyl]-1H-indole-3-propanamide

[4S-[4α,5α(R*)]] and [4S-[4α, 5α(S*)]]-α-amino-N-(2,2-dimethyl-4-phenyl-1,3-dioxan-5-yl)-α-methyl-1H-indole-3-propanamide Step A. A solution of the title compound of Example 95 (1.65 g, 2.8 mmol) in absolute ethanol was treated with catalytic amount of 10% palladium on carbon and stirred overnight under a positive pressure of hydrogen. The reaction mixture was then filtered over celite and washed with ethanol. The filtrate was concentrated and passed through small plug of silica gel to give a white foam (1.1 g, 100%). m.p. 182°–185° C.

[4S-[4α,5α(R*)]] and [4S-[4α, 5α(S*)]]-N-(2,2-dimethyl-4-phenyl-1.3-dioxan-5-yl)-α-methyl-α-[[[(1-phenyl-cyclopentyl)methyl]amino]carbonyl]-1H-indole-3-propanamide Step B. To a stirred solution of the product of Step A (0.49 g, 1.2 mmol) in dry THF (15 mL), was added 1-phenyl cyclopentylmethylisocyanate (0.26 g, 1.3 mmol) in dry THF (5 mL) at room temperature. The reaction mixture was concentrated, chromatographed and crystallized to give the title compound (0.21 g, 30%),
m.p. 125°–28° C.

Example 97

[1S-[1R*(R*),2R*]] and [1S-[1R*(S*),2R*]]-N-[2-hydroxy-1-(hydroxymethyl)-2-phenyl ethyl]-2-(1H-indol-3-ylmethyl)-2-methyl-$N^1$ tricyclo[3.3.1.1$^{3,7}$] dec-2-ylpropanediamide N,N,N-Trimethyl-1H-indole-3-methanaminium iodide Gramine methiodide (2) (JACS 66 200 (1944))

Gramine (1) (43.5 g, 0.29 mmol) (see Synthetic Scheme 23 for Compounds 1-23) was dissolved in absolute ethanol (200 mL) and methyl iodide (17 mL, 0.27 mmol) was added dropwise over 0.5 hour. A mild exotherm occurred with the formation of a white precipitate. The reaction mixture was stirred overnight at room temperature and then cooled to 0° C. for 2 hours. The white solid was collected by filtration, washed four times with ethanol (50 mL), three times with diethyl ether (50 mL), and dried in vacuo. The product was obtained as a white solid. 70.4 g (83t). IR (KBr) 3306, 1483, 1346, 810, 760 cm$^{-1}$.

Diethyl(1H-indol-3-ylmethyl)methylpropanedioate (3)

Sodium hydride (4.0 g, 0.1 mmol) was added in portions over 10 minutes to a mixture of diethylmethyl malonate (17.4 g, 0.1 mmol) in DMF (200 mL) at room temperature. The reaction mixture was stirred 5-minutes and gramine methiodide (33.5 g, 0.11 mmol) was added and the whole mixture warmed to 50° C. for 0.5 hour and was then stirred overnight at room temperature. Water (200 mL) was carefully added to quench the reaction. The entire mixture was diluted with diethyl ether (500 mL) and water (300 mL). The layers were separated and the organic layer was washed with water (3×200 mL) The combined aqueous layers were extracted with diethyl ether (1×500 mL), the ether layer washed with water, the organic extracts combined, dried (MgSO$_4$), filtered and concentrated. The residue was filtered through silica gel (70–230 mesh) using hexane/ethyl acetate, 1/1, as eluant. The product containing fractions were combined, concentrated, and filtered through silica gel (70–230) using 8/2 hexane/EtOAC as eluant. The product was obtained as a red viscous oil. 13.1 g (43%). IR (film) 3397, 2983, 1731, 1376, 1254, 1108 cm$^{-1}$.

Ethyl hydrogen(1H-indol-3-ylmethyl)-methylpropanedioate (4)

To a solution of diester (4.85 g, 0.016 mmol) in 95% ethanol (50 mL) at room temperature was added 1N aqueous sodium hydroxide solution (16 mL) and enough water until the solution just became cloudy. Water was added as the reaction proceeded. After 2 hours the reaction mixture was concentrated on the rotary evaporator to remove ethanol, diluted with water, washed with ethyl acetate, made acidic with 10% citric acid solution, brine was added, and the entire mixture extracted with ethyl acetate. The ethyl acetate solution was dried (MgSO$_4$), filtered and concentrated to a brown oil. The brown oil was chromatographed on silica gel (70–230 mesh) using ethyl acetate as eluant and then rechromatographed on silica gel (70–230 mesh) using hexane/ethyl acetate, 1/1, as eluant. The product 4 was obtained as an orange/tan oil. 2.92 g (66%) IR (film) 3402, 2982, 1718, 1458, 1098, 742 cm$^{-1}$.

Ethyl(±)-α-methyl-α-[(tricyclo[3,3,1.1$^{3,7}$]dec-2-ylamino) carbonyl]-1H-indole-3-ipropanoate (5)

A mixture of acid (1.41 g, 0.005 mmol), adamantanamine hydrochloride (0.95 g, 0.005 mmol) 1-hydroxybenzotriazole-H$_2$0 (0.68 g, 0.005 mmol), and CH$_2$Cl$_2$ (50 mL) was cooled to 0° C. and triethylamine (0.8 mL, 0.0057 mmol) was added and the mixture stirred 5 minutes. Then dicyclohexylcarbodiimide (1.04 g, 0.005 mmol) was added all at once. The reaction mixture was stirred 3 days at room temperature, concentrated to dryness, the residue taken up in ethyl acetate, washed with 10% citric acid, sodium carbonate and sodium chloride solutions. The organic layer was dried (MgSO$_4$), filtered, and concentrated to an orange oil. Addition of 1/1, hexane/ethyl acetate caused the oil to solidify. The solid was collected by filtration. 2.05 g (98%). IR (KBr) 3418, 3327, 2907, 1713, 1630, 1540, 1457, 1113 cm$^{-1}$ (±)-α-methyl-α-[( tricyclo[3.3.1.1$^{3,7}$]dec-2-ylamino) carbonyl]-1H-indole-3-propanoic acid (6)

The ester (1.04 g, 2.5 mmol) was dissolved in ethanol (10 mL) and 1N sodium hydroxide solution (3.5 mL) was added and just enough water to make the solution cloudy. The reaction mixture was briefly warmed to 50° C. to get solution. The reaction mixture was allowed to sit 14 days at room temperature. The reaction mixture was concentrated to remove ethanol, diluted with water, washed the aqueous solution with ethyl acetate, made the aqueous layer acidic with 10% citric acid solution, extracted with ethyl acetate, washed the ethyl acetate solution with brine, dried (MgSO$_4$), filtered, and concentrated to an off-white foam. The foam was filtered through silica gel (70–230 mesh) using ethyl acetate as eluant. The product was obtained as an off-whit solid. 0.87 g (90%). IR (KBr) 3411, 2908, 1716, 1617, 1540, 740 cm$^{-1}$.

[4S-[4α,5α(R*)]] and [4S[4α,5α(S*)]]N-(2,2-dimethyl-4-phenyl-1,3-dioxan-5-yl)-2-(1H-indol-3-ylmethyl)-2-methyl-$N^1$-(tricyclo[3.3.1.1$^{3,7}$]dec-2-yl)propanediamide (7)

Dicyclohexylcarbodiimide (0.30 g, 1.46 mmol) was added to a mixture of (4S,5S)-(+)-5-amino-2,2-dimethyl-4-phenyl-1,3-dioxane (0.31 g, 1.44 mmol), acid (0.53 g, 1.39 mmol), and 1-hydroxybenzotriazole (0.22 g, 1.63 mmol) in a mixture 10/1, CH$_2$Cl$_2$/DMF, (30 mL) at 0° C. The reaction mixture was allowed to sit 1 hour at 0C and then 3 days at room temperature. The reaction mixture was concentrated to dryness, the residue taken up in ethyl acetate, the ethyl acetate solution washed with saturated sodium chloride solution, dried (MgSO$_4$), filtered and concentrated to an orange oil. The oil was purified by filtration through silica gel (70–230 mesh) using hexane/ethyl acetate, 7/3, as eluant. The product was obtained as a white solid. 0.247 g (31%). IR (KBr) 3341, 2910, 1665, 1508, 1201, 742 cm$^{-1}$.

[1S-[1R*(R*),2R*]] and [1S-[1R*(S*),2R*]]-N-[2-hydroxy-1-(hydroxymethyl)-2-phenyl ethyl]-2-(1H-indol-3-ylmethyl)-2-methyl-$N^1$tricyclo[3.3.1.1$^{3,7}$]dec-2-ylpropanediamide (8)

A mixture of the acetonide (0.16 g, 0.28 mmol), methanol (10 mL), and 1N HCl (1 mL) was allowed to sit at room temperature for 4 hours. The reaction mixture was concentrated to dryness without heating. Ethyl acetate was added, the ethyl acetate dried (MgSO$_4$), filtered, concentrated, and the residue chromatographed on silica gel (70–230 mesh) using ethyl acetate as eluant. The product was obtained as a white foam. 0.0727 g (49%).

Example 98

[1S-[R*(R*),2R*]] and [1S-[1R*(S*),2R*]]-N-[2-hydroxy-1-(hydroxymethyl)-2-phenylethyl]-2-(1H-indol-3-ylmethyl) -2-methyl-N'-(tricyclo[3.3.1.1$^{3,7}$] dec-1-ylmethyl)propanediamide Ethyl α-methyl-α-[[(tricyclo[3.3.1.1$^{3,7}$]dec-1-ylmethyl) amino]carbonyl]-1H-indole-3-propanoate (9)

Compound 9 was prepared from Compound 4 according to the procedure for Compound 5. The product was obtained as an off-white solid. 3.49 g (58%). IR (KBr) 3402, 3337, 2913, 2904, 1718, 1652, 1116 cm$^{-1}$.

(±)α-methyl-α- [[(tricyclo[3.3.1.1$^{3,7}$]dec-1-ylmethyl)-amino]carbonyl]-1H-indole-3-propanoic acid (10)

Compound 10 was prepared from Compound 9 according to the procedure for Compound 6. The product was obtained as a white solid. 1.95 g (71%) IR (KBr) 3440, 2912, 1713, 1652, 1621, 1189, 746 cm$^{-1}$.

[4S-[4α,5α(R*)]] and [4S-[4α,5α(S*)]]-N-(2,2-dimethyl-4-phenyl-1,3-dioxan-5-yl)-2-(1H-indol-3-ylmethyl)-2-methyl-N'-(tricyclo[3.3.1.1$^{3,7}$]dec-1-ylmethyl-propanediamide (11)

Compound 11 was prepared from Compound 10 according to the procedure for Compound 7. The product was obtained as a white foam. 0.83 g, (72%). IR (KBr) 3418, 2904, 1666, 1558, 1106 cm$^{-1}$.

[1S-[1R*(R*), 2R*]] and [1S-[1R*(S*), 2R*]]-N-[2-hydroxy-1-(hydroxymethyl)-2-phenylethyl]-2-(1H-indol-3-ylmethyl)-2-methyl-N'-(tricyclo[3.3.1.1$^{3,7}$]dec-1-ylmethyl) propanediamide (12)

Compound 12 was prepared from Compound 11 according to the procedure for Compound 8. The product was obtained as a white foam. 0.2633 g (91%). IR (KBr) 3341, 1652, 1588, 1544, 1477, 699 cm$^{-1}$.

Example 99

[1S-[1R*(R*),2R*]] and [1S-[1R*(S*),2R*[[α-[[[2,6-bis(1-methylethyl)phenyl]amino]carbonyl]amino]-N-[2-hydroxy-1-(hydroxymethyl)-2-phenylethyl]-α-methyl-1H-indole-3-propanamide

[4S-[4α,5α(R*)]] and [4S-[4α,5α(S*)]]-1.1-dimethyl-ethy] [2-[(2,2-dimethyl-4-phenyl-1,3-dioxan-5-yl)-amino]-1-(1H-indol-3-ylmethyl)-1-methyl-2-oxoethyl]-carbamate (14)

Compound 14 was prepared according to the procedure of Compound 7. The product was obtained as a white foam. 4.70 g (98%). IR (KBr) 3413, 1707, 1663, 1507, 1501, 1458, 1168, 743 cm$^{-1}$.

[4S-[4α,5α(R*)]] and [4S-[4α,5α(S*)]]-α-amino-N-(2,2-dimethyl-4-phenyl-1.3-dioxan-5-yl)-α-methyl-1H-indole-3-propanamide (15)

Anhydrous hydrogen chloride gas was bubbled through a solution of t-butyloxy carbonyl amine 14 (3.4 g, 6.7 mmol) in dichloromethane (80 ml) for 5 minutes. The reaction mixture was allowed to sit at room temperature for 1 hour and was then poured into saturated aqueous sodium bicarbonate solution. Sodium chloride solution was added and the aqueous solution as extracted two times with ethyl acetate. The organic extracts were combined, dried (MgSO$_4$), filtered and concentrated. The residue was filtered through silica gel (70–230 mesh) using ethyl acetate as eluant to give the product as an off-white solid. 2.18 g (80%). IR (KBr) 3356, 3244, 1646, 1514, 744 cm$^{-1}$.

[4S-[4α,5α(R*)]] or [4S-[4α,5α(S*)]]-α-[[[[2,6-bid(1-methylethyl)phenyl]amino]carbonyl]amino]-N-(2,2-dimethyl-4-phenyl-1,3-dioxan-5-yl)-α-methyl-1H-indole-3-propanamide (16a)

[4S-[4α, 5α(R*)]] or [4S-[4α,5α(S*)]]-α-[[[[2,6-bis(1-methylethyl)phenyl]amino]carbonyl]amino]-N-(2.2-dimethyl-4-phenyl-1,3-dioxan-5-yl)-α-methyl-1H-indole-3-propanamide (16b)

A mixture of amine 15 (0.40 g, 1 mmol) and 2,6-diisopropylphenyl isocyanate (0.23 g, 1.1 mmol) in ethyl acetate (30 mL) was heated briefly to achieve solution. The reaction mixture was allowed to sit 2 days at room temperature. The reaction mixture was concentrated to a viscous oil, which was chromatographed on silica gel (70–230 mesh) using ethyl acetate as eluant. The less polar diastereomer, 16a, was obtained as a white solid. 0.2876 g. The more polar diastereomer, 16b, was obtained as a white solid. 0.2369 g. Total yield (87%). IR (Kbr) 3431, 2964, 1675, 1500, 1239, 741 cm$^{-1}$.

[1S-[1R*(R*),2R*]] and [1S-[1R*(S*), 2R*]]α-[[[[2,6-bis(1-methylethyl)phenyl]amino]carbonyl]amino]-N-[2-hydroxy-1-(hydroxymethyl)-2-phenylethyl]-α-methyl-1H-indole-3-propanamide (17a)

Compound 17a was prepared from 16a according to the procedure for Compound 8. The product was obtained as a white foam. 0.0893 g (48%). IR (KBr) 3400, 3343, 1733, 1663, 1513, 742 cm$^{-1}$.

Example 100

[1S-[1R*(R*), 2R*]] or [1S-[1R*(S),2R*]]α-[[[[2.6-bis(1-methylethyl)phenyl]amino]carbonyl]amino]-N-[2-hydroxy-1-(hydroxymethyl)-2-phenylethyl]-α-methyl-1H-indole-3-propanamide (17b)

Compound 17b was prepared from 16b according to the procedure for Compound 8. The product was obtained as a white foam. 0.096 g (66%). IR (KBr) 3420, 3299, 1734, 1716, 1662, 1507, 1058 cm$^{-1}$.

Example 101

N- [(1,1-dimethylethoxy)carbonyl]-L-phenylalanyl-α-methyl-N-tricyclo[3.3.1.1$^{3,7}$]dec-2-yl-DL-tryptophanamide

[4S-[4α,5α(R*)]] and [4S-[4α,5α(S*)]]-[2-[(2,2-dimethyl-4-phenyl-1,3-dioxan-5-yl)amino]-1-(1H-indol-3-ylmethyl)-1-methyl-2-oxoethyl]carbamate (18)

The amine 15 (0.4 g, 1 mmol) and 2,6-diisopropylphenyl chloroformate (0.51 g, 2 mmol) were taken up in tetrahydrofuran (50 mL) and triethylamine (0.34 mL, 2.4 mmol) was added. The reaction mixture was stirred 5 days at room temperature and then concentrated to dryness. The residue was filtered through silica gel (70–230 mesh) using hexane/ethyl acetate, 1/1, as eluant. The product was obtained as a foam/solid. 0.395 g (66%). IR (KBr) 3326, 1654, 1636, 1520, 1257, 742 cm$^{-1}$.

N-[N[(1,1-dimethylethoxy)carbonyl]-L-phenylalanyl]-α-methyl-DL-tryptophan methyl ester (19)

Compound 19 was prepared from BOC-L-phenylalanine and RS-α-Me tryptophan methyl ester according to the procedure for Example 7. 4.74 g (99%). IR (KBr) 3408, 3353, 1734, 1696, 1617, 1507, 1457, 1165 cm$^{-1}$.

α-methyl-N-L-phenylalanyl-DL methylester, monohydrochloride (20)

Anhydrous hydrogen chloride gas was bubbled through a solution of 19 (1.50 g, 3.1 mmol) in dichloromethane (50 mL) for 2 minutes at room temperature. The reaction mixture was allowed to sit overnight at room temperature. The solvent was removed in vacuo. Ether was added twice and concentrated. The residue was taken up in methanol and then concentrated. Ether was added and then removed on the rotary evaporator yielding the product as a tan foam. 1.32 g (100%). IR KBr) 3403, 3396, 3343, 3231, 1734, 1684, 1677, 1498, 1216, 743 cm$^{-1}$.

N-[N- [(1,1-dimethylethoxvy)carbonyl]-L-phenylalanyl]-α-methyl-DL-tryotophyl (21)

Compound 21 was prepared from 19 according to the procedure for Compound 6. The product was obtained as a white foam. 2.34 g (96%). IR (KBr) 3375, 1716, 1708, 1702, 1498, 1457, 1368, 1164, 743 cm$^{-1}$.

N-[(1,1-dimethylethoxy)carbonyl]-L-phenylalanyl-α-methyl-N-tricyclo[3.3.1.1$^{3,7}$]dec-2-yl-DL-tryptophanamide (22)

Compound 22 was prepared from 21 and 2-adamantamine according to the procedure for Compound 7. The product was obtained as a white solid. 0.585 g (38%). IR (KBr) 3411, 3333, 1696, 1672, 1653, 1519, 1165 cm$^{-1}$.

Example 102

N-[N-[(tricyclo[3.3.1.1$^{3,7}$]dec-2-yloxy)carbonyl]-L-phenylalanyl]-DL-tryptophan methylester (23)

Compound 20 (1.25 g, 3.0 mmol) was added to 2-adamantyl chloroformate (0.70 g, 3.3 mmol) in THF (80 mL), then triethyl amine (0.9 mL, 6.5 mmol) was added and the reaction mixture cooled to 0° C. After 0.5 hour the reaction mixture was concentrated to dryness, the residue was dissolved in ethyl acetate. The ethyl acetate solution was washed with 10% aqueous citric acid and saturated sodium chloride solutions, dried (MgSO$_4$), filtered and concentrated. The residue was filtered through silica gel (70–230 mesh) using hexane/ethyl acetate as eluant. The product was obtained as a white foam. 1.12 g (67%). IR (KBr) 3342, 2912, 1672, 1663, 1507, 1361, 1254, 1101 cm$^{-1}$.

Example 103

Tricyclo[3.3.1.1$^{3,7}$]dec-2-yl(±)-[2-[(3,4-dihydro-2H-1-benzopyran-3-yl)amino]-1-(1H-indol-3-ylmethyl)-1-methyl-2-oxoethy]1carbamate A solution of 2-adamantyl oxycarbonyl αmethyl, DL tryptophane (0.79 g , 0.002 mmol) in ethyl acetate (60 mL) was treated with dicyclohexylcarbodiimide (0.495 g, 0.002 mmol) and 1-hydroxybenzotriazole hydrate (0.3 g, 0.0023 mmol). After stirring for 2 hours at room temperature the precipitated dicyclohyexyl urea was removed by filtration. To the clear filtrate was added 3,4-dihydro-2,4-1-benzopyran-3-amine (0.37 g, 0.002 mmol). The reaction mixture was stirred at room temperature overnight. The ethyl acetate solution was washed with 5% citric acid, 5% NdHCO$_3$ and brine. The organic phase was dried over MgSO$_4$ and concentrated in vacuo to yield a white foam. The product was chromatographed over silica using 50% ethyl acetate, 50% hexane as eluant to give the title compound (0.66 g, 61%).
Analysis for C$_{32}$H$_{37}$N$_3$O$_4$ $_{O3}$½H$_2$O MW 536.679;
Calc.: C, 71.61; H, 7.13; N, 7.82;
Found: C, 71.67; H, 6.93; N, 7.75.

Example 104

Tricyclo[3.3.1.1$^{3,7}$]dec-2-yl(±)-[1-(1H-indol-3-ylmethyl)-1-methyl-2-oxo-2-[[(1,2,3,4-tetrahydro-1-naphthalenyl)methyl]amino]carbamate In a process analogous to Example 103 by substituting 1,2,3,4-tetrahydro-1-naphthalene-methenamine (0.32 g, 0.002 mmol) for 3,4-dihydro-2,4-1 benzopyran-3-amine one obtains the title compound (0.76 g, 69%).
Analysis for C$_{34}$H$_{41}$N$_3$O$_3$ ½H$_2$O MW 548.734:
Calc.: C, 74.42; H, 7.71; N, 7.65;
Found: C, 74.27; H, 7.57; N, 7.36.

Example 105

Tricyclo[3.3.1.1$^{3,7}$]dec-2-yl(±)-[1-(1H-indol-3-ylmethyl)-1-methyl-2-oxo-2-(9H-xanthen-9-ylmethyl)-amino]ethyl]carbamate A solution of 2-adamantyl oxycarbonyl-α-methyl DL tryptophane (0.79 g, 0.002 mmol) in methylene chloride (60 mL) was treated with hydroxybenzothiazole hydrate (0.3 g, 0.0022 mmol), 1-(2-dimethylamino propyl)-3-ethylcarbodiimide·HCl (0.38 g, 0.002 mmol) and triethyl amine (0.202 g, 0.002 mmol). After stirring at room temperature for 2 hours a solution of 3H-xanthane-9-methenamine (0.495 g, 0.002 mmol) in methylene chloride (10 mL) was added. The reaction mixture was stirred at room temperature overnight. The clear solution was concentrated in vacuo. The resulting oil was taken up in ethyl acetate. The ethyl acetate solution was washed with 1 NHCl, saturated NdHCO$_3$ and brine. The organic phase was dried over MgSO$_4$ and concentrate in vacuo to give a white foam. the product was chromatographed over silica using 500 ethyl acetate; 500 hexane as eluant to give the title compound (0.72 g, 59%). Analysis for C$_{37}$H$_{39}$N$_3$O$_4$·H$_2$O MW 607.761:
Calc.: C, 73.13; H, 6.79; N, 6.91;
Found: C, 73.53; H, 6.80; N, 6.61.

Example 106

Carbamic acid, [2-[(hexahydro-1H-azepin-1-yl)amino]-1-(1H-indol-3-ylmethyl)-1-methyl-2-oxoethyl]-,tricyclo[3.3.1.1$^{3,7}$]dec-2-yl ester. (R)-

The title compound was synthesized as in Example 103 by substituting 1-aminohomopiperidine for 3,4-dihydro-2, 4-1-benzopyran 3-amine and -R-2-adamantyl oxocarbonyl α-methyl tryptophane for 2-adamantyl oxycarbonyl-α-methyl-DL-tryptophan. Following completion of reaction, precipitated solid was filtered yielding title compound, m.p. 184°–186° C.
Analysis for C$_{29}$H$_{40}$N$_4$O$_3$·0.75 H$_2$O:
Calc.: C, 68.81; H, 8.26; N, 11.06;
Found: C, 68.78; H, 8.26; N, 11.27.

Example 107

Carbamic acid, [1-(1H-indol-3-ylmethyl)-1-methyl-2-oxo-2- (1-piperidinylamino)ethyl]-,tricyclo [3.3.1.1$^{3,7}$]dec-2-ylester,(R)-

The title compound was synthesized as described in Example 106 by substituting 1-aminopiperidine for 1-aminohomopiperidine, m.p. 242°–244° C.
Analysis for C$_{28}$H$_{38}$N$_4$O$_3$·0.25 H$_2$O:
Calc.: C, 69.60; H, 8.03; N, 11.59;
Found: C, 69.68; H, 8.09; N, 11.66.

Example 108

Carbamic acid, [1-(1H-indol-3-ylmethyl)-1-methyl-2-(4-morpholinylamino) -2-oxoethyl]-,tricyclo [3.3.1.1$^{3,7}$]dec-2-ylester,(R)-

The title compound was synthesized as described in Example 106 by substituting 4-aminomorpholine for 1-aminohomopiperidine, m.p. 257°–259° C.
Analysis for C$_{27}$H$_{36}$N$_4$O$_4$:
Calc.: C, 67.48; H, 7.55; N, 11.66;
Found: C, 67.13; H, 7.72; N, 11.67.

Example 109

Carbamic acid, N-[2-[(2-hydroxvcyclohexyl)-amino]-1-(1H-indol-3-ylmethyl)-1-methyl-2-oxoethyl]-,tricyclo[3.3.1.1$^{3,7}$]dec-2-ylester, [1α(R) 2β]

The title compound was synthesized as described in Example 106 by substituting trans-2-amino-cyclohexanol for 1-aminohomopiperidine.

Analysis for C$_{29}$H$_{39}$N$_3$O$_4$0.5 H$_2$O:
Calc.: C, 69.29; H, 8.02; N, 8.35;
Found: C, 69.38; H, 8.46; N, 8.00.

Examples 110 and 111

Carbamic acid, [2-[(2-hydroxvcyclohexyl)amino]-1-(1H-indol-3-ylmethyl)-1-methyl-2-oxoethyl]-, tricyclo-[3.3.1.1$^{3,7}$]dec-2-ylester Isomer 1

TRP Center R: Ring center unknown

Carbamic acid. [2-[(2-hydroxycyclohexyl)amino]-1-(1H-indol-3-ylmethyl)-1-methyl-2-oxoethyl]-, tricyclo-[3.3.1.1$^{3,7}$]dec-2-ylester Isomer 2

TRP Center is R: Other center unknown

Individual diastereomers of Example 109 were separated by Waters Model 46K HPLC using 6 μm silica column (Prep Nova Pak®). The mobile phase was ethyl acetate-hexane (60:40) and flow rate was 15 mL/min. The first diastereomer (Example 110) (m.p. 130°–137° C.) had retention time of 11.92 min. The second diastereomer (Example 111) (m.p. 125°–130° C.) had retention time of 13.87 min.

Example 112

Tricyclo[3.3.1.1$^{3,7}$]dec-2-yl ester [2S-(R*,S*)]1 N-[1-(1H-indol-3-ylmethyl)-2-[[2-(methoxymethyl)-1-pyrrolidinyl]amino]-1-methyl-2-oxoethyl]carbamate

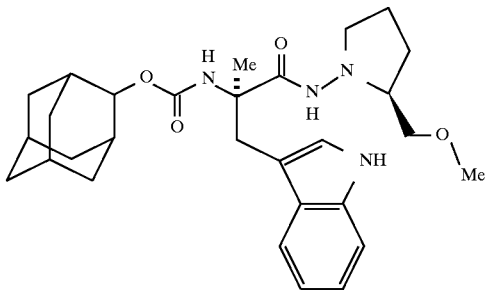

A solution of 2-adamantyloxycarbonyl·α-methyl, DL tryptophane (0.79 g, 0.002 mmol) in ethyl acetate (60 mL) was treated with dicyclohexylcarbodiimide (0.495 g, 0.002 mmol) and 1-hydroxybenzotriazole hydrate (0.3 g, 0.0023 mmol). After stirring for 2 hours at room temperature, the precipitated dicyclohexyl urea as removed by filtration. To the clear filtrate was added (—S—)-1-amino-2-(methoxymethyl)pyrrolide. The reaction mixture was stirred at room temperature overnight. The ethyl acetate solution was washed with 5% citric acid, 5% NaHCO$_3$, and brine. The organic phase was dried over MgSO$_4$ and concentrated in vacuo to yield a white foam. The product was chromatographed over silica using 50% ethyl acetate, 50% hexane as eluant to give the title compound, mp 125°–130° C.

Analysis calculated for C$_{29}$H$_{40}$N$_4$O$_4$ 0.25H$_2$O: C, 67.87; H, 7.95; N, 10.91.
Found: C, 67.54; H, 7.95; N, 11.04.

Example 113

Tricyclo [3.3.1.1$^{3,7}$]dec-2-yl [R-(R*,R*)]-[-(1H-indol-3-ylmethyl)-2-[[2-(methoxymethyl)-1-pyrrolidinyl]amino]-1-methyl-2-oxoethyl]carbamate

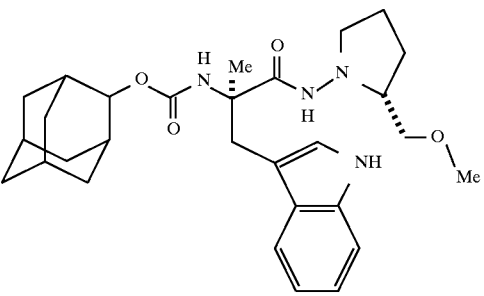

The title compound was synthesized as described in Example 1 above by substituting -R-1-amine-2-(methoxymethyl)pyrrolidine for (—S—)-1-amine-2-(methoxymethyl) pyrrolide; mp 115°–120° C.
Analysis calculated for C$_{29}$H$_{40}$N$_4$O$_4$: C, 68.48; H, 7.93; N, 11.01.
Found: C, 68.65; H, 7.83; N, 10.74.

Example 114

(R)-1-[[3-(1H-indol-3-yl)-2-methyl-1-oxo-2-[[(tricyclo[3.3.1.1$^{3,7}$]dec-2-yloxy)carbonyl]amino]propyl]amino]cyclohexaneacetic acid

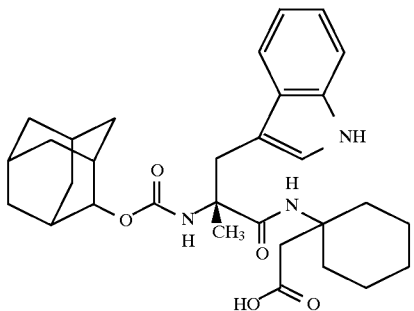

Step 1
To a stirred solution of 1-aminocyclohexane-1-carboxylic acid (5.0 g, 34.92 mmol) in 1N NaOH (39 mL) was added 1,4-dioxan (40 mL) followed by sodiumbicarbonate (3.52 g, 41.9 mmol). Di-tert-butyldicarbonate (9.15 g, 41.9 mmol) in 1,4-dioxan (40 mL) was then added dropwise over 30 minutes and the mixture stirred rapidly overnight at room temperature. The 1,4-dioxan was removed in vacuo and the residue diluted with water (50 mL) and extracted once with Et$_2$O (50 mL)). The aqueous solution was made pH4 with 5% citric acid and the mixture extracted into EtOAc (3×100 mL). The combined EtOAc extracts were dried over MgSO$_4$, filtered, and the solvent removed in vacuo to give the product as a white solid (4.42 g, 52%); mp 174° C.; IR(film)3313, 1713, and 1655 cm$^{-1}$; δ NMR (DMSO-d$^6$) 1.15–1.65 (8H, m), 1.36 (9H, s), 1.87–1.98 (2H, m), 6.84 (1H, bs), 12.08 (1H, s).
Analysis calculated for (C$_{12}$H$_{21}$NO$_4$0.1H$_2$O): C, H, N.
Step 2
N-methylmorpholine (0.497 mL, 4.52 mmol) was added to a stirred solution of the BOCaminoacid (1.0 g, 4.11 mmol) in THF (25 mL) cooled to −10° C. A solution of ethylchloroformate (0.432 mL, 4.52 mmol) in THF (10 mL) was then added dropwise over 10 minutes and the mixture stirred for a further 30 minutes. N-methylmorpholine hydrochloride was filtered and a solution of diazamethane (0.42 g, 10 mmol) in Et$_2$O (25 mL) was added in one portion to the stirred solution cooled in an ice bath. The yellow mixture was stirred overnight with slow rewarming to room temperature, CaCl$_2$ added to destroy excess diazamethane, the mixture filtered, and the solvent removed in vacuo. Purification of the residue by recrystallization from EtOAc gave the product as a yellow solid (0.671 g, 61%); mp 157°–160°C.; IR(film)2098, 1687, and 1643 cm$^{-1}$; 6 NMR (CaCl$_3$) 1.25–1.50 (2H, m), 1.44 (9H, s), 1.59–2.00 (7H, m), 4.73 (1H, s), 5.60 (1H, s).

Analysis calculated for (C$_{13}$H$_{21}$N$_3$O$_3$ 0.25EtOAc): C, H, N.

Step 3

To a stirred solution of the diazaketone (0.639 g, 2.39 mmol) in MeOH (20 mL) was added 1.0 mL of a solution of silver(I) benzoate (0.137 g, 0.60 mmol) in Et$_3$N (2.0 mL) and the mixture heated at reflux for 1 hour. The mixture was filtered through celite and the solvent removed in vacuo. The residual syrup was dissolved in EtOAc (25 mL), washed with 5% citric acid solution (2×25 mL), saturated NaHCO$_3$ (25 mL), and brine (25 mL). The EtOAc solution was dried over MgSO$_4$, filtered, and the solvent removed in vacuo to give the product as a syrup (0.495 g, 76%); IR(film)3382, 2933, and 1718 cm$^{-1}$; 6 NMR (CaCl$_3$) 1.22–1.53 (10H, m), 1.44 (9H, s), 2.75 (2H, s), 3.65 (3H, s), 4.50 (1H, s).

Analysis calculated for (C$_{14}$H$_{25}$NO$_4$): C, H, N.

Step 4

To a stirred solution of the ester (0.297 g, 1.1 mmol) in CH$_2$Cl$_2$ (2 mL) was added trifluoroacetic acid (2 mL) and the mixture stirred for 1 hour at room temperature. The solvent was removed in vacuo giving the product as a syrup which was used without further purification (0.314 g, 100%); IR(film)2946 and 1677 cm$^{-1}$.

Step 5

N,N$^1$-dicyclohexylcarbodiimide (0.25 g, 1.21 mmol) was added to a stirred solution of 2-Adoc-R-α-Me-Trp-OH (0.436 g, 1.10 mmol) and 1-hydroxybenzotriazole monohydrate (0.202 g, 1.32 mmol). The mixture was stirred for 2 hours at room temperature and the N,N$^1$-dicyclohexylurea filtered off. The amine salt (0.314 g, 1.10 mmol) dissolved in EtOAc (10 mL) containing Et$_3$N (0.169 mL, 1.21 mmol) was then added dropwise over 5 minutes. This was followed by a catalytic amount of 4-dimethylaminopyridine and the mixture stirred at reflux for 32 hours. The solution was washed with 5% citric acid (2×25 mL), saturated NaHCO$_3$ (2×25 mL), 5% citric acid (25 mL), and brine (25 mL). The EtOAc solution was dried over MgSO$_4$. filtered, and the solvent removed in vacuo. Purification of the residue by chromatography on silica using 67% n-hexane/33% EtOAc as eluant gave the product as a white solid (0.128 g, 21%); mp 128°–132° C.; [α]$_D^{20}$+77.1° (C =0.28, acetone); IR(film)2928, 2856, 1713, and 1665 cm$^{-1}$; δ NMR (CDCl$_3$) 1.23–2.01 (22H, m), 1.50 (3H, s), 2.13–2.16 (1H, m), 2.30–2.34 (1H, m), 2.74 (1H, d, J 14.7 Hz), 2.94 (1H, d, J 14.7 Hz), 3.32 (1H, d, J 14.9 Hz), 3.59 (3H, s), 3.62 (1H, d, J 16.4 Hz), 4.82 (1H, s), 5.14 (1H, s), 6.47 (1H, s), 7.03 (1H, s), 7.07–7.20 (2H, m), 7.36 (1H, d, J 7.9 Hz), 7.64 (1H, d, J 7.9 Hz), 8.19 (1H s).

Analysis calculated for (C$_{32}$H$_{43}$N$_3$O$_5$ 0.25H$_2$O): C, H, N.

Step 6

LiOH·H$_2$O (0.011 g, 0.26 mmol) was added to a stirred solution of the methyl ester (0.129 g, 0.24 mmol) in THF:H$_2$O (20 mL, 3:1) cooled in an ice bath. The cold solution was stirred with gradual rewarming to room temperature for 29 hours. The mixture was diluted with water (10 mL) and the THF removed in vacuo. The aqueous solution was acidified with 0.1N HCl (3.0 mL) and the product extracted into EtOAc (2×25 mL), the combined extracts dried over MgSO$_4$, filtered, and the solvent removed in vacuo. The residue was purified by reverse phase chromatography on silica using 70% MeOH/30% H$_2$% as eluant giving the product as a white solid (0.049 g, 38%); mp 111°–133° C.; [α]$_D^{20}$+48.9° (C=0.18, acetone); IR(film)2929, 2855, 1708, and 1660 cm$^{-1}$; δ NMR (DMSO-d$^6$) 1.22 (3H, s), 1.10–2.08 (24H, m), 2.32–2.42 (1H, m), 2.78 (1H, d, J 14.3 Hz), 3.08 (1H, d, J 14.5 Hz), 3.54 (1H, d, J 14.4 Hz), 4.70 (1H, s), 6.65 (1H, s), 6.84 (1H, s), 6.88–6.93 (1H, m), 7.01–7.04 (2H, m), 7.31 (1H, d, J 8.1 Hz), 7.49 (1H, d, J 8.0 Hz), 10.87 (1H, s), 11.95 (1H, b).

Analysis calculated for (C$_{31}$H$_{44}$N$_3$O$_5$): C, H, N.

Example 115

[1S-[α(S*),2B]] and [1R-[α(R*),28β]]$^{sP}$2-[[3-(1H-indol-3-yl)-2-methyl-1-oxo-2-[(tricyclo[3.3.1.1$^{3,7}$] dec-2-yloxy)carbonyl]amino]propyl]amino] cyclhexanecarboxylic acid

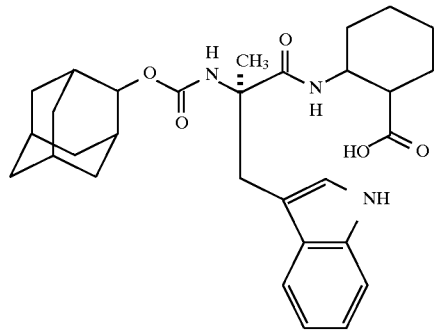

Step 1

Trans-2-cyanoaminocyclohexane (0.242 g, 1.98 mmol) was heated at reflux in 6N HCl (15 mL, 90 mmol) for 18 hours. The cooled mixture was extracted with Et$_2$O (2×25 mL) and the aqueous solution evaporated to dryness. The residue was purified by ion-exchange resin (IR 120H) using 12% aqueous NH$_3$ as the eluant giving the product as an off-white solid (0.148 g, 42%), δ NMR (D$_2$O) 1.26–1.48 (4H, m), 1.80–1.92 (2H, m), 2.04–2.26 (3H, m), 3.21–3.28 (1H, m).

Step 2

To a stirred solution of the acid (0.067 g, 0.17 mmol) in EtOAC (5 mL) was added pentafluorophenol (0.031 g, 0.17 mmol) followed by N,N$^1$dicyclohexylcar-bodiimide (0.039 g, 0.19 mmol). The mixture was stirred for 2 hours and the N,N$^1$-dicyclohexylurea filtered and the solvent removed in vacuo. The residual pentafluorophenylester was stirred and dissolved in DMF (1 mL) and a solution of the amino acid (0.024 g, 0.17 mmol) and Et$_3$N (0.027 mL, 0.19 mmol) in DMF:H$_2$O (2 mL, 1:1) was added and the mixture stirred at room temperature for 77 hours. Five percent aqueous citric acid (10 mL) was added and the mixture extracted with EtOAc (2×25 mL). The combined EtOAc extracts were washed once with brine (10 mL), dried over MgSO$_{41}$ filtered, and the solvent removed in vacuo. The residue was purified by reverse phase chromatography on silica using 70% MeOH/30% H$_2$O as eluant giving the product as a mixture of diastereoisomers (0.022 g, 25%); mp 109°–134° C.; IR(film)3340, 2930, 1708, and 1657 cm$^{-1}$; δ NMR (CDCl$_3$) 1.10–1.98 (25H, m), 2.20–2.30 (1H, m), 3.15–3.44 (2H, m), 3.93–4.07 (1H, m) 4.79, 4.83 (1H, 2s), 5.05 (1H, b), 5.41 (1H, bs) 6.43–6.50 (0.5H, m), 6.58–6.65 (0.5H, m), 6.96–7.15 (3H, m), 7.31–7.36 (1H, m), 7.50–7.58 (1H, m), 8.55–8.80 ((1H, 2s).

Anaylsis calculated for (C$_{30}$H$_{39}$N$_3$O$_5$ 0.9EtOAc): C, H, N.

Example 116

Carbamic acid [2-[(2-cyanocyclohexyl)amino]-1-(1H-indol-3-ylmethyl)-1-methyl-2-oxoethyl]-1H-tricyclo-[3.3.1.1$^{3,7}$]dec-2-yl ester

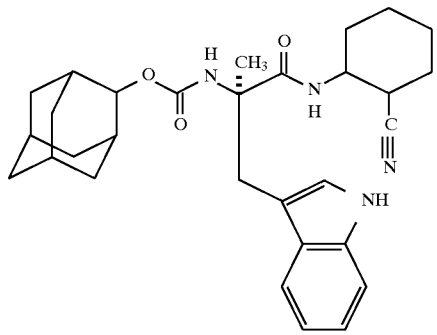

Step 1

Potassium cyanide (0.67 g, 10.29 mmol) was added to a stirred solution of 7-azabicyclo[[4.1.0]heptane (1.0 g, 10.29 mmol) in DMF:water (20 mL, 1:1). After heating at 100° C. for 17 hours, the mixture was cooled and poured into water (100 mL) and extracted with EtOAC (3×50 mL). The combined EtOAc extracts were washed with water (3×50 mL), dried over MgSO$_4$, filtered, and the solvent removed in vacuo giving the product as a syrup (0.485 g, 38%); IR(film) 3370, 2935, 2860, and 2238 cm$^{-1}$; δ NMR (CDCl$_3$) 1.01–1.31 (3H, m), 1.44–1.69 (5H, m), 1.83–2.15 (3H, m), 2.68–2.78 (1H, m).

Step 2

To a stirred solution of the acid (0.397 g, 1.0 mmol) in EtOAc (40 mL) was added 1-hydroxybenzo-triazole monohydrate (0.191 g, 1.25 mmol) followed by N,N$^1$-dicyclohexylcarbodiimide (0.227 g, 1.1 mmol) and the mixture stirred at room temperature for 2 hours. A solution of trans-2-cyanoaminecylcohexane (0.122 g, 1.0 mmol) in EtOAc (2.0 mL) was added and the mixture stirred at room temperature for 67 hours. The N,N$^1$-dicyclohexylurea was filtered off and the EtOAc solution washed with 5% citric acid solution (2×25 mL), saturated NaHCO$_3$ (2×25 mL), 5% citric acid (25 mL), and brine (25 mL). The EtOAc solution was dried over MgSO$_{41}$ filtered, and the solvent removed in vacuo. The residue was purified by chromatography on silica using 506 n-hexane/50% EtOAc as eluant giving the product as a white solid (0.206 g, 41%); mp 120°–154° C.; IR(film) 3346, 2918, 2242, 1700, and 1659 cm$^{-1}$; δ NMR (CDCl$_3$) 1.18–2.00 (25H, m), 2.60–2.66 (1H, m), 3.23–3.33 (1H, m), 3.56 (1H, d, J 14.8 Hz), 3.96–4.02 (1H, m), 4.81–4.83 (1H, m), 5.11 (0.5H, s), 5.23 (0.5H, s), 6.68–6.76 (1H, m), 7.03–7.21 (3H, m), 7.36 (1H, d, J 7.9 Hz), 7.61 (1H, d, J 7.8 Hz), 8.27–8.29 (1H, m).

Analysis calculated for (C$_{30}$H$_{38}$N$_4$O$_3$): C, H, N.

Example 117

Tricyclo[3.3.1.1$^{3,7}$]dec-2-yl ester[1-(1H-indol-3-ylmethyl)-1-methyl-2 [(2-methylcyclohexyl) amino]-2- oxoethyl]carbamate

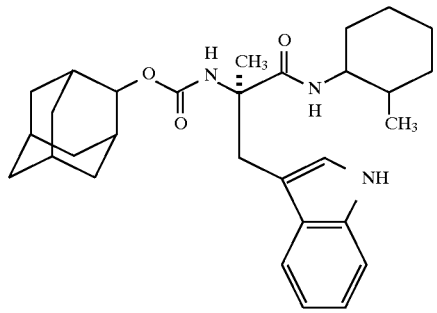

To a stirred solution of 2-Adoc-αMe-Trp-OH (100 mg, 0.25 mmol) was added hydroxybenzotriazole hydrate (38 mg, 0.25 mmol) followed by dicyclohexyl-carbodiimide (52 mg, 0.25 mmol). After stirring for 2 hours, the mixture was filtered and to the filtrate was added a solution of 2-methylcyclohexylamine (30 mg, 0.27 mmol) in ethyl acetate. After stirring at room temperature overnight, the mixture was evaporated to dryness and the residue purified by flash chromatography eluting with CH$_2$Cl$_2$/EtOAc 9:1 to give a colorless foam (88 mg, 72% yield); mp 105°–110° C.

NMR (300 MHz, CDCl$_3$); δ 0.75–2.05 (m, 29H, α-CH$_3$ CHCH$_3$, 9×CH$_2$+4×CH), 3.25–3.65 (m, 2.5H, CH$_2$-indole, +CH for two of the isomers), 3.95–4.05 (m, 0.5H, CH for two of the isomers), 4.82 (s, 1H, CHOCONH), 5.11 (s) and 5.25–5.30 (m, 1H, OCONH), 6.03 and 6.11 (pair of d), 6.45 (bd), and 6.5–6.6 (m, 1H, CONH for four isomers), 7.02 (d, J 2.2 Hz, 1H, 2C-H), 7.11 (t, J 7.2 Hz, IH, 5C-H), 7.18 (t, J 7.9 Hz, 1H, 6C-H), 7.35 (d, J 8.0 Hz, 1H, 7C—H), 7.63 (d, J 7.7 Hz, 1H, 4C-H), 8.12 (s, 1H, indole NH).

Analysis calculated for C$_{30}$H$_{41}$N$_3$O$_3$0.25H$_2$O: C, 72.62; H. 8.43; N, 8.47.
Found: C, 72.68; H, 8.35; N, 8.18.

Example 118

Tricyclo[3.3.1.1$^{3,7}$]dec-2yl ester [2-(bicyclo[2.2.1] hept-2-ylamino)-1-(1H-indol-3-ylmethyl)-1-methyl-2-oxoethyl]carbamate H

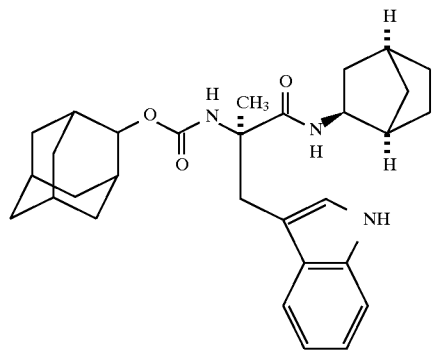

Step 1

N,N$^1$-dicyclohexylcarbodiimide (0.229 g, 1.11 mmol) was added to a stirred solution of 2-Adoc-R-α-Me-Trp-OH (0.401 g, 1.01 mmol) and 1-hydroxybenzotriazole monohydrate (0.186 g, 1.21 mmol) in EtOH (50 mL). The mixture was stirred for 2 hours at room temperature and the N,N¹-dicyclohexylurea filtered off. 2-Aminonorbornane (0.139 g, 1.25 mmol) in EtOAc (25 mL) was then added dropwise over 10 minutes and the mixture stirred at room temperature for 24 hours. The EtOAc solution was washed with 5% citric acid (2×25 mL), saturated NaHCO₃ solution (2×25 mL), 5% citric acid solution (25 mL) and brine (25 mL). The EtOAc solution was dried (MgSO₄), filtered, and the solvent removed in vacuo to give the product as a white solid (0.438 g, 89%); mp 111°–117° C.; IR(film)3338, 2910, 1700, and 1650 cm⁻¹; 6 NMR (CDCl₃) 1.03–1.06 (9H, m), 1.56 (3H, s), 1.65–2.04 (15H, m), 2.19 (1H, s) 3.29 (1H, d, J 14.7 Hz), 3.49 (1H, d, J 14.5 Hz), 3.58–3.65 (1H, m), 4.83 (1H, s), 5.25 (1H, b), 6.05 (1H, b), 7.01 (1H, d, J 8.0 Hz), 7.08–7.20 (2H, m), 7.36 (1H, d, J 8.0 Hz), 7.60 (1 H, d, J 7.8 Hz), 8.23 (1H, s).

Analysis calculated for ($C_{30}H_{39}N_3O_3 0.5H_2O$): C, H, N.

Example 119

Tricyclo[3.3.1.1³,⁷]dec-2-yl ester (R) [2-[[1-(hydroxymethyl)cyclopentyl]amino]-1-(1H-indol-3-ylmethyl)-1-methyl-2-oxoethyl]carbamate

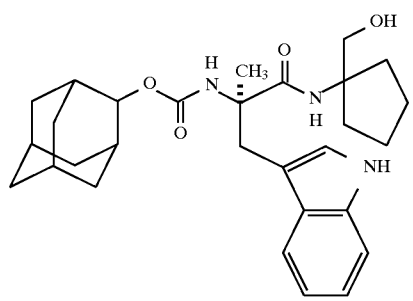

Step 1

N,N¹-dicyclohexylcarbodiimide (0.232 g, 1.12 mmol) was added to a stirred solution of 2-Adoc-R-α-Me-Trp-OH (0.404 g, 1.02 mmol) and 1-hydroxybenzotriazole monohydrate (0.186 g, 1.21 mmol in EtOAc (50 mL). The mixture was stirred for 2 hours at room temperature and the N,N¹-dicyclohexylurea filtered off. 1-Amino-1-hydroxymethylcyclopentane (0.147 g, 1.28 mmol) in EtOAc (20 mL) was added dropwise over 15 minutes and the mixture stirred at room temperature for 48 hours. The EtOAc solution was washed with 50 citric acid (2×25 mL), saturated NaHCO₃ solution (2×25 mL), 5% citric acid (25 mL), and brine (25 mL). The EtOAc was dried over MgSO₄, filtered, and the solvent removed in vacuo. Purification of the residue by chromatography on silica using 50% n-hexane/50% EtOAc as eluant gave the product as a white solid (0.301 g, 60%); mp 95°–104°–C.; [α]$_D$²⁰+45.9° (C=0.28, acetone); IR(film)3308, 2917, 1694, and 1667 cm⁻¹; δ NMR (CDCl₃) 1.51 (3H, s), 1.56–2.01 (23H, m), 3.29 (1H, d, J 14.76 Hz), 3.46 (1H, d, J 14.7 Hz), 3.57 (1H, d, J 11.5 Hz), 3.77 (1H, d, J 11.5 Hz), 4.82 (1H, s), 5.12 (1H, s), 6.26 (1H, s), 7.03 (1H, d, J 2.2 Hz), 7.09–7.14 (1H, m), 7.17–7.22 (1H, m), 7.38 (1H, d, J 8.0 Hz), 7.61 (1H, d, J 7.8 Hz), 8.30 (1H, s).

Analysis calculated for ($C_{29}H_{39}N_3O_4$): C, H, N.

Example 120

(R)-1-[[2-(1H-indol-3-ylmethyl)-2-methyl-1-oxo-2-[[(tricyclo[3.3.1.1³,⁷]dec-2-yloxy) carbonyl]amino]ethyl]amino]cyclohexanoic acid

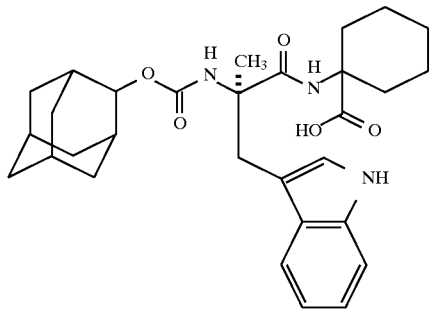

Step 1

Thionyl chloride (7.3 mL, 100 mmol) was added dropwise over 15 minutes to anhydrous MeOH (100 mL) cooled to −10° C. 1-Amino-1-cyclohexanecarboxylic acid (1.43 g, 10 mmol) was added in one portion and the cold solution stirred for 18 hours with slow rewarming to room temperature and then at reflux for 2.5 hours. The MeOH was reduced to low volume and Et₂O added causing the product to precipitate. This was recrystallized from MeOH:Et₂O as a white solid (1.15 g, 59%); mp 203°–208° C.; δ NMR (DMSO-d⁶) 1.39–1.97 (10H, m), 3.73 (3H, s), 8.79 (3H, bs).

Analysis calculated for ($C_8H_{16}ClNO_2 0.25H_2O$): C, H, Cl, N.

Step 2

N,N¹-dicyclohexylcarbodiimide (0.454 g, 2.20 mmol) was added to a stirred solution of 2-Adoc-R-a-Me- Trp-OH (0.793 g, 2.00 mmol) and 1-hydroxybenzotriazole monohydrate (0.383 g, 2.50 mmol) in EtOAc (100 mL). The mixture was stirred at room temperature for 2 hours and the N,N¹-dicyclohexylurea filtered off. The aminoester hydrochloride (0.426 g, 2.20 mmol) was added followed by dropwise addition of Et₃N (0.307 mL, 2.20 mmol) in EtoAC (25 mL) added over 10 minutes and then a catalytic amount of 4-dimethylaminopyridine. The mixture was heated at reflux for 10 hours and the cooled solution washed with 5% citric acid (2×25 mL)), saturated NaHCO₃ (2×25 mL)), 5% citric acid (25 mL), and brine (25 mL). The EtOAc was dried over MgSO₄, filtered, and the solvent removed in vacuo. The residue was purified by chromatography on silica using 50% n-hexane/50% EtOAc as eluant giving the product as a white solid (0.458 g, 43%); mp 110°–118° C.; [α$_d$²⁰+37.9° (C=0.13, acetone), IR(film) 3369, 2926, 1724, and 1668 cm⁻¹; δ NMR (DMSO-d⁶) 1.25–2.18 (24H, m), 1.29 (3H, s), 3.13 (1H, d, J 14.6 Hz), 3.51–3.56 (4H, m), 4.70 (1H, s), 6.68 (1H, bs), 6.90–6.95 (1H, m), 7.01–7.06 (2H, m), 7.33 (1H, d, J 8.0 Hz), 7.46 (1H, s), 7.52 (1H, d, J 7.8 Hz), 10.89 (1H, s).

Analysis calculated for (C33H₄₁N₃O₅ 0.1n-C₆H₁₄): C, H, N.

Step 3

LiOH-H₂O (0.042 g, 1.00 mmol) was added to a stirred solution of the methylester (0.327 g, 0.61 mmol) in THF:H₂O (25 mL, 4:1 mixture) cooled to 0° C. The mixture was stirred for 72 hours at room temperature and then a further portion of the LiOH-H₂O (0.013 g, 0.31 mmol) was added. The mixture was stirred a further 8 hours at room temperature and then the THF removed in vacuo. The aqueous solution was acidified with 1N HCl (2.0 mL) and the product extracted into EtOAc (2×25 mL). The EtOAc was dried over MgSO₄, filtered, and the solvent removed in vacuo. The residue was purified by reverse phase chromatography on silica using 30% H₂O/70% MeOH as eluant giving the product as a white solid (0.151 g, 48%); mp 233°–235° C.; IR(film 3354, 2918, and 1718 cm⁻¹; δ NMR (DMSO-d⁶) 1.15–2.00 (26H, m), 2.10–2.20 (1H, m), 3.10 (1H, d, J 14.6 Hz), 3.55 (1H, d, J 14.7 Hz), 4.69 (1H, s), 6.70 (1H, b), 6.89–6.94 (1H, m), 7.00–7.05 (2H, m), 7.27–7.33 (2H, m), 7.50 (1H, d, J 7.6 Hz), 10.88 (1H, s), 12.08 (1H, s).
Analysis calculated for (C₃₀H₃₉N₃O₅): C, H, N.

Example 121

2-[[3-(1H-indol-3-yl)-2-methyl-1-oxo-2-[[(tricyclo-[3.3.1.1³,⁷]dec-2-yloxy)carbonyl]amino]propyl] amino]cyclohexanecarboxylic acid

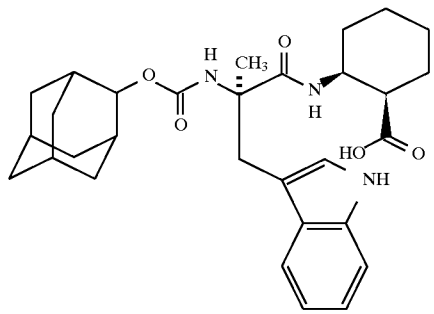

Step 1

(–)-Cis-2-benzamidecyclohexanecarboxylic acid (1.0 g, 4.04 mmol) was heated at reflux in GN HCl (40 mL, 240 mmol) for 24 hours. The cooled mixture was extracted with EtOAc (2×25 mL) to remove benzoic acid. The acidic solution was then evaporated to dryness and the residue recrystallized from MeOH/Et₂O giving the product as a white solid (0.518 g, 71%); mp 230°–234° C.; δ NMR (DMSO-d⁶) 1.29–1.98 (8H, m), 2.89–2.90 (1H, m), 3.29 (1H, m), 8.09 (3H, bs), 12.90 (1H, bs).
Analysis calculated for (C₇H₁₄ClNO₂ 0.25H₂O): C, H, N.

Step 2

N,N¹-dicyclohexylcarbodiimide (0.285 g, 1.38 mmol) was added to a stirred solution of 2-Adoc-R-α-Me-Trp-OH (0.500 g, 1.26 nmol) and pentafluorophenol (0.255 g, 1.39 mmol) in EtOAc (50 mL). The mixture was stirred for 2 hours at room temperature, the N,N¹-dicyclohexylurea filtered off and the solvent removed in vacuo. The pentafluorophenylester was stirred and dissolved in anhydrous DMF (20 mL) and the amino acid hydrochloride (0.270 g, 1.5 mmol) was added followed by Et₃N (0.418 mL, 3.0 mmol) and the mixture stirred at room temperature for 72 hours. The mixture was diluted with 5% citric acid solution (50 mL) and extracted with EtOAc (3×50 mL). The combined EtOAc extracts were washed with brine (3×50 mL), dried (MgSO₄), filtered, and the solvent removed in vacuo. The residue was purified by reverse phase chromatography on silica using 70%MeOH/30%H₂O as eluant giving the product as a white solid (0.115 g, 18%); mp 135°–143° C.; [α]_d^{20}+21.6° (C=0.10, acetone); IR(film) 3348, 2920, 1703, and 1655 cm⁻¹; δ NMR (DMSO-d⁶) 1.26 (3H, s), 1.26–1.95 (23H, m), 3.10–3.17 (1H, m), 3.35–3.40 (1H, m), 3.88–4.00 (1H, m), 4.67 (1H, s), 6.91–7.05 (4H, m), 7.31 (1H, d, J 8.0 Hz), 7.38 (1H, bs), 7.46 (1H, d, J 7.9 Hz), 10.87 (1H, s), 12.30 (1H, b).
Analysis calculated for (C₃₀H₃₉N₃O₅ 0.3H₂0): C, H, N.

Example 122

Tricyclo[3.3.1.1³,⁷]dec-2-yl ester (R) [2-[1-(hydroxymethyl)cvclohexyl]amino]-1-(1H-indol-3-ylmethyl)-1-methyl-2-oxoethyl]carbamate

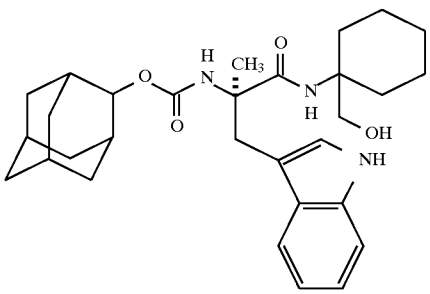

Step 1

1-Aminocyclohexanecarboxylic acid (5.0 g, 34.92 mmol) was stirred and dissolved in 1N NaOH (39 mL, 39.0 mmol) and 1,4-dioxan (40 mL) was added. To this mixture was added NaHCO₃ (3.52 g, 44.9 mmol) followed by a solution of di-tert-butyl-dicarbonate (9.15 g, 41.9 imol) in 1,4-dioxan (40 mL) added dropwise over 30 minutes. The mixture was stirred rapidly overnight at room temperature and the 1,4-dioxan removed in vacuo. The residue was diluted with water (50 mL) and the mixture extracted once with Et₂O (50 mL). The aqueous solution was made pH4 with 5% citric acid and the product extracted into EtOAc (3×100 mL). The EtOAc was dried over MgSO₄. filtered, and the solvent removed in vacuo to give the product as a white solid (4.42 g, 52%); mp 174° C.; IR(film) 3313, 1713, and 1655 cm⁻¹; δ NMR (DMSO-d⁶), 1.15–1.65 (8H, m), 1.36 (9H, s), 1.87–1.98 (2H, m), 6.84 (1H, bs), 12.08 (1H, s).
Analysis calculated for (C₁₂H₂₁NO₄ 0.1H₂O): C, H, N.

Step 2

N-methylmorpholine (0.230 mL, 2.06 mmol) was added to a stirred solution of the acid (0.50 g, 2.06 mmol) in THF (10 mL) cooled to –10° C. To this mixture was added ethyl chloroformate (0.20 mL, 2.06 mmol) and the cold solution stirred for 50 minutes. N-methyl-morpholine hydrochloride was filtered off and the solution recooled to –10° C. 2.0 M LiBH₄ (3.1 mL, 6.2 mmol) was added and the cold mixture stirred for 2.5 hours. 1N HCl (7.5 mL, 7.5 mmol) was added and the mixture extracted with EtOAC (2×20 mL). The combined EtOAc extracts were dried over MgSO₄, filtered, and the solvent removed in vacuo. The residue was purified by chromatography on silica using 67% n-hexane/33% EtOAc as eluant giving the product as a white solid (0.249 g, 53%); mp 94.5°–95.5° C.; IR(film) 2930 and 1686 cm⁻¹; δ NMR (CDCl₃) 1.44 (9H, s), 1.38–1.56 (8H, m), 1.75–1.83 (2H, m), 3.65 (2H, s), 4.10 (1H, b), 4.56 (1H, b).
Analysis calculated for (C₁₂H₂₃NO₃): C, H, N.

Step 3

Trifluoroacetic acid (1.0 mL, 12.78 mmol) was added to a stirred solution of the alcohol (0.221 g, 0.97 mmol) in CH₂Cl₂ (5.0 mL) and the mixture stirred at room temperature for 2 hours. The solvent was removed in vacuo giving a syrup which solidified from Et₂O/n-hexane. This gave the product as a white solid (0.236 g, 100%) which was used directly without further purification.

Step 4

N,N¹-dicyclohexylcarbodiimide (0.227 g, 1.1 mmol) was added to a stirred solution of 2-Adoc-R-α-Me-Trp-OH (0.397 g, 1.0 mmol) and 1-hydroxybenzotriazole monohydrate (0.184 g, 1.20 nmol) in EtOAc (40 mL). The mixture was stirred for 2 hours at room temperature and the N,N$^1$-dicyclohexylurea filtered off. A solution of the amine salt (0.253 g, 1.04 mmol) in EtOAc (10 mL) containing Et$_3$N (0.160 mL, 1.14 mmol) was added dropwise over 10 minutes and the mixture stirred at room temperature for 48 hours. The EtOAc solution was washed with 5% citric acid (2×25 mL), saturated NaHCO$_3$ (2×25 mL), 5% citric acid (25 mL), and brine (25 mL), dried over MgSO$_4$, filtered, and the solvent removed in vacuo. The residue was purified by chromatography on silica using 67% n-hexane/33% EtOAc and 50% n-hexane/50% EtOAc as eluants giving the product as a white solid (0.099 g, 20%); mp 94°–105° C.; [α]$_D^{20}$+ 48° (C=0.50, acetone); IR(film) 2929, 1695, and 1670 cm$^{-1}$; δ NMR (CDCl$_3$) 1.31–2.00 (2Hd, m)/ 1.53 (3H, s), 3.29 (1H, d, J 14.7 Hz), 3.49–3.58 (2H, m), 3.78 (1H, d, J 11.7 Hz), 4.10 (1H, b), 4.82 (1H, s), 5.18 (1H, s), 6.15 (1H, s), 7.03 (1H, s), 7.09–7.21 (2H, m), 7.38 (1H, d, J 8.0 Hz), 7.61 (1H, d, J 7.8 Hz), 8.53 (1H, 5).

Analysis calculated for (C$_{30}$H$_{41}$N$_3$O$_4$): C, H. N.

Example 123

Carbamic acid, [1-[1H-indol-2-ylmethyl)-1-methyl-2-[[2-[(methylamino)carbonyl]cyclohexyl]amino]-2-oxoethyl]-, tricyclo[3.3.1.1>3,7]dec-2-yl ester

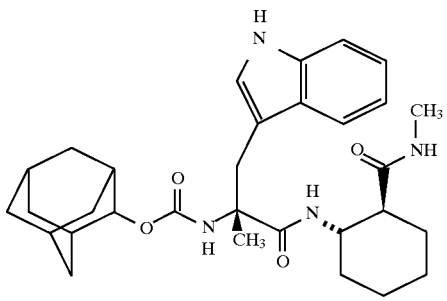

Step 1

N,N$^1$-dicyclohexylcarbodiimide (0.027 g, 0.13 mmol) was added to a stirred solution of the acid (0.055 g, 0.11 mmol) and 1-hydroxybenzotriazole monohydrate (0.020 g, 0.13 mmol) in EtOAC (10 mL). The mixture was stirred for 2 hours at room temperature and the N,N$^1$-dicyclohexylurea filtered off. Methylamine hydrochloride (0.011 g, 0.17 mmol) was added followed by Et$_3$N (0.024 mL, 0.17 mmol) and the mixture stirred at room temperature for 19 hours. A further portion of methylamine hydrochloride (0.024 g, 0.36 mmol) was added followed by Et$_3$N (0.05 mL, 0.36 mmol) and the mixture stirred for a further 48 hours. The mixture was washed with 5% citric acid (2×10 mL), saturated NaHCO$_3$ (10 mL)), and once with brine (10 mL). The EtOAc was dried over MgSO$_{41}$ filtered, and the solvent removed in vacuo. The residue was purified by chromatography on silica using 2% MeOH/98% CH$_2$Cl$_2$ as eluant giving the product as a white solid (0.021 g, 36%); mp 146°–156° C.; IR(film) 3315, 2927, 2856, 1700, and 1647 cm$^{-1}$; δ NMR (CDCl$_3$) 1.15–2.04 (25H, m), 2.16–2.28 (1H, m), 2.70–2.72 (3H, m), 3.27–3.50 (2H, m), 3.81–3.90 (1H, m), 4.80 (1H, s), 5.23 (0.5H, s), 5.26 (0.5H, s), 6.47 (0.5H, d, J 8.5 Hz), 6.55 (1H, b), 6.64 (0.5H, d, J 8.5 Hz), 6.97–6.99 (1H, m), 7.05–7.19 (2H, m), 7.35 (1H, d, J 8.0 Hz), 7.60 (1H, d, J 7.8 Hz), 8.48 (1H, s).

Analysis calculated for (C$_{31}$H$_{42}$N$_4$O$_4$ 0.75H$_2$0): C, H, N.

We claim:
1. A compound of formula

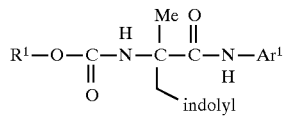

wherein

R$^1$ is a cyclo or polycycloalkyl hydrocarbon with from 0 to 4 substituents each independently selected from a straight or branched alkyl of from 1to 6 carbon atoms, halogen, CN, OR*, SR*, CO$_2$R*, CF$_3$, NR$^5$R$^6$, or (CH$_2$)$_n$OR$^5$ wherein R*, R$^5$, and R$^6$ are each independently hydrogen or a straight or branched alkyl of from 1 to about 6 carbon atoms; and Ar$^1$ is phenyl or substituted phenyl.

2. A compound of formula

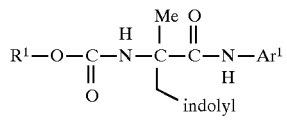

wherein

R$^1$ is

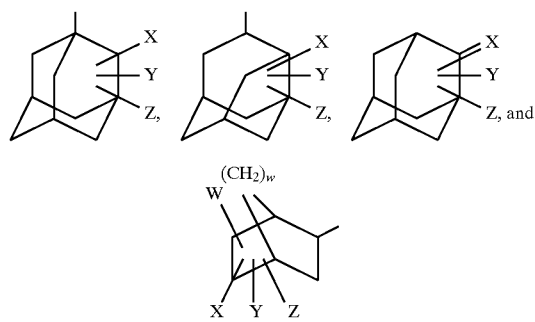

wherein W, X, Y and Z are each independently hydrogen, a straight or branched alkyl of from one to six carbon atoms, CF$_3$, NR$^5$R$^6$, —(CH$_2$)$_n$CO$_2$R*, CN, F, Cl, Br, OR*, SR* wherein R*, R$^5$ and R$^6$ are each independently hydrogen or a straight or branched alkyl of from 1 to about 6 carbon atoms and w is an integer of from 1 to 3: and Ar is
2- or 3-thienyl,
2- or 3-furanyl,
2-, 3-, or 4-pyridinyl,

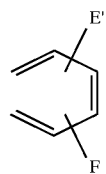

wherein E' and F are each independently hydrogen, fluorine, chlorine, bromine, iodine, methyl, methoxy, trifluoromethyl, nitro, hydroxy, NH$_2$, and OCF$_3$.

3. A compound of formula $$R^1-O-\underset{\underset{O}{\|}}{C}-\underset{H}{N}-\underset{\underset{\text{indolyl}}{|}}{\overset{\overset{Me}{|}}{C}}-\overset{\overset{O}{\|}}{\underset{H}{C}}-N-Ar^1$$

wherein the $R^1$ is polycycloalkyl a is selected from the group consisting of

[three adamantyl structures with substituents X, Y, Z]

[bicyclic structure with $(CH_2)_w$ bridge and substituents W, X, Y, Z]

wherein W, X, Y, and Z are each independently hydrogen, a straight or branched alkyl of from one to six carbon atoms, $CF_3$, $NR^5R^6$, $-(CH_2)_nCO_2R^*$, CN, F, Cl, Br, $OR^*$, $SR^*$, wherein , $R^*$, $R^5$, and $R^6$ are each independently hydrogen or a straight or branched alkyl of from 1to about 6 carbon atcs and w is an integer of from 1to 3 and $Ar^1$ is phenyl,
pyrrolidinyl,
substituted pyrrolidinyl,
heterocycle,
2- or 3-thienyl,
2- or 3-furanyl,
2-, 3- or 4-pyridinyl,

[phenyl ring with E' and F substituents]

wherein E' and F are each independently hydrogen, fluorine, chlorine, bromine, iodine, methyl, methoxy, trifluoromethyl, nitro, hydroxy, $NH_2$, and $OCF_3$.

4. A compound named:

Carbamic acid, [2-[[1-(hydroxymethyl)-2-phenylethyl]amino]-1-(1H-indol-3-ylmethyl)ethyl]-, tricyclo[3.3.1.1$^{3,7}$]dec-2-yl ester, [S-(R*,S*)]-, Carbamic acid, [2-[[1-(hydroxymethyl)-2-phenylethyl]amino]-1-(1H-indol-3-ylmethyl)ethyl-, tricyclo[3.3.1.1$^{3,7}$]dec-2-yl ester, [S-(R*,R*)]-, Tricyclo[3.3.1.1$^{3,7}$]dec-2-yl[1- [[[1-hydroxy-methyl)-2-phenylethyl]carbonyl]amino]-2-(1H-indol-3-yl)ethyl] carbamate, Carbamic acid, [2-[(2-hydroxy-2-phenylethyl)-amino]-1-(1H-indol-3-ylmethyl)-1-methylethyl]-, tricyclo [3.3.1.1$^{3,7}$]dec-2-yl ester (hydroxy center is RS, other center is R), Carbamic acid, [2-[[1-(hydroxymethyl)-2-phenyl-ethyl]amino]-1-(1H-indol-3-ylmethyl)-1-methylethyl]-, tricyclo[3.3.1.1$^{3,7}$]dec-2-yl ester, [R-(R*,S*)]-, 4-methylbenzenesulfonate (1:1) (salt), ester, [R-(R*,S*)]-, 4-methylbenzenesulfonate (1:1) (salt), Benzenepropanol,:δ-[[2-(1H-indol-3-yl)-2- [[(tricyclo[3.3.1.1$^{3,7}$]dec-2-yloxy)carbonyl]-amino]propyl]amino]-, acetate (ester), [R-(R*,S*)]-, 4-methylbenzenesulfonate (1:1) (salt), Carbamic acid, [[2-[acetyl[1-(hydroxymethyl)-2-phenylethyl]amino]-1-(1H-indol-3-ylmethyl)-1-methyl]ethyl]-, tricyclo[3.3.1.1$^{3,7}$]dec-2-yl ester, [R-(R*,S*)]-, 5,13-Dioxa-2,8-diazatetradec-10-enoic acid, 3-(1H-indol-3-ylmethyl)-3-methyl-4,9,12-trioxo-7-phenyl-, tricyclo[3.3.1.1$^{3,7}$]dec-2-yl ester, [S- (R*,S*)]-, 5,13-Dioxa-2,8-diazatetradecanoic acid, 3-(1H-indol-3-ylmethyl)-3-methyl-4,9,12-trioxo-7-phenyl-, tricyclo[3.3.1.1$^{3,7}$]dec-2-yl ester, [R-(R*,R*)]-, Carbamic acid, [1-(1H-indol-3-ylmethyl)-1-methyl-2-[(1-oxo-4-phenylbutyl)amino]ethyl]-, tricyclo[3.3.1.1$^{3,7}$]dec-2-yl ester (R)-, Carbamic acid, [2-(benzoylamino)-1-(1H-indol-3-ylmethyl)-1-methylethyl]-, tricyclo[3.3.1.1$^{3,7}$]-dec-2-yl ester, (R)-, Carbamic acid, [1-(1H-indol-3-ylmethyl)- 1-methyl-2-[(1-oxo-3-phenylpropyl)amino]ethyl]-, tricyclo[3.3.1.1$^{3,7}$]dec-2-yl ester, (R)-, Carbamic acid, [1-(1H-indol-3-ylmethyl)- 1-methyl-2-[(2-phenylacetyl)amino]ethyl]-, tricyclo-[3.3.1.1$^{3,7}$]dec-2-yl ester, (R)-, Carbamic acid, [2-[[3-[[1-(hydroxymethyl)-2-phenylethyl]amino]-3-oxopropyl]amino]-1-(1H-indol-3-ylmethyl)-1-methyl-2-oxoethyl]-, [R, (R*,S*)]-, Carbamic acid, [1-(1H-indol-3-ylmethyl)-2-[[3-[[1-(hydroxymethyl)-2-phenylethyl]amino]-3-oxopropyl]amino]-1-methyl-2-oxoethyl]-, tricyclo-[3.3.1.1$^{3,7}$]dec-2-yl ester, [S-(R*,R*)]-, D-Phenylalaninamide, α-methyl-N-[(tricyclo-[3.3.1.1$^{3,7}$]dec-2-yloxy)carbonyl] -D-tryptophyl-β-alanyl-, L-Phenylalaninamide, α-methyl-N-[(tricyclo-[3.3.1.1$^{3,7}$]dec-2-yloxy)carbonyl) -D-tryptophyl-β-alanyl-, L-Phenylalaninamide, α-methyl-N-[(tricyclo-[3.3.11.1$^{3,7}$]dec-2-yloxy)carbonyl] -L-tryptophyl-β-alanyl-, D-Phenylalaninamide, α-methyl-N-[tricyclo-[3.3.1.1$^{3,7}$]dec-2-yloxy)carbonyl]-L-tryptophyl-β-alanyl-, 12-Oxa-2,5,9-triazatridecanoic acid, 3-(1H-indol-3-ylmethyl)-3-methyl-4,8,11-trioxo-10-(phenylmethyl)-, tricyclo[3.3.1.1$^{3,7}$]dec-2-yl ester, [R,(R*,R*)]-, L-Phenylalanine, N-[N-[α-methyl-N-[(tricyclo-[3.3.1.1$^{3,7}$]dec-2-yloxy)carbonyl]-D-tryptophyl]-β-alanyl]-, phenylmethyl ester, Propanoic acid, 2-[[3-[[3-(1H-indol-3-yl)-2-methyl-1-oxo-2-[[(tricyclo[3.3.1.1$^{3,7}$]dec-2-yloxy)carbonyl]amino]propyl]amino]-1-oxopropyl]-amino]-3-phenyl-, phenylmethyl ester, [S-(R*,R*)]-, D-Phenylalanine, N- [N- [α-methyl-N- [(tricyclo-[3.3.1.1$^{3,7}$]dec-2-yloxy)carbonyl]-D-tryptophyl]-β-alanyl]-, L-Phenylalanine, N-[N-[α-methyl-N-[(tricyclo-[3.3.1.1$^{3,7}$]dec-2-yloxy)carbonyl] -D-tryptophyl]-β-alanyl]-, L-Phenylalanine, N-[N-[α-methyl-N-[(tricyclo-[3.3.1.1$^{3,7}$]dec-2-yloxy)carbonyl]-L-tryptophyl]-β--alanyl]-, Benzenepropanoic acid, α-[[3-[[3-[(1H-indol-3-yl)-2-methyl-1-oxo-2-[[(tricyclo[3.3.1.1$^{3,7}$]dec-2-yloxy)carbonyl]amino]propyl]amino]:-1-oxopropyl]-amino]-, [S-(R*,S*)]-, Glycine, N-[2-methyl-N-[(tricyclo-[3.3.1.1$^{3,7}$]dec-2-yloxy)carbonyl]-D-tryptophyl]-, phenylmethyl ester, Carbamic acid, [3-(1H-indol-3-ylmethyl)-2,5-dioxo-1-(2-phenylethyl)-3-pyrrolidinyl]-, tricyclo[3.3.1.1$^{3,7}$]dec-2-yl ester, (±)-, Carbamic acid, [1-(1H-imidazol-4-ylmethyl)- 1-methyl-2-oxo-2-[(2-phenylethyl)amino]ethyl]-, 1,1-dimethylethyl ester, (±)-, Carbamic acid, [3-(1H-indol-3-yl)-1-methyl-1-[[(2-phenylethyl)amino]carbonyl]propyl]-, tricyclo[3.3.1.1$^{3,7}$]dec-2-yl ester, (±)-, Carbamic acid, [1-[[[1-hydroxymethyl)-2-phenylethyl]amino]carbonyl]-3-(1H-indol-3-yl)-1-methylpropyl]-, tricyclo[3.3.1.1$^{3,7}$]dec-2-yl ester (hydroxymethyl center is S, other center is RS), 13-Oxa-2,5,9-triazatetradec-10-enoic acid, 3-[2-(1H-indol-3-yl)ethyl]-3-methyl-4,5,12-trioxo-7-phenyl-, tricyclo[3.3.1.1$^{3,7}$]dec-2-yl ester [TRP center is R/S mixture, other center is R], L-Phenylalaninamide, N-[[(1,1-dimethyl-ethoxy)-carbonyl]-α-methyl]-L-tryptophyl]-L-methionyl-L-α-aspartyl-, Glycine, N-[2-methyl-N-[(tricyclo-[3.3.1.1$^{3,7}$]dec-2-yloxy)carbonyl]-D-tryptophyl]-L-phenylalanyl-, Carbamic acid, [1-[[[1-(hydroxymethyl)-2-phenylethyl]amino]carbonyl]-2-(1H-indol-3-yl)-propyl]-, tricyclo[3.3.1.1$^{3,7}$]dec-2-yl ester (hydroxymethyl center S, other centers RS), 2,4-Heptadienoic acid, 6-[[3-(1H-indol-3-yl)-2-methyl-1-oxo-2-[[(tricyclo[3.3.1.1$^{3,7}$]dec-2-yloxy)carbonyl]aminolpropyl]amino]-7-phenyl-, [R,R*,S*-(E,E)]]-, Glycine, N-[2-methyl-N-[(tricyclo-[3.3.1.1$^{3,7}$]dec-2-yloxy)carbonyl]-D-tryptophyl]-, phenylmethyl ester, Tricyclo[3.3.1.1$^{3,7}$]dec-2-yl-R-(R*,S*)]-[1-[4,5-dihydro-4-(phenylmethyl)-2-thiazolyl]-2-(1H-indol-3-yl)-1-methylethyl]carbamate, Carbamic acid, [2-[(hexahydro-1H-azepin-1-yl)amino]-1-(1H-indol-3-ylmethyl)-1-methyl-2-oxoethyl]-,tricyclo[3.3.1.1$^{3,7}$]dec-2-yl ester,(R)-, Carbamic acid, N-[2-[(2-hydroxycyclohexyl)-amino]-1-(1H-indol-3-ylmethyl)-1-methyl-2-oxoethyl]-,tricyclo[3.3.1.1$^{3,7}$]dec-2-ylester,[1α(R),2α], Carbamic acid, [1-(1H-indol-3-ylmethyl)-1-methyl-2-(4-morpholinylamino)-2-oxo-ethyl] -,tricyclo[3.3.1.1$^{3,7}$]dec-2-ylester, (R)-, Carbamic acid, [1-(1H-indol-3-ylmethyl)-1-methyl-2-oxo-2-(1-piperidinylamino)-ethyl]-,tricyclo[3.3.1.1$^{3,7}$]dec-2-ylester, (R)-, Tricyclo[3.3.1.1$^{3,7}$]dec-2-yl ester [2S-(R*,S*)], N-[1-(1H-indol-3-ylmethyl)- 2-[[2-(methoxymethyl)-1-pyrrolidinyl]amino]-1-methyl-2-oxoethyl]carbamate, Tricyclo[3.3.1.1$^{3,7}$]dec-2-yl[R-(R*,R*)]-[1-(1H-indol-3-ylmethyl)-2-[[2-(methoxymethyl)-1-pyrrolidinyl]amino]-1-methyl-2-oxoethyl]-carbamate, (R)-1-[[3-(1H-indol-3-yl)-2-methyl-1-oxo-2-[[(tricyclo[3.3.1.1$^{3,7}$]dec-2-yloxy)carbonyl]amino]propyl]amino]cyclohexaneacetic acid,

[1S-[[1α(S*),2B]] and [1R-[α(R*),2 β]]$^{sp}$2 -[[3-(1H-indol-3-yl)-2-methyl-1-oxo-2-[(tricyclo-[3.3.1.1$^{3,7}$]dec-2-yloxy)carbonyl]amino]propyl]-amino]cyclohexanecarboxylic acid, Carbamic acid [2-[(2-cyanocyclohexyl)amino]-1-(1H-indol-3-ylmethyl)-1-methyl-2-oxoethyl]-1H-tricyclo[3.3.1.1$^{3,7}$]dec-2-yl ester, [Tricyclo[3.3.1.1$^{3,7}$]dec-2-yl ester-[[1-(1H-indol-3-ylmethyl)-1-methyl-2[(2-methyl cyclohexyl) amino]-2-oxoethyl]carbamate, Tricyclo[3.3.1.1$^{3,7}$]dec-2yl ester [2-(bicyclo[2.2.1]hept-2-ylamino)-1-(1H-indol-3-ylmethyl)-1-methyl-2oxoethyl]carbamate, Tricyclo[3.3.1.1$^{3,7}$]dec-2-yl ester (R)[2-[[1-(hydroxymethyl)cyclopentyl]amino]-1-(1H-indol-3-ylmethyl)-1-methyl-2-oxoethyl]-carbamate, 2-[[3-(1H-indol-3-yl)-2-methyl-1-oxo-2-[[(tricyclo[3.3.1.1$^{3,7}$]dec-2-yloxy)-carbonyl]amino]propyl]amino]cyclohexanecarboxylic acid(R)$^{sp}$ 1- [[2- (1H-indol-3-ylmethyl) -2-methyl-1-oxo-2-[[(tricyclo[3.3.1.1$^{3,7}$]dec-2-yloxy)-carbonyl]amino]ethyl]amino] -cyclohexanoic acid, Tricyclo[3.3.1.1$^{3,7}$]dec-2-yl ester (R) [2-[1-(hydroxymethyl)cyclohexyl]amino]-1-(1H-indol-3-ylmethyl)-1-methyl-2-oxoethyl]-carbamate, and Phenylmethyl ester [2S-[1(2S*,3R*),2R*]]-[3-[2-[[(1,1-dimethylethyl)amino]carbonyl]-1-piperidinyl]-2-hydroxy-1-(phenylmethyl)-propyl]carbamate.

5. A pharmaceutical composition comprising an amount of a compound according to any one of claims 1–4, effective to suppress the appetite, to reduce gastric acid secretion, reduce anxiety, treat gastrointestinal ulcers, treat psychotic behavior, block the reaction caused by withdrawal from drug or alcohol use, potentate the effects of morphine and other opioids in treating pain, and treat and/or prevent panic in a mammal, and a pharmaceutically acceptable carrier.

6. A method of reducing anxiety in a mammal, comprising administering an effective anxiety reducing amount of a compound according to any one of claims 1–4.

* * * * *

UNITED STATES PATENT AND TRADEMARK OFFICE
CERTIFICATE OF CORRECTION

PATENT NO. : 5,846,942
DATED : December 8, 1998
INVENTOR(S) : Horwell, et. al.

It is certified that error appears in the above-identified patent and that said Letters Patent is hereby corrected as shown below:

Column 144, line 13, insert -- -- between "from 1" and "to 6".

Column 144, line 52, "Ar" should read "$Ar^1$".

Column 144, line 60, delete " 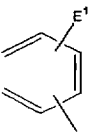 "

and insert -- 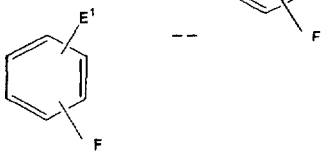 --

Column 145, line 8, "a" should read "and".

Column 145, line 27, delete "," after "wherein".

Column 145, line 28, insert -- -- between "1" and "to".

Column 145, line 29, "atos" should read "atoms".

Column 146, line 1, delete "δ" insert -- β --.

Column 146, line 64, delete ":".

Column 147, line 31, "aminolpropyl]" should read "amino]propyl]".

UNITED STATES PATENT AND TRADEMARK OFFICE
CERTIFICATE OF CORRECTION

PATENT NO. : 5,846,942
DATED : December 8, 1998
INVENTOR(S) : Horwell, et. al.

It is certified that error appears in the above-identified patent and that said Letters Patent is hereby corrected as shown below:

Column 146, line 40, "[3.3.11.1$^{3,7}$]" should read "[3.3.1.1$^{3,7}$]".

Column 146, line 61, "β--alanyl]-" should read "β-alanyl]-"

Column 147, line 10, "[1-[[[1-hydroxymethyl)" should read "[1-[[[(1-hydroxymethyl)".

Column 148, line 10, insert "1" between "[" and "α".

Column 147, line 42, "[1α(R),2α]" should read "[1α(R),2β]".

Column 148, line 15, after "ester," delete "[" and begin a new paragraph with "Tricyclo".

Column 148, line 16, "ester-[[1-" should read "ester-[1-".

Column 148, line 42, "potentate" should read "potentiate".

Signed and Sealed this

Twenty-seventh Day of June, 2000

Attest:

Q. TODD DICKINSON

*Attesting Officer*      *Director of Patents and Trademarks*